(12) United States Patent
Philippe et al.

(10) Patent No.: US 10,463,062 B2
(45) Date of Patent: Nov. 5, 2019

(54) MICROBIAL PRODUCTION OF STEVIOL GLYCOSIDES

(71) Applicant: Manus Biosynthesis, Inc., Cambridge, MA (US)

(72) Inventors: Ryan Philippe, Cambridge, MA (US); Ajikumar Parayil Kumaran, Cambridge, MA (US); Jason Donald, Cambridge, MA (US); Krishna Patel, Cambridge, MA (US); Swati Gupta, Cambridge, MA (US); Ryan Lim, Cambridge, MA (US); Liwei Li, Cambridge, MA (US)

(73) Assignee: MANUS BIO INC., Cambridge, MA (US)

( * ) Notice: Subject to any disclaimer, the term of this patent is extended or adjusted under 35 U.S.C. 154(b) by 177 days.

(21) Appl. No.: 15/524,015

(22) PCT Filed: Nov. 5, 2015

(86) PCT No.: PCT/US2015/059273
§ 371 (c)(1),
(2) Date: May 3, 2017

(87) PCT Pub. No.: WO2016/073740
PCT Pub. Date: May 12, 2016

(65) Prior Publication Data
US 2017/0332673 A1 Nov. 23, 2017

Related U.S. Application Data

(60) Provisional application No. 62/075,644, filed on Nov. 5, 2014.

(51) Int. Cl.
| *A23L 2/60* | (2006.01) |
| *C12P 19/56* | (2006.01) |
| *C12N 9/10* | (2006.01) |
| *A23L 27/30* | (2016.01) |
| *C12N 9/02* | (2006.01) |

(52) U.S. Cl.
CPC .............. *A23L 2/60* (2013.01); *A23L 27/36* (2016.08); *C12N 9/0073* (2013.01); *C12N 9/1048* (2013.01); *C12N 9/1051* (2013.01); *C12P 19/56* (2013.01); *C12Y 114/13079* (2013.01); *C12Y 204/01017* (2013.01); *A23V 2002/00* (2013.01)

(58) Field of Classification Search
CPC ...... A23V 2250/262; A23L 27/36; A23L 2/60
See application file for complete search history.

(56) References Cited

U.S. PATENT DOCUMENTS

| 8,703,225 B2 | 4/2014 | Morita et al. |
| 9,243,273 B2 | 1/2016 | Markosyan et al. |
| 9,562,251 B2 | 2/2017 | Kishore et al. |
| 9,848,632 B2 | 12/2017 | Morita et al. |
| 9,957,540 B2 | 5/2018 | Mikkelsen et al. |
| 2008/0064063 A1 | 3/2008 | Brandle et al. |
| 2014/0357588 A1 | 12/2014 | Markosyan et al. |

FOREIGN PATENT DOCUMENTS

| JP | 3277275 | 12/1991 |
| WO | 2011153378 | 12/2011 |
| WO | 2012075030 | 7/2012 |
| WO | 2013022989 | 2/2013 |
| WO | 2014122227 | 8/2014 |

OTHER PUBLICATIONS

International Search Report and Written Opinion, International Application No. PCT/US2015/059273, dated Mar. 30, 2016, 10 pages.
Ohta, et al., "Characterization of Novel Steviol Glycosides from Leaves of Stevia rebaudiana Morita", J. Appl. Glycosci., 2010 57, pp. 199-209.
Brandle, et al., "Steviol glycoside biosynthesis", Phytochemistry, 2007, vol. 68, pp. 1855-1863.
Richman et al., Functional genomics uncovers three glucosyltransferases involved in the synthesis of the major sweet glucosides of Stevia rebaudiana, The Plant Journal, 2005 vol. 41, pp. 56-67.
Li et al., "Phylogenetic Analysis of the UDP-glycosyltransferase Multigene Family of *Arabidopsis thaliana*", The Journal of Biological Chemistry, 2001, vol. 276, No. 6, pp. 4338-4343.
Shibata et al., Glucosylation of Steviol and Steviol-Glucosides in Extracts from Stevia rebaudiana Bertoni, Plant Physiol., 1991, vol. 95, pp. 152-156.
Lim, et al., The Activity of *Arabidopsis* Glycosyltransferases toward Salicylic Acid, 4-Hydroxybenzoic Acid, and Other Benzoates, 2002, The Journal of Biological Chemistry, vol. 277, No. 1, pp. 586-592.
Ko, et al., "Glycosylation of Flavonoids with a Glycosyltransferase from Bacillus cereus," FEMS Microbiol Lett, 2006, vol. 258, pp. 263-268.

*Primary Examiner* — Karen Cochrane Carlson
(74) *Attorney, Agent, or Firm* — Morgan, Lewis & Bockius LLP

(57) ABSTRACT

The invention provides methods for making steviol glycosides, including RebM and glycosylation products that are minor products in stevia leaves, and provides enzymes, encoding polynucleotides, and host cells for use in these methods. The invention provides engineered enzymes and engineered host cells for producing steviol glycosylation products, such as RebM, at high purity and/or yield. The invention further provides methods of making products containing steviol glycosides, such as RebM, including food products, beverages, oral care products, sweeteners, and flavoring products.

24 Claims, 69 Drawing Sheets

Specification includes a Sequence Listing.

MICROBIAL PRODUCTION OF STEVIOL GLYCOSIDES

RELATED APPLICATIONS

This application claims priority to and the benefit of U.S. Provisional Application No. 62/075,644, filed Nov. 5, 2014, which is hereby incorporated by reference in its entirety.

TECHNICAL FIELD

The present disclosure relates to enzymes, including engineered enzymes, encoding polynucleotides, host cells, and methods for producing steviol glycosides.

BACKGROUND

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in Stevia leaves, composing approximately 10% to 20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

The minor glycosylation product rebaudioside M is estimated to be about 200-350 times more potent than sucrose, and is described as possessing a clean, sweet taste with a slightly bitter or licorice aftertaste. Prakash I. et al., *Development of Next Generation Stevia Sweetener: Rebaudioside M, Foods* 3(1), 162-175 (2014). RebM is of great interest to the global food industry.

Although methods are known for preparing steviol glycosides from *Stevia rebaudiana*, many of these methods are unsuitable for use commercially and/or are not sustainable. Accordingly, there remains a need for simple, efficient, and economical methods for preparing compositions comprising steviol glycosides, including highly purified steviol glycoside compositions. Further, methods are needed for producing substantial amounts of the minor glycosylation products, including products having a plurality of glycosylations, such as Reb A, Reb D, Reb E, Reb I, RebM, and others.

SUMMARY OF THE INVENTION

In various aspects, the invention provides methods for making steviol glycosides, including Reb D and RebM and glycosylation products that are minor products in stevia leaves, and provides enzymes, encoding polynucleotides, and host cells for use in these methods. The invention provides engineered enzymes and engineered host cells for producing steviol glycosylation products, such as Reb D and RebM, at high purity and/or yield. The invention further provides methods of making products containing steviol glycosides, where the products include food products, beverages, oral care products, sweeteners, flavoring products, among others.

In various aspects and embodiments, the invention provides enzymes, encoding polynucleotides, host cells, and methods for producing steviol glycosides having a plurality of glycosylations at C13 and/or C19. The steviol glycosides may have 2, 3, 4, 5, 6, 7, 8 or more glycosylations. In various embodiments, the glycosylations are selected from: C13-O, C19-O, 1-2' (at C-13 and/or C19 of steviol), and 1-3' (at C13 and/or C19 of steviol). Exemplary enzymes to perform these glycosylations are listed in Table 8, and include enzymes that catalyze C13-O glycosylations of steviol (e.g., SrUGT85C2), C19-O glycosylations of steviol (e.g., SrUGT74G1), 1-2' glycosylations of steviol glycosides (e.g., SrUGT91D1, SrUGT91D2, OsUGT1-2), and 1-3' glycosylations of steviol glycosides (e.g., SrUGT76G1). Numerous derivatives that can be used in various embodiments are disclosed herein, including enzymes identified herein as MbUGTc13 (SEQ ID NO:51), MbUGTc19 (SEQ ID NO:8), MbUGTc19-2 (SEQ ID NO:46), MbUGT1-2 (SEQ ID NO:9), MbUGT1,2-2 (SEQ ID NO:45), and MbUGT1-3 (SEQ ID NO:10), and derivatives thereof. In some embodiments, the invention provides host cells that express at least 2, 3, or 4 UGT enzymes for performing these glycosylations in vivo on the steviol substrate. Various steviol glycoside products that can be produced according to embodiments of the invention are shown in FIGS. 28-31 and Table 10, and these include Reb M, Reb D, Reb E, and Reb I. In accordance with embodiments of the invention, these steviol glycosides can be produced at high yields in bacterial host cells, such as *E. coli*, including at temperatures suitable for *E. coli* growth and metabolism.

In some aspects, the invention provides modified UGT enzymes having an increase in 1-2' glycosylating activity at C19 of Rebaudioside A (RebA) as compared to its parent UGT enzyme, and without substantial loss of 1-2' glycosylating activity at C13 of steviolmonoside. Such enzymes can provide for increased carbon flux to RebD. Further, the invention provides modified UGT enzymes having an increase in 1-3' glycosylating activity at C19 of Rebaudioside D (RebD) as compared to its parent UGT enzyme, without substantial loss of 1-3' glycosylating activity at C13 of stevioside. Such enzymes can provide for increased carbon flux to RebM.

In accordance with the present disclosure, production of steviol glycosides is engineered in host cells through the production of various pathway modules from glycolysis to steviol, and further to steviol glycosides, and which can be optimized and balanced to promote carbon flux to steviol and then to Reb D or RebM (or other glycosylation product) as the main glycosylation product.

In another aspect, the invention provides a method for making RebD. The method comprises providing a host cell producing RebD from steviol through a plurality of uridine diphosphate dependent glycosyltransferase enzymes (UGT), and culturing the host cell under conditions for producing the RebD. The UGT enzymes comprise a modified UGT enzyme having an increase in 1-2' glycosylating activity at C19 of Rebaudioside A (RebA) as compared to its parent UGT enzyme, without substantial loss of 1-2' glycosylating activity at C13 of steviolmonoside. In certain embodiments, the 1-2' glycosylating activity at C19 of Rebaudioside A (RebA) is equal to or better than the 1-2' glycosylating activity at C13 of steviolmonoside.

In another aspect, the invention provides a method for making RebM. The method comprises providing a host cell producing RebM from steviol through a plurality of uridine diphosphate dependent glycosyltransferase enzymes (UGT), and culturing the host cell under conditions for producing the RebM. The UGT enzymes comprise one or more of: (a) a modified UGT enzyme having an increase in 1-2' glycosylating activity at C19 of Rebaudioside A (RebA) as compared to its parent UGT enzyme, without substantial loss of 1-2' glycosylating activity at C13 of steviolmonoside; and (b) a modified UGT enzyme having an increase in 1-3' glycosylating activity at C19 of Rebaudioside D (RebD) as compared to its parent UGT enzyme, without substantial loss of 1-3' glycosylating activity at C13 of stevioside. In certain embodiments, the 1-2' glycosylating activity at C19 of Rebaudioside A (RebA) is equal to or better than the 1-2' glycosylating activity at C13 of steviolmonoside. Alternatively or in addition, the 1-3' glycosylating activity at C19 of Rebaudioside D (RebD) is equal to or better than the 1-3' glycosylating activity at C13 of stevioside.

In some embodiments, the invention provides modified SrUGT76G1 enzymes, which provide for 1-3' glycosylating activity of stevioside and RebD, including enzymes having an amino acid substitution at position 200 of the wild type enzyme (e.g., L200A or L200G), which exhibit substantial improvement in activity.

In other aspects and embodiments, the invention provides circular permutants of UGT enzymes (as well as encoding polynucleotides), which can provide novel substrate specificities, product profiles, and reaction kinetics over the wild-type enzymes. The circular permutants can be expressed in host cells for production of steviol glycosides as described herein. Thus, in various embodiments the microbial cell expresses at least one UGT enzyme that is a circular permutant of a wild-type or parent UGT enzyme. A circular permutant retains the same basic fold of the parent enzyme, but has a different position of the N-terminus (e.g., "cut-site"), with the original N- and C-termini connected, optionally by a linking sequence. For example, in the circular permutants, the N-terminal Methionine is positioned at a site in the protein other than the natural N-terminus. For example, the invention provides circular permutants of OsUGT1-2 and SrUGT74G1, which can be further modified as described herein for production of glycosylation products of steviol.

In another aspect, the invention provides a method for production of steviol glycosides having at least 4 glycosylations in *E. coli*. In accordance with the invention, the *E. coli* cell comprises a plurality of UGT enzymes, which may include one or more enzymes described herein, that together perform at least 4, at least 5, or at least 6, sequential glycosylation reactions. As disclosed herein, the glycosylation substrates and lower glycosylation products accumulate in the *E. coli* cell sufficiently to allow downstream reactions to proceed at an acceptable rate, with a high majority of the glycosylation products ultimately accumulating extracellularly. The steviol glycosides can be purified from media components. Thus, *E. coli* is a desirable host for production of steviol glycosides that require several glycosylation reactions of the steviol scaffold.

In still other aspects, the invention provides methods for production of steviol glycosides (including RebM, Reb D, Reb E, Reb I, and others) in *E. coli*. While many of the enzymes known for production of steviol in host cells are plant enzymes, which often have optimal temperatures in the range of 20-24° C., *E. coli* growth rate and metabolism are optimal at higher temperatures. The present disclosure enables production of steviol glycosides at high yield in *E. coli*, by enabling enzyme productivity at temperatures above 24° C., such as from 24° C. to 37° C., or from 27° C. to 37° C., or from 30° C. to 37° C. In various embodiments, the disclosure provides alternative or engineered GGPPS, KS, CPPS, KO, and KAH enzymes for production of steviol or steviol glycosides in *E. coli* or other microbial host.

Other aspects and embodiments of the invention will be apparent from the following detailed disclosure.

DESCRIPTION OF THE FIGURES

FIG. 38 shows UGT alignment and secondary structure, anchored to 2VCE which is an *Arabidopsis* UGT with a solved crystal structure. Alignments include 2VCE (SEQ ID NO:58), 2ACW (SEQ ID NO:59), 2C1Z (SEQ ID NO:60), 2PQ6 (SEQ ID NO:61), 3HBF (SEQ ID NO:62), 3WC4 (SEQ ID NO:63), SrUGT85C2 (SEQ ID NO:1), SrUGT74G1 (SEQ ID NO:2), Q0DPB7-ORYSJ is OsUGT1-2 (SEQ ID NO:7), SrUGT76G1 (SEQ ID NO:3). Boxed is the position of the 76G1-L200A point mutation, which promotes significantly improved activity. Also shown in boxes is the conserved PSPG motif

DETAILED DESCRIPTION OF THE INVENTION

In various aspects, the invention provides methods for making steviol glycosides, including RebM, RebD, and glycosylation products that are minor products in stevia leaves, and provides enzymes, encoding polynucleotides, and host cells for use in these methods. The invention provides engineered enzymes and engineered host cells for producing steviol glycosylation products at high purity and/or yield. The invention further provides methods of making products containing steviol glycosides, such as RebM or RebD, including food products, beverages, oral care products, sweeteners, flavoring products, among others. Such steviol glycoside-containing products can be made at reduced cost by virtue of this disclosure.

Figure 1:
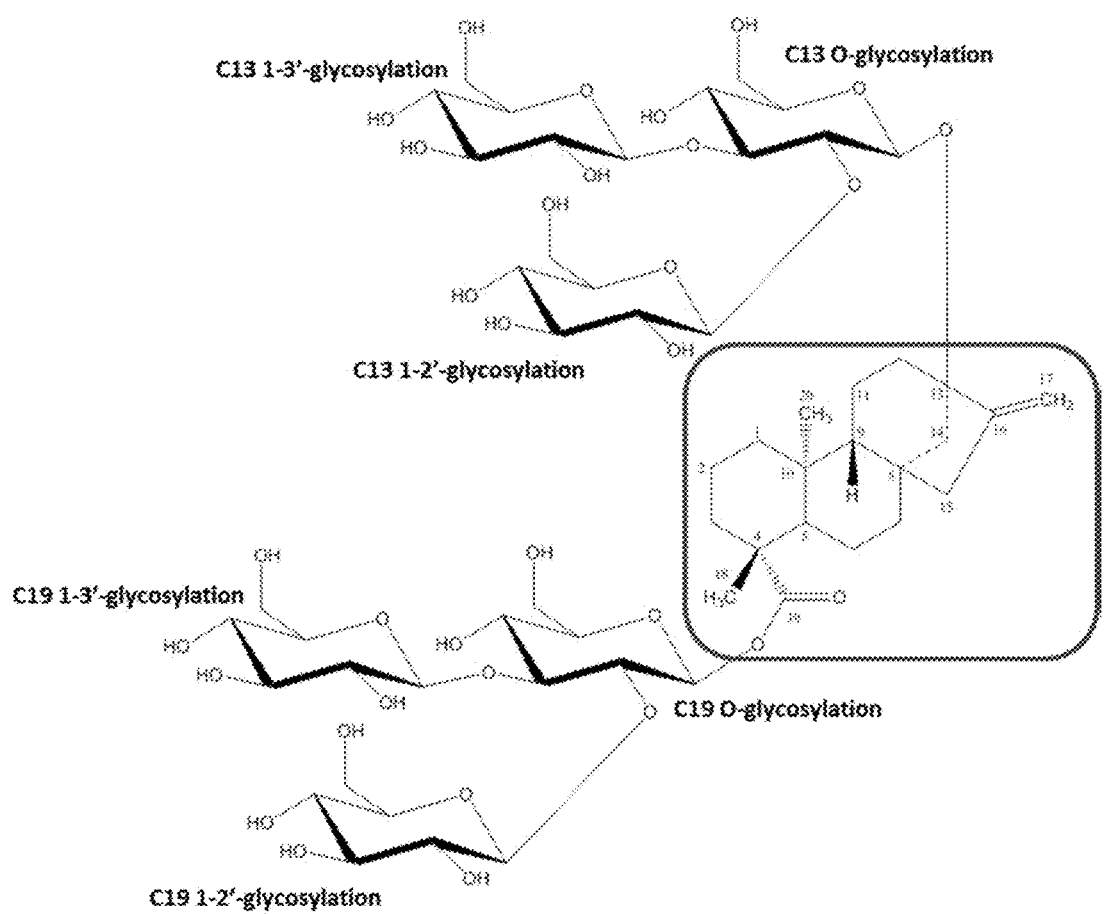
FIG. 1 shows the chemical structure of Rebaudioside M (RebM), a minor component of the steviol glycoside family, and which is a derivative of the diterpenoid steviol (box) with six glucosyl-modification groups.
Figure 3:
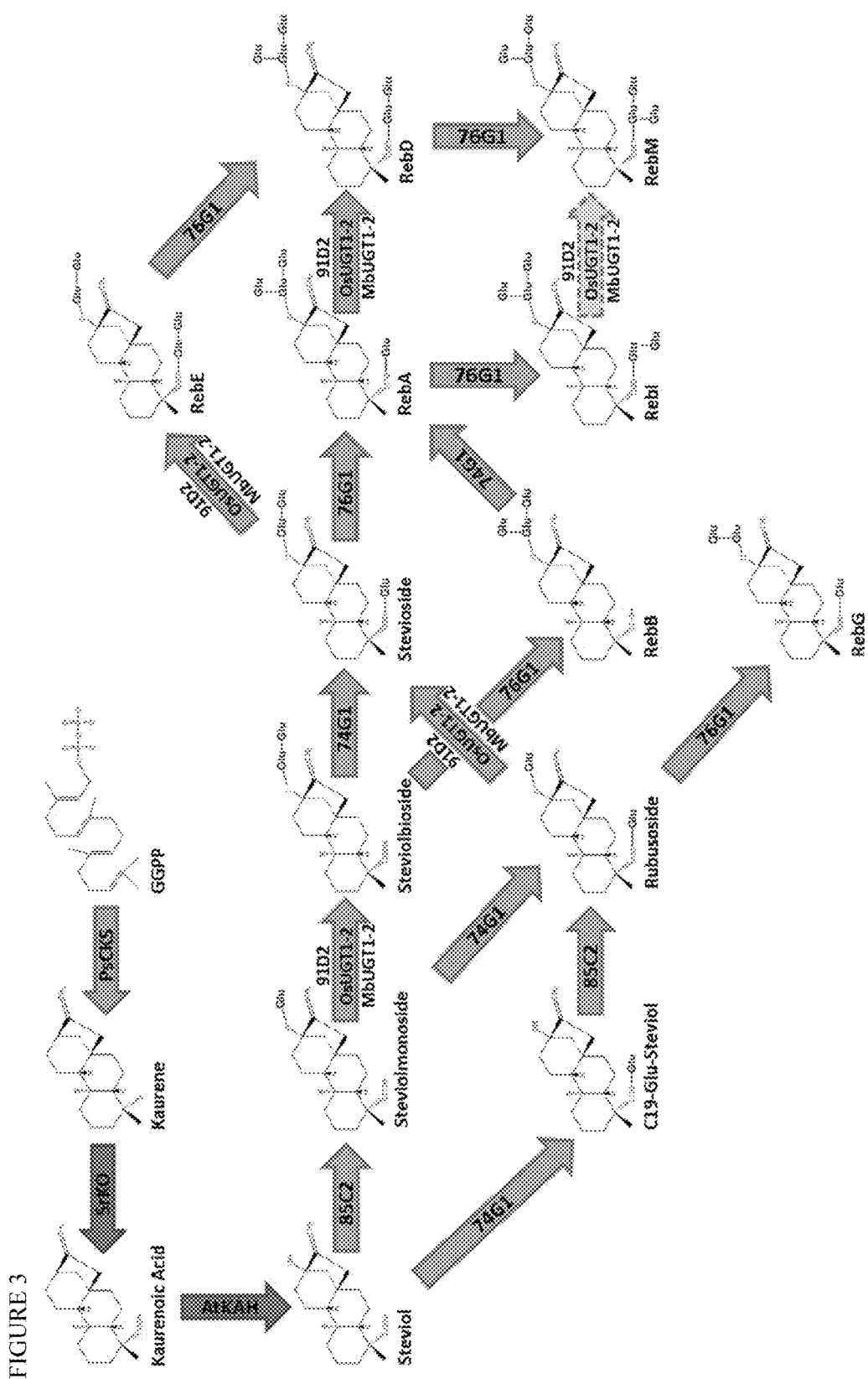
FIG. 3 shows an exemplary pathway for steviol glycoside production, including to RebM. PsCKS is a bifunctional copalyl diphosphate and kaurene synthase (from *Phaeosphaeria* sp.) which acts on geranylgeranyl diphosphate (synthesized from IPP and DMAPP by *Taxus canadensis* GGPP synthase, not shown). SrKO is *Stevia rebaudiana* kaurene oxidase and AtKAH is an *Arabidopsis thaliana* P450 with steviol monooxygenase activity. Solid arrows are known UGT activities. Arrows with dotted line borders are predicted reactions based on demonstrated activities on other substrates in vitro. MbUGT1-2 is a novel UGT enzyme designed in this disclosure.

RebM is illustrated in FIG. 1, with the steviol scaffold (a diterpenoid) shown boxed. RebM contains six glycosylations: (1) a C13 O-glycosylation, (2) a C13 1-2' glycosylation, (3) a C13 1-3' glycosylation, (4) a C19 O-glycosylation, (5) a C19 1-2' glycosylation, and (6) a C19 1-3' glycosylation. Pathways from geranylgeranyl pyrophosphate (GGPP) to RebM are illustrated in FIG. 3. GGPP produced from IPP and DMAPP (products of the MEP or MVA pathways), is converted to kaurene by the action of copalyl synthase and kaurene synthase, which can be present as a bifunctional enzyme in some embodiments. Steviol is produced from kaurene by the action of two P450 enzymes, kaurene oxidase and kaurenoic acid hydroxylase, which are regenerated by one or more P450 reductase enzymes. After production of steviol, a series of glycosylation reactions at C13 and C19 are capable of producing various steviol glycoside products, including the hexaglycosylated RebM. Various other glycosylation products are possible (as shown in FIG. 3), and as illustrated in FIGS. 28-31, known UGT glycosylation enzymes are each capable of acting on a number of substrates. Thus the fidelity, relative reaction rates, expression levels, and availability of substrate will affect the relative yields of the glycosylation products. For example, both UGT91D2 and OsUGT1-2 are 1-2' glycosylating enzymes that can produce steviolbioside from steviolmonoside (by action at C13), as well as RebD from RebA (by action at C19). Further, UGT76G1 is a 1-3' glycosylating enzyme that can produce RebA from stevioside (by action at C13), as well as RebM from RebD (by action at C19). Tables 8, 9, and 10 show the various possible steviol glycosides that may result from the six glycosylation reactions, as well as enzymes for each reaction. Table 1 lists various enzymes that may be used for the production of steviol glycosides. Amino acid sequences are also provided herewith, each of which can optionally include an alanine inserted or substituted at position 2 to decrease turnover in the cell. Certain GGPPS sequences further contain two additional residues (VD) at the end of the sequence, which are not believed to have any deleterious effect, and may be omitted in certain embodiments.

Thus, in some aspects, the invention provides enzymes, encoding polynucleotides, and host cells engineered for maximizing the production of the desired steviol glycoside (e.g., RebM). For example, this disclosure provides modified UGT enzymes having an increase in 1-2' glycosylating activity at C19 of Rebaudioside A (RebA) as compared to the parent UGT enzyme, and without substantial loss of 1-2' glycosylating activity at C13 of steviolmonoside. Such enzymes may provide for increased carbon flux to RebD. Further, this disclosure provides modified UGT enzymes having an increase in 1-3' glycosylating activity at C19 of Rebaudioside D (RebD) as compared to the parent UGT enzyme, without substantial loss of 1-3' glycosylating activity at C13 of stevioside. Such enzymes may provide for increased carbon flux to RebM. In some aspects and embodiments, and without wishing to be bound by theory, the invention provides for modified UGT enzymes with substrate binding pockets that are better able to accommodate substrates (including larger substrates), thereby increasing the rate of activity (e.g., rate of substrate binding and turnover) with more highly glycosylated steviol substrates such as RebA or RebD.

The invention in some aspects provides for a controlled glycosylation pathway that produces largely RebM as a glycosylation product. For example, in some embodiments, the invention provides a method for making RebM in microbial cells, where the RebM:RebD ratio is greater than about 1:1, or greater than about 1:0.5, or greater than about 1:0.25, or greater than about 10:1, or greater than about 25:1, or greater than about 50:1. In some embodiments, RebD is produced at less than about 20%, or at less than about 10%, or at less than about 5%, or at less than about 1% of the RebM yield, or is not detectable in the isolated steviol glycosylation products. Because RebD can be difficult to separate from RebM, or can add significant purification costs if such separation is necessary, products with low levels of RebD are desirable in some embodiments. In some embodiments, RebM represents at least about 25% by weight of the steviol glycosylation products produced by the cell, or at least about 50% by weight of the glycosylation products, or at least about 75% by weight of the glycosylation products, or at least about 80% by weight of the glycosylation products, or at least about 85% by weight of the glycosylation products, or at least about 90% by weight of the glycosylation products, or at least about 95% by weight of the steviol glycosylation products.

The glycosylation pathways involve a 13-O glycosylation, a 19-O glycosylation, as well as one or more 1-2' glycosylations and/or one or more 1-3' glycosylations at C13 and/or C19 of steviol. The term "steviol glycoside(s)" refers to a glycoside of steviol, including, but not limited to, steviolmonoside, steviolbioside, rubusoside, dulcoside B, dulcoside A, rebaudioside B, rebaudioside G, stevioside, rebaudioside C, rebaudioside F, rebaudioside A, rebaudioside E, rebaudioside H, rebaudioside L, rebaudioside K, rebaudioside J, rebaudioside M, rebaudioside D, rebaudioside N, rebaudioside O. The chemical identities of these steviol glycosides are known, and are described for example, in Table 10, as well as in WO 2014/122227, which is hereby incorporated by reference in its entirety.

Figure 2:
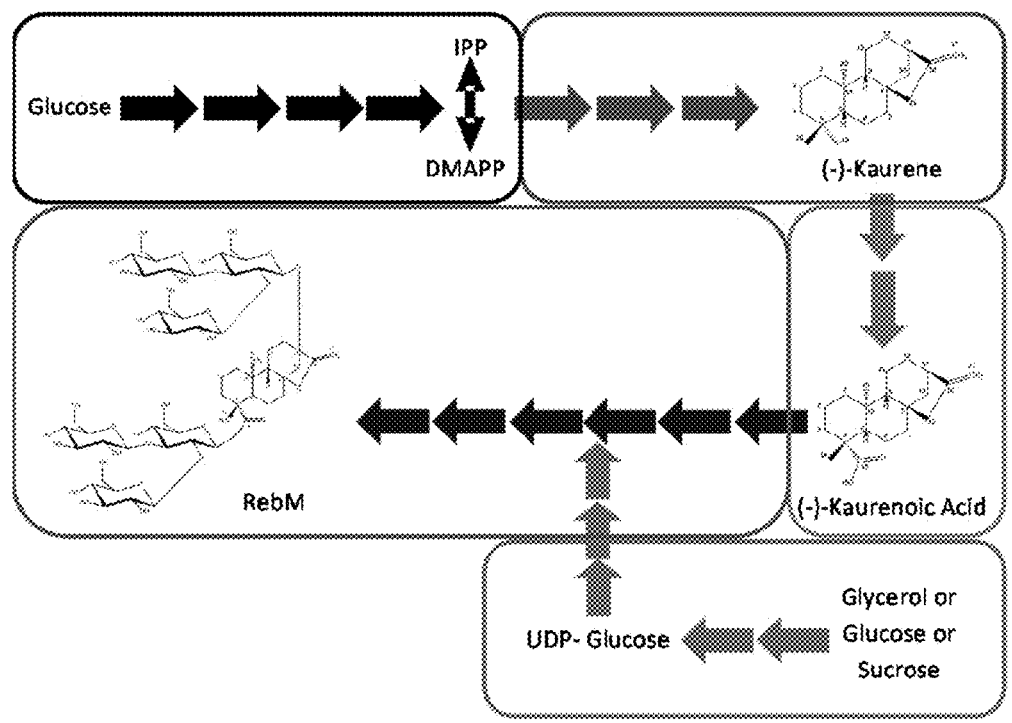
FIG. 2 shows pathway modules to RebM. Glycolysis and MEP pathways are treated as one module, and the downstream kaurene biosynthesis pathway is shown as the second module. Biosynthesis of steviol is shown as the third module. The fourth module is for the glycosylation of steviol and the RebM biosynthetic pathway. The fifth module to support enhanced UDP-glucose production is also shown.

In accordance with the present disclosure, production of steviol glycosides is engineered in host cells through the production of various pathway "modules," as illustrated in FIG. 2, and which can be optimized and balanced to promote carbon flux to steviol and then a desired glycosylation product (such as RebM or RebD) as the main glycosylation product. By grouping enzymes with similar turnovers into a subset, or module, and equalizing the turnover of the different subsets by adjusting concentrations/activities of enzymes, the ratio of pathway turnover to resource expenditure can be optimized.

The first pathway module comprises enzymes in the MEP or MVA pathways, which produce IPP and DMAPP. The MEP and MVA pathways may be endogenous to the organism, and these pathways may be increased and balanced with downstream pathways by providing duplicate copies of certain rate-limiting enzymes. IPP and DMAPP act as a substrate for the production of (−)-kaurene (e.g., by separate copalyl synthase and kaurene synthase enzymes, or a bifunctional enzyme), which is the second pathway module. A third pathway module converts (−)-kaurenoic acid to steviol by the action of two P450 enzymes (e.g., kaurene oxidase (KO) and kaurenoic acid hydroxylase (KAH)) and one or more P450 reductase enzymes. Exemplary enzymes that catalyze production of GGPP and its conversion through to steviol are listed in Table 1. Steviol is then glycosylated to the final product by a UDP enzyme module. An additional module includes genes that enhance production of the UDP-glucose substrate. In various embodiments of the invention, these modules are each present as mono- or poly-cistronic operons, which are each harbored on plasmids or are chromosomally integrated. In certain embodiments, the modules are configured for increased production of the desired end-product.

In one aspect, the invention provides a method for making a steviol glycoside, which is optionally RebM or RebD. The method comprises providing a host cell producing the steviol glycoside from steviol through a plurality of uridine diphosphate dependent glycosyltransferase enzymes (UGT), and culturing the host cell under conditions for producing the steviol glycoside. The UGT enzymes comprise one or more of: (a) a modified UGT enzyme having an increase in 1-2' glycosylating activity at C19 of Rebaudioside A (RebA) as compared to its parent UGT enzyme, without substantial loss of 1-2' glycosylating activity at C13 of steviolmonoside (e.g., when evaluated at 22° C., 27° C., or 30° C.); and (b) a modified UGT enzyme having an increase in 1-3' glycosylating activity at C19 of Rebaudioside D (RebD) as compared to its parent UGT enzyme, without substantial loss of 1-3' glycosylating activity at C13 of stevioside (e.g., when evaluated at 22° C., 27° C., or 30° C.).

In certain embodiments, the 1-2' glycosylating activity at C19 of Rebaudioside A (RebA) is equal to or better than the 1-2' glycosylating activity at C13 of steviolmonoside. Alternatively or in addition, the 1-3' glycosylating activity at C19 of Rebaudioside D (RebD) is equal to or better than the 1-3' glycosylating activity at C13 of stevioside.

In some embodiments, the modified UGT enzyme having 1-2' glycosylating activity and/or the UGT enzyme having 1-3' glycosylating activity does not exhibit a substantial loss of activity at C13, as compared to the parent enzyme. For example, the modified enzyme retains at least 50% of its activity at C13, or at least about 75% of its activity at C13, or at least about 80%, at least about 90%, or at least about 95% of its activity at C13 as compared to the parent (e.g., wild-type) enzyme (e.g., when evaluated at 22° C., 27° C., or 30° C.). In some embodiments, the enzyme has improved activity at C13, such as at least 2-fold or at least 3-fold improved activity at C13. The loss of, or improvement in, a glycosylation activity can be determined in vitro, for example in cell extracts with the substrate of interest added, or other in vitro or in vivo assay. For example, relative reaction rates may be determined in a strain that produces the steviol or steviol glycoside substrate(s) of interest. Exemplary assays for quantifying glycosylation activity are disclosed herein as well as in WO 2014/122227, which is hereby incorporated by reference.

While in some embodiments, the 1-2' and 1-3' glycosylation activities at C13 are sufficiently functional with the enzyme that performs these reactions at C19 (e.g., without any additional enzyme to perform these enzymatic steps), in other embodiments, the cell further expresses an enzyme to perform 1-2' and/or 1-3' glycosylation at C13. In some embodiments, a second enzyme is engineered to perform the 1-2' and/or 1-3' reactions at C13, even with loss of activity at C19.

In some embodiments, the cell expresses only one UGT enzyme having 1-2' glycosylating activity at C13 of steviolmonoside, and/or expresses only one UGT enzyme having 1-3' glycosylating activity at C13 of stevioside. In such embodiments, the enzyme can be engineered to enhance the reaction at C19, thereby pulling product toward C19 glycosylation products such as RebM, without the need for expression of additional enzymes that place a further metabolic burden on the cell.

In aspects and embodiments, the invention provides circular permutants of UGT enzymes (as well as encoding polynucleotides and methods of making circular permutants of UGT enzymes), which can provide novel substrate specificities, product profiles, and reaction kinetics over the parent (e.g., wild-type) enzymes. Without wishing to be bound by theory, circular permutants provide the opportunity to make the UGT binding pocket more open or accessible for larger substrates, such as steviol substrates having one or more glycosyl groups. In this manner, the invention allows for the glycosylation reactions on more glycosylated forms of steviol to proceed at rates similar to or even greater than reactions on less glycosylated (and thus smaller) substrates. The circular permutants can be expressed in host cells for production of steviol glycosides as described herein. Thus, in various embodiments the microbial cell producing the steviol glycoside (e.g., RebM or RebD) expresses at least one UGT enzyme that is a circular permutant of a parent (e.g., wild-type) UGT enzyme.

Figure 20A:
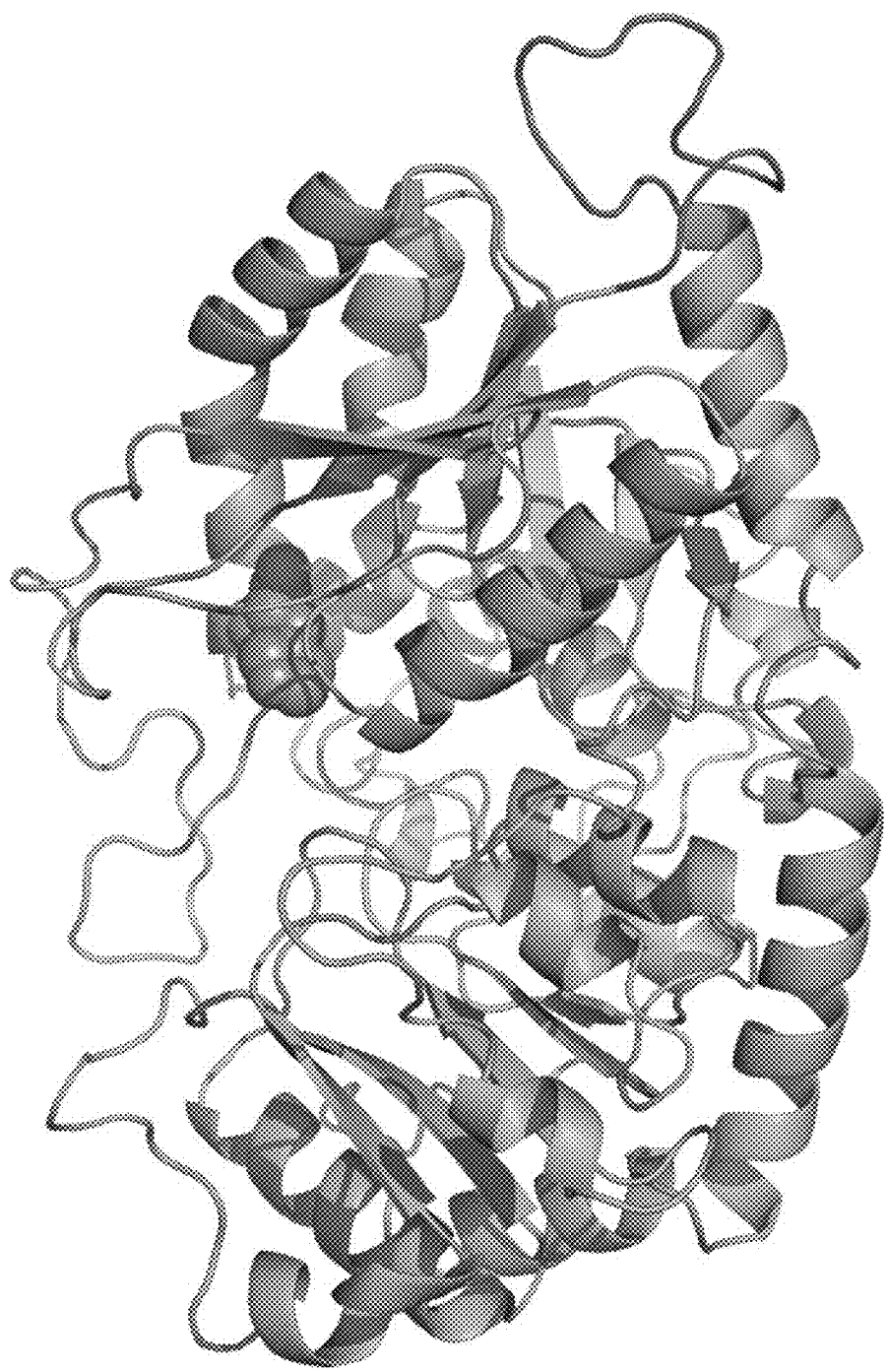
FIG. 20 shows linkers for UGT circular permutants, to connect the natural N and C-termini. Three different linkers are shown: (A) YKDDSGYSSSYAAAAGM (SEQ ID NO:48) attaching the existing sequence, (B) YKDAAGM (SEQ ID NO:49), creating an intermediate-length loop, and (C) YGSGM (SEQ ID NO:50), creating a minimal loop.
Figure 20B:
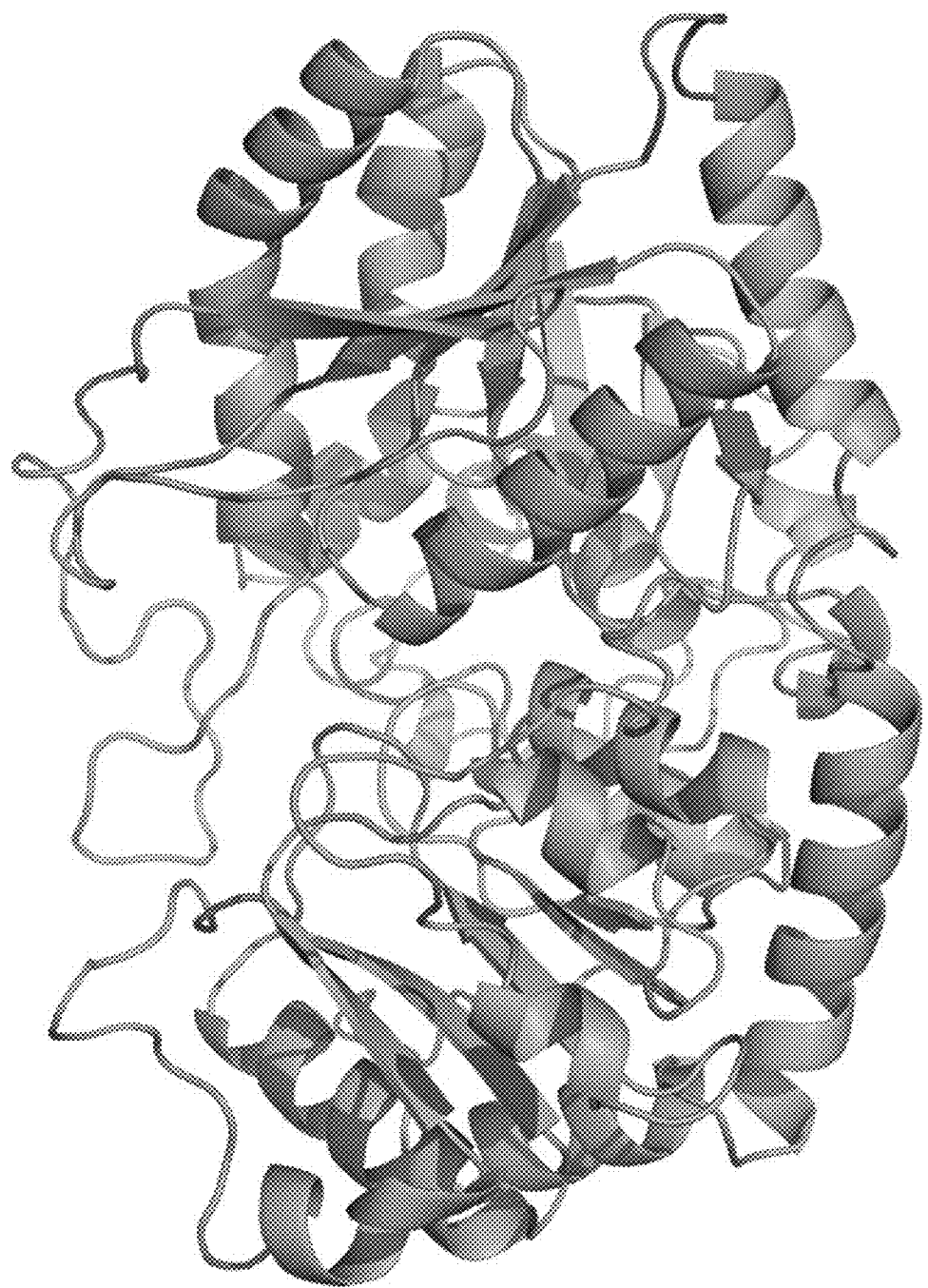
Figure 20C:
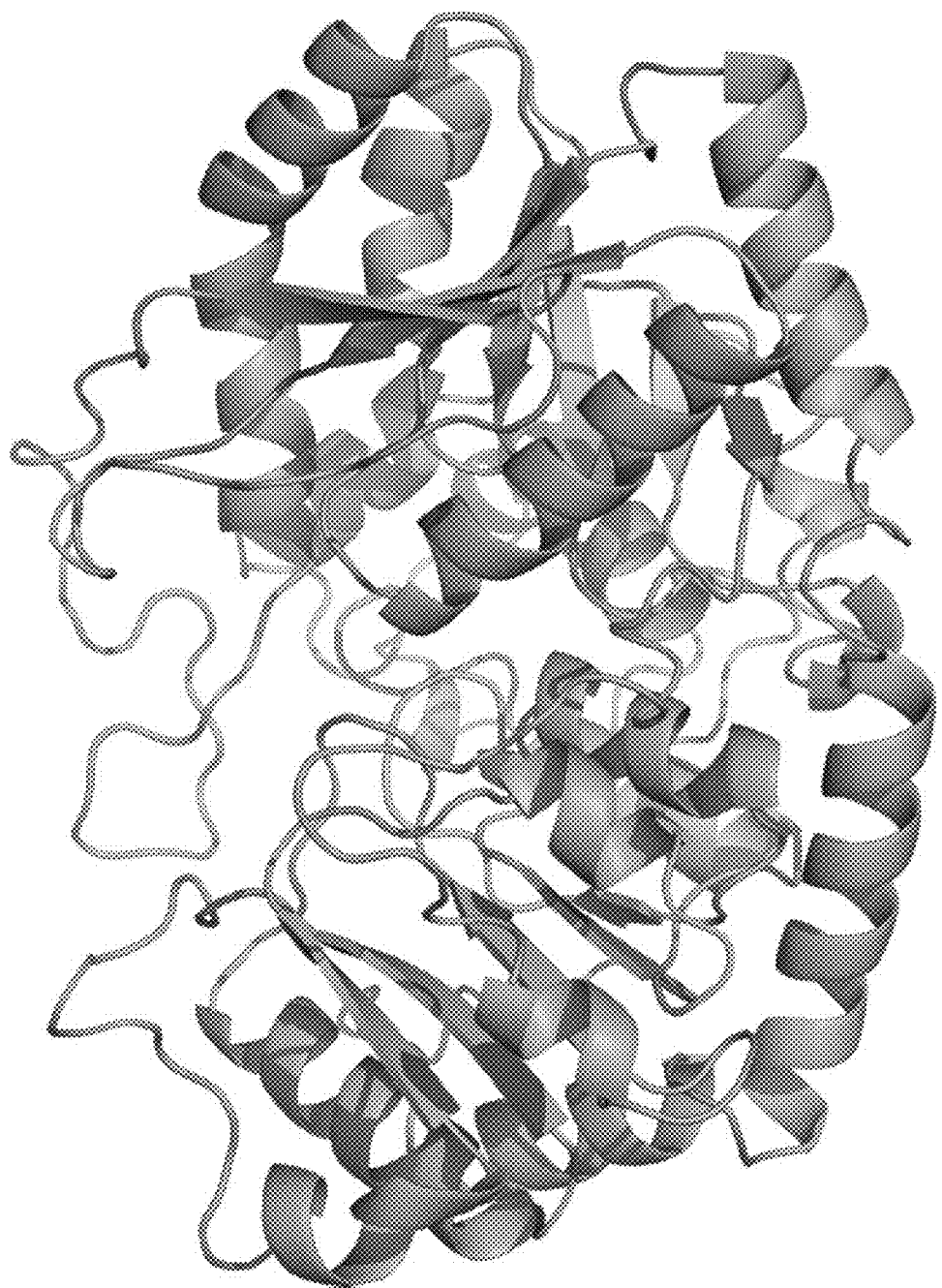
Figure 38:
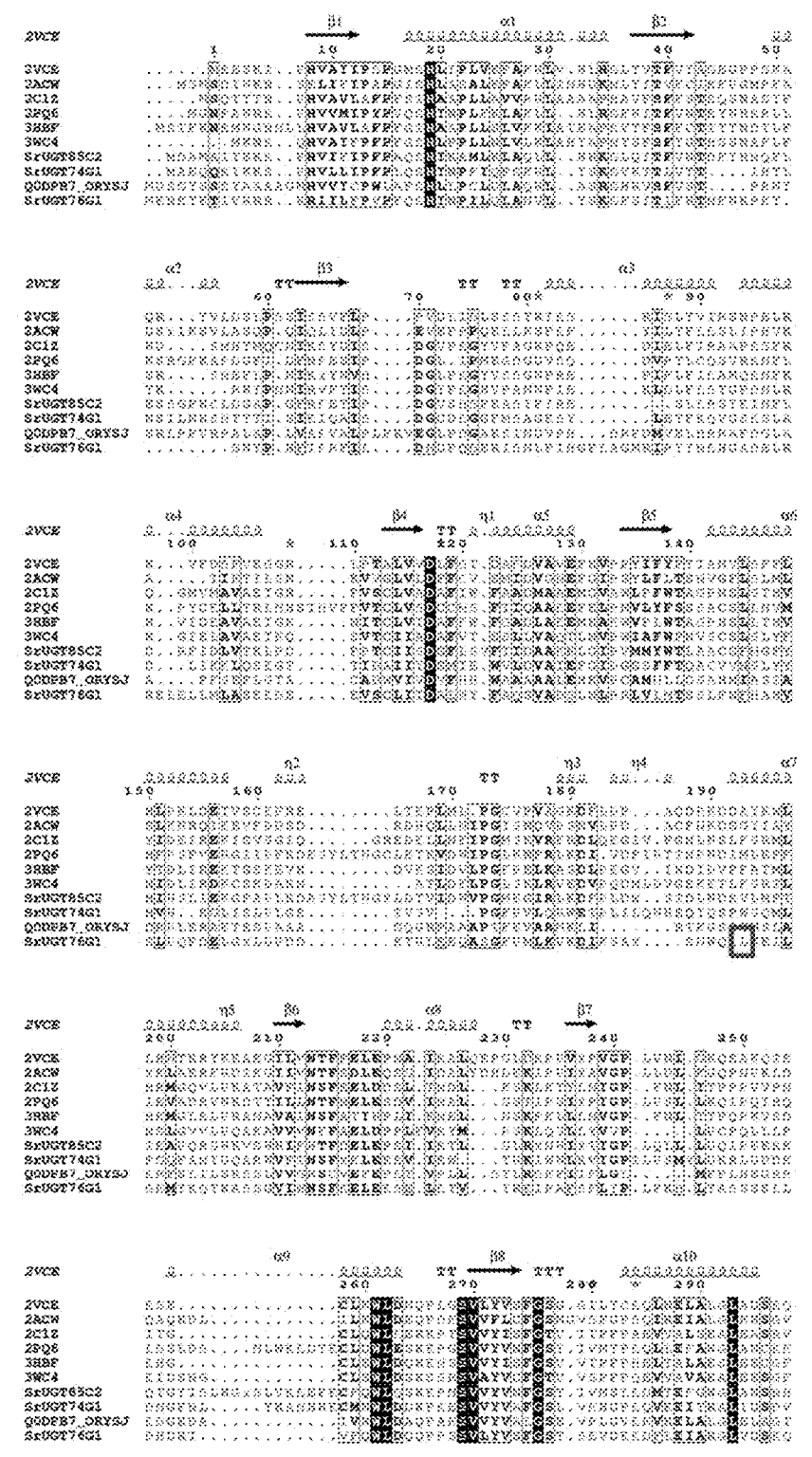
Figure 38:
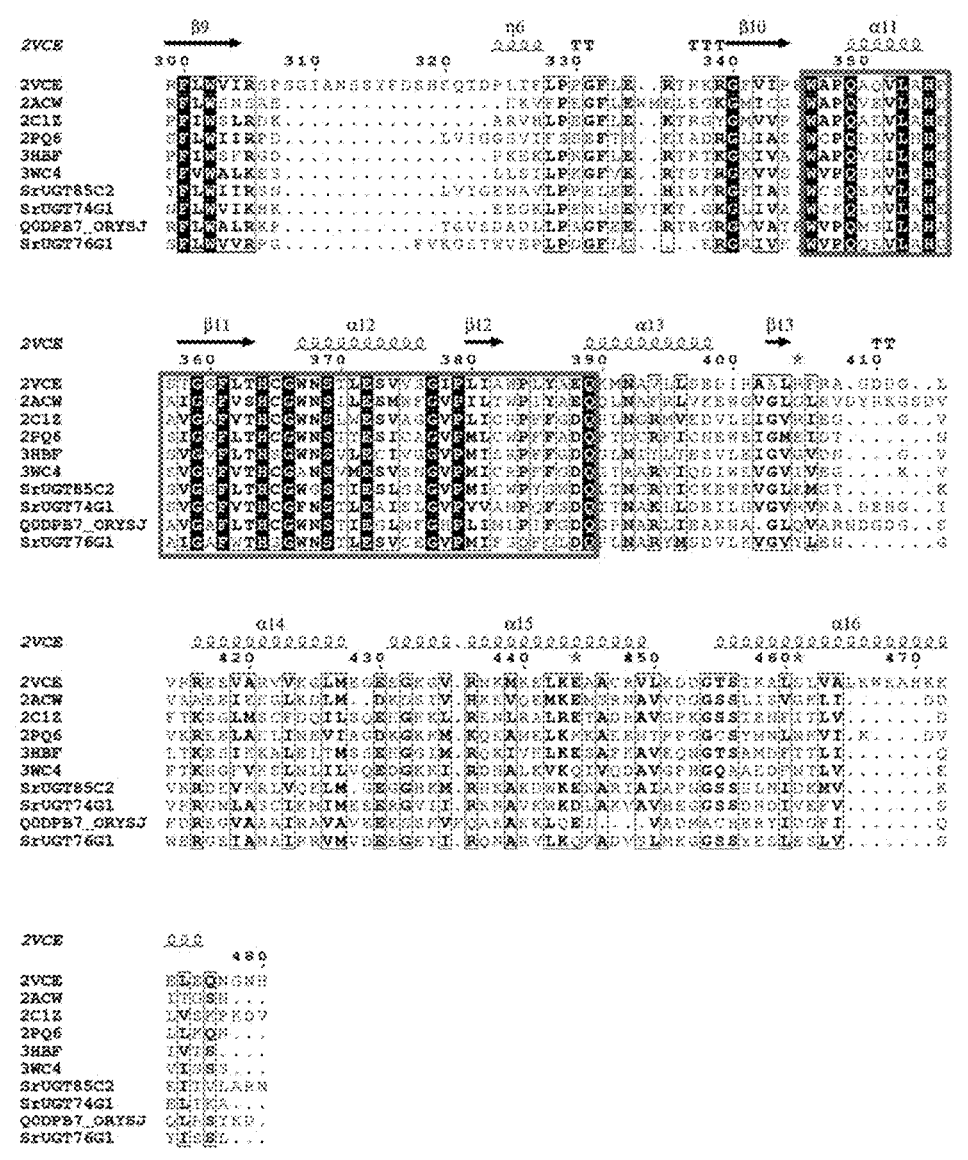

A circular permutant retains the same basic fold of the parent enzyme, but has a different position of the natural N-terminus (e.g., "cut-site"), with the original N- and C-termini connected, optionally by a linking sequence. An exemplary structure of a UGT enzyme (e.g., based on OsUGT1-2) is shown in FIG. 20. A UGT alignment and secondary structure elements are shown in FIG. 38. For each circular permutant, the cut-site can be described with reference to the corresponding position of the parent sequence (e.g., wild-type sequence), by alignment of the permutant's N-terminal amino acids (e.g., N-terminal 50 or 100 amino acids) with the parent or wild-type sequence. As used herein, the "cut site" of a given circular permutant refers to the original position of the amino acid that is positioned at position 2 in the circular permutant (e.g., after the initiating Met), or position 3 of the circular permutant when an Alanine is inserted at position 2 to decrease protein turnover. Alignments for comparing global UGT sequences should be anchored around the conserved PSPG motif shown in FIG. 38. The PSPG (plant secondary product glycosyltransferase) motif is a conserved region within plant UGTs that plays a role in binding the nucleotide-diphosphate-sugar donor molecule. Gachon et al., *Plant secondary metabolism glycosyltransferases: the emerging functional analysis*, Trends Plant Sci. 10:542-549 (2005). The most conserved residues in this motif in the UDPGT family show the pattern: WXPQXXX-LXHXXXXAFXXHXGXXXXXEXXXXGXPXXXXPX-FXXQ (SEQ ID NO:52), of which the underlined histidine makes a critical contact to the diphosphate region. Finn R D, et al. *Pfam: the protein families database*, Nucleic Acids Res. 42:D222-230 (2014). Further, alignment around this motif is useful for describing point mutations that translate to beneficial properties for the UGT proteins as a class. For example, anchoring alignments to the tryptophan at the beginning of the motif, or the important histidine in the middle, may be used to describe point mutations relative to this sequence, which will be universal in plant GT1 UDP-glucose glycosyltransferases.

In some embodiments, the circular permutant is a circular permutant of UGT85C2 from *Stevia rebaudiana*. SrUGT85C2 is provided herein as SEQ ID NO:1. In some embodiments, the circular permutant is a circular permutant of OsUGT1-2 (SEQ ID NO:7). In some embodiments, the circular permutant is of UGT91D2 of *Stevia rebaudiana* (SEQ ID NO:5). In some embodiments, the circular permutant is of UGT74G1 of *Stevia rebaudiana* (SEQ ID NO:2). In some embodiments, the circular permutant is of UGT76G1 of *Stevia rebaudiana* (SEQ ID NO:3). In this manner, by changing the position of the N-terminus of the UGT enzyme, enzymes with novel substrate specificities and activity profiles can be created. For example, in some embodiments, the cut site is between amino acids 150 to 300, or in some embodiments between amino acids 190 and 260, or in some embodiments between residues 190 and 210, when the N-terminus of the circular permutant (e.g., N-terminal 50 amino acids) is aligned with the parent or wild-type enzyme. In other embodiments, the circular permutant has a cut site between amino acids 245 and 280 (e.g., position 272), or between amino acids 260 to 275, when the N-terminal 50 amino acids of the circular permutant are aligned with the parent or wild-type enzyme. In some embodiments, the new N-terminus is placed between local secondary structure elements (such as α-helices or β-sheets), and/or is placed at a loop structure of the wild-type enzyme. When selecting the desired position of the N-terminus, a Met is added to the cut-site as the initiating amino acid, and an Ala is optionally placed at the second position to decrease cellular turnover. The natural N and C-termini are linked, optionally with a linking sequence. Generally, the linking sequence is selected to provide flexibility (e.g., no defined secondary structure other than a potential loop), for example, using a sequence consisting predominately or essentially of Gly, Ser, and/or Ala. In some embodiments, the linking amino acid sequence is from about 2 to about 25 amino acids in length, which may form a loop. The circular permutant may further comprise from 1 to about 30, or from about 1 to about 20, or from 1 to about 10, or from 1 to about 5 amino acid substitutions, deletions, or insertions with respect to the corresponding position of the parent or wild-type enzyme (e.g., based on the highest score local alignment). In some embodiments, the natural N-terminal Met is maintained at its new position in the molecule, or in other embodiments is deleted.

In some embodiments, at least one UGT enzyme is a chimeric UGT enzyme, in which the N-terminal domain of one UGT is combined with the C-terminal domain of a different UGT enzyme. For example, the N-terminal and C-terminal domains are of two different enzymes selected from Table 9, and each domain may further comprise from one to ten amino acid substitutions, deletions, and/or insertions relative to the parent domain sequence. UGTs have two domains, a more variable N-terminal substrate binding (sugar acceptor) domain and a more conserved C-terminal UDP-glucose binding (sugar donor) domain. The N-terminal domain is mostly determinant of substrate specificity for the enzyme, but some specificity is controlled by the C-terminal domain. Each of these domains makes up roughly half of the protein.

In some embodiments, the UGT enzyme having 1-2' glycosylating activity is OsUGT1-2 (SEQ ID NO:7), SrUGT91D2 (SEQ ID NO:5), SrUGT91D1 (SEQ ID NO:4), SrUGT91D2e (SEQ ID NO:6) (see Table 9) or derivative thereof. In some embodiments, the derivative has increased glycosylating activity at C19 of RebA. The UGT enzyme may generally have a level of identity that is greater than about 50%, greater than about 60%, greater than about 70%, greater than about 80%, greater than about 90%, or greater than about 95%, or greater than about 96, 97, 98, or 99% to one or more of OsUGT1-2, SrUGT91D2, SrUGT91D1, and SrUGT91D2e.

The similarity or identity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J. Mol. Biol.* 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

In some embodiments the UGT enzyme having 1-2' glycosylating activity is OsUGT1-2 or derivative thereof, and which is optionally a circular permutant of OsUGT1-2 comprising one or more amino acid substitutions, deletions, and/or insertions that increase 1-2' glycosylating activity at C19 of RebA. For example, the 1-2' glycosylating enzyme may have a cut site that aligns with or corresponds to a position within amino acids 190 to 210 of OsUGT1-2 (SEQ ID NO:7), and may be a position within amino acids 194 to 200 of SEQ ID NO:7 in some embodiments, such as position 195, 196, 197, or 199. The circular permutant may optionally have a linker sequence between the amino acids that correspond to the N-terminal and C-terminal residues of OsUGT1-2. The linker may vary in length, such as in the range of 2 to about 25 amino acids. For example, the linker may be from about 8 to about 20 amino acids in length, such as about 17 amino acids in some embodiments. In some embodiments, the circular permutant does not contain any linking sequence. The circular permutant may further contain from 1 to 20, or from 1 to 10, or from 1 to 5 amino acid substitutions, additions, or deletions from the wild-type sequence (determined by local alignment of the mutated sequence to OsUGT1-2). In some embodiments, an Ala is inserted or substituted at position 2 to decrease enzyme turnover in the cell. In some embodiments, the mutations collectively increase 1-2' glycosylating activity at C19 of RebA (e.g., when evaluated at 22° C., 27° C., or 30° C.).

In some embodiments, the UGT enzyme having 1-2' glycosylating activity is a circular permutant of OsUGT1-2, with a cut-site corresponding to position 195, 196, 197, 198, or 199 of OsUGT1-2. An exemplary circular permutant, named MbUGT1-2, is disclosed herein. The circular permutant may have amino acid substitutions at one or more of positions corresponding to positions 14, 16, 89, 185, 365, 366, 395, 396, 417, 420, 421, 422, 424, 427, 428, 430, 431, 432, 434 and/or 463 of the wild-type enzyme. In some embodiments, the circular permutant has an amino acid substitution at position 14, and such substitution may be an aromatic amino acid, such as Trp or Tyr. In these or other embodiments, the circular permutant has an amino acid substitution at position 366, and the substituted amino acid is optionally Pro. In these or other embodiments, the circular permutant has an amino acid substitution at position 420, and the substituted amino acid is optionally Glu. In these or other embodiments, the circular permutant has an amino acid substitution at position 421, and the substituted amino acid is optionally Phe. In these or other embodiments, the circular permutant has an amino acid substitution at position 424, and the substituted amino acid is optionally Asp. In these or other embodiments, the circular permutant has an amino acid substitution at position 427, and the substituted amino acid is optionally Glu. In these or other embodiments, the circular permutant has an amino acid substitution at position 428, and the substituted amino acid is optionally Glu. In these or other embodiments, the circular permutant has an amino acid substitution at position 432, and the substituted amino acid is optionally Tyr, His, Trp, Asp, or Glu. In some embodiments, the enzyme contains an insertion of from 2-5 amino acids between amino acids 424 and 427, such as the sequence Gly-Pro-Ser. In some embodiments, the UGT having 1-2' glycosylating activity comprises the amino acid sequence of SEQ ID NO:9 (MbUGT1-2), or an enzyme having at least about 50% identity, at least about 60% identity, at least about 70% identity, at least about 80% identity, at least about 85% identity, or at least about 90% identity, or at least about 95% identity, or at least 96%, 97%, 98% or 99% identity to SEQ ID NO:9, and having 1-2' glycosylating activity at one or more of C19 of RebA or C13 of steviolmonoside.

In some embodiments, the UGT enzyme having 1-2' glycosylating activity is a circular permutant of OsUGT1-2, with a cut site corresponding to position 196 of OsUGT1-2. An exemplary circular permutant, named MbUGT1,2-2 (SEQ ID NO:45), is disclosed herein. The circular permutant has amino acid substitutions at one or more of positions 16, 422, 430, and 434 of the wild-type enzyme. In some embodiments, the circular permutant has an amino acid substitution at position 16, and such substitution may be an aromatic amino acid, such as Trp. In these or other embodiments, the circular permutant has an amino acid substitution at position 422, and the substituted amino acid is optionally Glu. In these or other embodiments, the circular permutant has an amino acid substitution at position 430, and the substituted amino acid is optionally Glu. In these or other embodiments, the circular permutant has an amino acid substitution at position 434, and the substituted amino acid is optionally His. In some embodiments, the enzyme does not contain any linking sequence between the natural N- and C-termini amino acids, and the natural N-terminal Met may be optionally deleted. In some embodiments, the UGT having 1-2' glycosylating activity comprises the amino acid sequence of SEQ ID NO:45, or an enzyme having at least about 50% identity, at least about 60% identity, at least about 70% identity, at least about 80% identity, at least about 85% identity, or at least about 90% identity, or at least about 95% identity, or at least 96%, 97%, 98% or 99% identity to SEQ ID NO:45, and having 1-2' glycosylating activity at one or more of C19 of RebA or C13 of steviolmonoside.

In some embodiments, the UGT enzyme having 1-3' glycosylating activity is SrUGT76G1, or derivative thereof having the same or increased glycosylation activity at C19 of RebD or C13 of stevioside. In some embodiments, the UGT enzyme having 1-3' glycosylating activity is a derivative of SrUGT76G1 that includes an amino acid substitution at one or more of positions 77, 78, 81, 82, 93, 94, 155, 192, 200, 202, 205, 283, 284, 379, and 397 of SEQ ID NO: 3 (see Table 13). In some embodiments, the derivative has an amino acid substitution at position L200 (numbered according to the wild type enzyme), and which is optionally Ala or Gly. In these embodiments, the derivative may further have an amino acid substitution at position 284 (e.g., Ala) and/or 379 (e.g., Gly), and/or 192 (e.g., Ala). In some embodiments, an Ala is inserted or substituted at position 2 to decrease turnover in the cell. In some embodiments, the UGT enzyme has at least about 80% identity, at least about 85% identity, at least about 90% identity, or at least about 95%, 96%, 97%, 98%, or 99% identity to SEQ ID NO: 3, with the proviso that the amino acid corresponding to position 200 of SEQ ID NO:3 is Ala or Gly. As shown in Table 13, the substitution of L200A or L200G provides for large improvements in activity at both C19 and C13.

Additional modification to UGT76G1 include modification at one or more of positions 22, 25, 145, 154, 256, and 282, such as one or more of Q22G, Q22H, I25F, I25W, T145A, T145G, T145P, H154R, L256P, L256W, L256T, L256G, L256A, L256R, L256E, S281G and S282N. These modifications are disclosed in WO 2014/122227, which is hereby incorporated by reference. In some embodiments, these additional modifications to UGT76G1 exhibit superior properties in combination with the modifications at positions 77, 78, 81, 82, 83, 93, 94, 155, 192, 200, 202, 205, 283, 284, 378, 379, and 397.

In some embodiments, the UGT enzyme having 1-3' glycosylating activity is a circular permutant of SrUGT76G1, with a cut-site corresponding to a position within amino acids 170 to 290 (e.g, 190-210, 196-200 or 260-280) of SrUGT76G1. In some embodiments, the cut site corresponds to position 196 or 264 of the wild-type enzyme. The circular permutant (e.g., MbUGT1-3), may have from 1 to 30, or from 1 to 20, or from 1 to 10, or from 1 to 5 amino acid substitutions, deletions, and/or insertions with respect to the corresponding position of the wild-type sequence. In some embodiments, the UGT having 1-3' glycosylating activity comprises the amino acid sequence of SEQ ID NO: 10 (MbUGT1-3), or comprises an amino acid sequence having at least about 50% identity, at least about 60% identity, at least about 70% identity, at least about 80% identity, at least about 85% identity, or at least about 90% identity, or at least about 95% identity, or at least 96%, 97%, 98% or 99% identity to SEQ ID NO: 10, and having 1-3' glycosylating activity at one or more of C19 of RebD or C13 of stevioside. In some embodiments, Ala is substituted or inserted at position 2 to decrease turnover in the cell.

In various embodiments, the host cell or method of the invention further involves a UGT enzyme that converts steviol to steviolmonoside. In some embodiments, the UGT enzyme that converts steviol to steviolmonoside is SrUGT85C2, or derivative thereof. In some embodiments, the enzyme contains from 1 to about 50, or from 1 to about 20, or from 1 to about 10 amino acid substitutions, deletions, and/or insertions with respect to SEQ ID NO: 1. For example, the derivative may have at least about 65% identity, or at least about 70% identity, or at least about 80% identity to SEQ ID NO: 1, or at least 90% identity to SEQ ID NO: 1, or at least 95%, 96%, 97%, 98%, or 99% identity to SEQ ID NO: 1, while maintaining the same or similar activity for converting steviol to steviolmonoside (e.g., in vitro or in vivo). Exemplary amino acid modifications are shown in Table 11. In some embodiments, the enzyme that converts steviol to steviolmonoside is a derivative of SrUGT85C2 having an amino acid substitution at position 215 of the wild type enzyme. In some embodiments, the amino acid at the position corresponding to 215 of the wild type enzyme is threonine, serine, glycine, or alanine (the wild type amino acid is Proline). In some embodiments, the amino acid at said position 215 is threonine. In these or other embodiments, the derivative of SrUGT85C2 has a mutation at one or more of positions 308, 311, 316, 349, and/or 414 (numbered in accordance with the wild type enzyme. In some embodiments, the amino acid at position 308 is threonine, and/or the amino acid at position 311 is glutamine, and/or the amino acid at position 316 is alanine, and/or the amino acid at position 349 is glutamic acid, and/or the amino acid at position 414 is glycine. In some embodiments, an Ala is inserted or substituted at the second position to limit turnover in the cell.

In various embodiments, the host cell or method further involves a UGT enzyme that converts steviolbioside to stevioside, which in some embodiments is SrUGT74G1, or derivative thereof. In some embodiments, the enzyme contains from 1 to about 50, or from 1 to about 20, or from 1 to 10 amino acid substitutions, deletions, and/or insertions with respect to SEQ ID NO: 2. For example, the derivative may have at least 80% identity to SEQ ID NO: 2, at least 90% identity to SEQ ID NO: 2, or at least 95%, 96%, 97%, 98%, or 99% identity to SEQ ID NO: 2, while maintaining the same or similar activity for converting steviolbioside to stevioside (e.g., in vitro or in vivo).

In some embodiments, the UGT enzyme that converts steviolbioside to stevioside is a circular permutant of SrUGT74G1 (e.g., MbUGTC19). In some embodiments, the circular permutant has a cut site corresponding to an amino acid within positions 180 to 280 (e.g., 250 to 270) of SrUGT74G1. The circular permutant may have a linking sequence between the original N- and C-termini of from 1 to 10 amino acids (e.g., GSG). The circular permutant may have from 1 to 30, or from 1 to 20, or from 1 to 10, or from 1 to 5 amino acid substitutions, deletions, and/or insertions with respect to the corresponding position of the wild-type sequence. In some embodiments, the SrUGT74G1 circular permutant comprises the amino acid sequence of SEQ ID NO: 8 (MbUGTC19) or SEQ ID NO: 46 (MbUGTC19-2), or comprises an amino acid sequence having at least about 50% identity, at least about 60% identity, at least about 70% identity, at least about 80% identity, at least about 85% identity, or at least about 90% identity, or at least about 95% identity, or at least 96%, 97%, 98% or 99% identity to SEQ ID NO: 8 or 46, and having activity for converting steviolbioside to stevioside.

In some embodiments, the host cell produces steviol substrate through one or more pathway modules comprising a kaurene synthase (KS), kaurene oxidase (KO), and a kaurenoic acid hydroxylase (KAH), the host cell further comprising a cytochrome P450 reductase (CPR) for regenerating one or more of the KO and KAH enzymes. In some embodiments, the KAH is KAH of *Stevia rebaudiana, Arabidopsis thaliana, Vitis vinifera*, or *Medicago trunculata*, or a derivative thereof (e.g., having at least 80%, or at least 90%, or at least 95%, or at least 97% sequence identity to the wild type sequence). In some embodiments, the KAH is an *Arabidopsis thaliana* KAH (AtKAH), or derivative thereof. The AtKAH may have one or more amino acid substitutions, insertions, and/or deletions that increase the rate of kaurenoic acid hydroxylase activity or otherwise improve enzyme productivity or expression, including for example an N-terminus engineered for functional expression in *E. coli*. In some embodiments, the AtKAH has an amino acid substitution at one or more positions (e.g., two-ten positions) of the parent sequence of SEQ ID NO:29 as shown in Table 6 that increases production of steviol or kaurenoic acid. Exemplary substitutions include substitutions corresponding to the following positions of SEQ ID NO:29: 25 (e.g., A25L), 79 (e.g., S79T), 119 (e.g., T119C), 137 (e.g., I137L), 142 (e.g., I142V), 155 (e.g., R155K), 180 (e.g., M180L), 193 (e.g., E193G), 196 (e.g. C196A), 197 (e.g., D197E), 226 (A226E), 235 (e.g., L235Q), 238 (e.g., I238M), 245 (F245L, F245V), 272 (e.g., L272I), 285 (e.g., I285R), 287 (e.g., C287S), 325 (e.g., C325I, C325M), 330 (e.g., F330L), 334 (e.g., D334E), 339 (e.g., S339T), 352 (e.g., S352E), 373 (e.g., E373D), 397 (e.g., I397F), 470 (e.g., V470L), 499 (e.g., Q499V), 506 (e.g., L506M), 507 (e.g., L507I, L507T, L507V). In some embodiments, the AtKAH enzyme is a derivative having an amino acid substitution at position 331 (with respect to the wild type sequence), which in some embodiments, improves the productivity of the enzyme at higher temperatures (e.g., higher than 22° C.). In some embodiments, the amino acid at position 331 is Ile.

Figure 9:
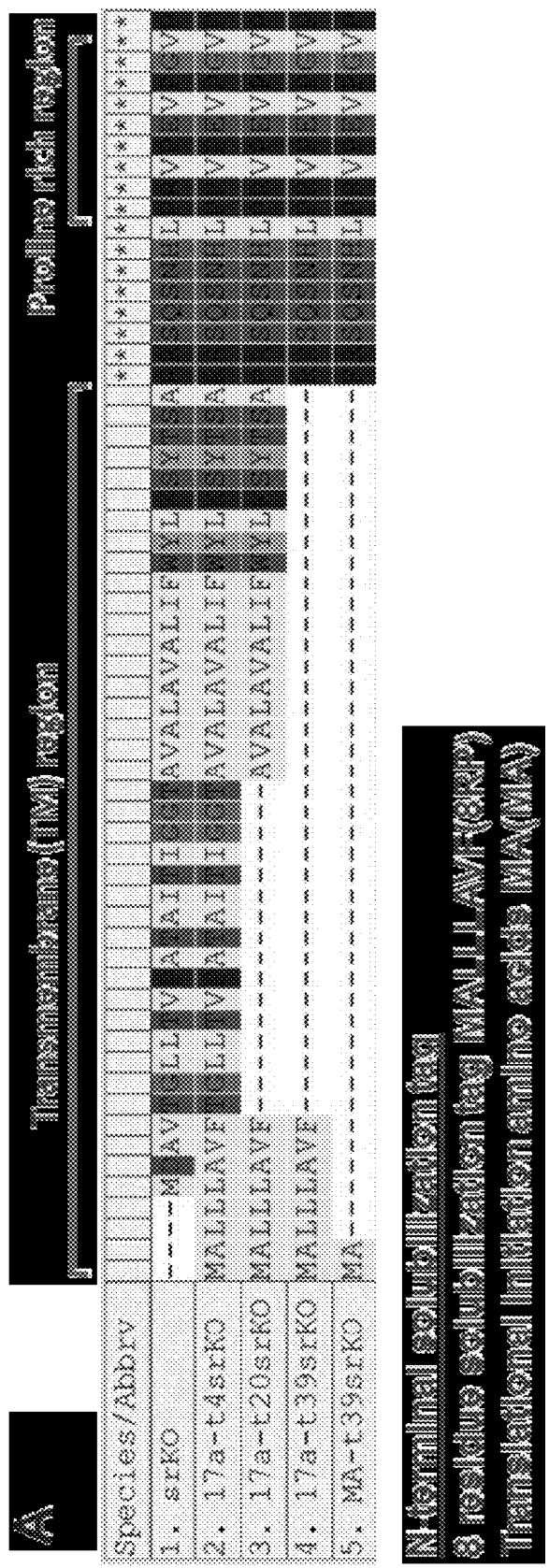
FIG. 9 shows redesign and characterization of SrKO enzyme. (A) The N-terminal transmembrane region analysis and truncations with modifications to SrKO. Alignments include SrKO (SEQ ID NO:53), 17a-t4srKO (SEQ ID NO:54), 17a-t20srKO (SEQ ID NO:55), 17a-t36srKO (SEQ ID NO:56), and MA-t39srKO (SEQ ID NO:57). MALL-LAVF (SEQ ID NO: 47) tag is also shown. (B) Schematics of designed SrKO/SrCPR enzyme constructs. (C) Protein expression from different engineered constructs in *E. coli*: (1) WT, (2) WT+(MA)KO-O-CPR, (3) WT+(MA)KO-O-CPR, (4) WT+(MA)KO-L-CPR, (5) WT+(MA)KO-L-CPR, (6) WT+(8RP)KO-O-CPR, (7) WT+(8RP)KO-O-CPR, (8) WT+(8RP)KO-L-CPR, (9) WT+(8RP)KO-L-CPR.
Figure 9:
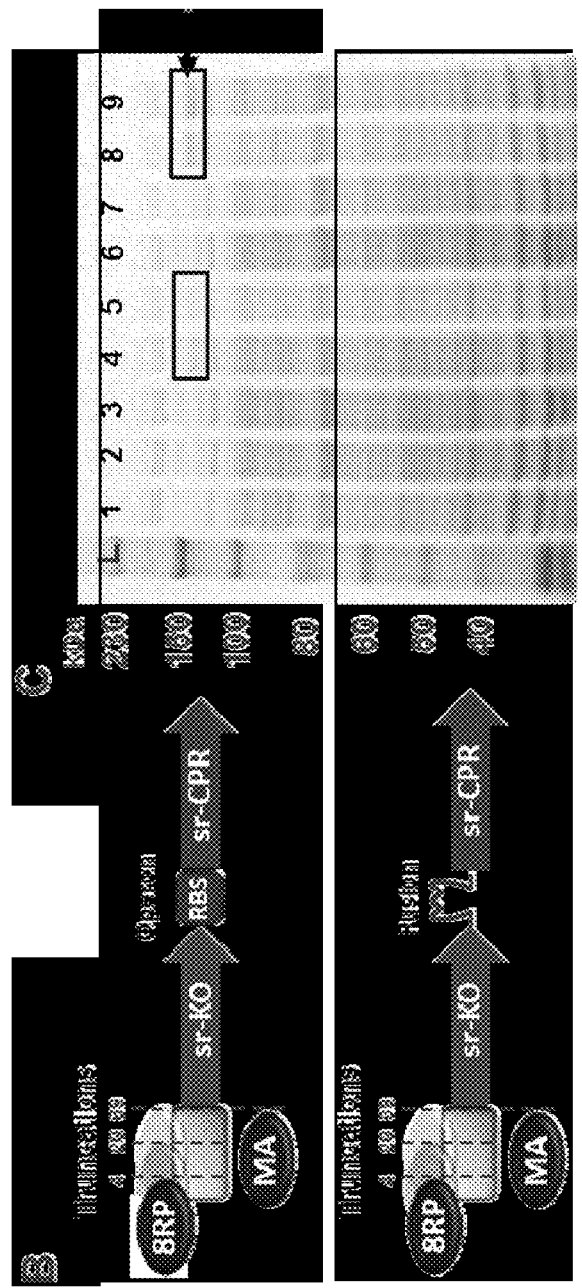

N-terminal modifications to achieve functional expression of the P450 enzyme SrKO are illustrated in FIG. 9. These modifications or similar modifications may be made to achieve functional expression of KAH, including AtKAH. For example, all or portions of the transmembrane region may be deleted, such as from 4 amino acids to about 39 amino acids, or in some embodiments, from about 6 amino acids to about 25 amino acids, or about 4 to about 20 amino acids, or about 29 amino acids, or about 39 amino acids. The deletions are preferably taken from the N-terminal portion of the transmembrane region. This portion is replaced with a solubilization tag of from about 4 to about 20 amino acid residues, such as from about 4 to about 12 residues (e.g., eight amino acid residues). The tag is constructed predominantly of hydrophobic amino acids, which are optionally selected from Ala, Leu, Ile, Val, and Phe. An exemplary sequence for the functional expression is the N-terminal tag: MALLLAVF (SEQ ID NO: 47). In some embodiments, the AtKAH has a truncation of 14 amino acids, with the addition of the N-terminal tag (e.g., SEQ ID NO: 29), optionally having the substitution C331I (position nomenclature based on the wild type enzyme).

Alternative N-terminal tag sequences for P450 enzymes are described in Provisional Application No. 62/208,166, filed Aug. 21, 2015, and which find use in certain embodiments of the present invention. For example, the transmembrane domain (or "N-terminal anchor") can be derived from an *E. coli* gene selected from waaA, ypfN, yhcB, yhbM, yhhm, zipA, ycgG, dj1A, sohB, lpxK, F11O, motA, htpx, pgaC, ygdD, hemr, and ycls. These genes were identified as inner membrane, cytoplasmic C-terminus proteins through bioinformatic prediction as well as experimental validation. The invention may employ an N-terminal anchor sequence that is a derivative of the *E. coli* wild-type transmembrane domain, that is, having one or more mutations with respect to the wild-type sequence. In exemplary embodiments, the membrane anchor sequence is from about 8 to about 75 amino acids in length. For example, the membrane anchor may be from about 15 to about 50, or from about 15 to about 40, or from about 15 to about 30, or from about 20 to about 40, or from about 20 to about 30 amino acids in length.

In some embodiments, the Kaurene Synthase (KS) is from *Stevia rebaudiana, Zea mays, Populus trichocarpa, Arabidopsis thaliana, Erwina tracheiphila* or derivative thereof (e.g., having at least 80%, or at least 90%, or at least 95%, or at least 97% sequence identity to the wild type sequence). Further, the cell may express a copalyl diphosphate synthase (CPPS) from *Stevia rebaudiana, Streptomyces clavuligerus, Bradyrhizobium japonicum, Zea mays, Arabidopsis thaliana, Erwina tracheiphila*, or derivative thereof (e.g., having at least 80%, or at least 90%, or at least 95%, or at least 97% sequence identity to the wild type sequence). In some embodiments, the host cell expresses a bifunctional CPPS and KS enzyme, which is optionally selected from *Phomopsis amygdali, Physcomitrella patens, Gibberella fujikuroi* enzyme, or derivative thereof. Such derivative may generally have at least about 75%, or at least about 80%, or at least about 85%, or at least about 90%, or at least about 95%, or at least 96%, 97%, 98%, or 99% identity to the parent sequence (e.g., see Table 1). In some embodiments, the cell expresses *Erwina tracheiphila* CPPS and KS enzymes, or derivatives thereof.

In some embodiments, the host cell expresses a Kaurene Oxidase from *Stevia rebaudiana* (SrKO), *Arabidopsis thaliana, Gibberella fujikoroi*, or *Trametes versicolor*, or a derivative thereof, which is optionally modified at the N-terminus for functional expression in *E. coli* (as described above and as shown in FIG. 9). In some embodiments, the CPR is an enzyme of *Stevia rebaudiana* (SrCPR), *Arabidopsis thaliana*, or *Giberella fujikuroi*, or a derivative thereof, which is optionally modified at the N-terminus for functional expression in *E. coli*.

The SrKO may have one or more amino acid modifications that improve its activity. Exemplary modifications are disclosed in U.S. Provisional Application No. 62/040,284, which is hereby incorporated by reference in its entirety. For example, the SrKO may comprise one or more amino acid modifications at positions (with respect to SEQ ID NO:22: 47 (e.g., L47I), 59 (e.g., Y59H), 60 (e.g., M60K), 63 (e.g., T63A), 67 (e.g., A67E), 76 (e.g., K76R), 80 (e.g., T80C), 82 (e.g., M82V), 85 (e.g., V85L, V85I), 86 (e.g., S86N), 100 (e.g., Q100S), 106 (e.g., N106K), 112 (e.g., K112T), 116 (A116R), 119 (e.g., T119S), 123 (e.g., M123T, M123Q, M123F, M123T), 127 (e.g., D127G), 129 (e.g., Y129F), 140 (e.g., A140R), 149 (e.g., K149R), 150 (e.g., H150F), 171 (e.g., N171D), 180 (e.g., L180F), 183 (e.g., I183V), 208 (e.g., D208E), 232 (e.g., D232E), 267 (e.g., S267A), 272 (e.g., H272Q), 284 (e.g., S284C), 286 (e.g., I286L), 294 (e.g., Q294K), 299 (e.g., Q299E), 310 (e.g., I310T, I310V), 371 (e.g., R371K, R371I), 375 (e.g., V375T, V375I, V375L), 378 (e.g., I378V), 382 (e.g., H382Y), 388 (e.g., V388Q, V388M), 393 (e.g., H393D), 400 (e.g., L400I), 413 (e.g., V413K, V413D), 434 (e.g., F434L), 442 (e.g., G442A), 450 (e.g., S450A), 454 (e.g., L454M), 460 (e.g., G460A), 464 (e.g., M464L), 475 (e.g., M475G), 487 (e.g., T487N), 492 (e.g., P492K), and 497 (e.g., I497L). In some embodiments, the SrKO contains a truncation of about 20 amino acids of the N-terminal transmembrane domain, with addition of an N-terminal tag sequence (described above). The SrKO may contain an Ala at the 2nd position to decrease enzyme turnover in the cell.

In some embodiments, the P450 reductase partner(s) include *Stevia rebaudiana* (Sr)CPR, *Stevia rebaudiana* (Sr) CPR1, *Arabidopsis thaliana* (At)CPR, *Taxus cuspidata* (Tc) CPR, *Artemisia annua* (Aa)CPR, *Arabidopsis thaliana* (At) CPR1, *Arabidopsis thaliana* (At)CPR2, *Arabidopsis thaliana* (At)R2, *Stevia rebaudiana* (Sr)CPR2, *Stevia rebaudiana* (Sr)CPR3, or *Pelargonium graveolens* (Pg)CPR. Any of these P450s can be derivatized in some embodiments, for example, to introduce from 1 to about 20 mutations, or from about 1 to about 10 mutations. These CPR proteins are further described in PCT/US15/46369, which disclosure is hereby incorporated by reference.

In some embodiments, the host cell is an *E. coli* that contains a single CPR enzyme (e.g., SrCPR), and which is chromosomally integrated, and supports both the SrKO and AtKAH enzymes, for example.

In some embodiments, the host cell expresses a geranylgeranyl pyrophosphate synthase (GGPPS), which is optionally of *Taxus canadensis, Abies grandis, Aspergillus nidulans, Stevia rebaudiana, Gibberella fujikuroi, Mus musculus, Thalassiosira pseudonana, Streptomyces melanosporofaciens, Streptomyces clavuligerus, Sulfulubus acidocaldarius, Synechococcus* sp. (e.g., JA-3-3Ab), *Arabidopsis thaliana*, Marine bacterium 443, *Paracoccus haeundaensis, Chlorobium tepidum* TLS, *Synechocystis* sp. (PCC 6803), *Thermotoga maritima* HB8, *Corynebacterium glutamicum, Therms thermophillus* HB27, *Pyrobaculum calidifontis* JCM 11548, or derivative thereof. See Table 1. Such derivative may generally have at least about 60%, or at least about 70%, or at least about 75%, or at least about 80%, or at least about 85%, or at least about 90%, or at least about 95%, or at least 96%, 97%, 98%, or 99% identity to the parent sequence (e.g., see Table 1). In some embodiments, the GGPPS is *Taxus canadensis* or derivative thereof. In some embodiments, the *Taxus* GGPPS is an N-terminal truncated sequence (e.g., with the N-terminal 70 to 110, such as about 98, amino acids truncated). The truncated sequence may further comprise from about 1 to about 10, such as from about 1 to about 5 amino acid substitutions, deletions, and/or insertions at the corresponding wild-type sequence. An exemplary truncated sequence is disclosed herein as SEQ ID NO: 12. In some embodiments, the GGPPS is from *Corynbacterium glutamicum* or derivative thereof, which can provide advantages in productivity at temperatures higher than 22° C.

In some embodiments, the host cell expresses a pathway producing iso-pentyl pyrophosphate (IPP) and dimethylallyl pyrophosphate (DMAPP). In some embodiments, the pathway is a methylerythritol phosphate (MEP) pathway and/or a mevalonic acid (MVA) pathway.

The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA. In some embodiments, steviol is produced at least in part by metabolic flux through an MEP pathway, and wherein the host cell has at least one additional copy of a dxs, ispD, ispF, and/or idi gene. As disclosed in U.S. Pat. No. 8,512,988, the level of the metabolite indole can be used as a surrogate marker for efficient production of terpenoid products in *E. coli* through the MEP pathway.

The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

The host cell may be prokaryotic or eukaryotic. For example, the host cell may be a bacteria selected from *E. coli, Bacillus subtillus,* or *Pseudomonas putida.* In some embodiments, the host cell is a species of *Saccharomyces, Pichia,* or *Yarrowia,* including *Saccharomyces cerevisiae, Pichia pastoris,* and *Yarrowia lipolytica.* The host cell may be an *E. coli* having a duplication or overexpression of dxs, idi, IspD, and IspF increasing production of IPP and DMAPP.

In some embodiments, the host cell is an *E. coli* having one or more genetic modifications increasing the production of UDP-glucose, for example, increasing UDP-glucose substrate availability. To improve availability of UDP-glucose for steviol glycosylation, a series of gene knock-outs and gene insertions can be introduced to increase carbon flux to UDP-glucose and decrease flux in pathways away from UDP-glucose (e.g., glycogen synthesis and carbon storage). For example, genetic modifications can increase importation of sucrose into the cell and split it into fructose and glucose via the activity of sucrose phosphorylase. A subsequent series of knock-outs can alter primary metabolism so as to force biomass to be synthesized using only fructose as carbon source, leaving glucose to be funneled exclusively towards UDP-glucose biosynthesis. Exemplary modifications to an *E. coli* strain to enact this strategy are listed in Table 7. Modifications are further described in PCT/EP2011/061891, which is hereby incorporated by reference in its entirety. In some embodiments, the one or more genetic modifications include ΔgalE, ΔgalT, ΔgalK, ΔgalM, ΔushA, Δagp, Δpgm, duplication of *E. coli* GALU, and expression of *Bacillus substillus* UGPA, BaSP.

In an exemplary embodiment, the host cell is an *E. coli* that comprises the following heterologously expressed genes: *Taxus canadensis* GGPPS or derivative thereof, *Phaeosphaeria* sp. PsCK or derivative thereof, *Stevia rebaudiana* KO or derivative thereof, *Arabidopsis thaliana* KAH or derivative thereof, *Stevia rebaudiana* CPR or derivative thereof (and which is the only CPR enzyme expressed by the host cell), *Stevia rebaudiana* UGT85C2 or derivative thereof, *Stevia rebaudiana* UGT74G1 of derivative thereof, *Stevia rebaudiana* UGT76G1 or derivative thereof, and MbUGT1-2 or derivative thereof. Various derivatives of these enzymes are disclosed herein. In some embodiments, the *E. coli* contains a polycistronic expression module of KAH-KO, and contains a single copy of SrCPR (or derivative) that is chromosomally integrated. In some embodiments, the *E. coli* is modified to increase availability of UDP-glucose as described above. In some embodiments, the *E. coli* has an additional copy of dxs, idi, ispD, and ispF genes. In some embodiments, one or more expressed proteins contain an Alanine at position 2, to provide additional stability in vivo.

In other embodiments, the host cell is an *E. coli* that comprises the following heterologously expressed genes: *Cornybacterium glutamicum* GGPPS or derivative thereof; *Erwina tracheiphila* CPPS and KS or derivative of one or both; *Stevia rebaudiana* KO or derivative thereof; *Arabidopsis thaliana* KAH or derivative thereof; a *Stevia rebaudiana* CPR or derivative thereof; *Stevia rebaudiana* UGT85C2 or MbUGTc13 or derivative thereof; *Stevia rebaudiana* UGT74G1 or derivative thereof (or MbUGTC19, MbUGTC19-2, or derivative thereof); *Stevia rebaudiana* UGT76G1 or derivative thereof (or MbUGT1-3 of derivative thereof); and OsUGT1-2, SrUGT91D2, or derivative thereof, or MbUGT1-2 or MbUGT1,1-2 or derivative thereof. Various derivatives of these enzymes are disclosed herein. In some embodiments, the *E. coli* contains a polycistronic expression module of KAH-KO, and contains a single copy of SrCPR that is chromosomally integrated. In some embodiments, the *E. coli* is modified to increase availability of UDP-glucose as described above. In some embodiments, the *E. coli* has an additional copy of one or more (or all) of dxs, idi, ispD, and ispF genes. In some embodiments, one or more expressed proteins contain an Alanine at position 2, to provide additional stability in vivo. In some embodiments, the *E. coli* provides increased productivity of Reb M or Reb D at temperatures above about 24° C., such as about 27° C. or more, or about 30° C. or more, or about 32° C. or more, or about 34° C. or more, or about 37° C.

In some embodiments, the method further comprises recovering the desired steviol glycoside(s) (e.g., RebM or RebD) from culture media. In some embodiments, the desired steviol glycoside (e.g., RebM or RebD) is produced in the culture media at a concentration of at least about 10 mg/L, or at least about 100 mg/L, or at least about 200 mg/L, or at least about 500 mg/L, or at least about 1 g/L, or at least about 10 g/L.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods. Fractions containing different glycoside fractions can be blended to prepare defined products. Alternatively, RebM and RebD, for example, can be prepared and purified from separate cultures, and blended at a predetermined ratio.

In another aspect, the invention provides a method for production of steviol glycosides having at least 4 glycosylations in *E. coli*. In accordance with the invention, the *E. coli* cell comprises a plurality of UGT enzymes, which may include one or more enzymes described herein, that together perform at least 4, at least 5, or at least 6 (including 7 or 8), sequential glycosylation reactions. As disclosed herein, the glycosylation substrates and lower glycosylation products accumulate in the *E. coli* cell sufficiently to allow downstream reactions to proceed at an acceptable rate, with a high majority of the glycosylation products ultimately accumulating extracellularly, most likely through the action of a membrane transporter. The steviol glycosides can be purified from media components. Thus, in some embodiments, the methods comprise separating growth media from the *E. coli* cells, for example using batch, continuous, or semi-continuous bioreactor processes, and isolating the desired glycosylation products (e.g, Reb M) from the growth media.

In still other aspects, the invention provides methods for production of steviol glycosides (including Reb D, Reb M, Reb E, Reb I and other glycosylation products) in *E. coli*. Generally, the desired steviol glycoside has at least 2 glycosylations, such as 2, 3, 4, 5, 6, 7, or 8 glycosylations. In some embodiments, the steviol glycoside is RebM or RebD. While many of the enzymes known for production of steviol in host cells are plant enzymes, which often have optimal temperatures in the range of 20-24° C., *E. coli* growth rate and metabolism are optimal at higher temperatures. The present disclosure enables production of steviol glycosides at high yield in *E. coli*, by enabling enzyme productivity at temperatures above 24° C., such as from 24° C. to 37° C., or from 27° C. to 37° C., or from 30° C. to 37° C.

While commercial biosynthesis in *E. coli* can often be limited by the temperature at which overexpressed and/or foreign enzymes are stable, the present disclosure in some embodiments allows for cultures to be maintained at higher temperatures, resulting in higher yields and higher overall productivity. In some embodiments, the culturing is conducted at about 30° C. or greater, or about 31° C. or greater, or about 32° C. or greater, or about 33° C. or greater, or about 34° C. or greater, or about 35° C. or greater, or about 36° C. or greater, or about 37° C.

The host cells and methods are further suitable for commercial production of steviol glycosides, that is, the cells and methods can be productive at commercial scale. In some embodiments, the size of the culture is at least about 100 L, at least about 200 L, at least about 500 L, at least about 1,000 L, or at least about 10,000 L. In an embodiment, the culturing may be conducted in batch culture, continuous culture, or semi-continuous culture.

In some aspects, the invention provides methods for making a product comprising a steviol glycoside ingredient, which is RebM or RebD in some embodiments. The method comprises culturing a strain described herein that produces the steviol glycoside, recovering the steviol glycoside, and incorporating the steviol glycoside into a product, such as a food, beverage, oral care product, sweetener, flavoring agent, or other product.

Purified steviol glycosides, prepared in accordance with the present invention, may be used in a variety of products including, but not limited to, foods, beverages, texturants (e.g., starches, fibers, gums, fats and fat mimetics, and emulsifiers), pharmaceutical compositions, tobacco products, nutraceutical compositions, oral hygiene compositions, and cosmetic compositions. Non-limiting examples of flavors for which RebM can be used in combination include lime, lemon, orange, fruit, banana, grape, pear, pineapple, mango, bitter almond, cola, cinnamon, sugar, cotton candy and vanilla flavors. Non-limiting examples of other food ingredients include flavors, acidulants, and amino acids, coloring agents, bulking agents, modified starches, gums, texturizers, preservatives, antioxidants, emulsifiers, stabilizers, thickeners and gelling agents.

Highly purified target steviol glycoside(s) obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s) obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Highly purified target steviol glycoside(s) obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, RebM can be used as a sweetener not only for drinks, foodstuffs, and other products dedicated for human consumption, but also in animal feed and fodder with improved characteristics.

Examples of products in which highly purified target steviol glycoside(s) may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

EXAMPLES

Steviol glycosides are the natural constituents of the plant *Stevia rebaudiana*, known commonly as Stevia. Steviol glycoside Rebaudioside M (RebM) (FIG. 1), whose taste profile drastically improves upon that of other steviol glycosides, is an ideal candidate to replace currently used steviol glycosides such Rebaudioside A, but hasn't fulfilled that promise because of its low levels in the Stevia plant (<0.01%). Steviol is a diterpenoid that forms the core chemical structure of steviol glycosides like RebM (1).

Terpenoid biosynthesis has been engineered in both prokaryotic (e.g., *E. coli*) and eukaryotic (e.g., yeast) cells for heterologous production of complex terpenoid molecules (2,3). The *E. coli* MEP-pathway is stoichiometrically superior and less byproduct accumulating compared to the yeast MVA-pathway (4,5). A new metabolic engineering approach, multivariate modular metabolic engineering (MMME), and a platform *E. coli* strain capable of overproducing terpenoid precursors has been described (4,6). MMME facilitates assessment and elimination of regulatory and pathway bottlenecks by re-defining the metabolic network as a collection of distinct modules (7). By grouping enzymes with similar turnovers into a subset, or module, and later equalizing the turnover of the different subsets by adjusting concentrations/activities, one can maximize the ratio of pathway turnover to resource expenditure.

MMME pathway engineering was applied in *E. coli* for the biosynthesis of kaurene, the unfunctionalized terpene scaffold precursor for steviol and steviol glycosides. Next, the downstream CYP450-mediated oxidation chemistry was engineered to demonstrate that the diterpenoid scaffold steviol can be biosynthesized in *E. coli*. Further, glycosylation chemistry for the conversion of steviol to steviol glycosides in *E. coli* was engineered to develop a technology platform for producing glycosylated natural products. Further still, *E. coli* were engineered to produce improved levels of UDP-glucose to support high levels of steviol glycoside production. This work provides for an economical, commercially-viable source for RebM (and other steviol glycosides described herein) in microbial systems from renewable resources.

Example 1: Biosynthesis of Steviol and Steviol Glycosides

Steviol glycosides are diterpenoid derivatives and their early biosynthetic pathways share common intermediates with gibberellic acid biosynthesis (8). The overall linear pathway is modularized into four parts: (1) the formation of starting precursor IPP and DMAPP from the central carbon metabolites derived from glucose, (2) the production of the first dedicated intermediate, kaurene; (3) biosynthesis of the key intermediate, steviol; and (4) the formation of various steviol glycosides. A further module (5) is independently engineered to support the increased production of UDP-glucose, the second substrate necessary for glycosylation of steviol. The five modules are shown in FIG. 2.

In plants, the formation of common isoprenoid precursors IPP and DMAPP can be derived from two biosynthetic routes; either the mevalonic acid (MVA) pathway or methylerythritol-phosphate (MEP) pathway (9). The first step in steviol diterpenoid biosynthesis is conversion of IPP and DMAPP into geranyl-geranyl diphosphate (GGPP). GGPP is the four subunit precursor for all diterpenoid molecules. Next, protonation-initiated cyclization of GGPP to copalyl diphosphate (CPP) is catalyzed by CPP synthase (CPPS). Kaurene is then produced from CPP by an ionization-dependant cyclization catalyzed by kaurene synthase (KS). These enzymes have been identified and characterized from the native biosynthetic pathway in Stevia. In addition to this, there are bi-functional enzymes characterized from the basal plant (*Physcomitrella patens*) and fungal species (e.g., *Gibberella fujikuroi* and *Phaeosphaeria* sp.) for conversion of GGPP into kaurene (10,11). Kaurene is then oxidized in a three-step reaction to kaurenoic acid, by kaurene oxidase (KO) a P450 mono-oxygenase. A full length KO cDNA was expressed in yeast and demonstrated that it could convert kaurene to kaurenoic acid (12). The next step in the pathway is the hydroxylation of kaurenoic acid by kaurenoic acid 13-hydroxylase (KAH). KAH, a cytochrome P450, was expressed in yeast and converted kaurenoic acid to steviol (13).

With the core steviol molecule assembled, a series of six glycosylations attach six glucose moieties to the steviol core. The glycosyltransferase enzymes (EC 2.4.1.17) responsible for these activities catalyze the transfer of the glucose component of UDP-glucose to a small hydrophobic molecule, in this case the steviol molecule (14). O-glycosylations occur at the C13 and C19 positions of steviol (FIG. 1), followed by 1-2' glycosylations and 1-3' glycosylations at both these O-glucosyls to result in six glycosylations in total. The order of glycosylations can be quite complex, with various intermediate products forming given variation in the order of C13 or C19 glycosylations, as well as 1-2' or 1-3' glycosylations (FIG. 3). Given the intermediate product pools accumulating in Stevia rebaudiana, a potential pathway for the production of RebM is Steviol>Steviolmonoside> Steviolbioside>Stevioside>Rebaudioside A>Rebaudioside D>Rebaudioside M. However, this does not preclude an alternate pathway in microbial biosynthetic systems (FIG. 3).

Detailed understanding and characterization of biochemical pathways for steviol glycosides and advancements in engineering of the upstream isoprenoid pathway to reroute the IPP and DMAPP through heterologous biosynthetic pathway engineering provides the basis for directed, sustainable production of purified and high quality steviol glycosides in a convenient microbial-based bioprocess. The current plant-based production and purification schemes present significant challenges to reducing costs. The microbial route described herein using plant pathways that have been reconstructed in microbial hosts offers superior opportunities for improving current processes and to generate superior quality steviol glycosides that are of very low abundance in nature.

(A) Engineering Kaurene Biosynthesis in E. coli

Kaurene is the cyclic diterpenoid precursor for steviol and plant growth hormone gibberellic acid. The biosynthesis of kaurene consists of three steps from the universal terpenoid precursor IPP and DMAPP. The three step reaction from IPP and DMAPP is catalyzed by enzymes GPPS, CPS and KS or bifunctional CPPS/KS enzymes. The overall pathway up to kaurene is grouped as two modules (FIG. 2). There have been several enzymes from different organisms characterized for the conversion of IPP and DMAPP to GGPP (15-18) and GGPP to kaurene (9-12,18) and kaurene to steviol (12,19-24) (Table 1). In higher plants, such as stevia, GGPP to kaurene biosynthesis is carried out as two step reaction mediated by enzymes called copalyl pyrophosphate synthase (CPPS) and kaurene synthase (KS). In the basal plant (Physcomitrella patens) and fungal (e.g., Gibberella fujikuroi and Phaeosphaeria sp.) species, the GGPP to kaurene biosynthesis is carried out by bi-functional enzymes characterized in these organisms. Similarly, there are multiple enzymes cloned and characterized as converting IPP and DMAPP to make GGPP. The first step towards engineering kaurene biosynthesis is therefore selection of enzymes. Enzymes from different species were selected to test for biosynthesis of kaurene (Table 1). Studies on MMME optimization of taxadiene biosynthesis show that the kinetics of TcGPPS are capable of supporting ~1 g/L production of taxadiene and therefore other diterpenes. To identify the best kaurene synthase ortholog, TcGPPS was selected as the upstream candidate enzyme. Operons were then selected containing KS-CPS-GGPPS (KCG) or bi-functional PsCK-GGPPS (CKG) to test the pathway in the upstream pathway engineered strains. To modulate the expression of the downstream kaurene pathway, the KS-CPPS-GGPPS (KCG) and CK-GGPPS (CKG) operons were cloned to a plasmid system with varying copy number and promoter strength (p5Trc, p10Trc, p20Trc and p5T7). Additionally, one copy of each kaurene operon was integrated into the E. coli chromosome under varying promoter strength, coupled with varying upstream pathway expression levels.

Figure 4:
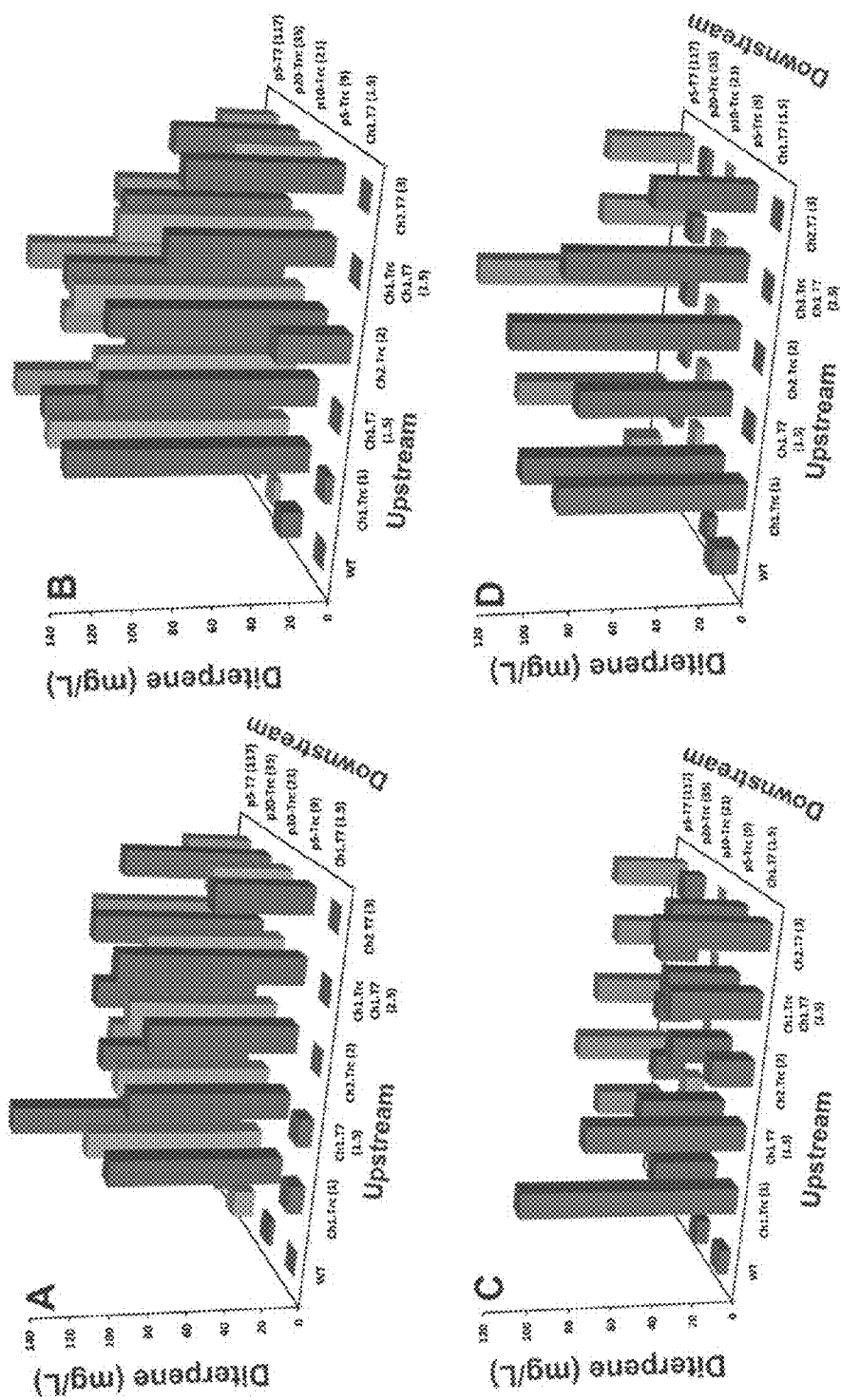
FIG. 4 shows kaurene production profiles from engineered *E. coli* cells. (A) and (B) are kaurene production from CPPS/KS enzymes selected from plant *Stevia rebaudiana* (SrCPPS and SrKS) and *Physcomitrella patens* (PpCK), respectively. (C) and (D) are strains constructed with enzymes selected from fungus species *Gibberella fujikuroi* (GfCK) and *Phaeosphaeria* sp. (PsCK), respectively.
Figure 5:
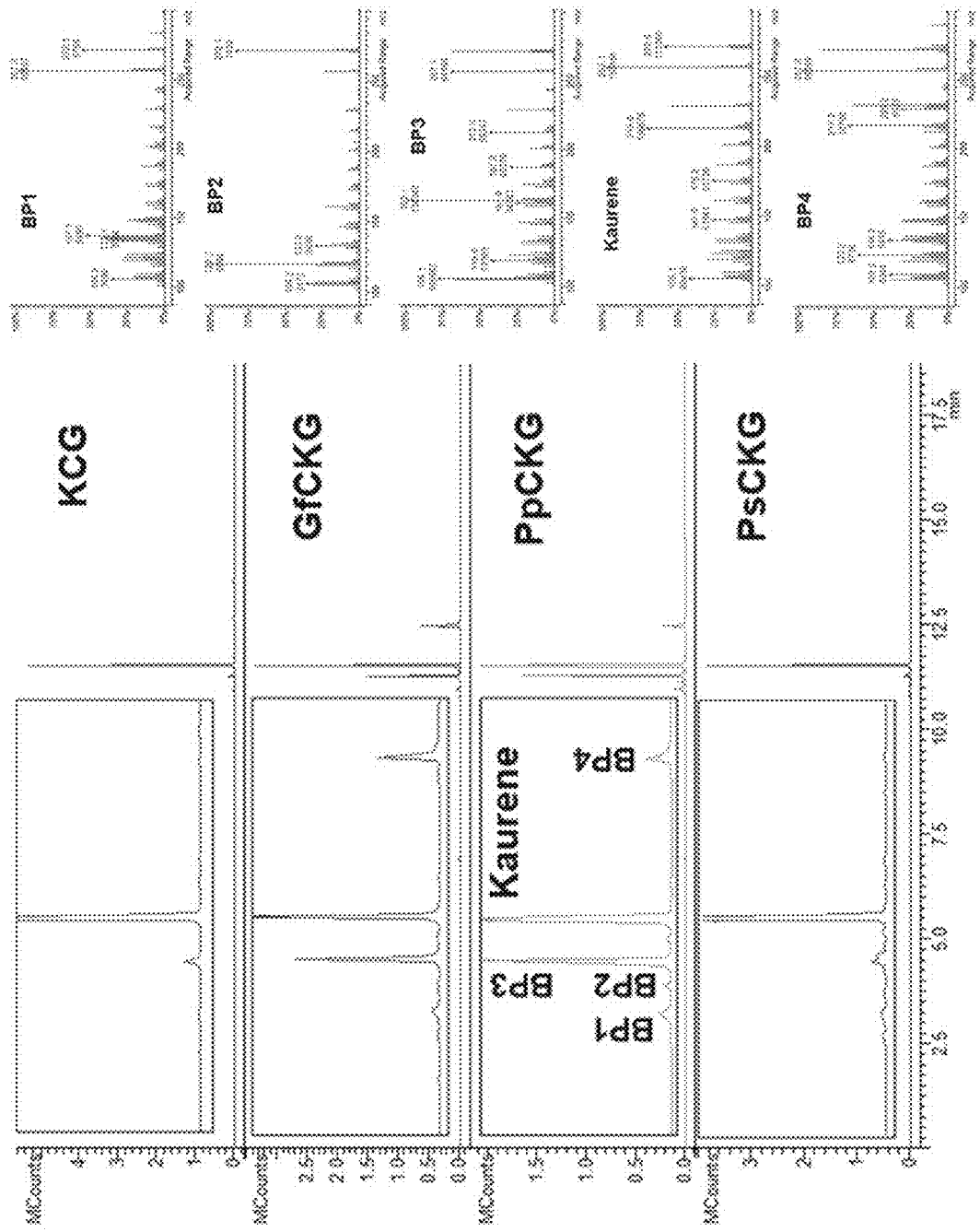
FIG. 5 shows GC profiles from strains constructed from different KS enzymes. The pathway is shown in FIG. 2. The figure in the box (left inset) is the magnified chromatograph to show the byproduct accumulation. The GC profile and corresponding MS spectra show that the KS enzymes can be non-specific vis-à-vis product profile. Other terpenoid byproducts were produced with similar MS characteristics as kaurene. In all three pathways the major product is kaurene. The authenticity of kaurene is confirmed by comparison to MS spectra and NMR data reported in previously published literature. The MS spectra from all the byproduct show a characteristic 272 molecular ion.
Figure 6:
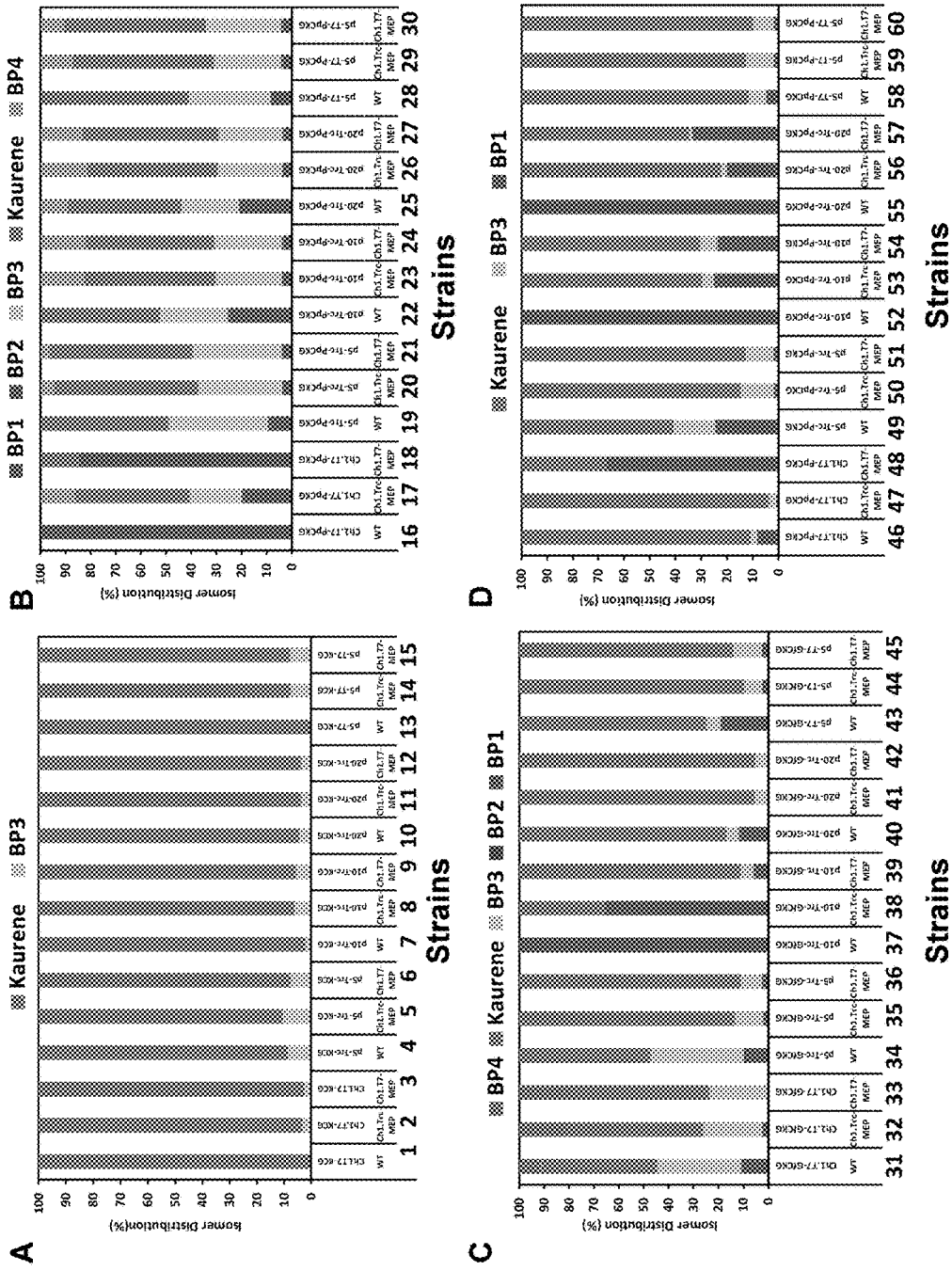
FIG. 6 shows the product profile from engineered strains. Shown are the production profiles from different downstream pathway expression levels under different upstream pathway modulation. The byproducts are the same as those shown in FIG. 5. Genotype details of each strain are in Table 2.
Figure 7:
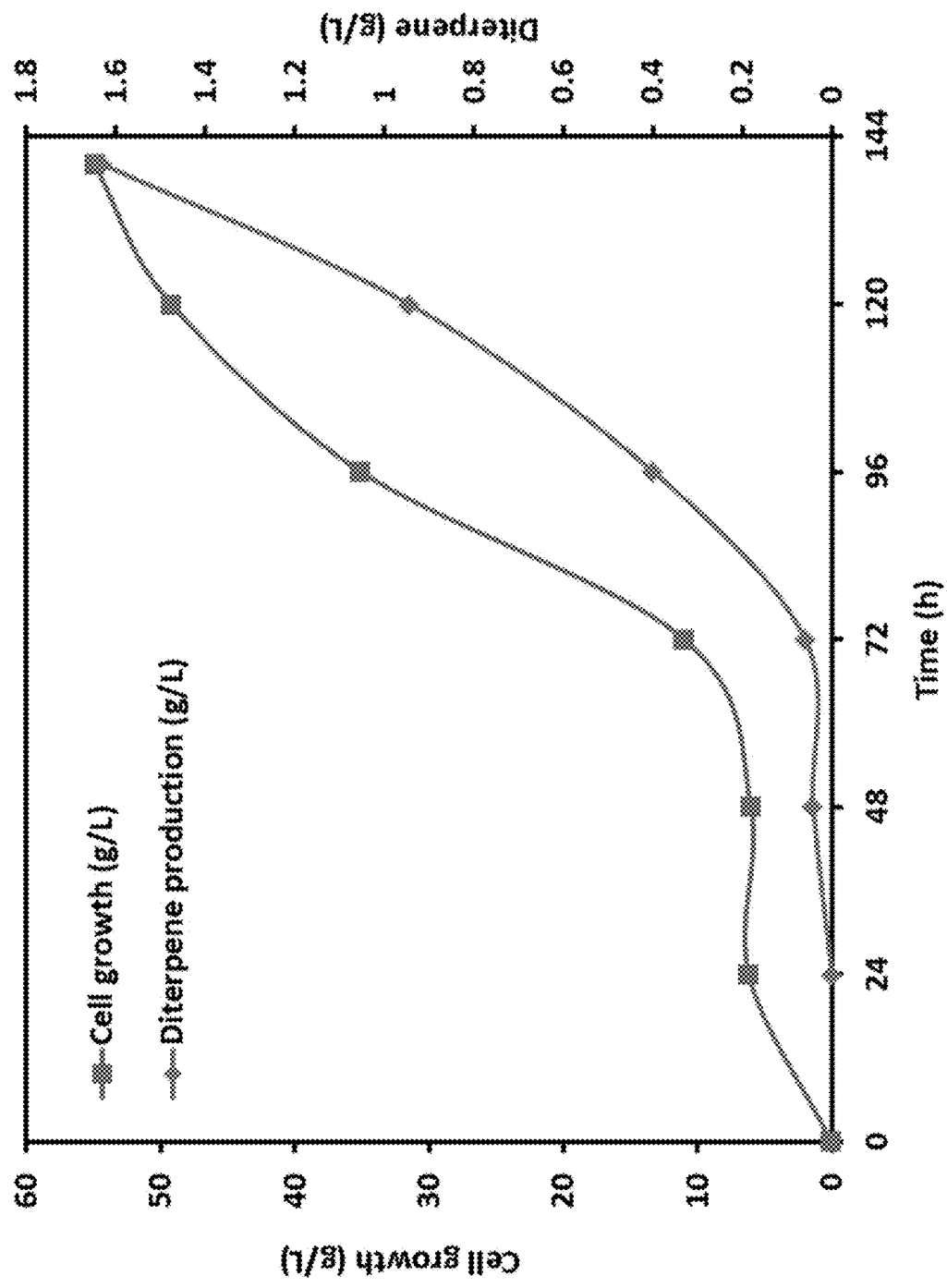
FIG. 7 shows that a strain (Strain 47 in table 2, Ch1TrcMEP-Ch1T7PsCKG) with properly balanced modules enabling kaurene biosynthesis, is capable of multi-gram-per-liter scale productivity of kaurene in a 2 L bioreactor.
Figure 8:
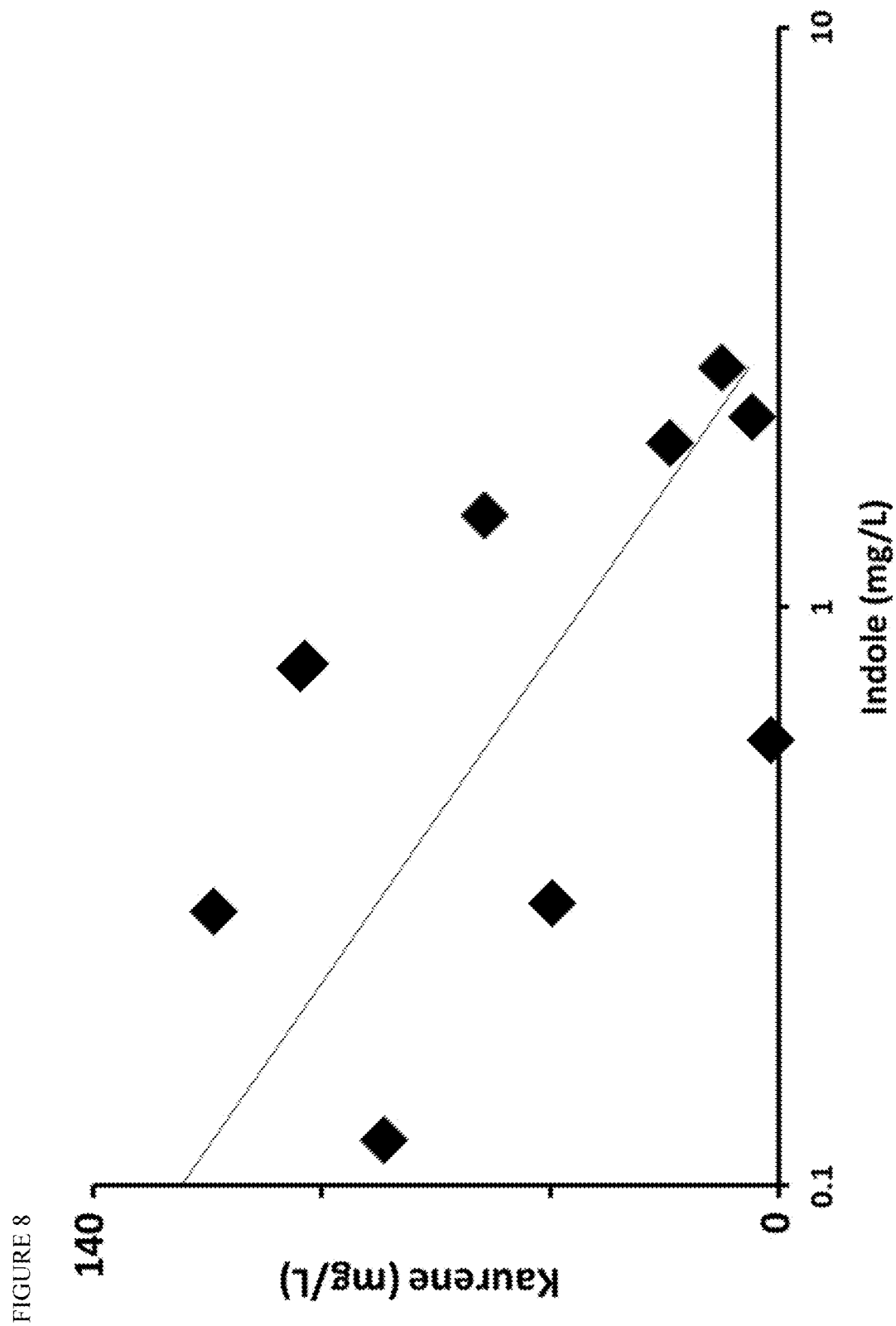
FIG. 8 shows that indole accumulation is inversely correlated to kaurene production across engineered strains.

Strains were selected with varying upstream and downstream expression to modulate the pathway and test the productivity of the various combinations. These strains were subjected to small scale (2 mL) Hungate tube fermentation to characterize the phenotypic characteristics and kaurene productivity. As shown in FIG. 4, a complex non-linear accumulation of kaurene was observed. Interestingly, KS from plant species (SrCPPS, SrKS and PpCK) showed similar profiles (FIG. 4A, B), whereas the pathways constructed with fungal enzymes (GfCK and PsCK) showed very similar patterns of product accumulation (FIG. 4C, D). Interestingly, the low-copy expression of pathways incorporating fungal enzymes showed relatively high productivity compared to the plant enzyme pathways. The global maximum in product titer (~140 mg/L) comes from a construct with exclusively plant enzymes (FIG. 4A, strain constructed with Stevia rebaudiana genes with upstream under Trc promoter and downstream in plasmid p20Trc). However, the completely chromosomally-integrated fungal pathway enzyme (PsCK) (FIG. 4D, strain with upstream Trc and downstream T7-PsCKG) produced ~100 mg/L of kaurene. Comparing the expression of the downstream components of these two strains, the Ch1T7PsCKG pathway is 23-fold less (1.5 a.u.) compared to the p20TrcSrKCG (35 a.u.) under the same upstream pathway Ch1TrcMEP strength (4). The key performance driver of a multistep/multi-module pathway is optimal balance in the flux. Here in the strain constructed with Ch1TrcMEP and Ch1T7PsCKG, with very low downstream expression we achieved kaurene production up to 100 mg/L. This demonstrated that the PsCK enzyme can support high flux under balanced pathway expression. In addition, this study also provided insights about the complex non-linear behavior on diterpene product profile under different pathway balance (FIGS. 5 and 6, Table 2). Such complex behavior on product selectivity of a pathway under varying flux modulations clearly demonstrates the power of multivariate-modular pathway optimization. Under optimal balance a strain can show high selectivity in product profile (FIG. 6D, strain 47). In addition, the multivariate-modular search allowed selection of the best variant kaurene enzyme (PsCK) to further engineer hyper-producing strains. When this optimal strain (i.e., Strain 47) was grown in a bioreactor system, we were able to—with minimal media or process improvements—generate a strain capable of 1.6 g/L production of kaurene (FIG. 7). MMME also provides insight towards further optimization of the pathway and helps identify the best variant of GGPPS enzyme (Table 1) using a similar approach. Furthermore, as observed in pathway engineering on taxadiene-producing strains, kaurene production also inversely correlated to the production of the inhibitory molecule indole (FIG. 8).

(B) Engineering Steviol Biosynthesis in *E. coli*

The biosynthesis of steviol involves two key oxidation reactions mediated by cytochrome P450 enzymes (FIG. 3). P450s are important oxidizing enzymes involved in the metabolic pathways of thousands of natural products (25). Until recently, the scientific community believed that when compared to native eukaryotic hosts (e.g. plants or yeast), bacterial hosts, such as *E. coli*, were not an ideal system for performing this important natural product chemistry. However, while optimizing taxol biochemistry in *E. coli*, an understanding was developed of the mechanistic structure-function relationships responsible for the biochemistry of P450 enzymes, specifically related to their use in *E. coli*. Optimal engineering of N-terminal membrane region and construction of optimal combinations of CYP450 and the co-factor P450 reductase (CPR) enzymes is key for functional expression. Several enzyme/pathway optimization techniques were developed for the functional expression CYP450 enzymes and in vivo oxidation of complex natural terpenoid natural products such as taxadiene, valencene, limonene or kaurene.

Steviol biosynthesis is mediated by two different CYP450 enzymes, kaurene oxidase (KO) and kaurenoic acid hydroxylase (KAH) with a CYP450 reductase (CPR). Several candidate genes/enzymes were identified and annotated as P450 enzymes for oxidation and hydroxylation reactions in steviol biosynthesis (Table 1). The functional expression of the enzymes KO and KAH for carboxylation and hydroxylation requires protein redesign and engineering. We started with redesigning and cloning the SrKO enzyme for improved functional expression in *E. coli*. After a thorough bioinformatics analysis, several N-terminal truncated and modified KO enzymes were constructed (FIG. 9A). Constructs were created that incorporate SrKO and co-factor cytrochrome P450 reductase enzyme (SrCPR) as a fusion protein ("linker" constructs) or as a polycistronic modules ("operon" constructs) (FIG. 9B) in the pET45d expression vector. The production and relative solubility of the protein in these constructs in *E. coli* was assessed using SDS-PAGE analysis (FIG. 9C).

These constructs were then transferred into our production vector p5Trc to test the in vivo functional activity of the pathway. These constructs were transformed into kaurene producing strains 3, 9 and 11 (Table 2) to test the conversion of kaurene to kaurenoic acid (Table 3). The designed chimeric enzymes were functionally active, but the incomplete reactivity of the enzymes resulted in the production of kaurenol and kaurenal. Among all various N-terminal truncated KO constructs, the 39AA truncation of KO was more functionally active compared to 4 and 20 amino acid truncated constructs. Additionally, the SrKO and SrCPR expressed as operons showed similar activity as fusion enzyme constructed from SrKO and SrCPR. Subsequent to this initial work, we further optimized the SrKO enzyme as part of a three-gene KAH-KO-CPR module, see below, and in this construct the optimal SrKO construct has 20 amino acid residues truncated from the N-terminus, resulting in complete conversion of kaurene to kaurenoic acid (see below).

Figure 10:
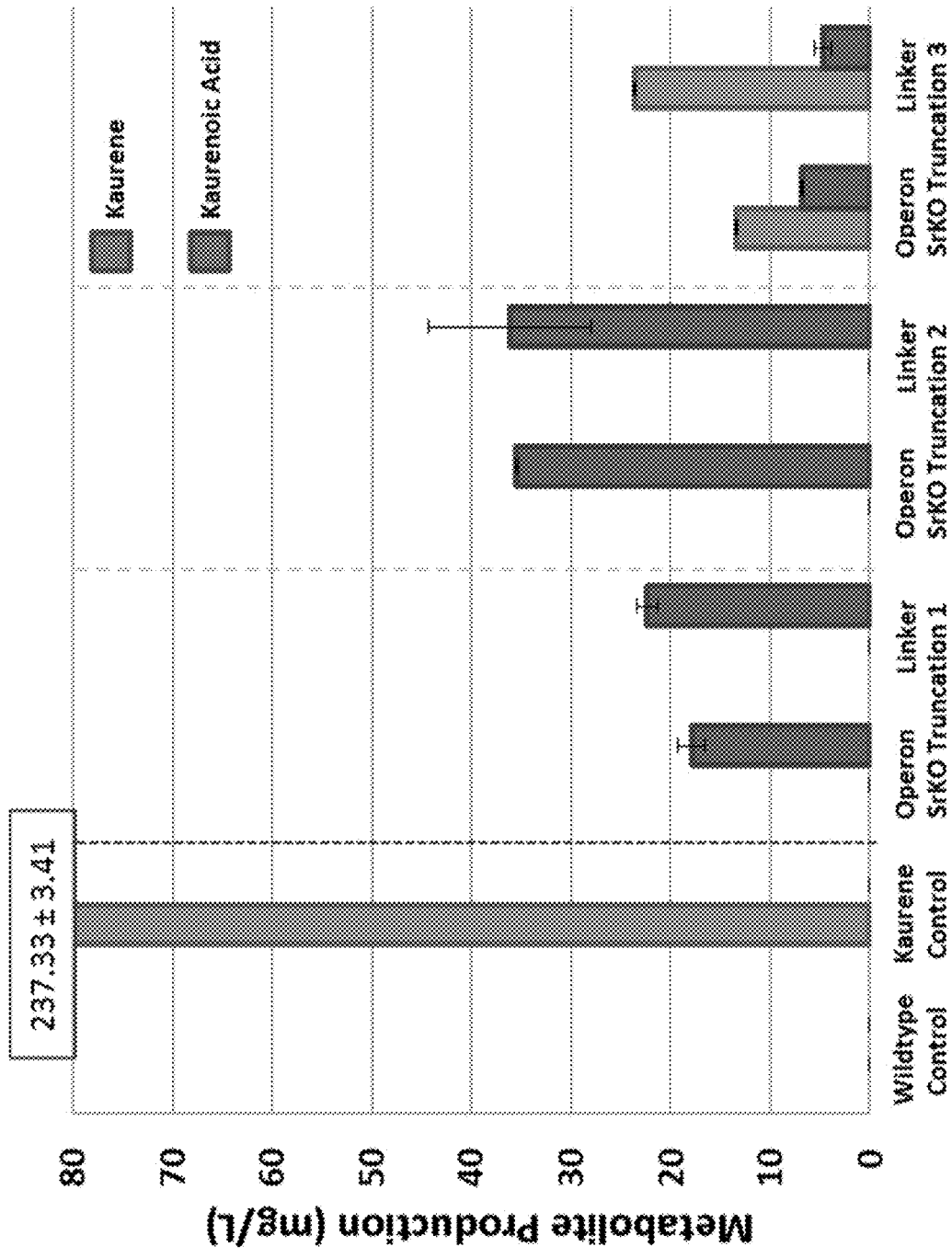
FIG. 10 shows the kaurenoic acid productivity of SrKO in linker or operon configuration with SrCPR in strain 47 background.
Figure 11:
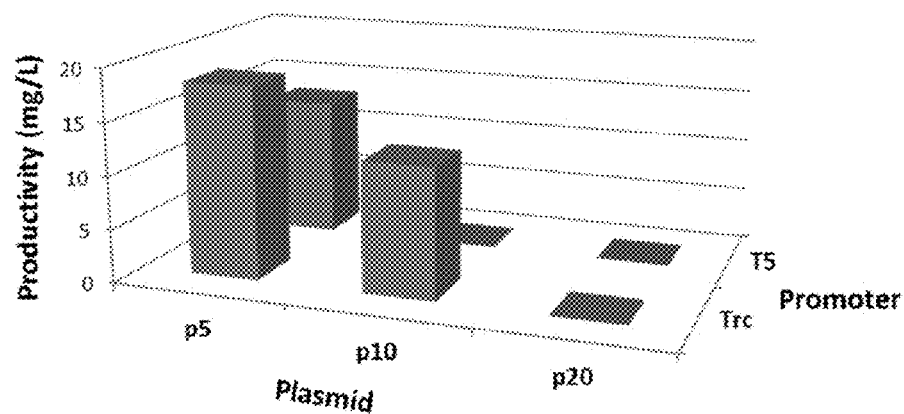
FIG. 11 illustrates the MMME landscape exploration of SrKO constructs under varying plasmid copy numbers and promoter strength. Imbalanced modules show less or no kaurenoic acid accumulation, with an associated increase in upstream kaurene accumulation instead.
Figure 11:
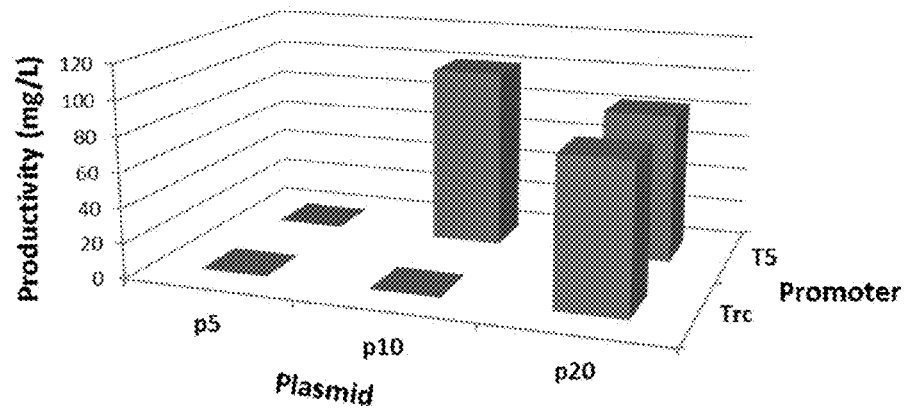

In the initial screening of the above SrKO strains, it was found that the availability of substrate pool for subsequent conversion to kaurenoic acid is important. When a high substrate (kaurene) pool was available (strain 9) the oxidation pathway converted kaurene to ~60 mg/L of oxygenated kaurene compounds. Previous in vitro studies on the enzymatic activity of the *Arabidopsis thaliana* KO enzyme demonstrated that the enzyme produces the alcohol, diol, and aldehyde derivatives of kaurene (12). Similar product diversity is seen with taxol P450 enzymes, however, in that work rebalancing of the entire pathway changed the product profile and produced the hydroxylated taxanes exclusively. Therefore, strain engineering studies were initiated to rebalance the KO P450 module and upstream modules. In order to rebalance the modules, the KO pathway was transferred into the high kaurene-producing chromosomally-integrated strain (Strain 47) and tested for activity and productivity (FIG. 10). Orthologous KO enzymes from different organisms were also designed, synthesized and tested (Table 1) to identify the best variant enzymes. Multivariate pathway optimization was performed, as with the kaurene pathway, to identify the best variant enzyme and their non-linear product profiles and product distributions under varying flux balances (FIG. 11). SrKO activity was subsequently improved by designing and testing a collection of point mutants in the wild-type background (Table 4).

Upon successful production of kaurenoic acid, the final enzymatic step in the biosynthetic pathway was incorporated and tested, hydroxylation at the C13 carbon of kaurenoic acid by the enzyme KAH to yield steviol (FIGS. 1 and 2). Studies on the polycistronic expression of SrKO and SrCPR proved that this enzymes can be expressed as independent components and remain functionally active. It was determined whether both KO and KAH could be functionally active with a single SrCPR enzyme. In order to limit the number of plasmids and balance the expression of KO and KAH, a single copy SrCPR was chromosomally integrated into a kaurene engineered strain. The KO and KAH was constructed as polycistronic expression under p5Trc plasmid. Detectable levels of steviol were detected in GC-MS analysis of all strains (Table 5) after four days fermentation and extraction with ethyl acetate.

Figure 12:
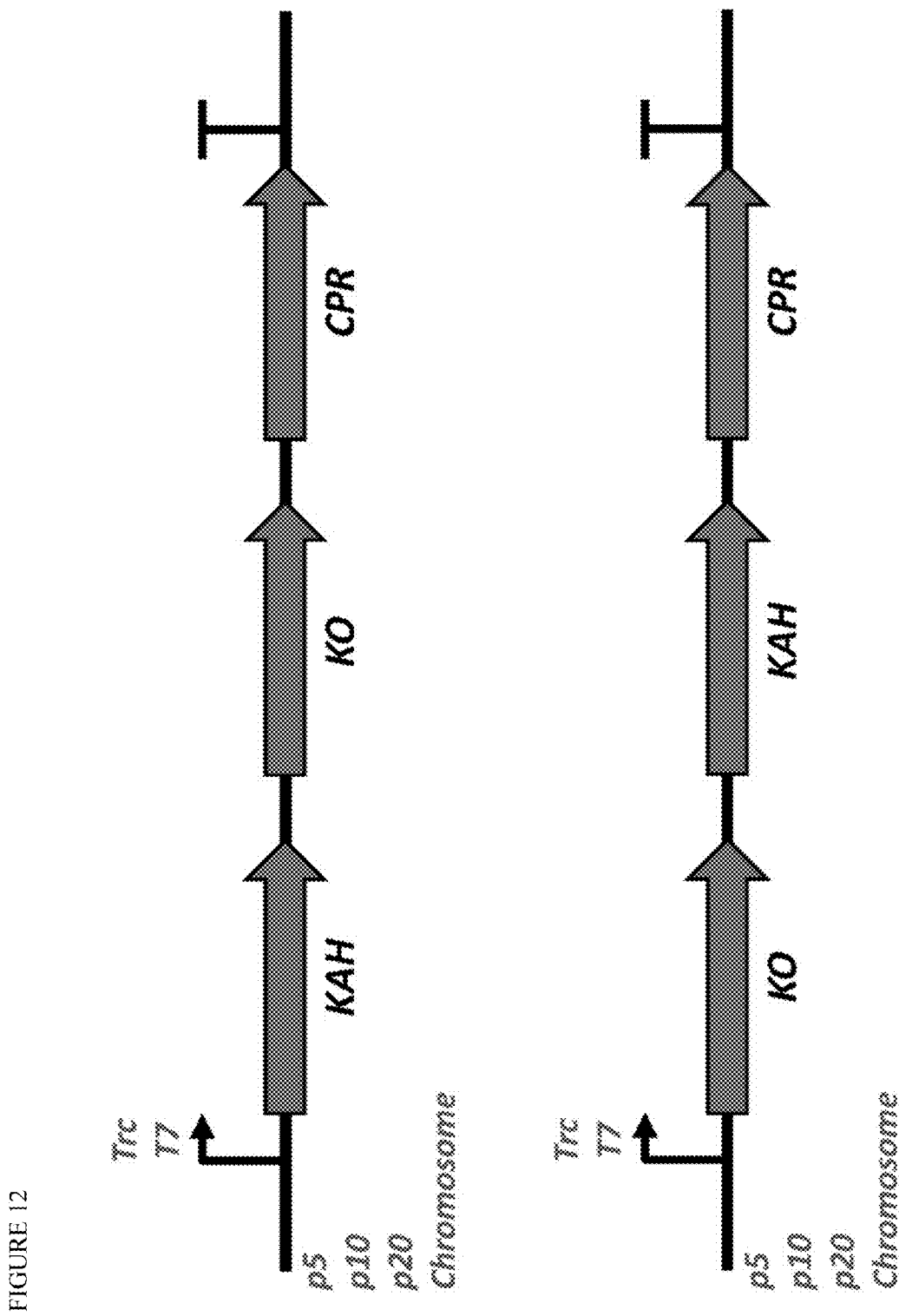
FIG. 12 shows design of a CYP450 expression module to screen for optimum enzyme variants, N-terminal truncations, and point mutations of KO, KAH, or CPR genes. The two P450s and the CPR enzyme are expressed in a polycistronic operon under various promoter strengths in either plasmid or chromosomally-integrated format.
Figure 13:
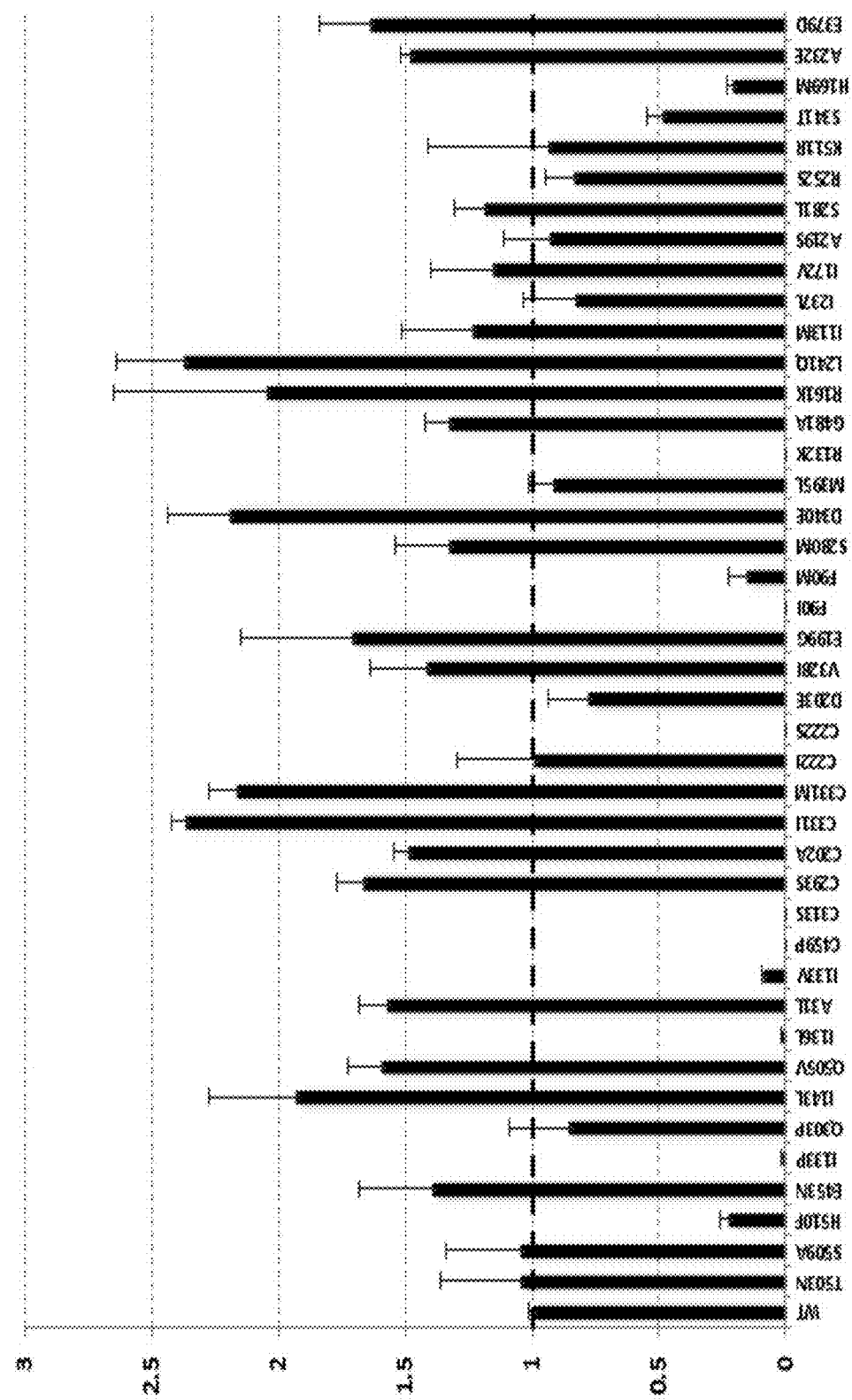
FIG. 13 shows point mutants of AtKAH enzyme, as represented by fold-change in kaurenoic acid hydroxylase activity relative to wild-type AtKAH.
Figure 13:
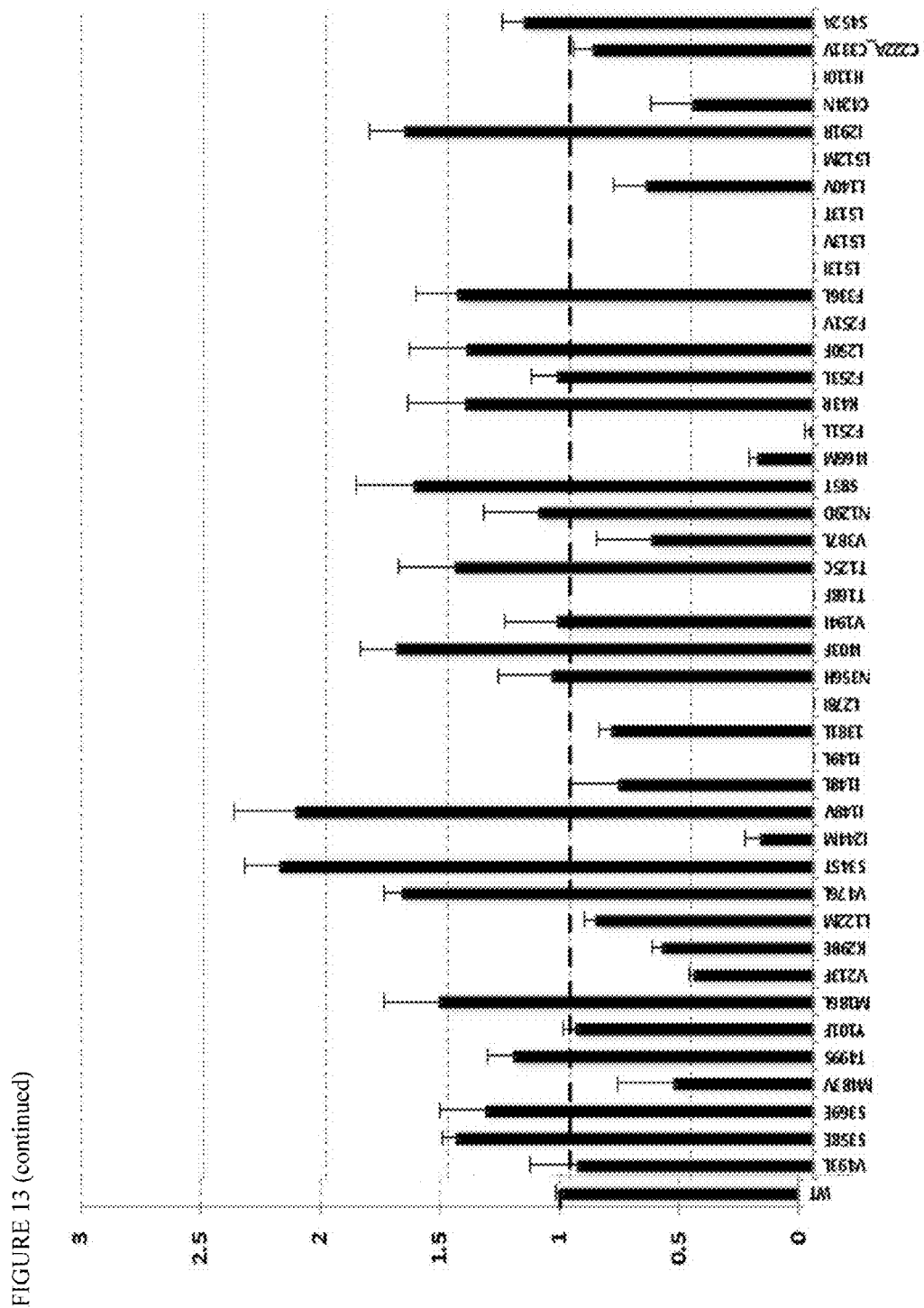
Figure 14:
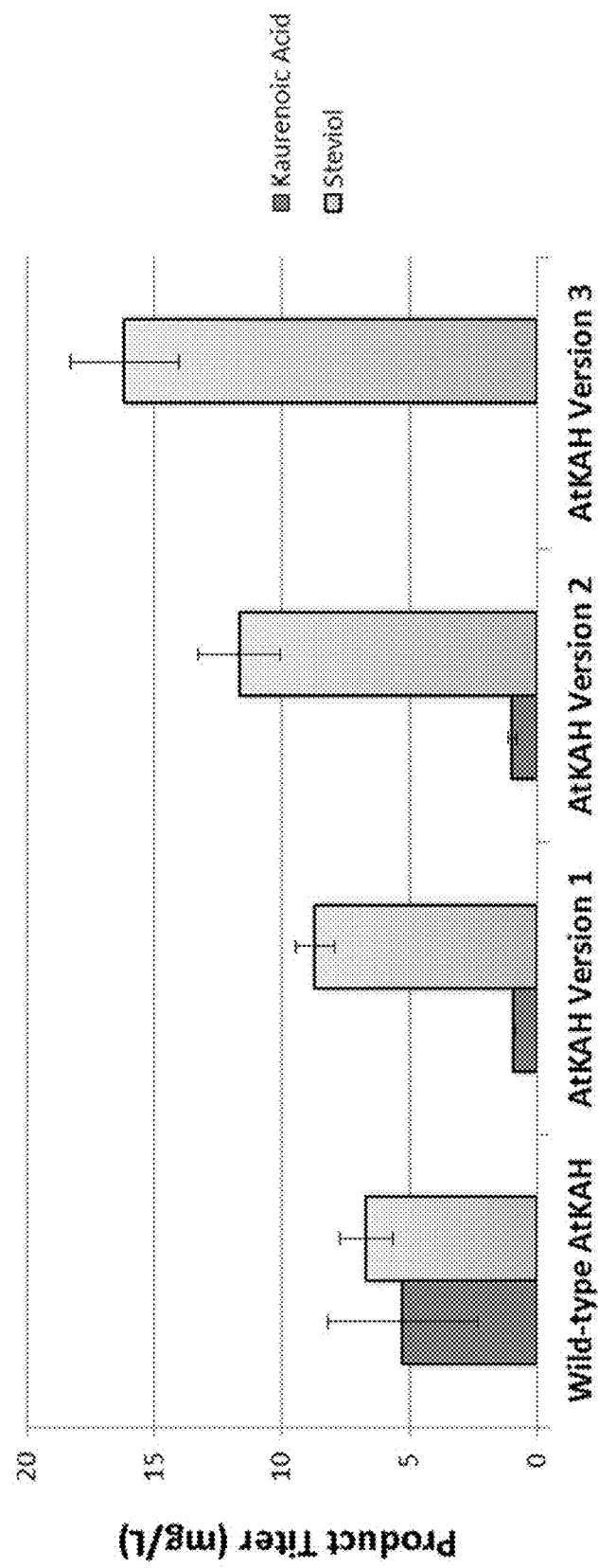
FIG. 14 shows a series of engineered AtKAH that demonstrate improved steviol productivity and eventual complete conversion of kaurenoic acid to steviol.
Figure 15:
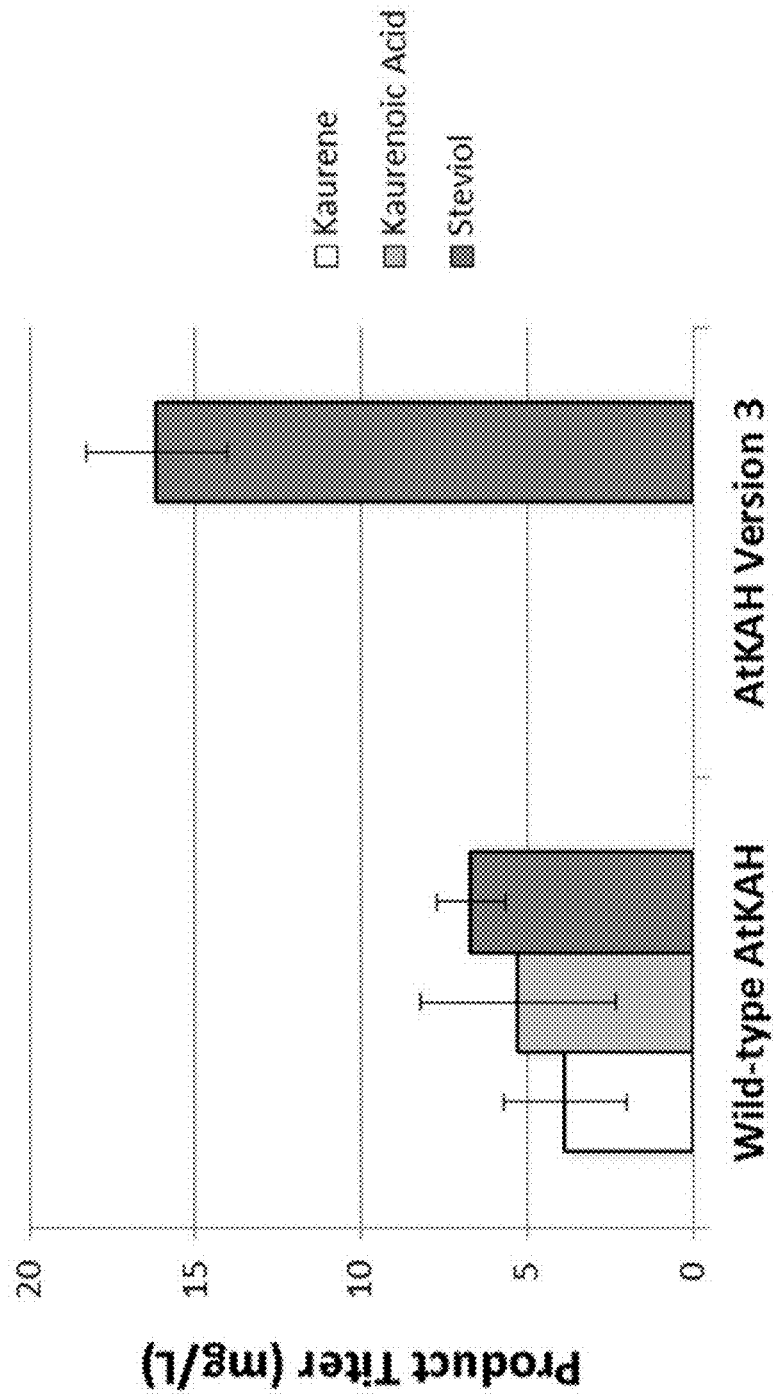
FIG. 15 shows that, in a properly balanced module, the two P450s (AtKAH and SrKO) and the co-factor CYP450 reductase (SrCPR) are capable of complete conversion of kaurene through kaurenoic acid through to steviol.

With this promising initial result in hand, the optimal enzymes for assembly into a biosynthetic pathway in *E. coli* were identified by in vivo expression of different engineered versions of both a KO and KAH candidate in a polycistronic operon with a CPR co-factor enzyme (FIG. 12). The AtKAH enzyme was further enhanced with a campaign of point mutations. A rational approach was used to design a collection of single point mutations in the AtKAH sequence, aimed at increasing stability, solubility, or activity of the wild-type enzyme for improved conversion of kaurenoic acid to steviol. The point mutations and corresponding fold-change improvements over wild-type AtKAH are summarized in Table 6, and are visualized in FIG. 13. Some of these point mutations were then recombined in the AtKAH enzyme, and a recombinant enzyme was identified that was capable of complete conversion of kaurenoic acid to steviol (FIG. 14). When expressed in an operon with optimal SrKO and SrCPR, complete conversion of kaurene to steviol was demonstrated (FIG. 15), further highlighting the importance of careful balancing of pathway components.

(C) Engineering Small Molecule Glycosylation in *E. coli*

Figure 16:
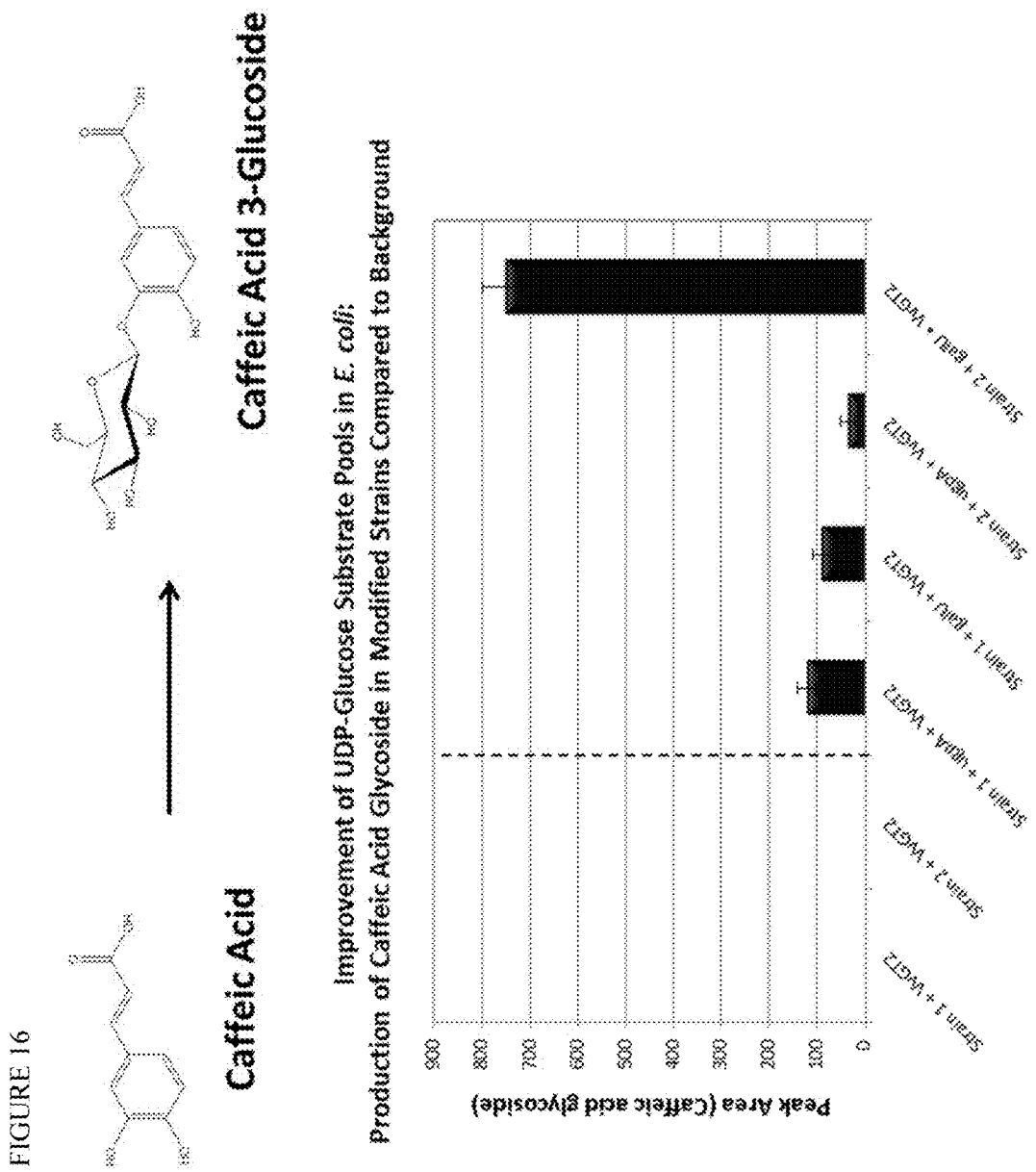
FIG. 16 demonstrates increased UDP-glucose production in *E. coli* using a model system: glycosylation of a small molecule caffeic acid with terpene producing *E. coli* strains engineered for increased UDP-glucose production, producing caffeic acid 3-glucoside using *Vitis vinifera* glycosyltransferase 2 (VvGT2) overexpressed from a pET plasmid. The improvement in glycosylated caffeic acid titers compared to the unmodified background strain shows an increase in the UDP-glucose substrate pool to support glycosylation. Strain 1 is Strain 47 (Table 2) with knock-outs of the galactose catabolic module (galETKM), UDP-sugar pyrophosphatase (ushA), phosphoglucomutase (pgm), glycose-1 phosphatase (agp), β-galactosidase (lacZ), and overexpressing sucrose phosphorylase (spl) under the Trc promoter (see Table 7). Strain 2 is Strain 47 (Table 2) with knock-outs of the galactose catabolic module (galETKM), UDP-sugar pyrophosphatase (ushA), phosphoglucomutase (pgm), glycose-1 phosphatase (agp), β-galactosidase (lacZ), and overexpressing and sucrose phosphorylase (spl) under the T7 promoter (see Table 7).

To support multiple glycosylation of steviol to rebaudioside M and all intermediate steviol glycosides, a series of modifications were introduced to the background *E. coli* strain intended to increase the amount of UDP-glucose available. A series of gene knock-outs and gene insertions were made aimed at increasing carbon flux to UDP-glucose and decreasing flux in pathways away from UDP-glucose not in keeping with small molecule glycosylation (i.e., glycogen synthesis and carbon storage). The design enables the import of sucrose into the cell and its splitting into fructose and glucose via the activity of sucrose phosphorylase. A subsequent series of knock-outs have altered primary metabolism so as to force biomass to be synthesized using only fructose as carbon source, leaving glucose to be funneled exclusively towards UDP-glucose biosynthesis when the cells are grown using sucrose as a carbon source. However, the cells are still capable of growth and improved UDP-glucose availability when grown on either glycerol or glucose as the carbon source. The specific modifications applied to the E. coli strain to enact this strategy are listed in Table 7. These modifications were tested to determine whether they enabled enhanced glycosylation of small molecules, and demonstrated that they indeed do by showing enhanced in vivo glycosylation of caffeic acid (supplemented in the media) by the engineered strains (FIG. 16).

Figure 17:
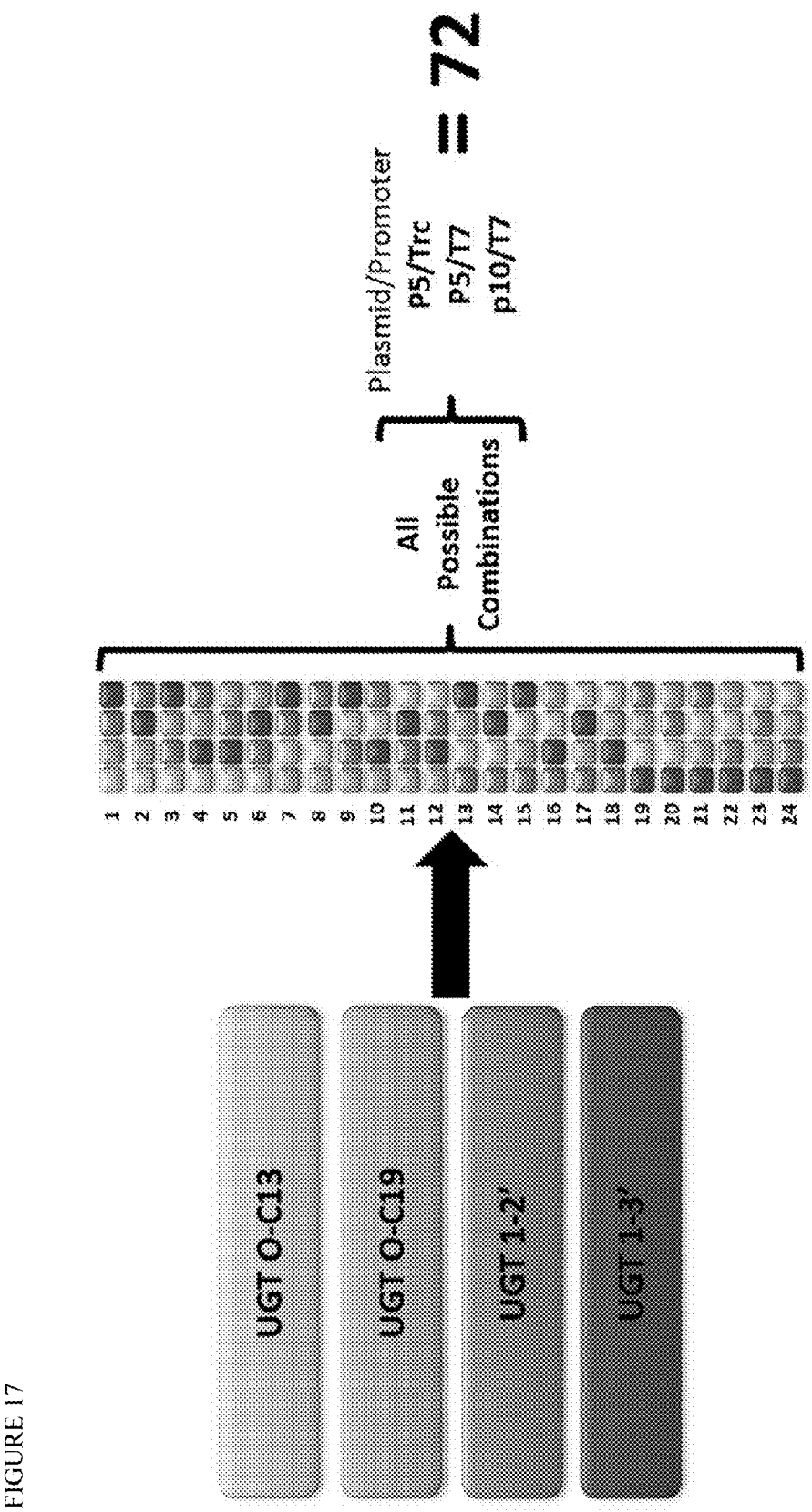
FIG. 17 shows the process for identification of an optimum glycosylation module incorporating all four UGT activities. All 24 possible combinations are rapidly assembled in three different plasmids, enabling expression at three different levels, for a total of 72 potential constructs.
Figure 18:
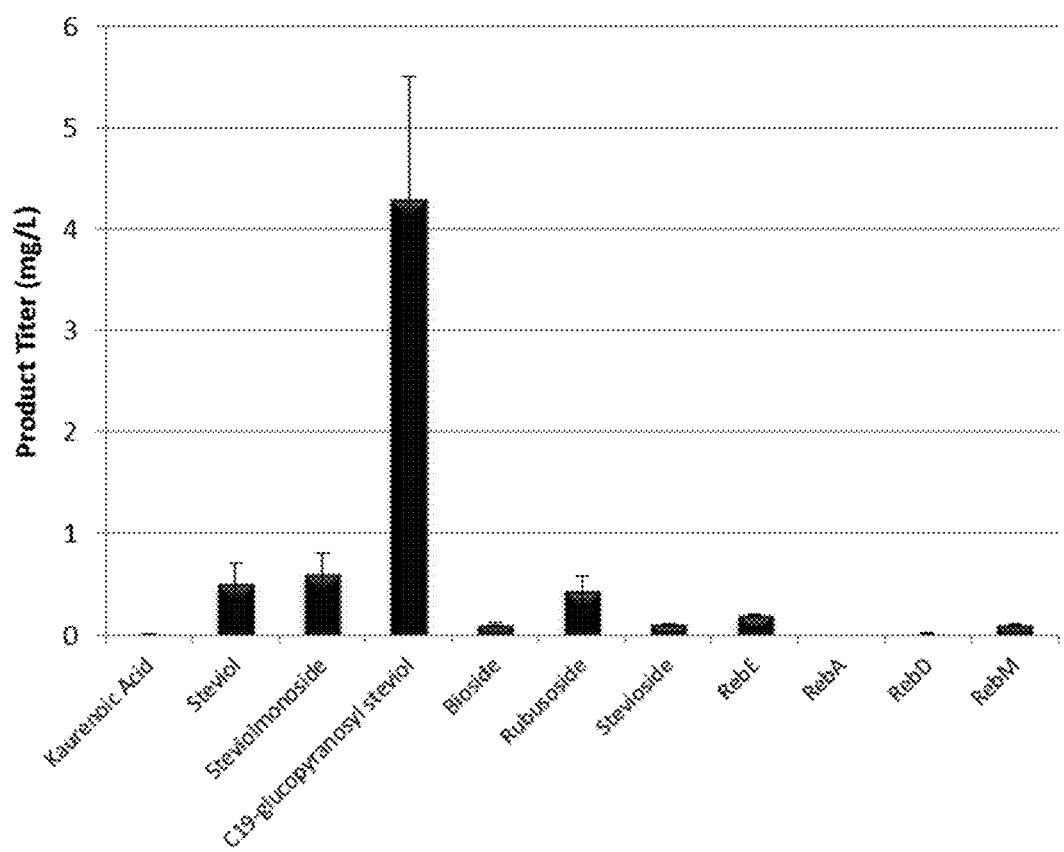
FIG. 18 shows in vivo production of RebM. (A) Product titers of steviol glycoside from *E. coli* culture. (B) LC/MS trace showing RebM identification. Negative control strain has been modified to produce steviol and increased UDP-glucose pools, while 4UGT strain is the negative control strain plus four UGTs.
Figure 18B:
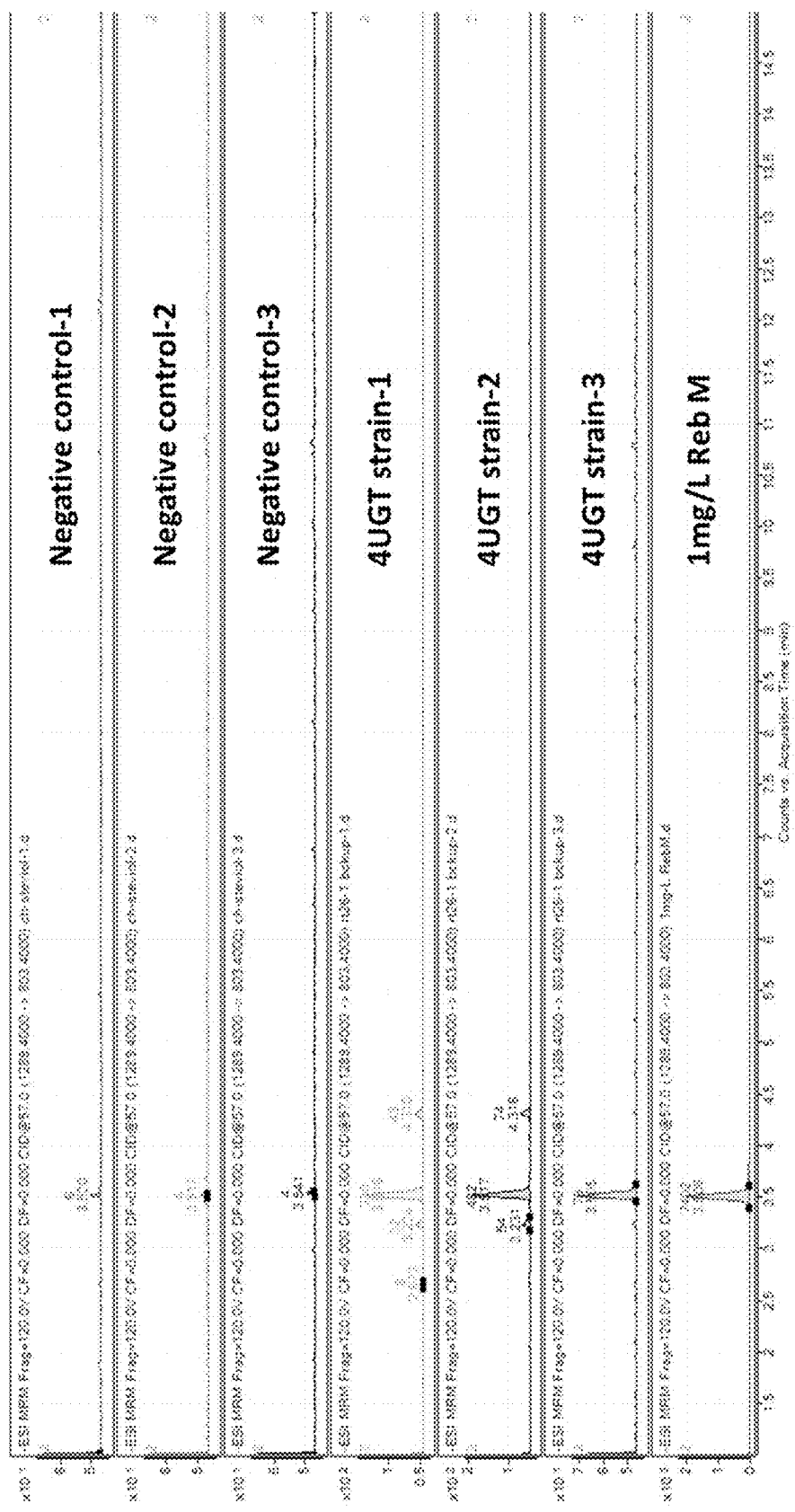

Having constructed the steviol core molecule, the core was glycosylated with UDP-glucose using an assembly of four UGTs, each capable of different glycosylation chemistries (Tables 8 and 9). These chemistries include (1) O-glycosylation at C13 of steviol, (2) O-glycosylation at C19 of steviol, (3) 1-2'-glycosylation at either the C13 or C19 O-glucose, and (4) 1-3'-glycosylation at either the C13 or C19 O-glucose (see FIG. 1 for an example incorporating all the above chemistries). Once one or both of the C13 and/or C19 oxygens are glycosylated, further glycosylations can be added to the O-glucose via 1-2' or 1-3' additions. As described below, these UGTs have been fundamentally modified by the shuffling of their domains, and further enhanced by point mutations aimed and enhancing flux through to the desired end product of RebM. The MMME approach was applied to rapidly combine the four UGTs in all possible combinations and screen the resulting constructs in vivo in a steviol-producing strain background (FIG. 17). The improved UGTs assembled in the optimum polycistronic configuration were combined with the four other modules in a single E. coli strain. We cultured the strain and demonstrated in vivo production of steviol glycosides leading to rebaudioside M (FIG. 18). The strain is capable of producing 5.7 mg/L of total steviol glycosides, which includes 100 μg/L of RebM. By generating all possible constructs and expressing them either in plasmids or integrated into the chromosome, under a variety of promoter strengths, steviol glycoside product profiles were obtained with RebD:RebM ratios ranging from 1:1 all the way to 0:1 (no RebD remaining).

To our knowledge, this is the first time two cytochrome P450 monooxygenases have been functionally expressed in E. coli for the production of a bifunctional oxygenated terpenoid molecule such as steviol. Additionally, a single CPR enzyme acted as co-factor for both P450 enzymes (KO and KAH) for converting kaurene to steviol. This is another significant leap in the engineering of P450 mediated oxidation chemistry in E. coli system. Moreover, to our knowledge, this is the first time four UGTs have been combined in a single E. coli strain and demonstrated to be capable of performing six sequential glycosylations of a terpenoid core molecule to produce rebaudioside M, let alone the intermediate steviol glycosides. This is a significant leap forward in the engineering of UGTs and the establishment of a platform for sustainable production of rare steviol glycosides.

Example 2: Construction of Circular Permutants of Glycosyltransferase Enzymes

Natural selection acting on an enzyme tends to select for sufficient stability and activity for the biological function. This process sends an enzyme down a specific evolutionary path that may make it not readily compatible with the stability and activity gains needed for industrial applications. As an example, enzymes specialized for a specific substrate tend to be more challenging to engineer for new substrates than enzymes that have not been specialized. Thus, 'shaking up' an enzyme by swapping domain connections might create an enzyme with the same protein fold, yet with novel folding and folded interactions that would make it newly-amenable to selection and evolution. In other words, we might be able to 'jump' a protein fold to another point in evolutionary space simply by shuffling the sequence, moving the enzyme away from its original evolutionary path without introducing any amino acid mutations.

UGTs (UDP-glucose glycosyltransferases) have two domains, a more variable N-terminal substrate binding (sugar acceptor) domain and a more conserved C-terminal UDP-glucose binding (sugar donor) domain. The N-terminal domain is mostly determinant of substrate specificity for the enzyme, but some specificity is controlled by the C-terminal domain. Each of these domains makes up roughly half of the protein. Given this two-domain structure, we hypothesized that cutting the protein in half to create new N- and C-termini and attaching the originals together (e.g., circular 'permutization') would 'shuffle' the enzyme and create new opportunities for engineering improved activity (since the resulting enzyme would not be the result of selective pressure).

Figure 19:
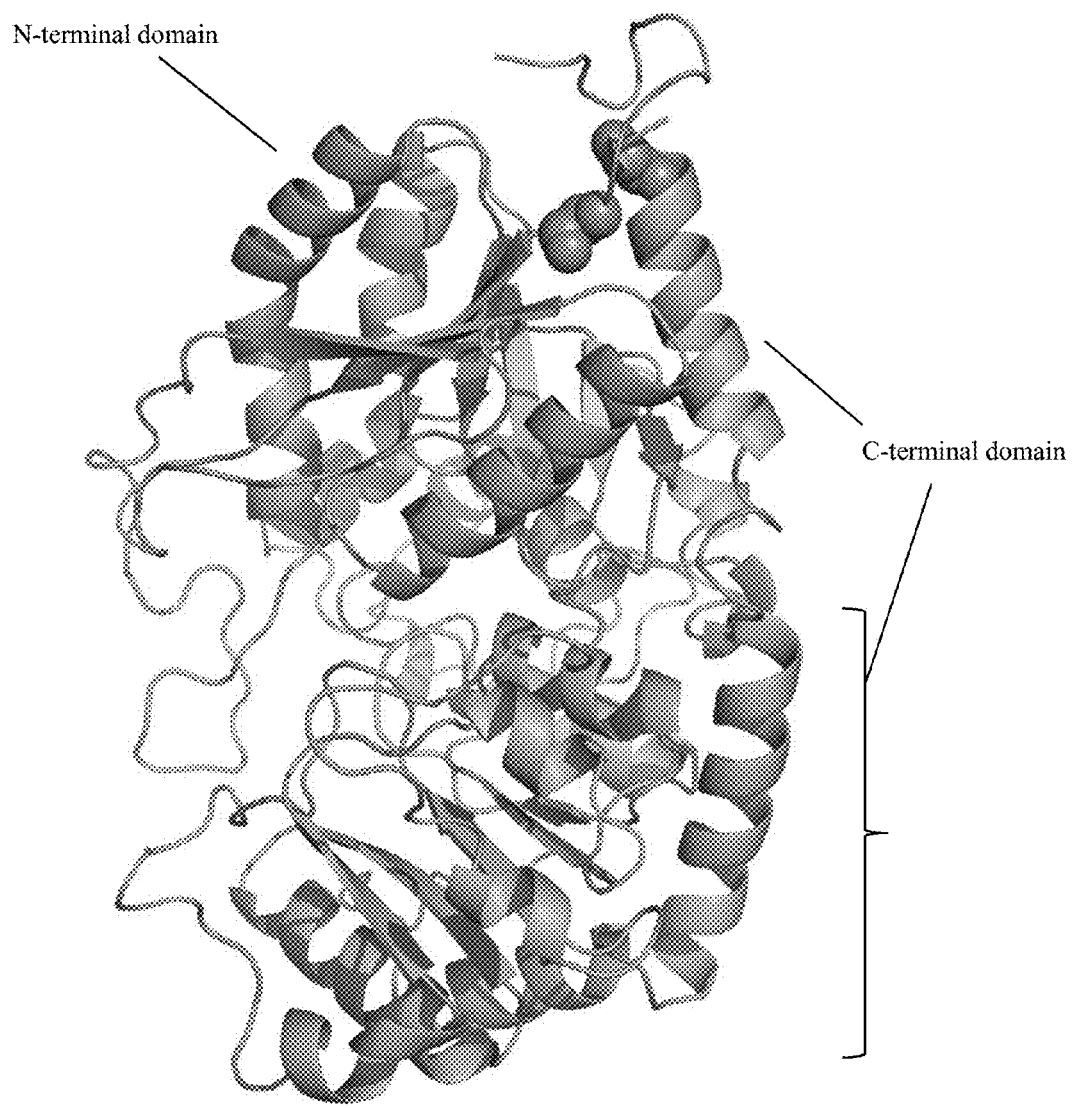
FIG. 19 shows a homology model of OsUGT1-2 (1-2' glycosylating enzyme from rice, *Oryza sativa*), as a starting point for circular permutant design.
Figure 21:
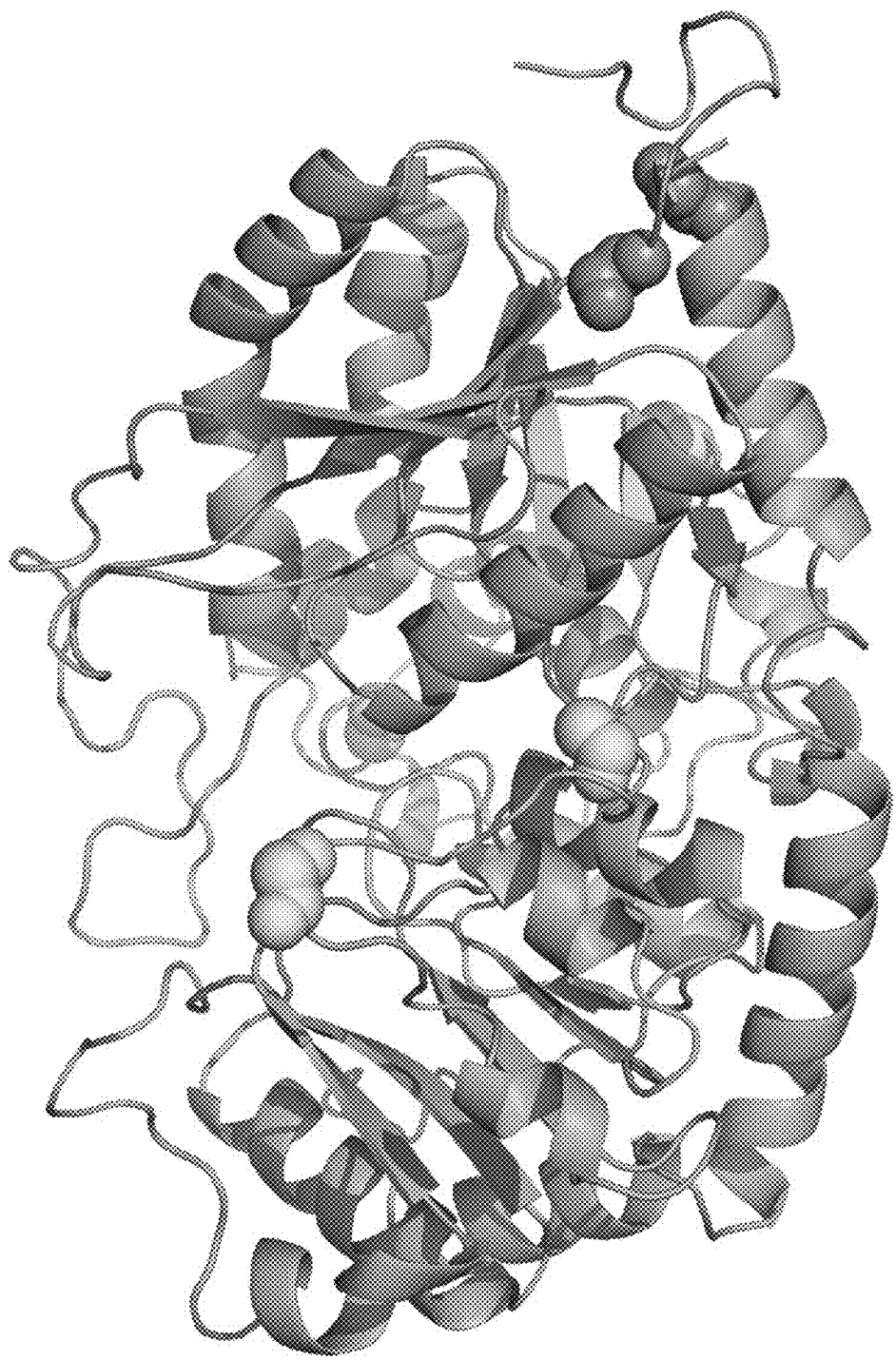
FIG. 21 illustrates criteria for selection of new N- and C-termini for the UGT circular permutant. Positions for new termini should be: (1) solvent exposed and away from the active site to minimize perturbation, (2) close to the middle of the sequence to maximize difference with the parental sequence, and (3) have amino acids often found at existing circular permutant division points (Lo, et al., 2012, PLoS One 7(2):e31791). New N-termini at G198, K240, G250, and G259 fit these criteria.

As a description of general procedure, designing a shuffled enzyme involves the following steps: (i) create a homology model to a known UGT with desired glycosylation activity (FIG. 19); (ii) using the homology model, estimate distance between N- and C-terminal residues; (iii) design linkers of various lengths to connect the existing N- and C-termini; (iv) select positions in the enzyme to become the new N- and C-termini; (v) synthesize the resulting sequences; (vi) express in vivo and in vitro and identify any shuffled enzymes that retain parent activity; (vii) modify designs via rational engineering, informed by a new homology model of the shuffled enzyme; and (viii) repeat step vii until desired activity improvement is achieved. When creating linkers (step iii), identify the N- and C-termini residues closest to ends, but predicted to be directly interacting with the rest of the protein based on the structure in the homology model (FIG. 20). When choosing cut sites for new N- and C-termini (step iv) (FIG. 21), choose a loop region between secondary structure elements, which maintains domain structure, is close to the middle of the sequence as possible, and which is solvent exposed and away from the active site.

Figure 22:
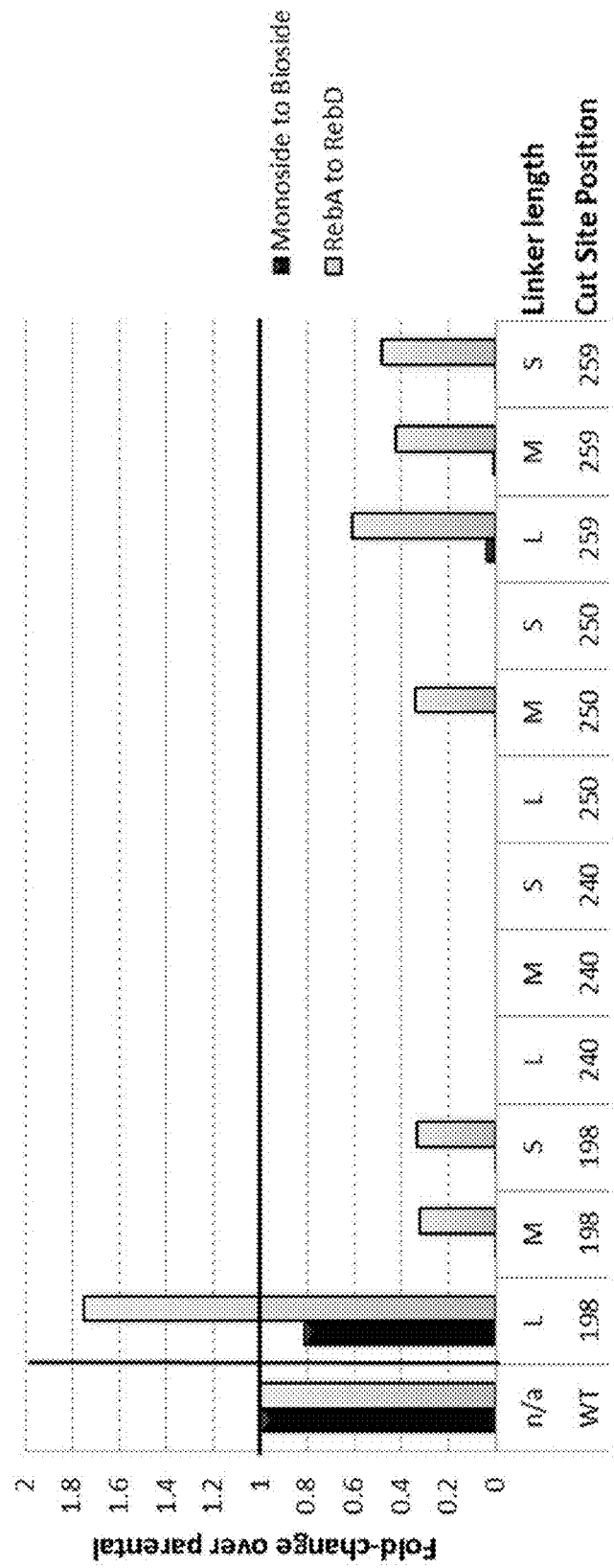
FIG. 22 shows 1-2' glycosylating activity for the first round of circular permutants of OsUGT1-2. The numbers indicate the location of the cut site in the parental sequence used to generate novel positions for N- and C-termini, while the L/M/S designation describes the long/medium/short linkers (which are described in FIG. 20).
Figure 23:
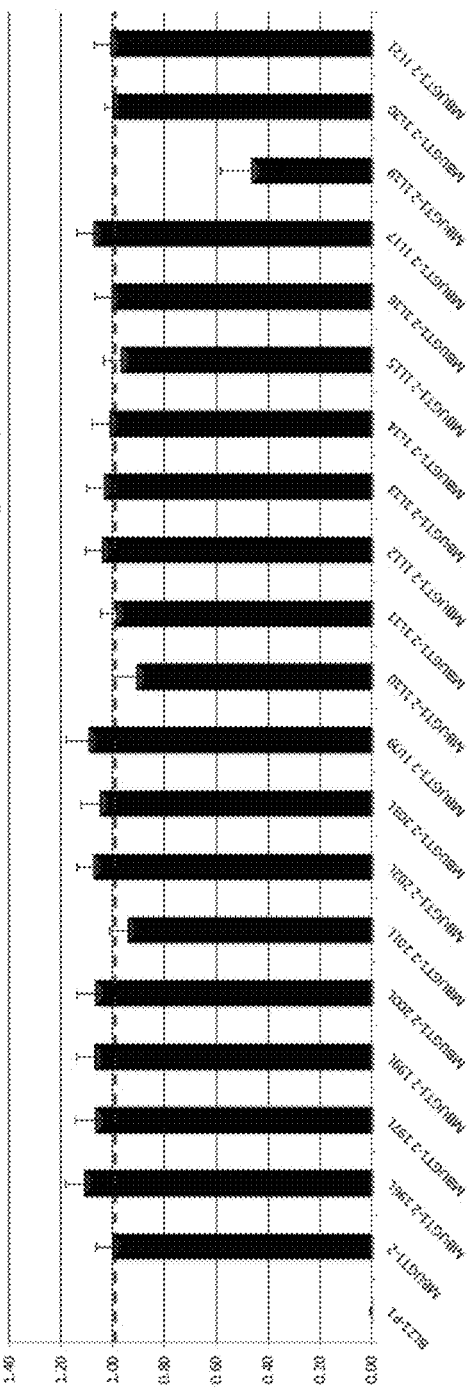
FIG. 23 shows refinement of the 1-2' UGT circular permutant (MbUGT1-2). Modifications to the cut site and linker length demonstrate significantly enhanced activity on at least one of the substrates possible for this enzyme. Number before L (eg. xxxL) indicates new cut site position, while number after L (eg. 1Lxx) indicates a new linker length in background with the 198 cut site [BL21=negative no UGT control].
Figure 23:
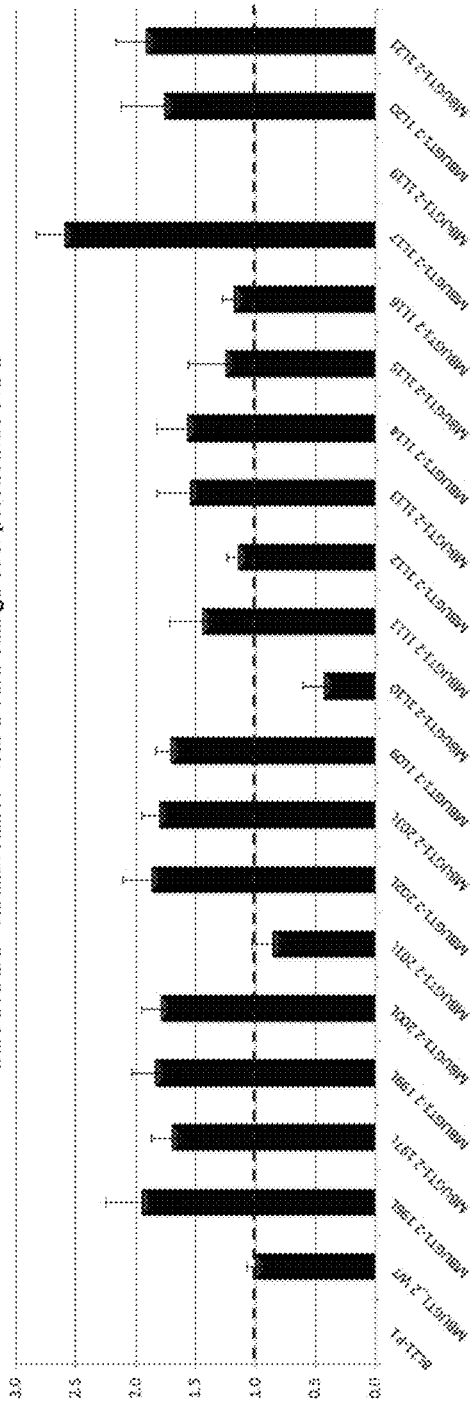

Circular permutants were designed, synthesized, and incorporated for each of the C13, C19, 1-2' and 1-3' glycosylating activities (parent enzymes are SrUGT85C2, SrUGT74G1, OsUGT1-2 (Q0DPB7_ORYSJ) (28), and SrUGT76G1, respectively). All four activities resulted in working circular permutants. As an example, data demonstrating the first round of circular permutant engineering resulting in the novel enzyme MbUGT1-2, showing equivalent activity with the parent enzyme OsUGT1-2 (FIG. 22). A subsequent round of refinement to the shuffled enzyme has generated enzymes with enhanced activities compared to the original parent sequence, demonstrating the potential for this shuffling approach to generate improved enzymes (FIG. 23). These refinements focus on finer-scale modifications to the position and specific residues forming the novel N and C-termini of the shuffled enzyme, as well as refining the length and amino acid sequence of the linker connecting the parental N and C-termini.

Figure 25:
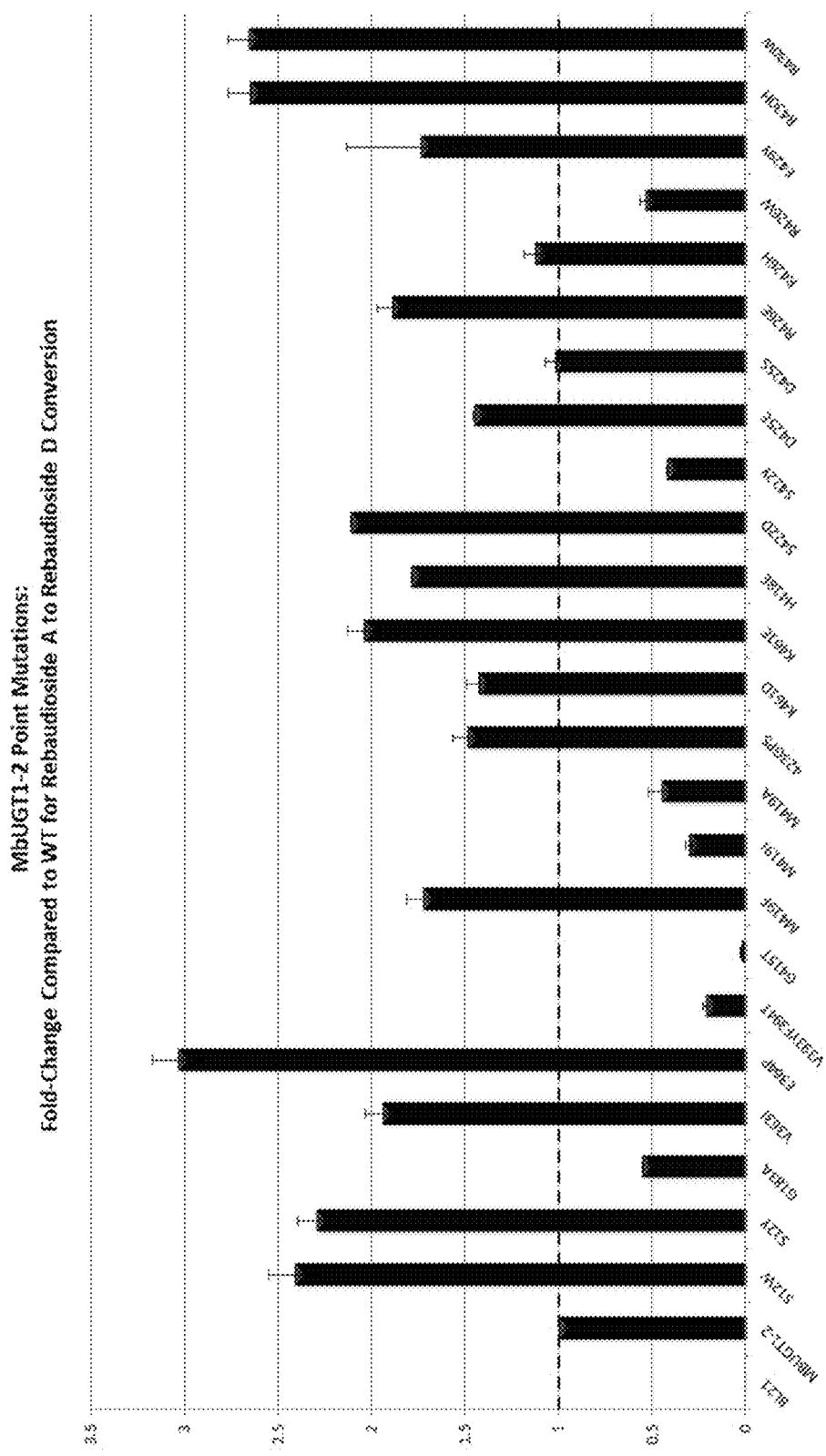
FIG. 25 shows point mutations in the MbUGT1-2 enzyme. Point mutations show increased activity on substrate rebaudioside A, demonstrating the potential for improving UGT enzymes generated by circular permutization. [BL21=negative no UGT control].
Figure 26:
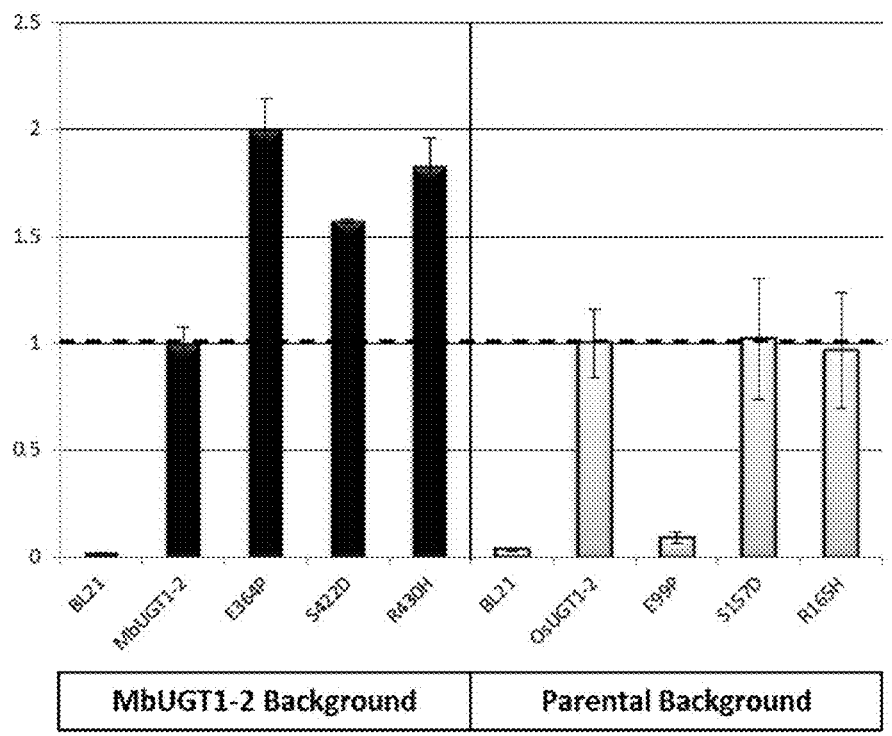
FIG. 26 shows that point mutations that are beneficial to the MbUGT1-2 enzyme do not, when translated to the appropriate amino acid residue in the parental UGT enzyme, result in neutral or even deleterious effects on activity. This demonstrates that circular permutants have the potential for unique improvements and evolution compared to the parent enzyme, brought about by shuffling of the sequence into a novel arrangement not previously selected for by natural selection. [BL21=negative no UGT control].

A series of point mutations to the MbUGT1-2 enzyme has resulted in further improvement to this novel sequence (FIGS. 24 and 25), confirming that the process has created opportunities for significant improvement by shuffling the enzyme sequence. However, when these point mutations conferring improved activity in MbUGT1-2 were tested in the parent OsUGT1-2 background, they were found to be either neutral or deleterious to activity (FIG. 26). The lack of transferability of point mutations between the novel enzyme and the parent sequence confirms that circular permutization is a valuable and general approach for creating opportunities for UGT enzyme improvement.

Example 3: Chimeric Fusions of Distinct Glycosyltransferases

Figure 27:
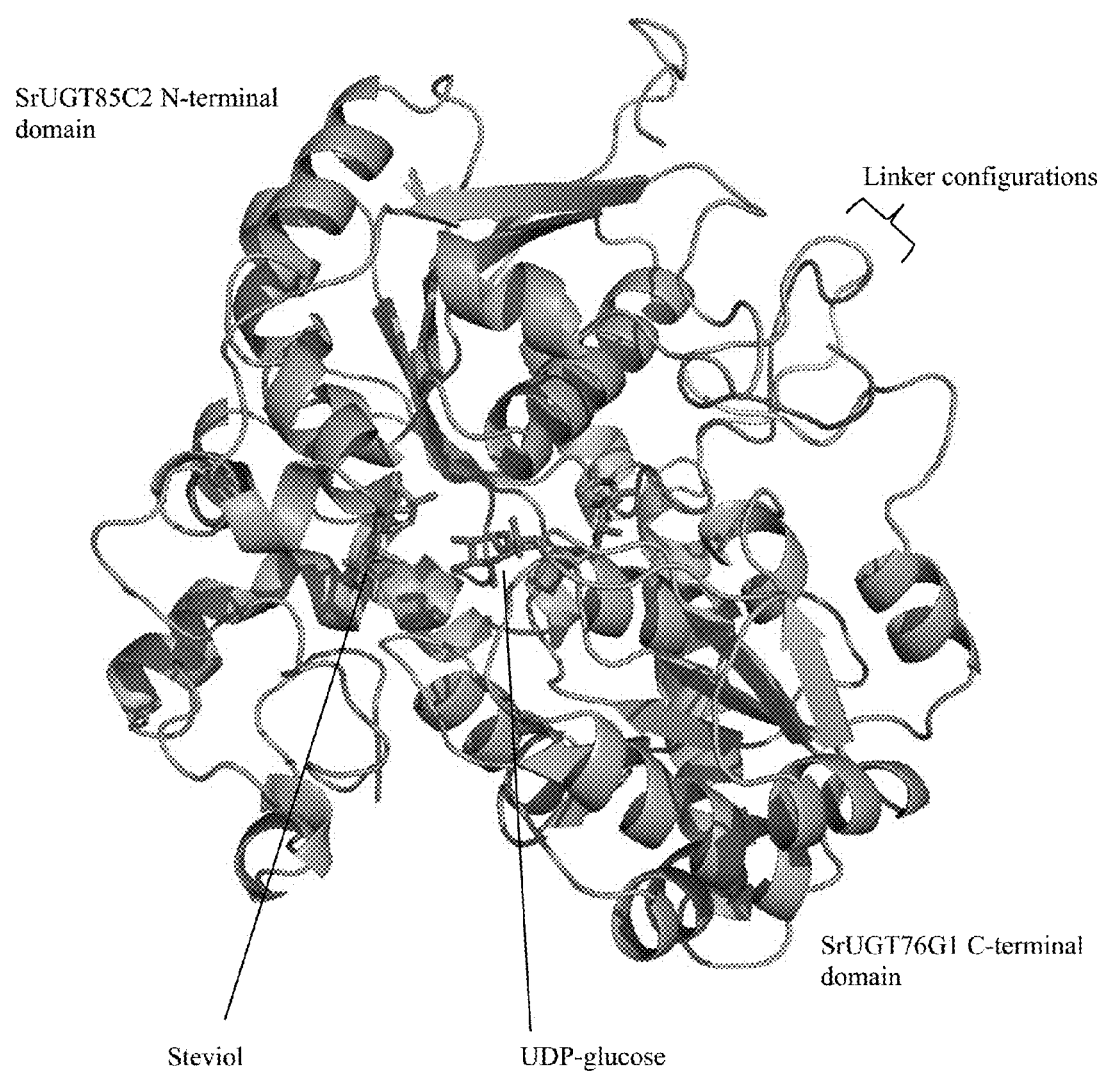
FIG. 27 shows a chimeric UGT with C13-O-glycosylating activity, created by fusing the N-terminus of SrUGT85C2 and the C-terminus of SrUGT76G1.
Figure 28:
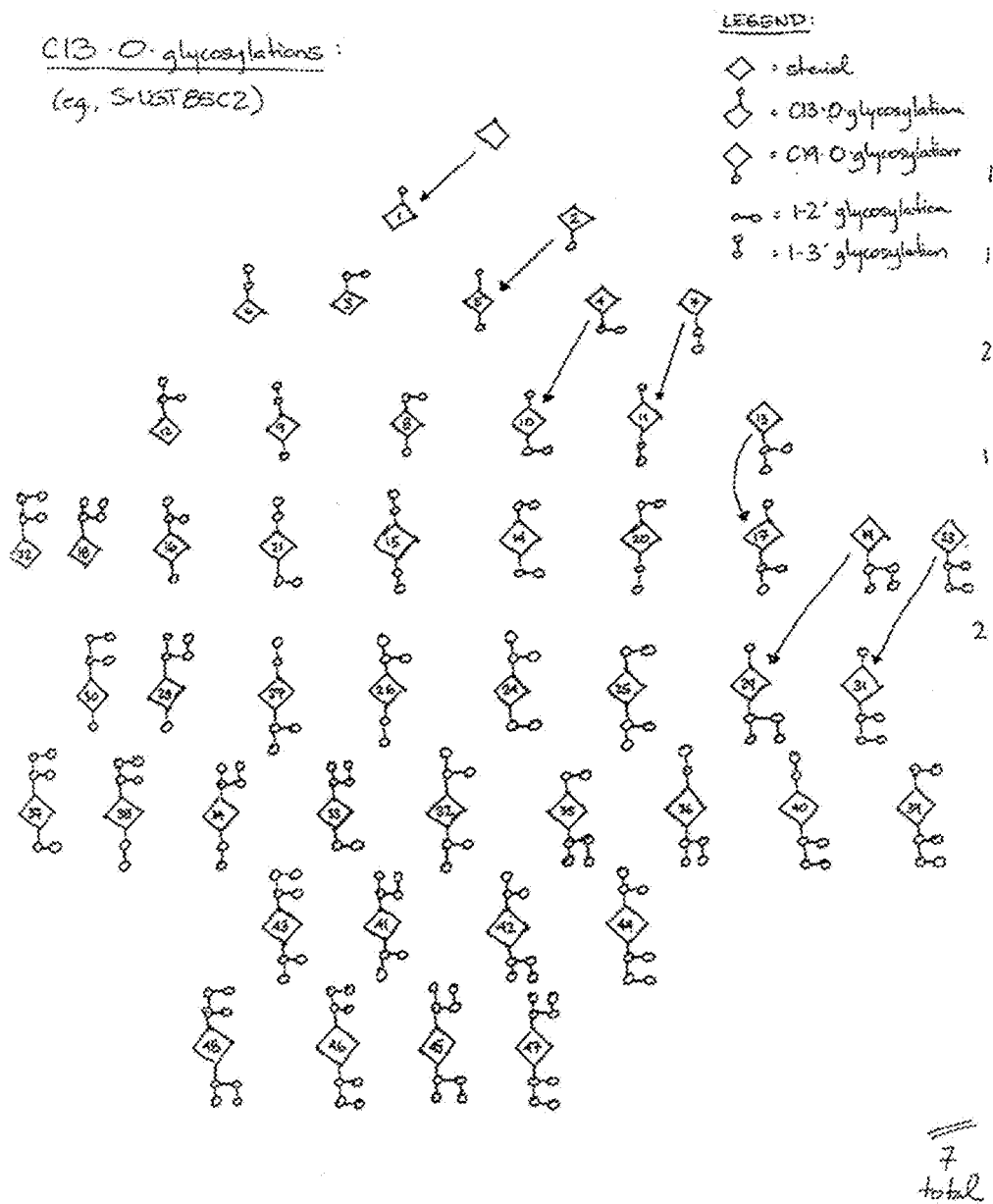
FIG. 28 is a summary of possible reactions (marked by arrows) catalyzed by SrUGT85C2 (i.e., C13-O-glycosylations).
Figure 29:
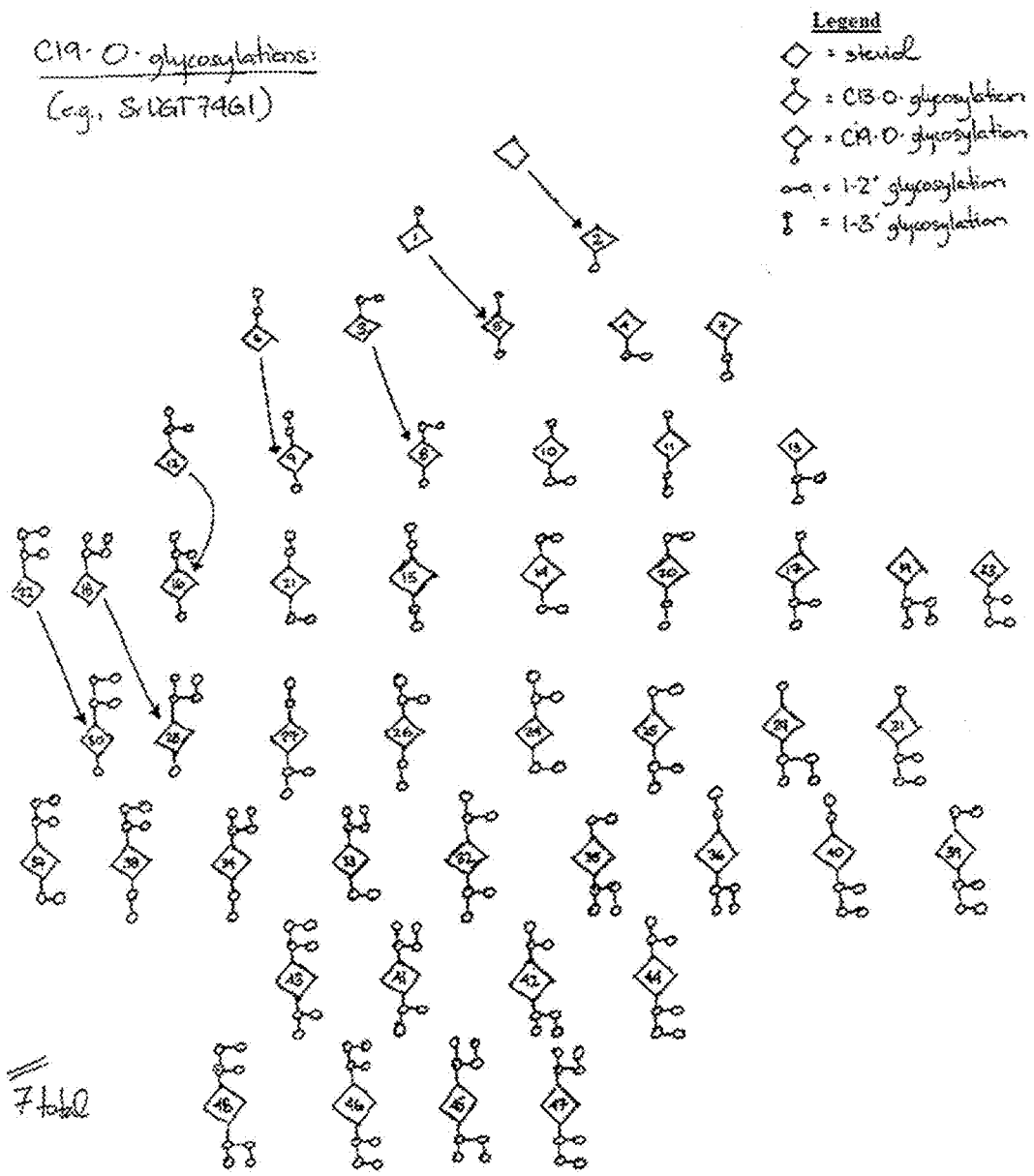
FIG. 29 is a summary of possible reactions (marked by arrows) catalyzed by SrUGT74G1 (i.e., C19-O-glycosylations).
Figure 30:
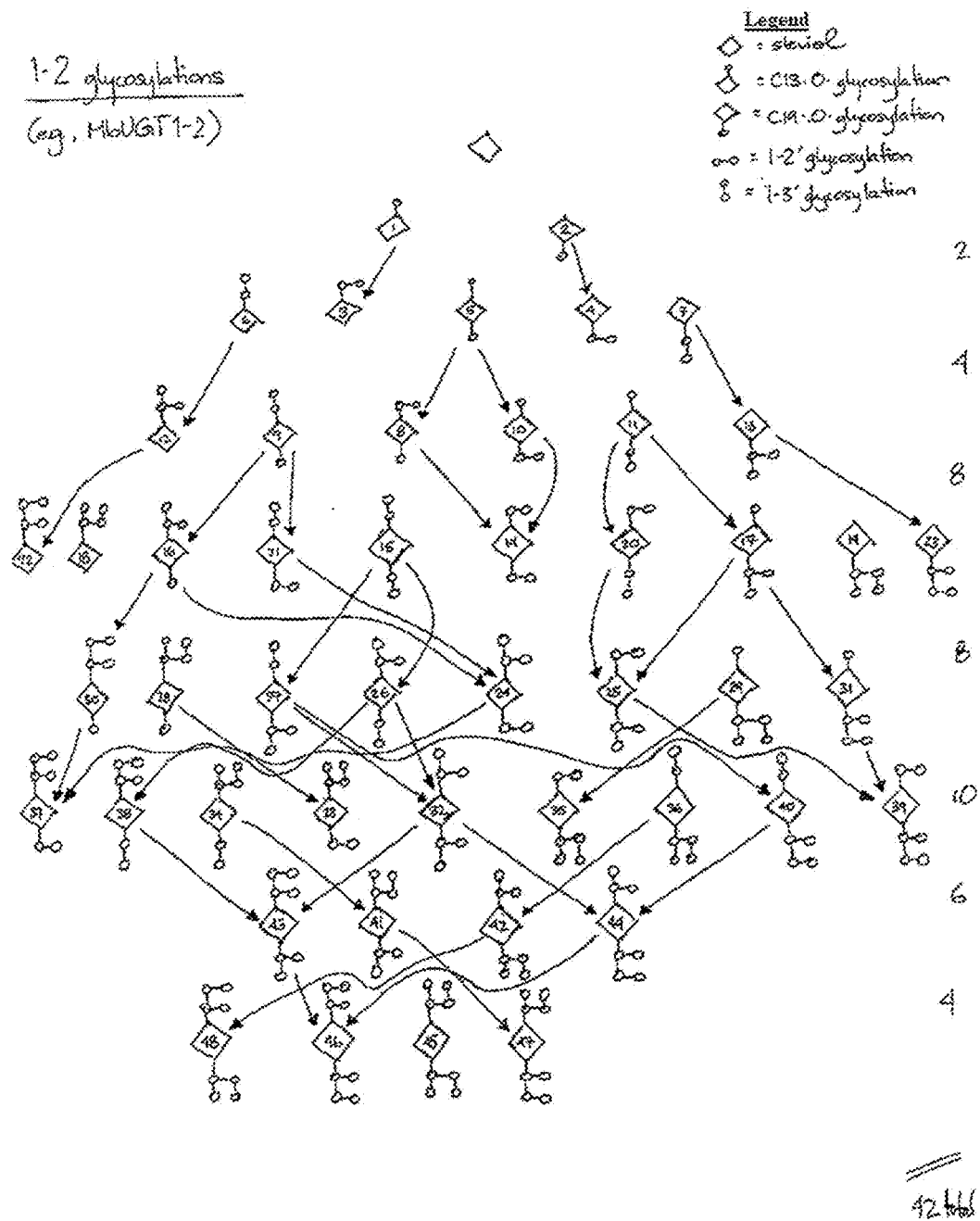
FIG. 30 is a summary of possible reactions (marked by arrows) catalyzed by MbUGT1-2 (i.e., 1-2-glycosylations).
Figure 31:
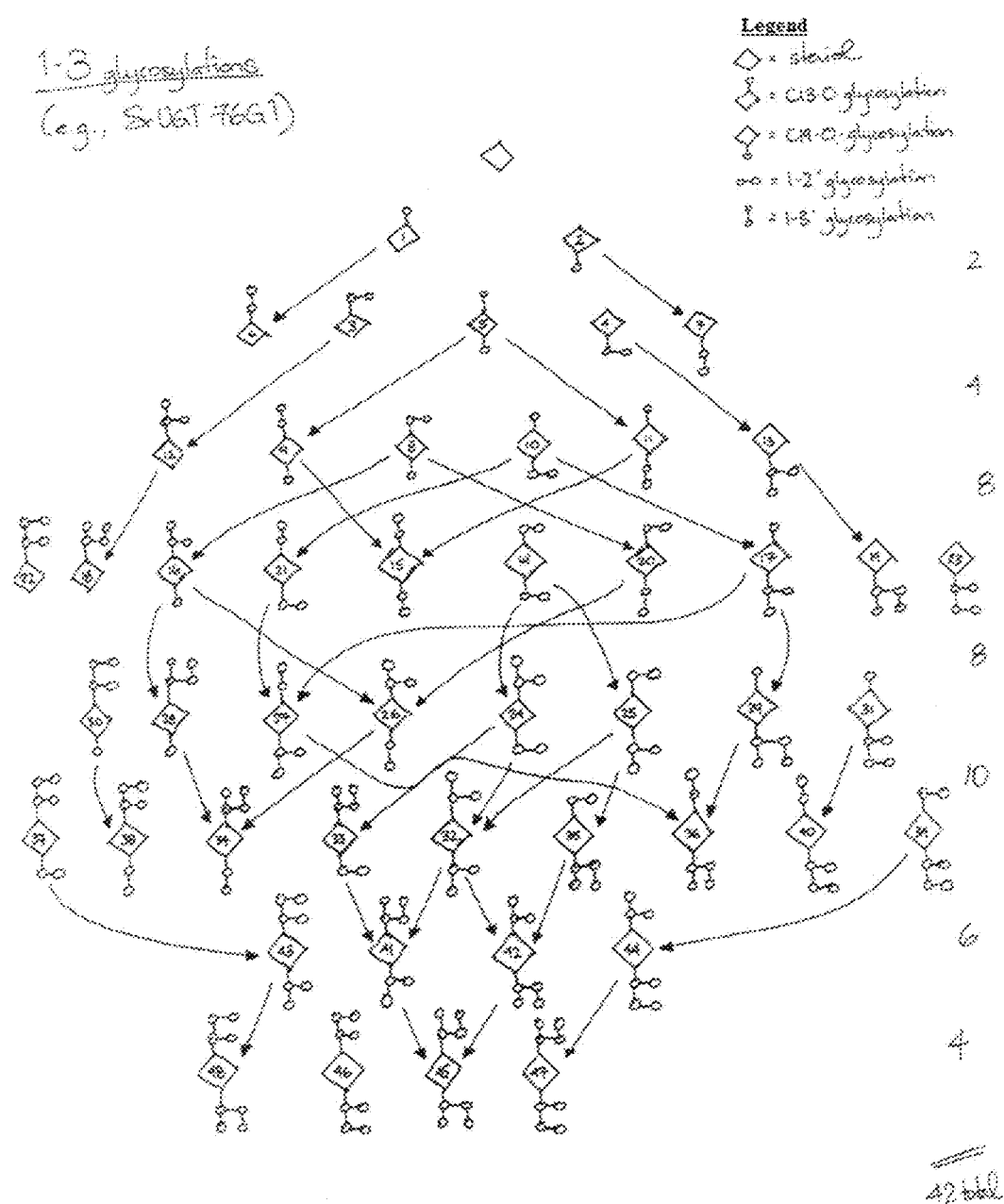
FIG. 31 is a summary of possible reactions (marked by arrows) catalyzed by SrUGT76G1 (i.e., 1-3-glycosylations).
Figure 32:
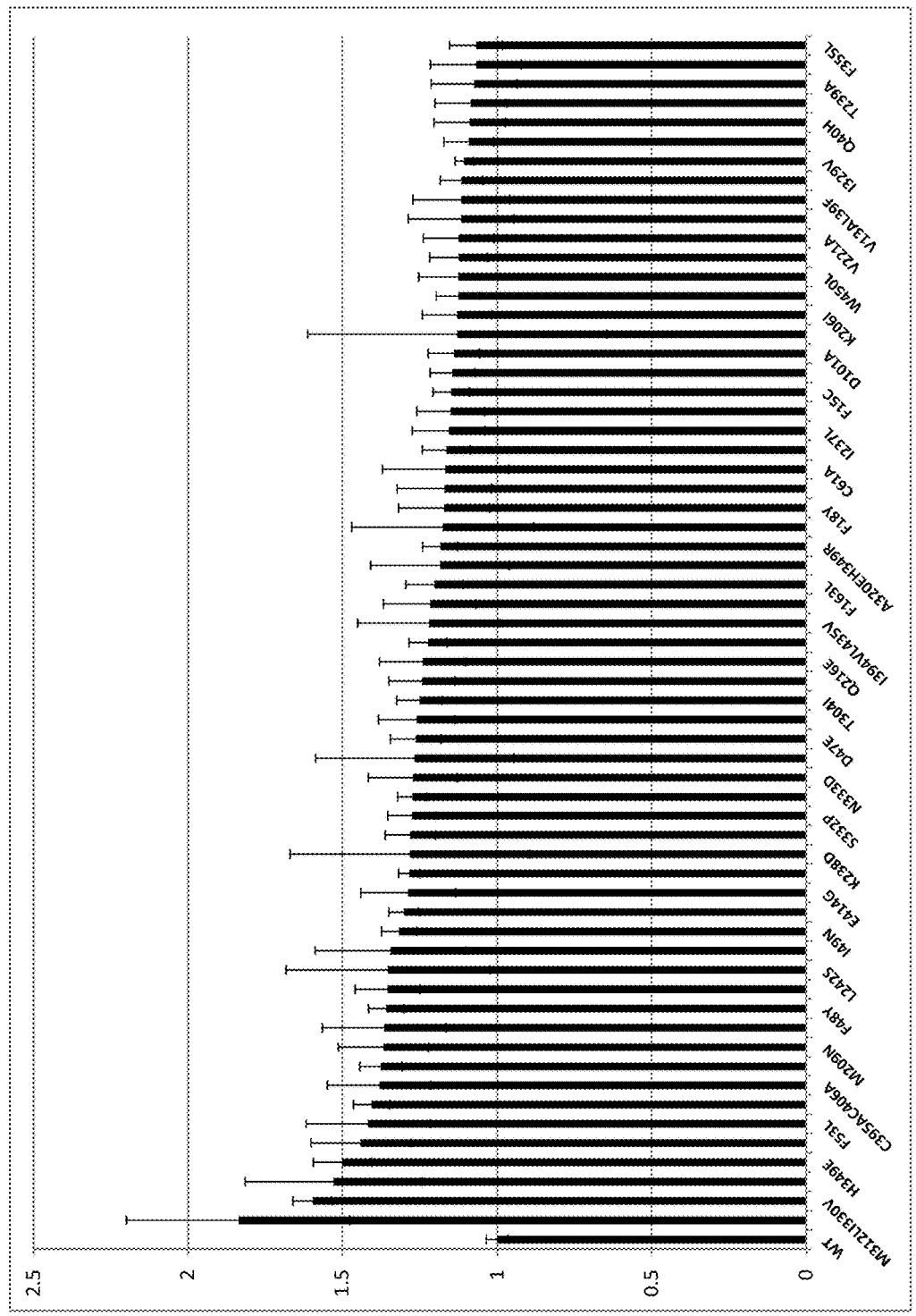
FIG. 32 shows point mutations in SrUGT85C2 enzyme versus altered activity on steviol substrate. [BL21=negative no UGT control].
Figure 32:
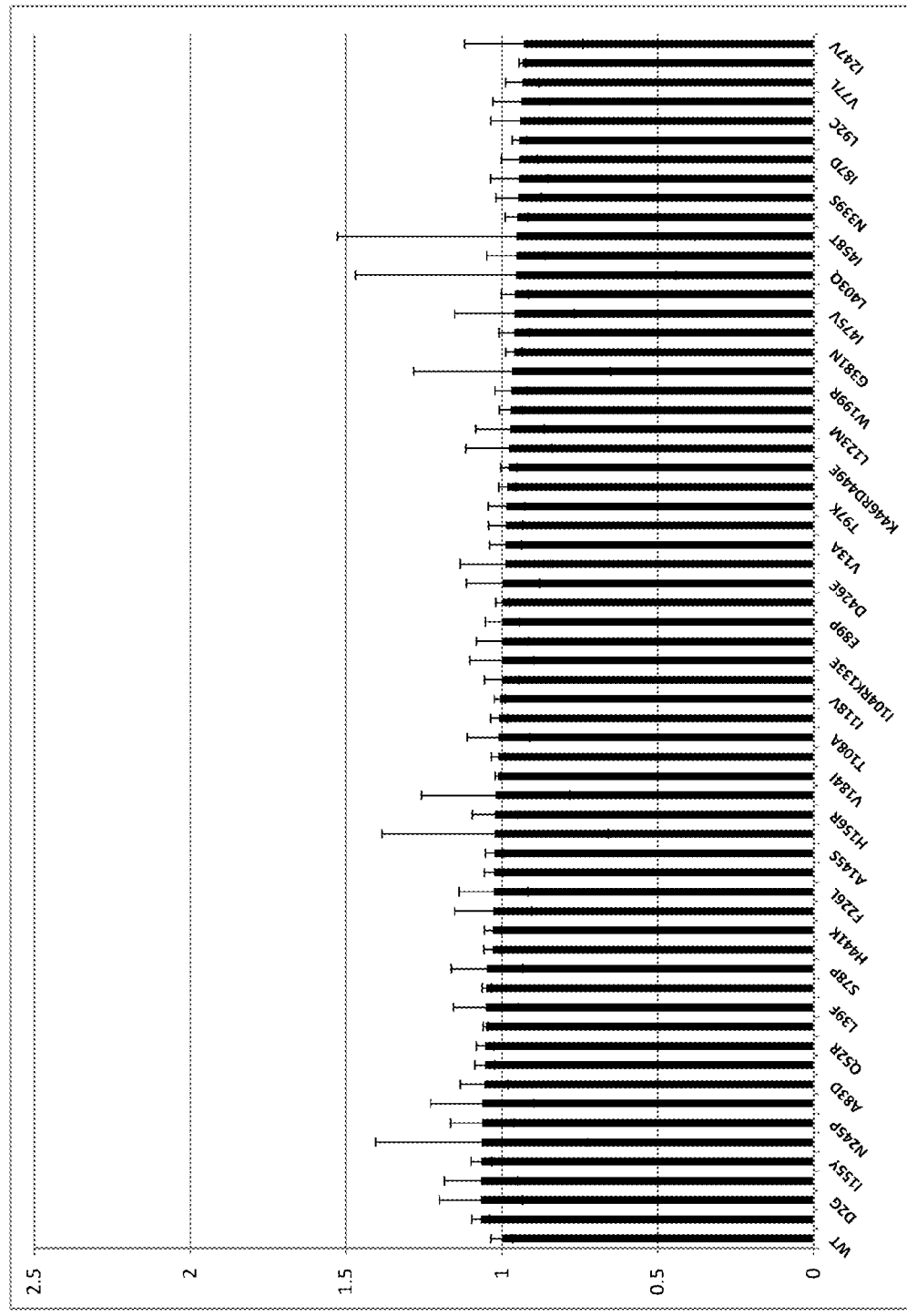
Figure 32:
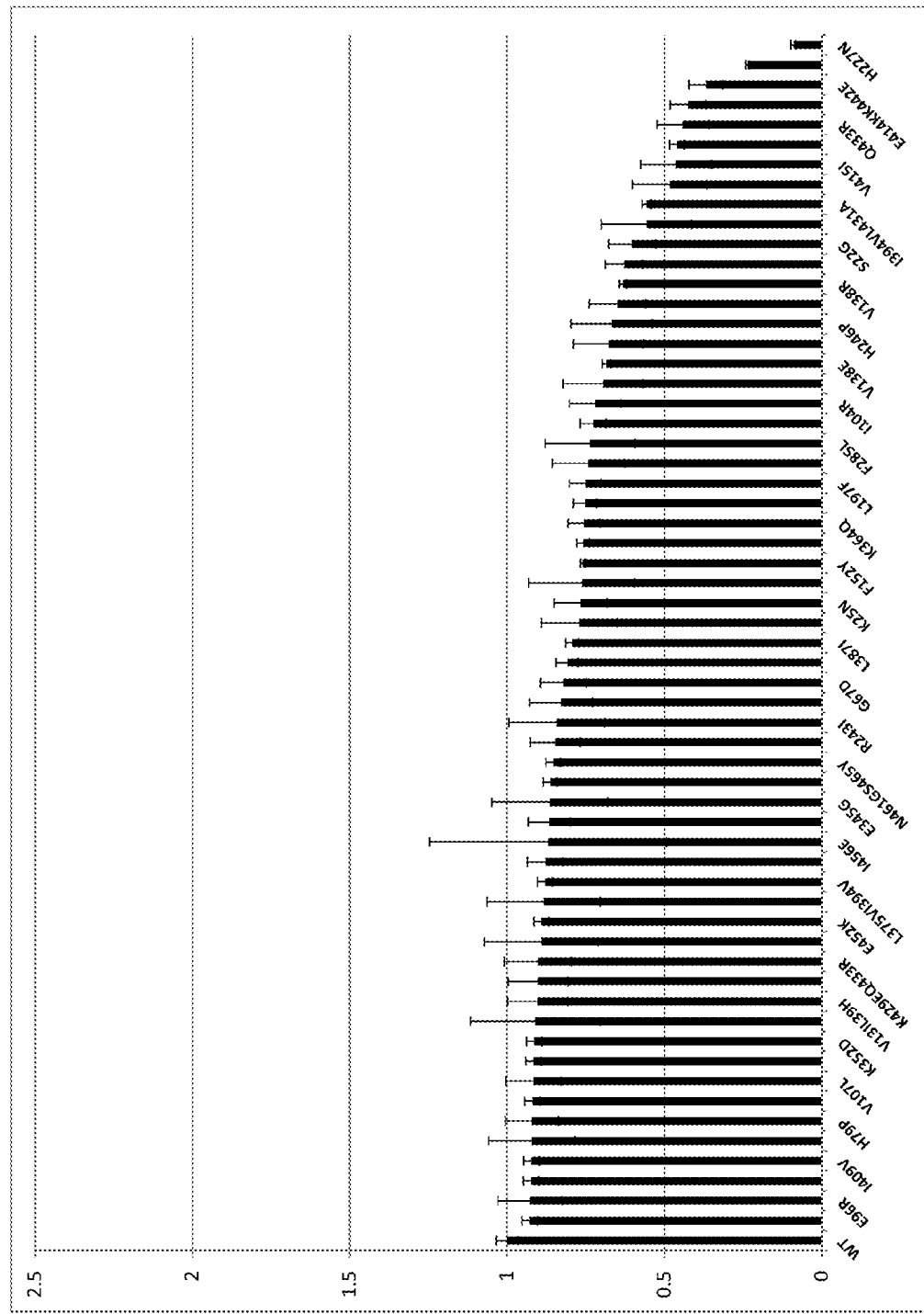

In a similar vein to the shuffling of enzymes engendered by circular permutization, an alternate method to shuffle glycosyltransferase enzymes was created by swapping the N-terminal small molecule sugar acceptor binding domain or the C-terminal sugar-donor binding domain between known UGTs. For example, a chimeric enzyme composed of the N-terminal domain of SrUGT85C2 and the C-terminal domain of SrUGT76G1 was created (FIG. 27). The rationale behind this approach rests on the concept of shuffling the domains of a UGT enzyme, only this time we add the nuance of shuffling domains between UGTs. The intent is to generate a non-optimized enzyme with a novel sequence, capable of further evolution away from the point in the energy landscape occupied by the parent enzyme, and towards a new optimum enzyme configuration in the production strain. Again, given that this enzyme is not a result of natural selection per se, the shuffled enzyme resulting from this chimeric approach should have increased evolutionary potential/greater potential to benefit positively from point mutations (i.e., with increased activity). Moreover, this approach can be used to generate chimeric protein with enhanced folding and/or stability.

In brief, this approach employs four broad steps: (1) identify two candidate UGTs; (2) select crossover positions for making a chimera between the two UGTs (i.e., select the point at which to join the two sequences); (3) mutate the C-terminal domain (the nucleotide-carbohydrate binding domain, e.g. UDP-glucose binding domain) to improve interaction with the small molecule substrate or the N-terminal small-molecule binding domain, based on structural considerations; (4) create and test chimeric constructs for activity. This approach is generalizable and applicable for improving the functional performance of potentially any UGT. Given the conserved domain structure of UGTs, domains from any two UGTs could be recombined.

Example 4: Modifying Glycosyltransferase Enzymes for Improved Activity and Biosynthesis of Rare Glycosides Although only around 20 steviol glycosides occur in sufficient quantities to have been characterized from stevia plants, there are several more possible steviol glycosides with different glycosylation patterns that can be created biosynthetically. Table 10 and FIGS. 29, 30, 31 and 32 summarize the known and potential steviol glycosides described in this section, which are abbreviated with the symbol SG#. Some of these glycosides exist in nature, and others are biosynthetically possible using UGTs that catalyze the four glycosylation chemistries described herein (i.e., C13-O-glycosylation, C19-O-glycosylation, 1,2'-glycosylation, and 1,3'-glycosylation).

Figure 33:
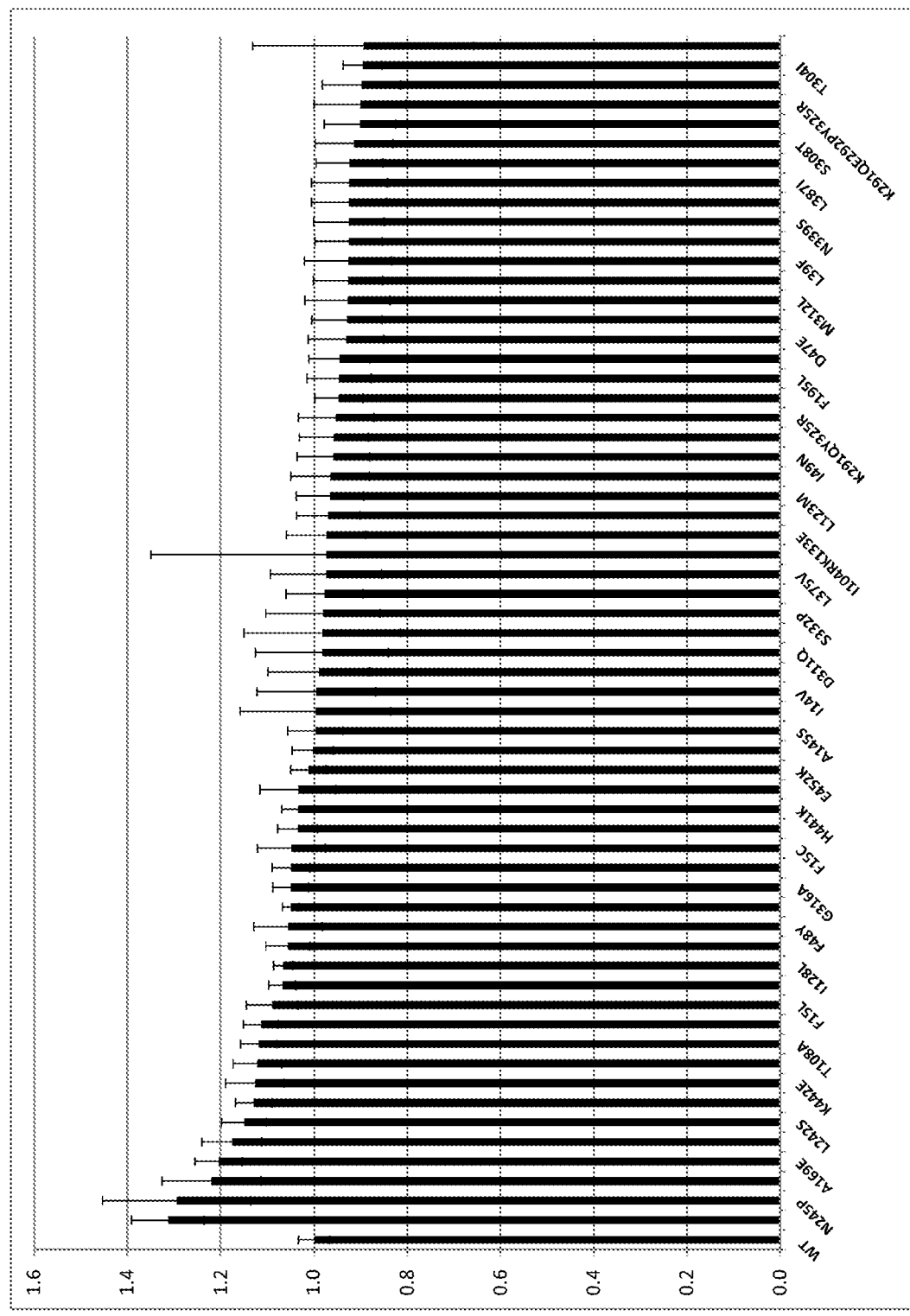
FIG. 33 shows point mutations in SrUGT85C2 enzyme versus altered activity on C19-glucopyranosyl steviol substrate. [BL21=negative no UGT control].
Figure 33:
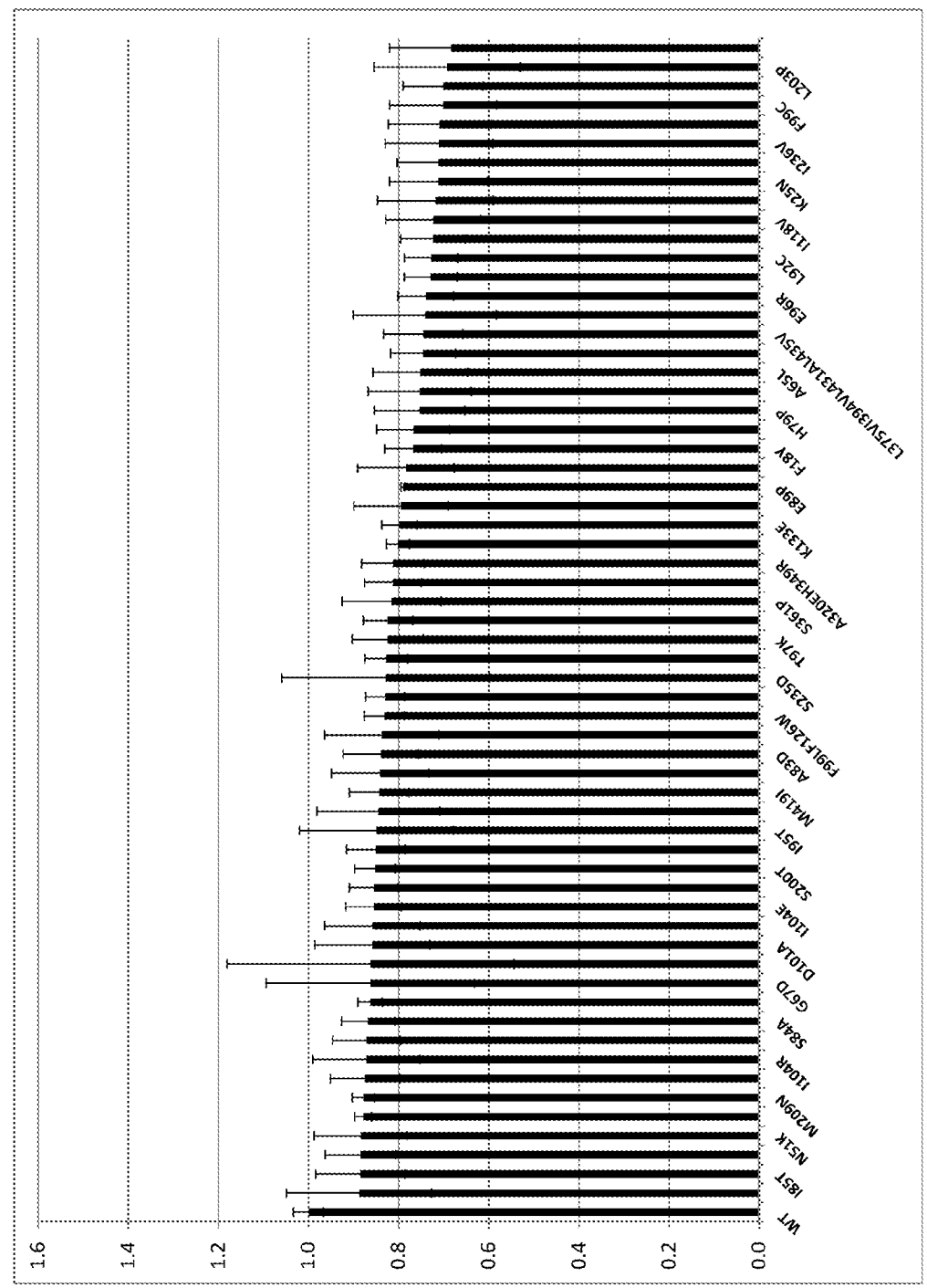
Figure 33:
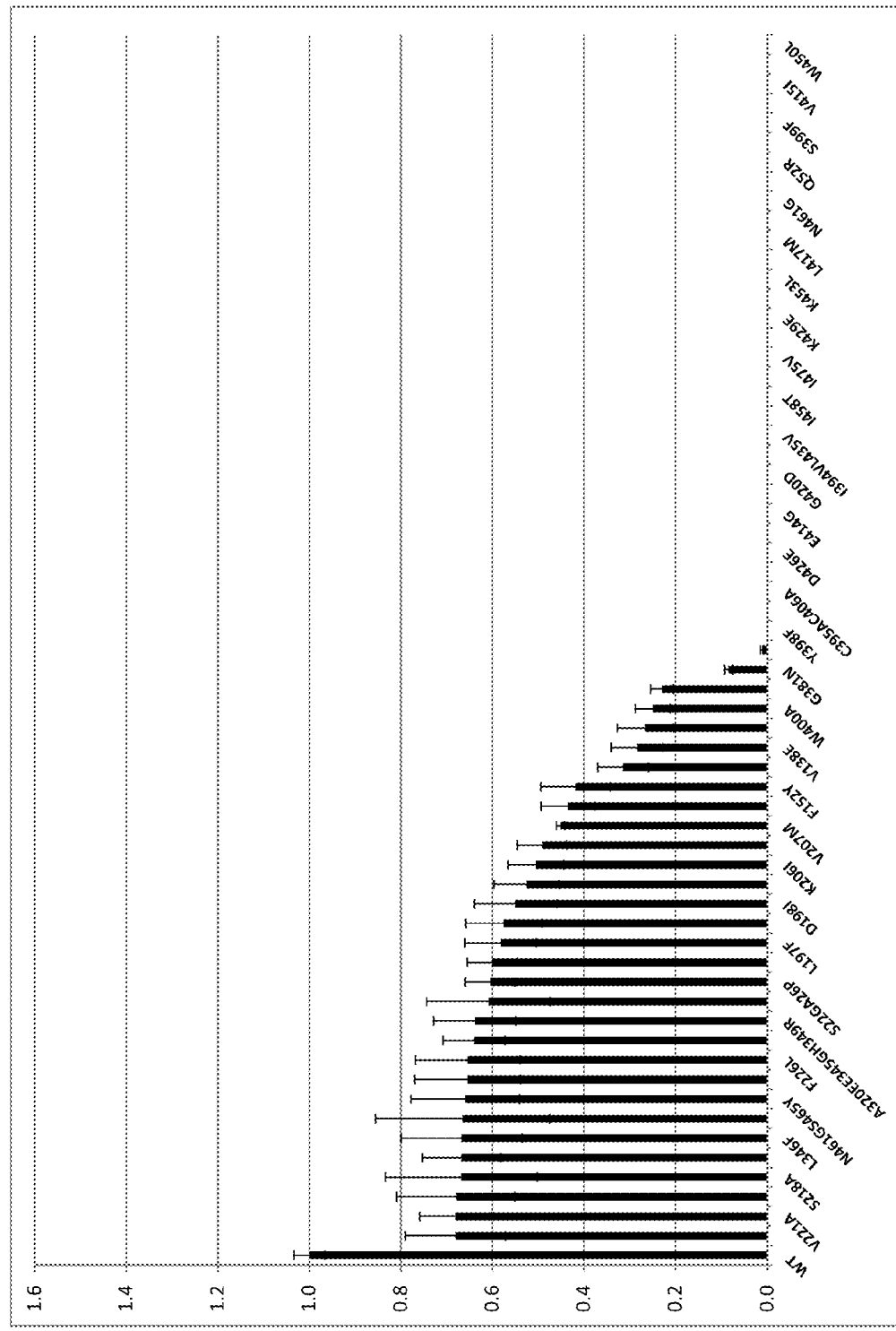
Figure 34:
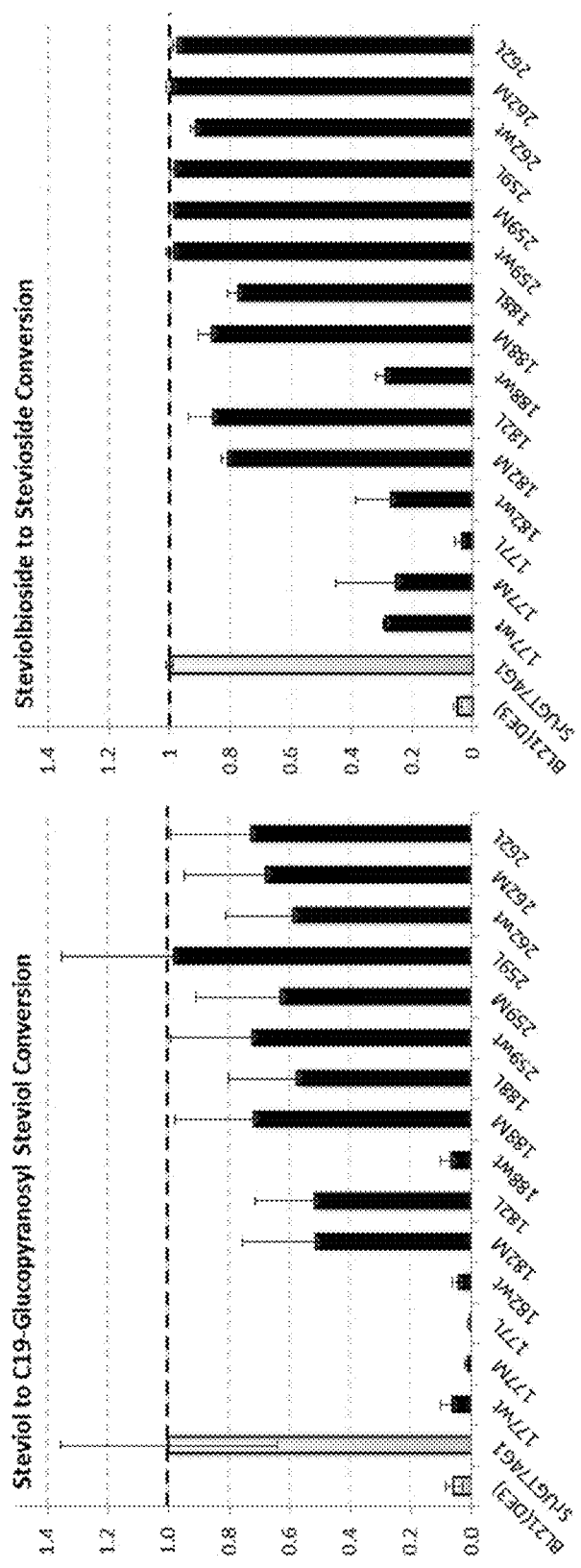
FIG. 34 shows C19-O-glycosylating activity for the first round of circular permutants of SrUGT74G1. The numbers indicate the location of the cut site in the parental sequence used to generate novel N- and C-termini, while the wt/L/S designation describes wild-type/long/short linkers (where 'wt' indicates a simple fusion of existing N- and C-termini sequences with no alteration).

A rational design approach was used to design a collection of single, double, and triple point mutations in the SrUGT85C2 sequence (possessing C13-O-glycosylating activity), aimed at increasing stability, solubility, or activity of the wild-type enzyme for improved conversion of steviol to steviolmonoside (SG1), and/or C19-glucopyranosyl steviol (SG2) to rubusoside (SG5), and/or SG4 to SG10, and/or SG7 to SG11, and/or SG13 to SG17, and/or SG19 to SG29, and/or SG23 to SG31. The point mutations and corresponding fold-change improvements over wild-type SrUGT85C2 are summarized in Table 11, and are visualized in FIGS. 32 and 33.

A rational design approach was used to design a collection of single, double, and triple point mutations in the SrUGT74G1 sequence (possessing C19-O-glycosylating activity), aimed at increasing stability, solubility, or activity of the wild-type enzyme for improved conversion of steviol to C19-glucopyranosyl steviol (SG2), and/or steviolmonoside (SG1) to rubusoside (SG5), and/or steviolbioside (SG3) to stevioside (SG8), and/or SG6 to rebaudioside G (SG9), and/or rebaudioside B (SG12) to rebaudioside A (SG16), and/or SG18 to SG28, and/or SG22 to SG30.

Figure 24:
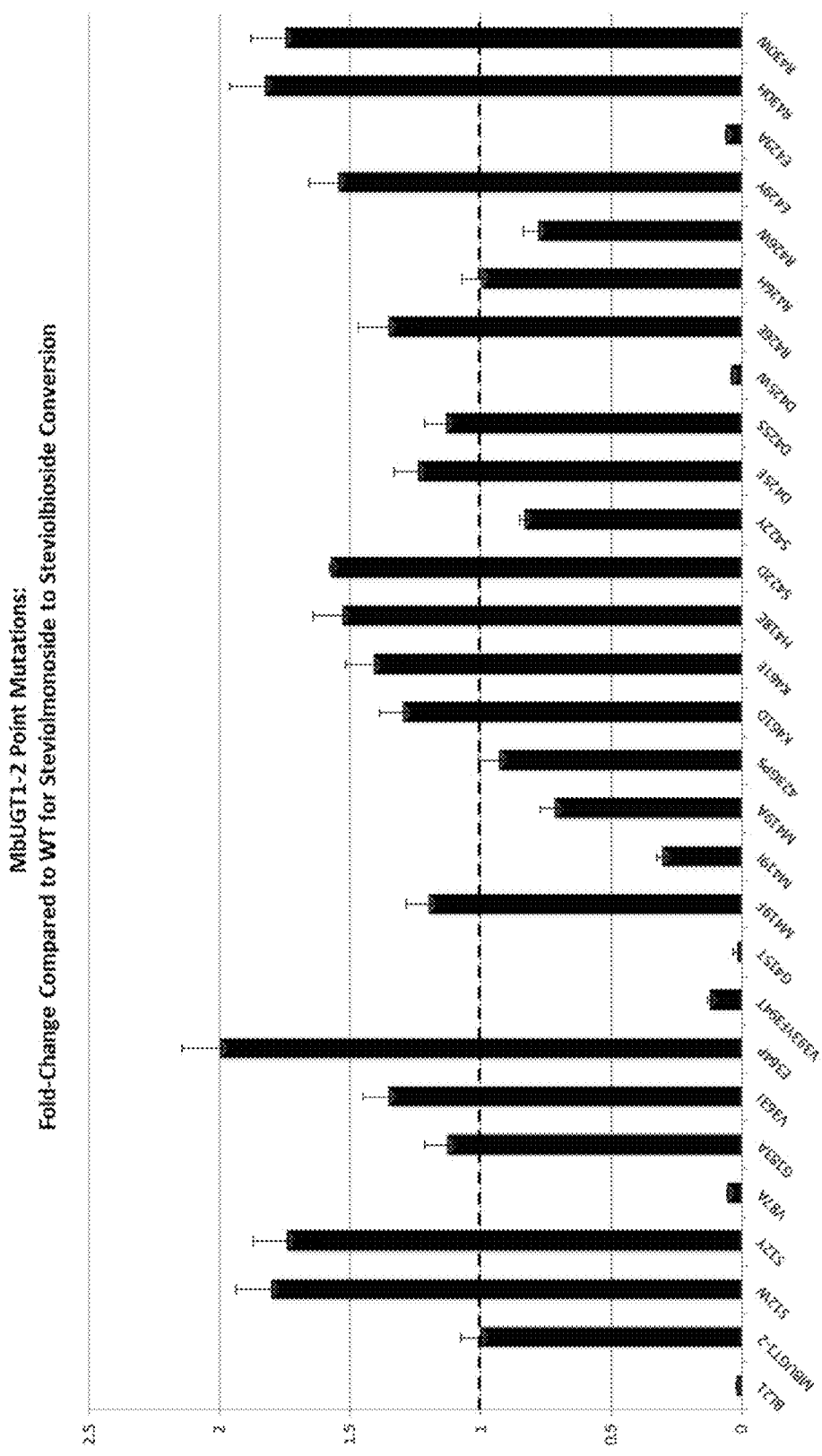
FIG. 24 shows point mutations in the MbUGT1-2 enzyme. Point mutations show increased activity on substrate steviolmonoside, demonstrating the potential for improving UGT enzymes generated by circular permutization [BL21=negative no UGT control].

A rational design approach was used to design a collection of single, double, and triple point mutations in the MbUGT1-2 sequence (possessing 1-2' glycosylating activity), aimed at increasing stability, solubility, or activity of the wild-type enzyme for improved conversion of steviolmonoside (SG1) to steviolbioside (SG3), and/or C19-glucopyranosyl steviol (SG2) to SG4, and/or rubusoside (SG5) to stevioside (SG8), and/or rubusoside (SG5) to SG10, and/or rubusoside (SG5) to rebaudioside E (SG14), and/or SG6 to rebaudioside B (SG12), and/or SG7 to SG13, and/or stevioside (SG8) to rebaudioside E (SG14), and/or SG10 to rebaudioside E (SG14), and/or rebaudioside G (SG9) to rebaudioside A (SG16), and/or rebaudioside G (SG9) to SG21, and/or SG11 to SG17, and/or SG11 to SG20, and/or rebaudioside B (SG12) to SG22, and/or SG13 to SG23, and/or SG15 to rebaudioside I (SG26), and/or SG15 to SG27, and/or rebaudioside A (SG16) to rebaudioside D (SG24), and/or rebaudioside A (SG16) to SG30, and/or SG17 to SG25, and/or SG17 to SG31, and/or SG20 to SG25, and/or SG21 to rebaudioside D (SG24), and/or rebaudioside D (SG24) to SG37, and/or SG25 to SG39, and/or rebaudioside I (SG26) to rebaudioside M (SG32), and/or rebaudioside I (SG26) to SG38, and/or SG27 to rebaudioside M (SG32), and/or SG27 to SG40, and/or SG28 to SG33, and/or SG29 to SG35, and/or SG30 to SG37, and/or SG31 to SG39, and/or rebaudioside M (SG32) to SG43, and/or rebaudioside M (SG32) to SG44, and/or SG34 to SG41, and/or SG36 to SG42, and/or SG38 to SG43, and/or SG40 to SG44, and/or SG41 to SG47, and/or SG42 to SG48, and/or SG43 to SG46, and/or SG44 to SG46. The point mutations and corresponding fold-change improvements over wild-type MbUGT1-2 are summarized in Table 12, and representative reactions are shown in FIGS. 24 and 25.

Figure 35:
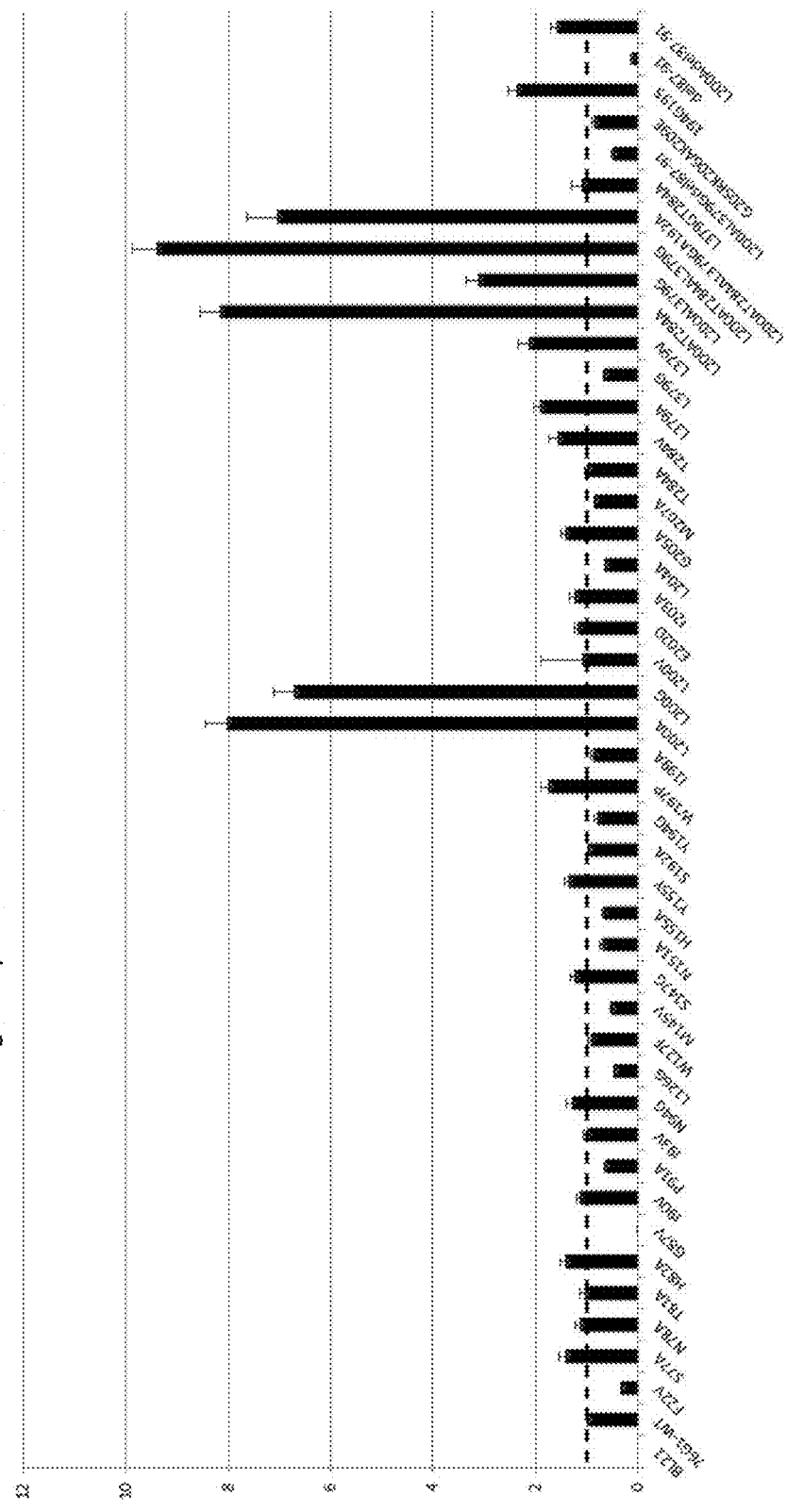
FIG. 35 shows point mutations in SrUGT76G1 enzyme versus altered activity on stevioside substrate. [BL21=negative no UGT control].
Figure 36:
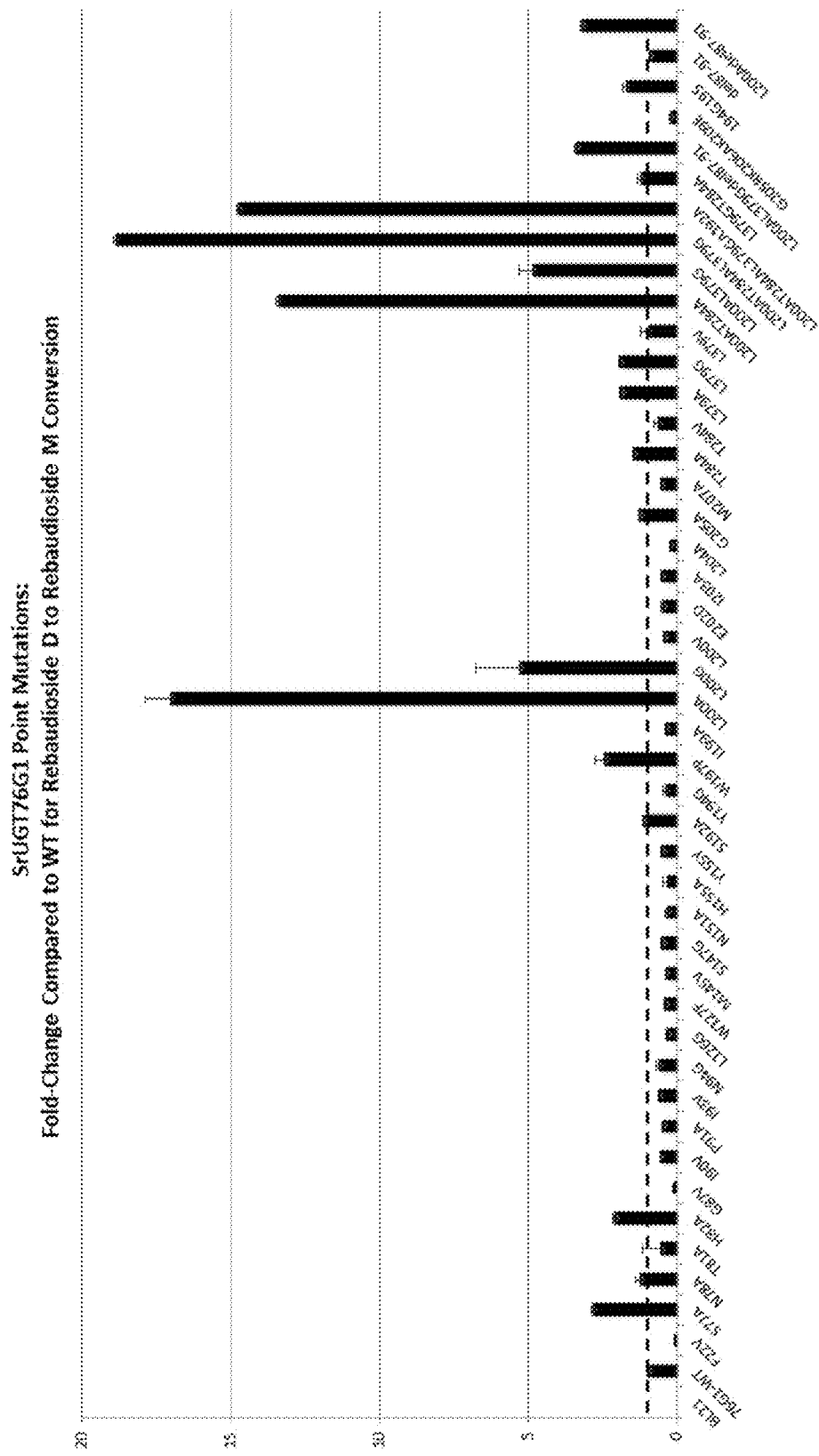
FIG. 36 shows point mutations in SrUGT76G1 enzyme versus altered activity on rebaudioside D substrate. [BL21=negative no UGT control].
Figure 37:
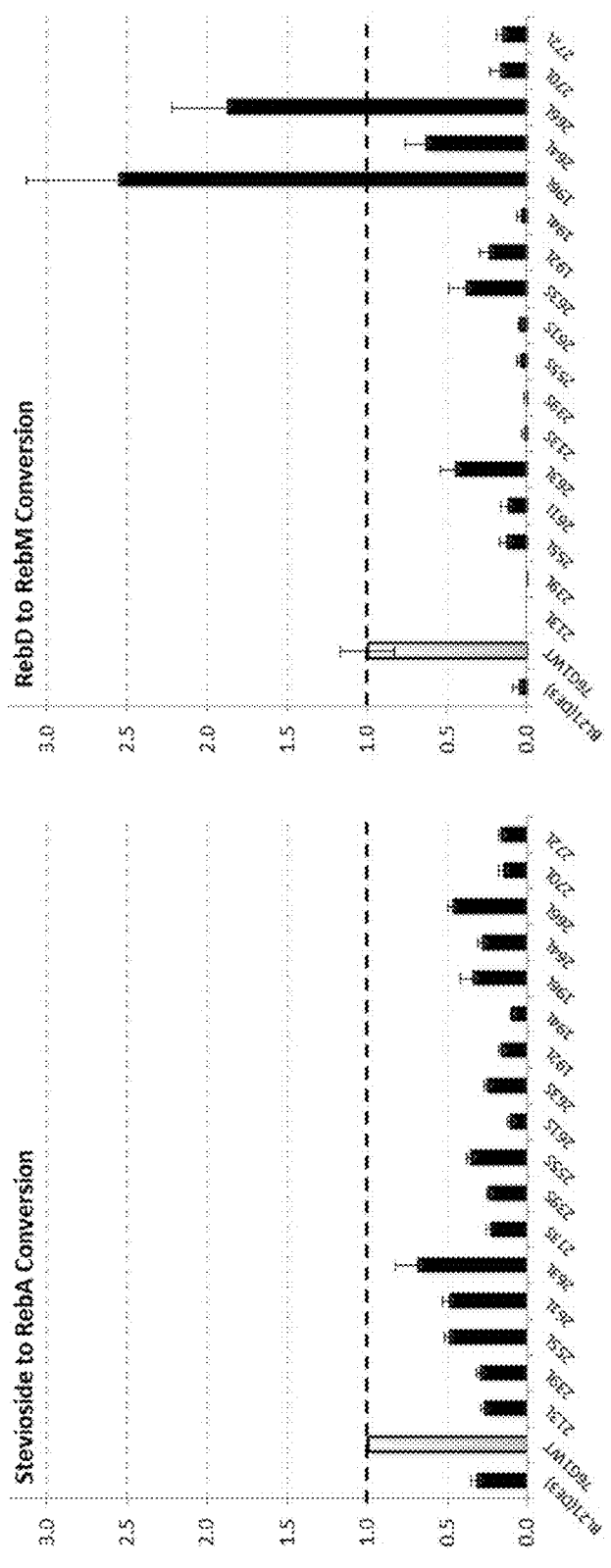
FIG. 37 shows 1-3' glycosylating activity for the first round of circular permutants of SrUGT76G1. The numbers indicate the location of the cut site in the parental sequence used to generate novel N- and C-termini, while the L/S designation describes long/short linkers.

A rational design approach was used to design a collection of single, double, triple, or quadruple point mutations in the SrUGT76G1 sequence (possessing 1-3' glycosylating activity), aimed at increasing stability, solubility, or activity of the wild-type enzyme for improved conversion of steviolmonoside (SG1) to SG6, and/or C19-glucopyranosyl steviol (SG2) to SG7, and/or steviolbioside (SG3) to rebaudioside B (SG12), and/or SG4 to SG13, and/or rubusoside (SG5) to rebaudioside G (SG9), and/or rubusoside (SG5) to SG11, and/or rubusoside (SG5) to SG15, and/or stevioside (SG8) to rebaudioside A (SG16), and/or stevioside (SG8) to SG20, and/or rebaudioside G (SG9) to SG15, and/or SG10 to SG17, and/or SG10 to SG21, and/or SG11 to SG15, and/or rebaudioside B (SG12) to SG18, and/or SG13 to SG19, and/or rebaudioside E (SG14) to rebaudioside D (SG24), and/or rebaudioside E (SG14) to SG25, and/or rebaudioside E (SG14) to rebaudioside M (SG32), and/or rebaudioside A (SG16) to rebaudioside I (SG26), and/or rebaudioside A (SG16) to SG28, and/or SG17 to SG27, and/or SG17 to SG29, and/or SG20 to rebaudioside I (SG26), and/or SG21 to SG27, and/or rebaudioside D (SG24) to rebaudioside M (SG32), and/or rebaudioside D (SG24) to SG33, and/or SG25 to rebaudioside M (SG32), and/or SG25 to SG35, and/or rebaudioside I (SG26) to SG34, and/or SG27 to SG36, and/or SG28 to SG34, and/or SG29 to SG36, and/or SG30 to SG38, and/or SG31 to SG40, and/or rebaudioside M (SG32) to SG41, and/or rebaudioside M (SG32) to SG42, and/or SG33 to SG41, and/or SG35 to SG42, and/or SG37 to SG43, and/or SG39 to SG44, and/or SG41 to SG45, and/or SG42 to SG45, and/or SG43 to SG48, and/or SG44 to SG47. The point mutations and corresponding fold-change improvements over wild-type SrUGT76G1 are summarized in Table 13, and representative reactions are shown in FIGS. 35 and 36.

Example 5: Improving Yield and Performance Above 22° C.

The performances of the enzymes in the kaurene module were determined to be suboptimal at temperatures above 22° C. A cluster of alternative enzymes were identified for the GGPPS (geranylgeranyl diphosphate) synthase enzyme and the bi-functional copalyl diphosphate (CPP)/kaurene synthase enzymes used in the previous examples. In particular, alternate enzymes from bacterial sources were considered, reasoning that these may function better in *E. coli* than plant and fungal enzymes. Enzymes from thermophilic bacteria were considered where possible. For the CPP synthase and kaurene synthase activities, genes from bacteria in the rhizosphere were identified, since they are often kaurene-producing due to their symbiotic lifestyle.

Figure 39:
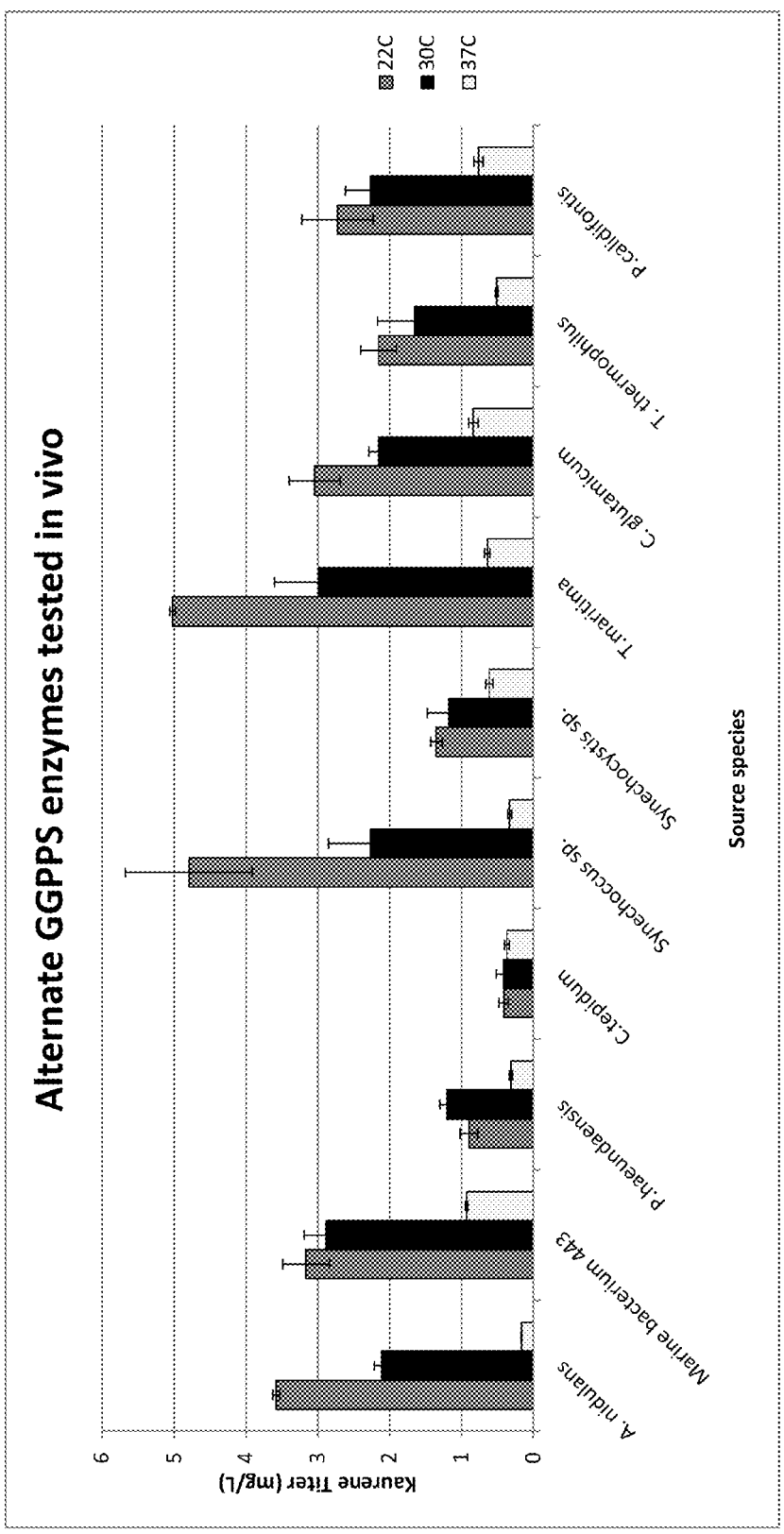
FIG. 39 shows alternate GGPPS enzymes tested in vivo for performance at 22° C., 30° C., and 37° C.

FIG. 39 shows the results for alternate GGPPS enzymes. Several enzymes show improved performance at higher temperatures, including Marine bacterium 443, *Synechoccus* sp., *Thermotoga maritima*, *Cornybacterium glutamicum*, and *Pyrobaculum calidifontis*.

Figure 40:
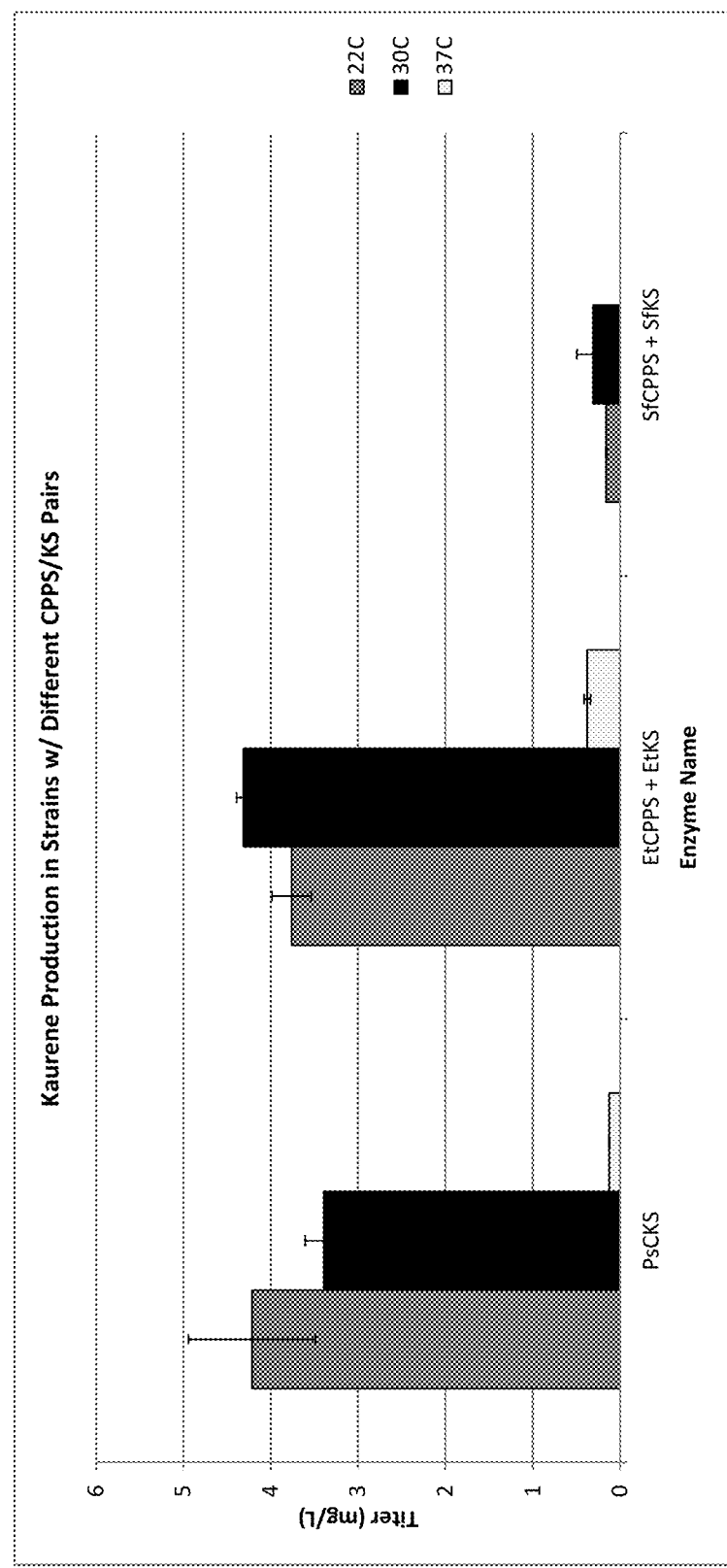
FIG. 40 shows alternate CPPS/KS pairs tested in vivo for performance at 22° C., 30° C., and 37° C.

FIG. 40 shows the results for alternate CPPS and KS enzymes. *Erwina tracheiphila* (Et)CPPS and EtKS showed improved activity at higher temperatures.

Figure 41:
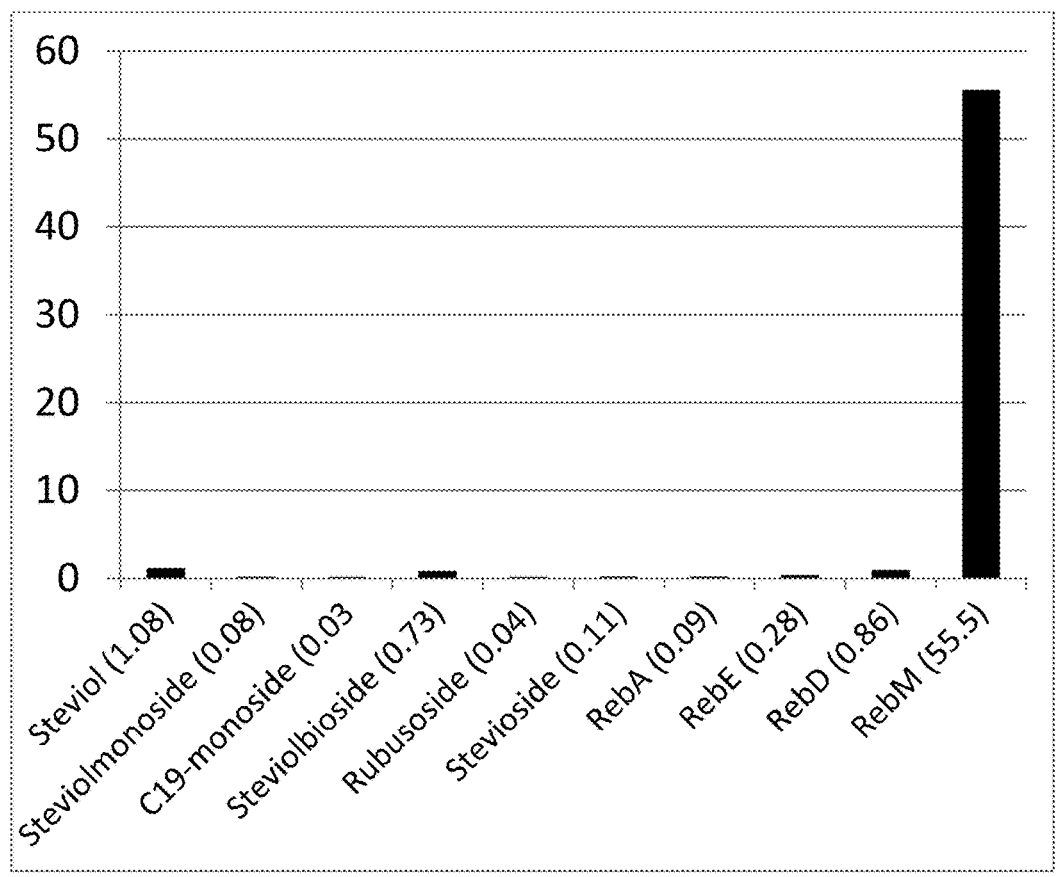
FIG. 41 shows the titer of Reb M in comparison to steviol and other glycosylation products, using a selected strain at 22° C.

Production of various steviol glycosides (including Reb M) was tested at 22° C. in a select strain. The strain was *E. coli* K12 with a pBAC single-copy chromosome containing FAB46-MEP, T7-PsCKS-AnGGPPS, T7-AtKAH-SrKO-SrCPR, T7-MbUGT1,3-MbUGT1,2-MbUGTc13-MbUGTc19. As shown in FIG. 41, Reb M titer was 55.5 mg/L with a total steviol glycoside titer of 58.3 mg/L, which is equal to 94.4% Reb M. The Reb M:Reb D ratio was 64.5:1 (in grams).

| Statistic | Quantity |
| --- | --- |
| Titer, Total Steviol Glycosides (mg/L) | 58.3 mg/L |
| Titer, Rebaudioside M (mg/L) | 55.5 mg/L |
| % Reb M (of total glycosides) | 94.4% |
| Reb M: Reb D (g/g) | 64.5:1 |

Figure 42:
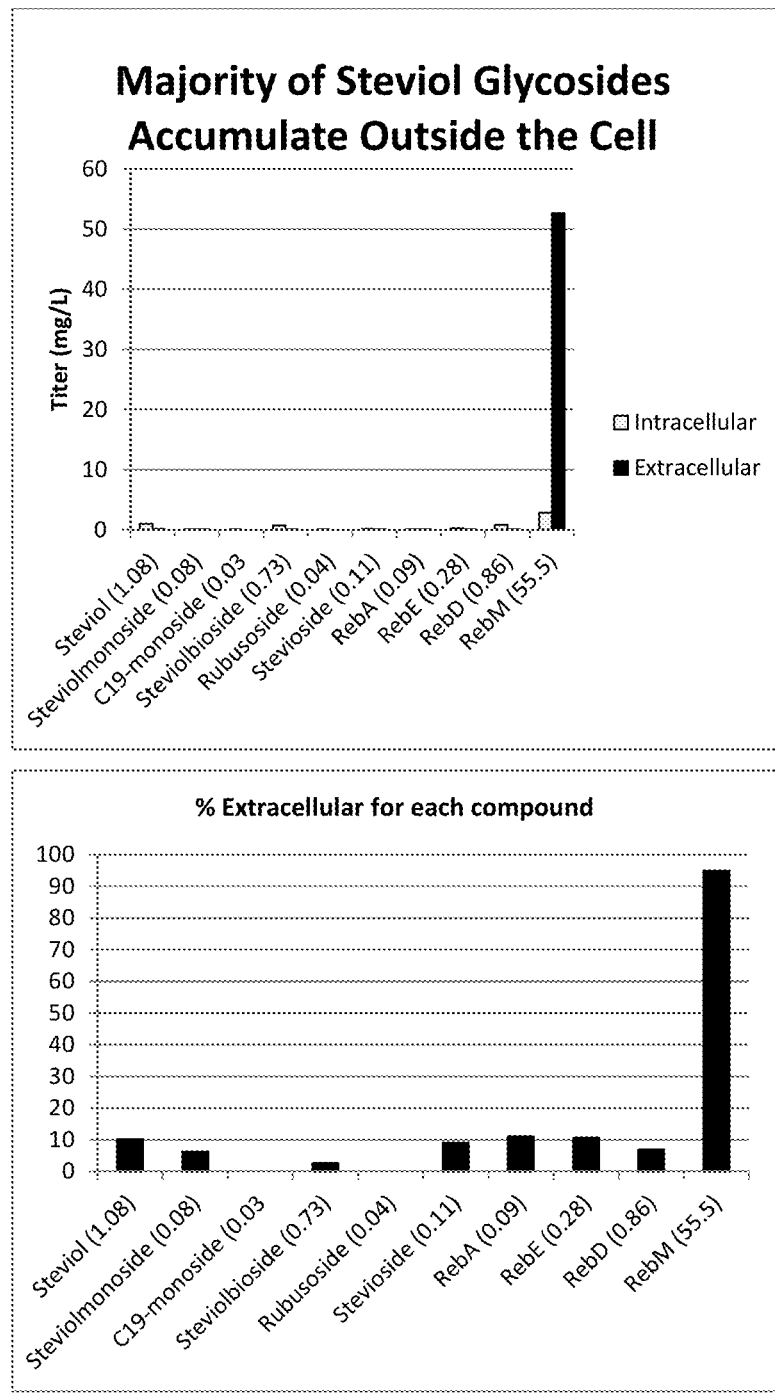
FIG. 42 shows that the majority of Reb M accumulates extracellularly. Left Panel shows the titer of Reb M and steviol glycosides inside and outside of the cell. Right Panel shows the same data as the percent of each compound observed extracellularly.

The intracellular accumulation of steviol glycosides was investigated. As shown in FIG. 42, the majority of the steviol glycosides are excreted from the cell. FIG. 42 shows the combined intracellular and extracellular material, as a percentage of product accumulating inside the cell versus outside. This was in contrast to initial studies having substantially less yield of steviol glycosides, which saw mostly intracellular accumulation. It s possible that the initial studies were of such low titer that accumulated product pools were insufficient for the active transport mechanisms required to pump the product out of the cells. Indeed, as the titer increased, a greater proportion of the product accumulated outside the cell, indicating that once above the threshold concentration for the putative pump activity, the rest of the products get moved out. These data are very promising from a strain engineering perspective and commercial production in *E. coli*, since if intermediate product pools are maintained below the Kb of the transporter, we can effectively push C-flux through to the end product without losing carbon to the outside (e.g., once a steviol glycoside intermediate is pumped out, it can no longer be further glycosylated to the desired product, such as RebM).

Figure 43A:
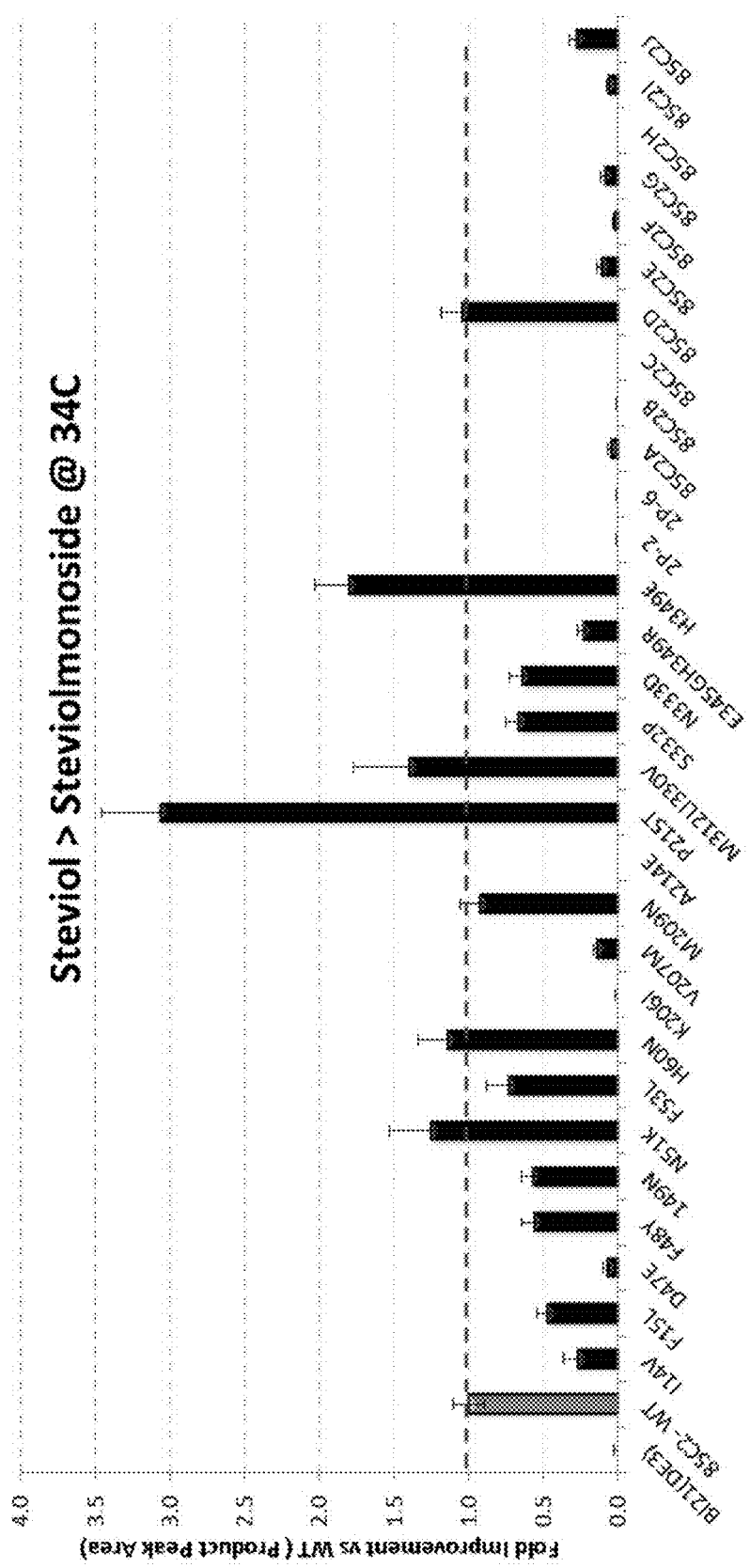
FIG. 43 shows screening of UGT85C2 mutants at 22, 30, and 34° C., based on production of steviolmonoside. Panels A and B show the panel of mutants at 34° C., and Panel C shows select mutations screened for steviolmonoside production at 22, 30, and 34° C.
Figure 43B:
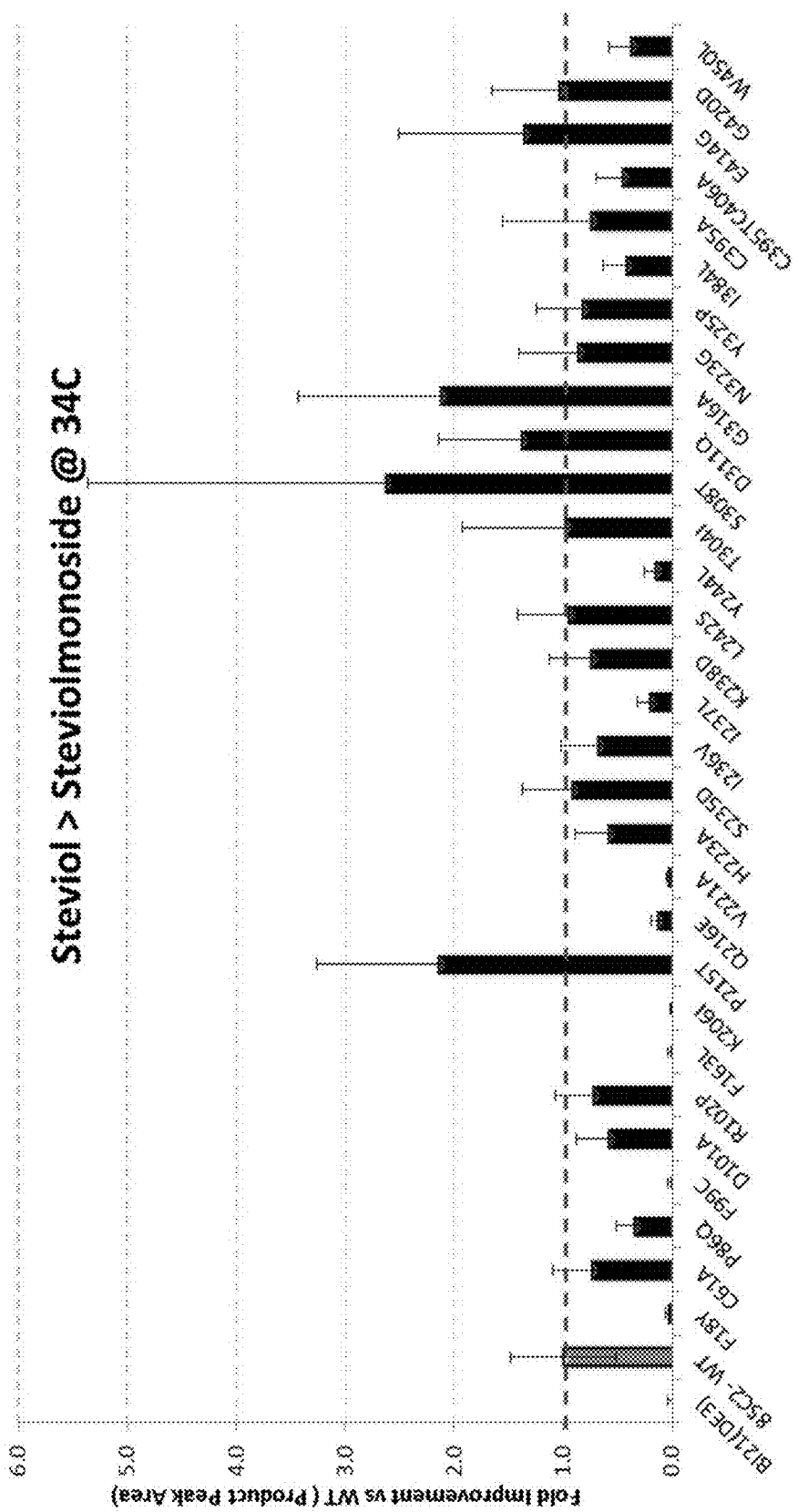
Figure 43C:
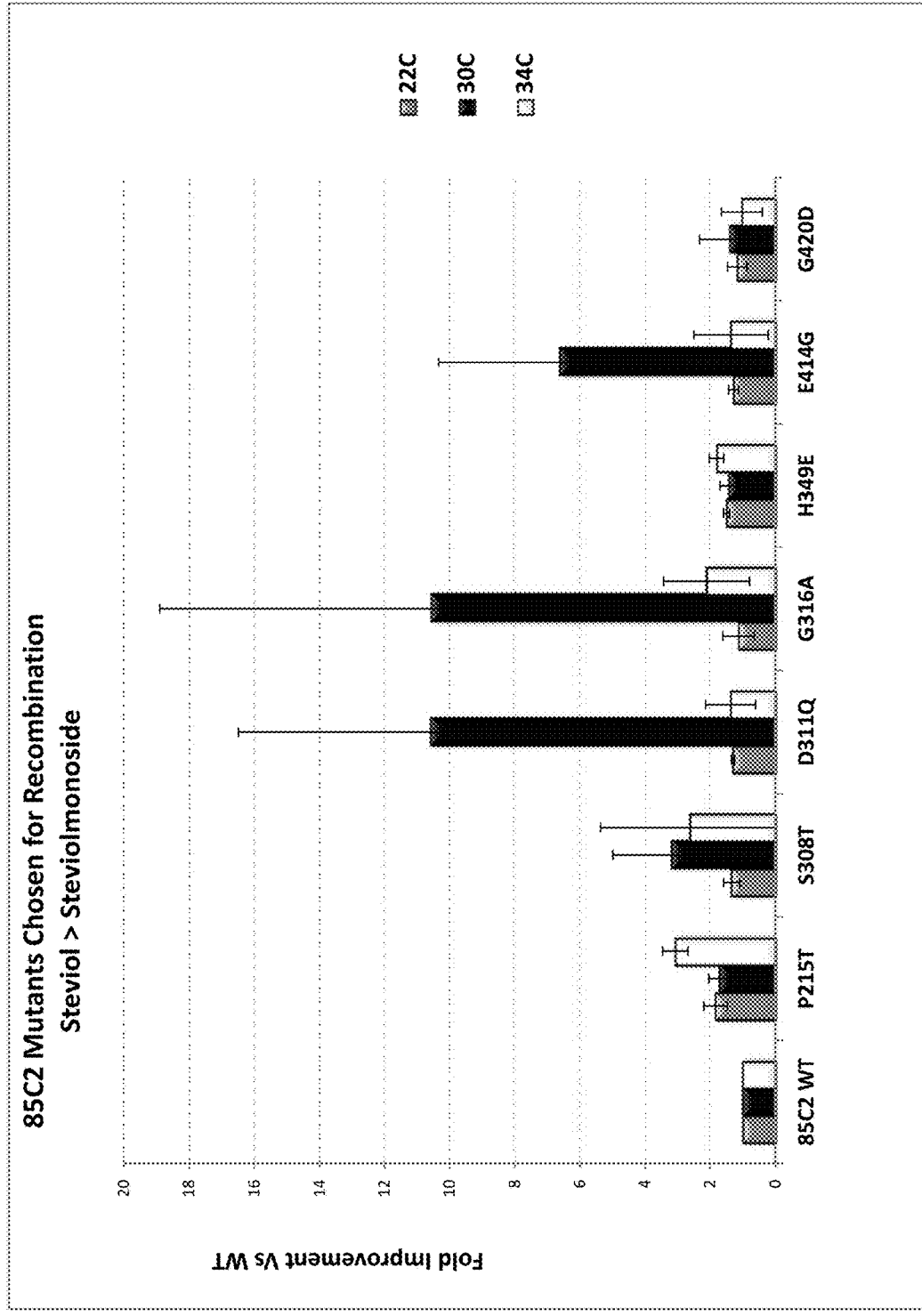

Point mutants of UGT85C2 were generated, and tested at 22, 30, and 34° C. FIG. 43A, B show steviol monoside production at 34° C. FIG. 43C shows production of steviolmonoside with selected mutants at 22, 30, and 34° C. Several mutations showed higher production of steviolmonoside at 34° C., with P215T being the highest producing mutation.

Figure 44A:
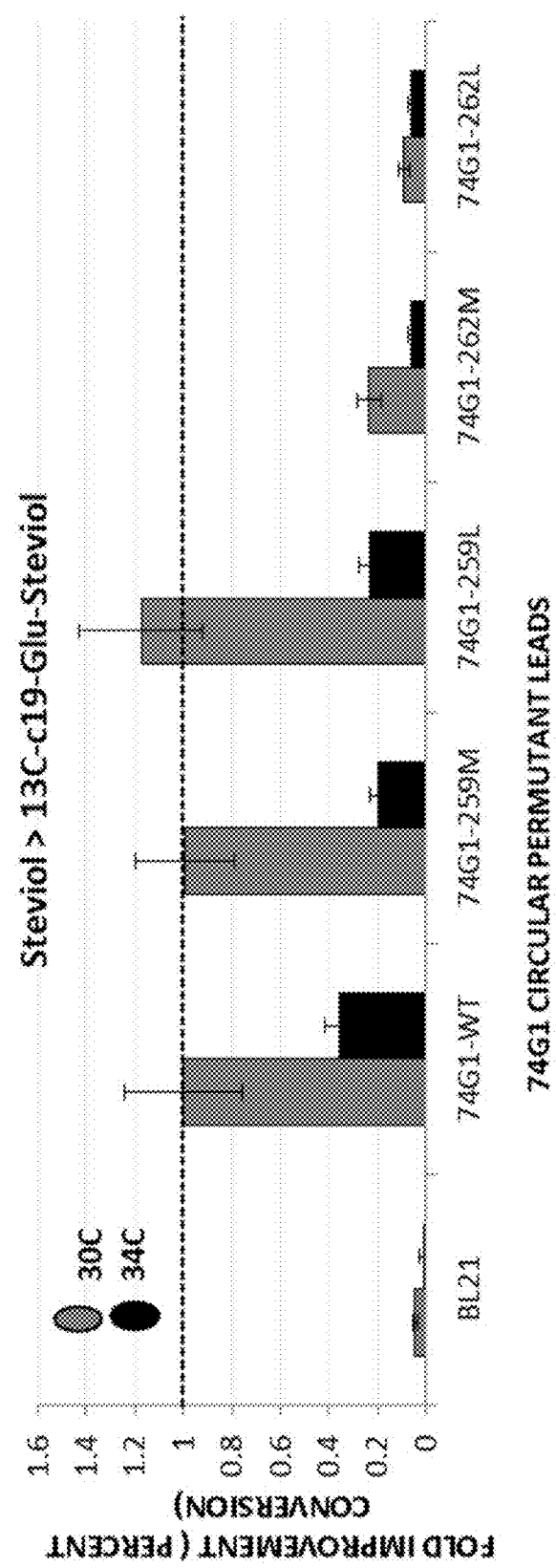
FIG. 44 shows screening of 74G1 circular permutants for activity at 30 and 34° C. Panel 44A shows activity on Steviol, and Panel 44B shows activity on steviolbioside.
Figure 44B:
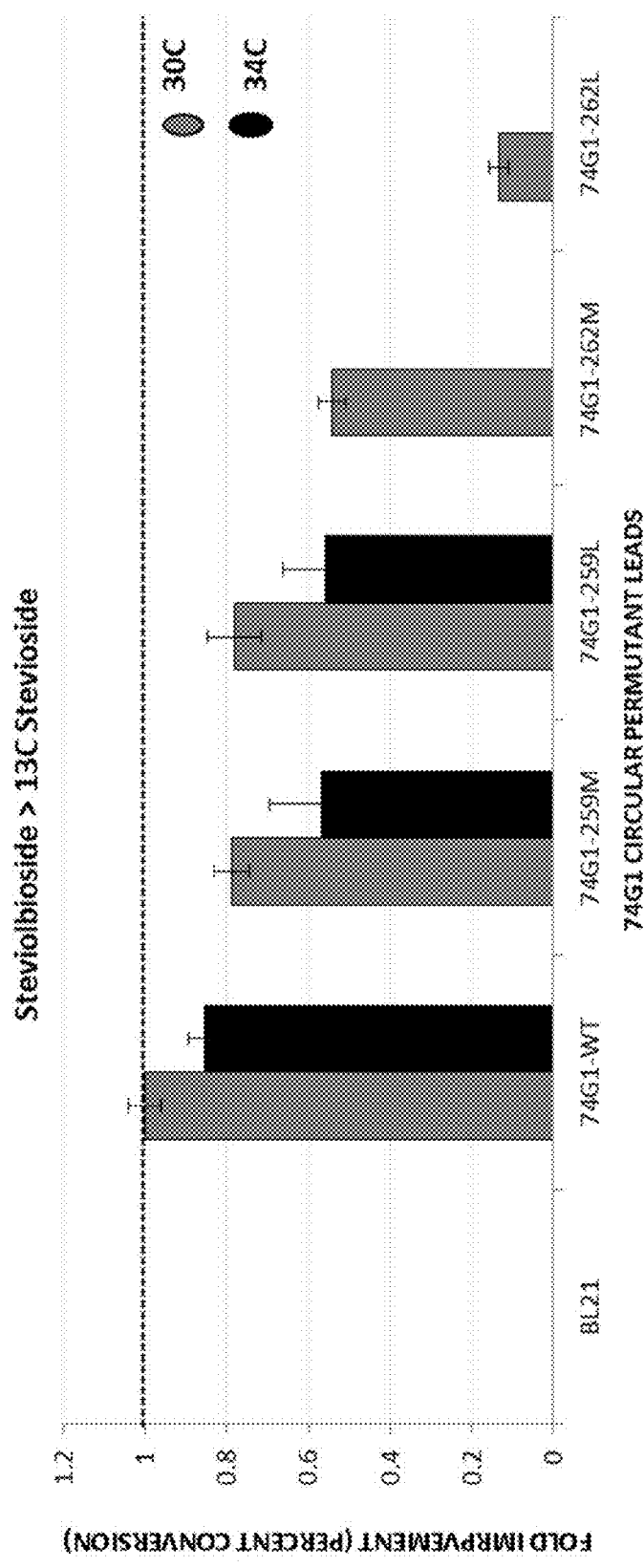

Circular permutants of 74G1 were also tested for activity at 30 and 34° C. FIG. 44A,B show conversion of steviol to 13C-c19-Glu-Steviol (FIG. 44A) and steviolbioside to 13C Stevioside (FIG. 44B).

Figure 45:
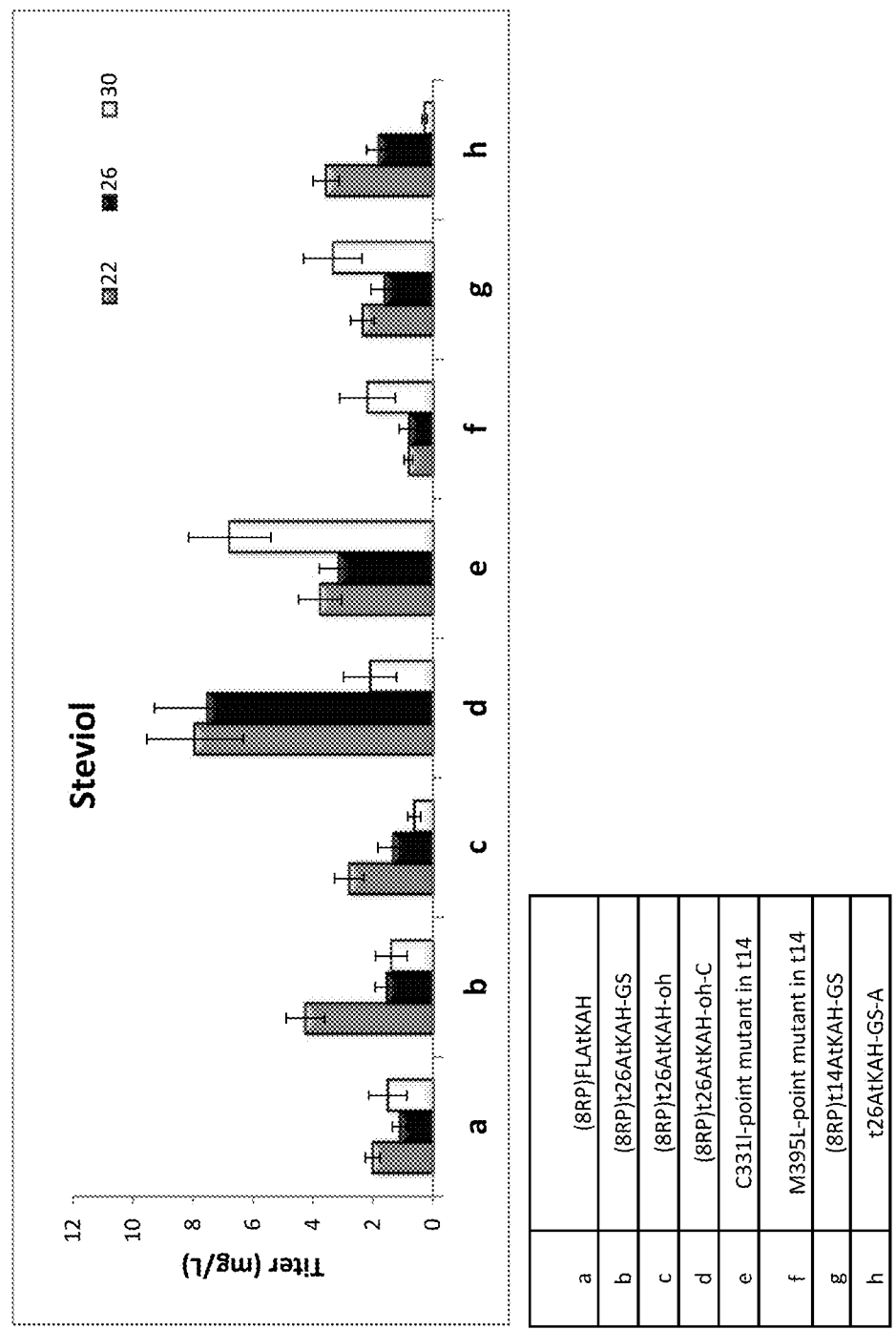
FIG. 45 shows screening of AtKAH point mutants for activity at 22, 26, and 30° C.

Mutations in AtKAH were screened for activity at 22, 26, and 30° C. C331I provided substantial thermostability, as shown in FIG. 45. C331I was made in the t14 background.

Figure 46A:
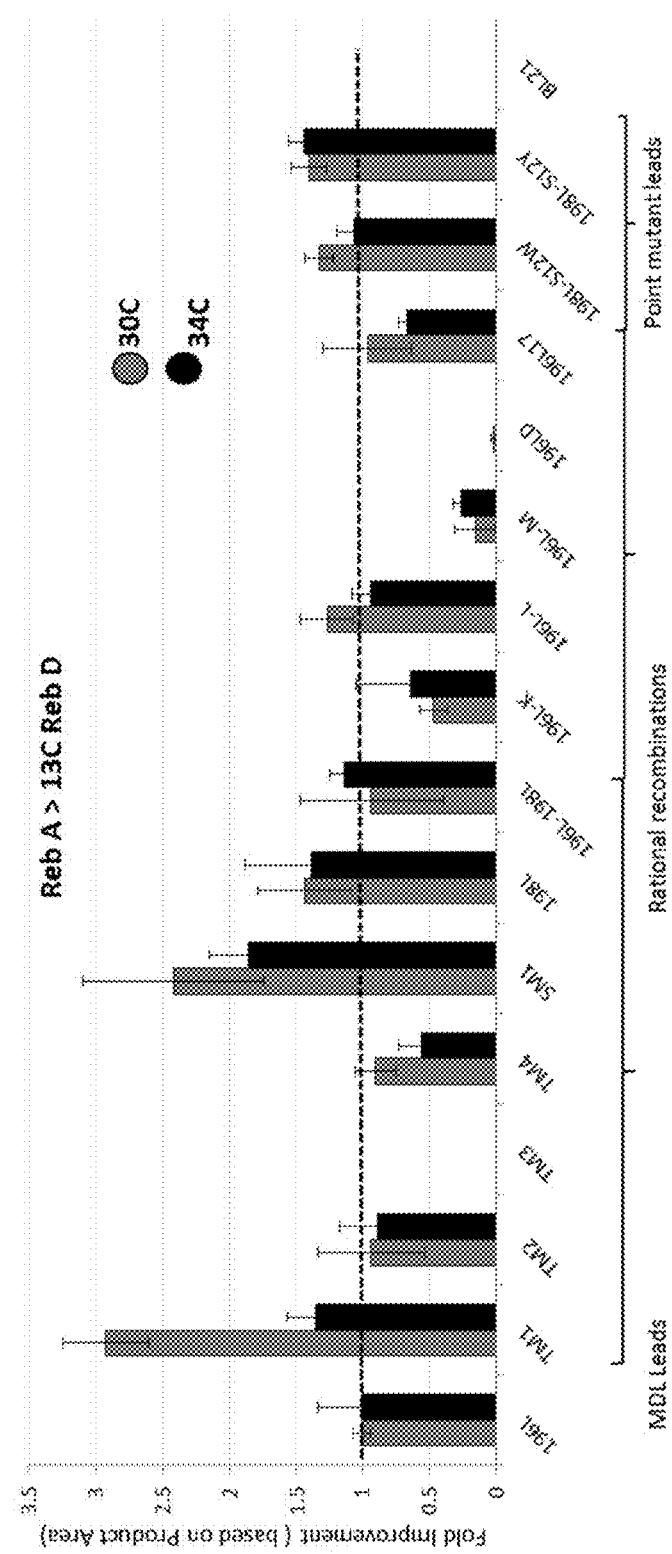
FIG. 46 shows in vitro screening of MbUGT1-2 recombination mutants at 30 and 34° C. Panel A shows conversion of Reb A to Reb D. Panel B shows conversion of Steviolmonoside to 13C Steviolbioside.
Figure 46B:
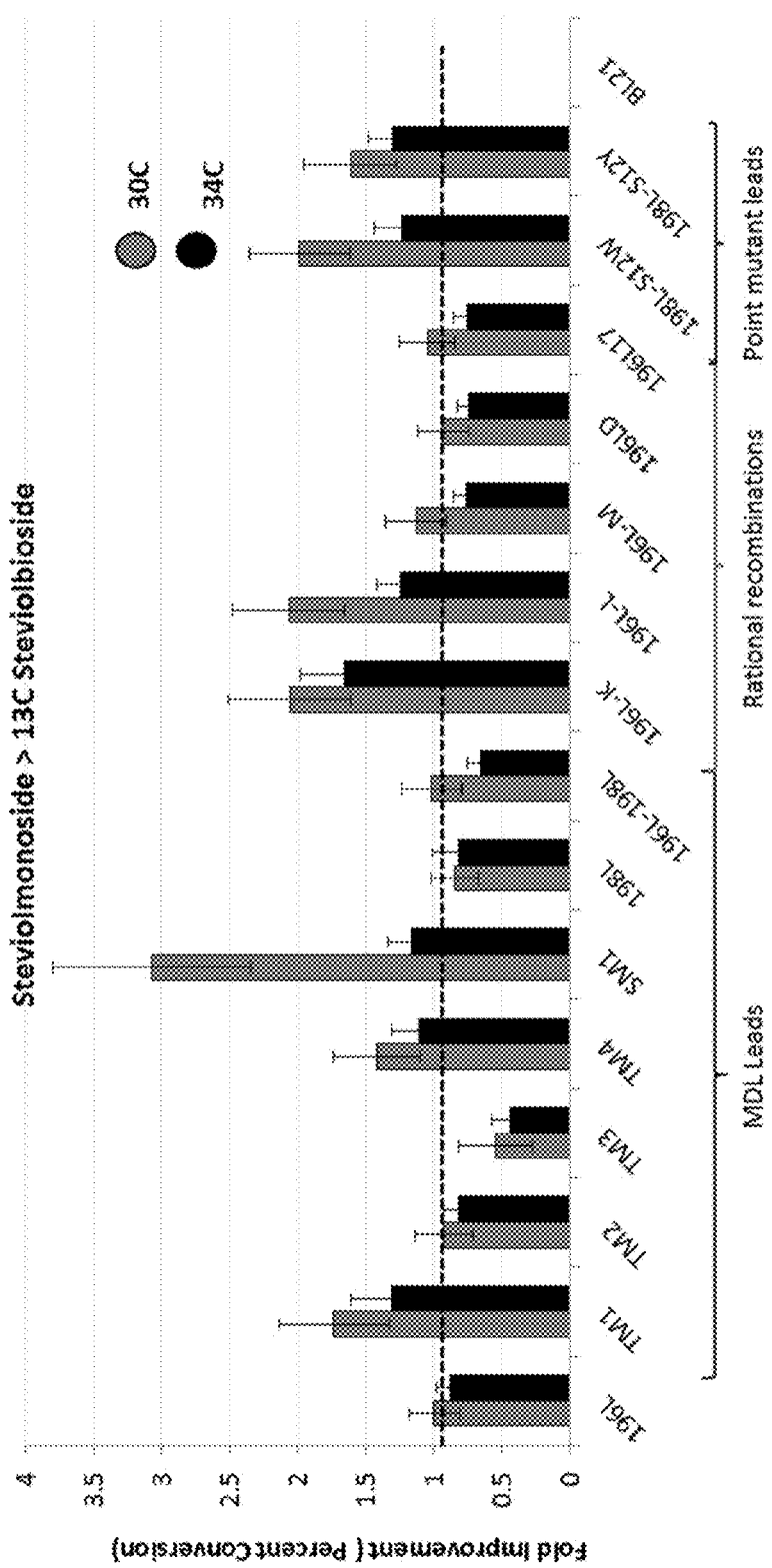

MbUGT1,2 rational recombinations were made, and screened at 30 and 34° C. for conversion of Reb A to Reb D (FIG. 46A), as well as for conversion of Steviolmonoside to 13c Steviolbioside (FIG. 46B). These studies resulted in a circular permutant truncated to create a new N-terminus at residue 196, with mutations introduced at S16W, H422E, R430E, R434H (MbUGT1,2-2). In these studies, cells producing these enzymes were induced for 4 hours of protein production at the listed temperature, extracted, and assayed in vitro overnight. Substrate concentration is 1 mM.

Figure 47:
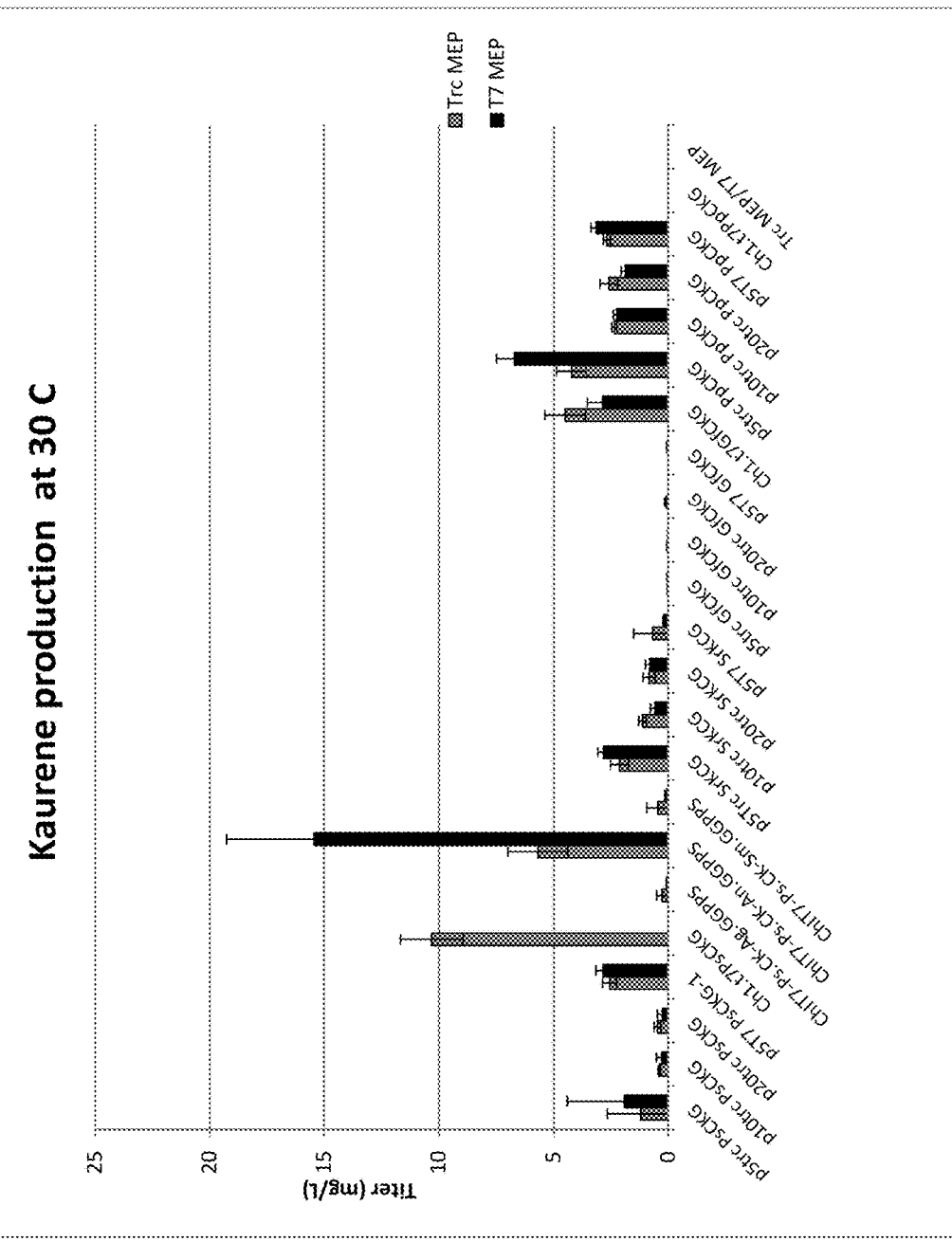
FIG. 47 shows kaurene production at 30° C. across various module constructs.
Figure 48:
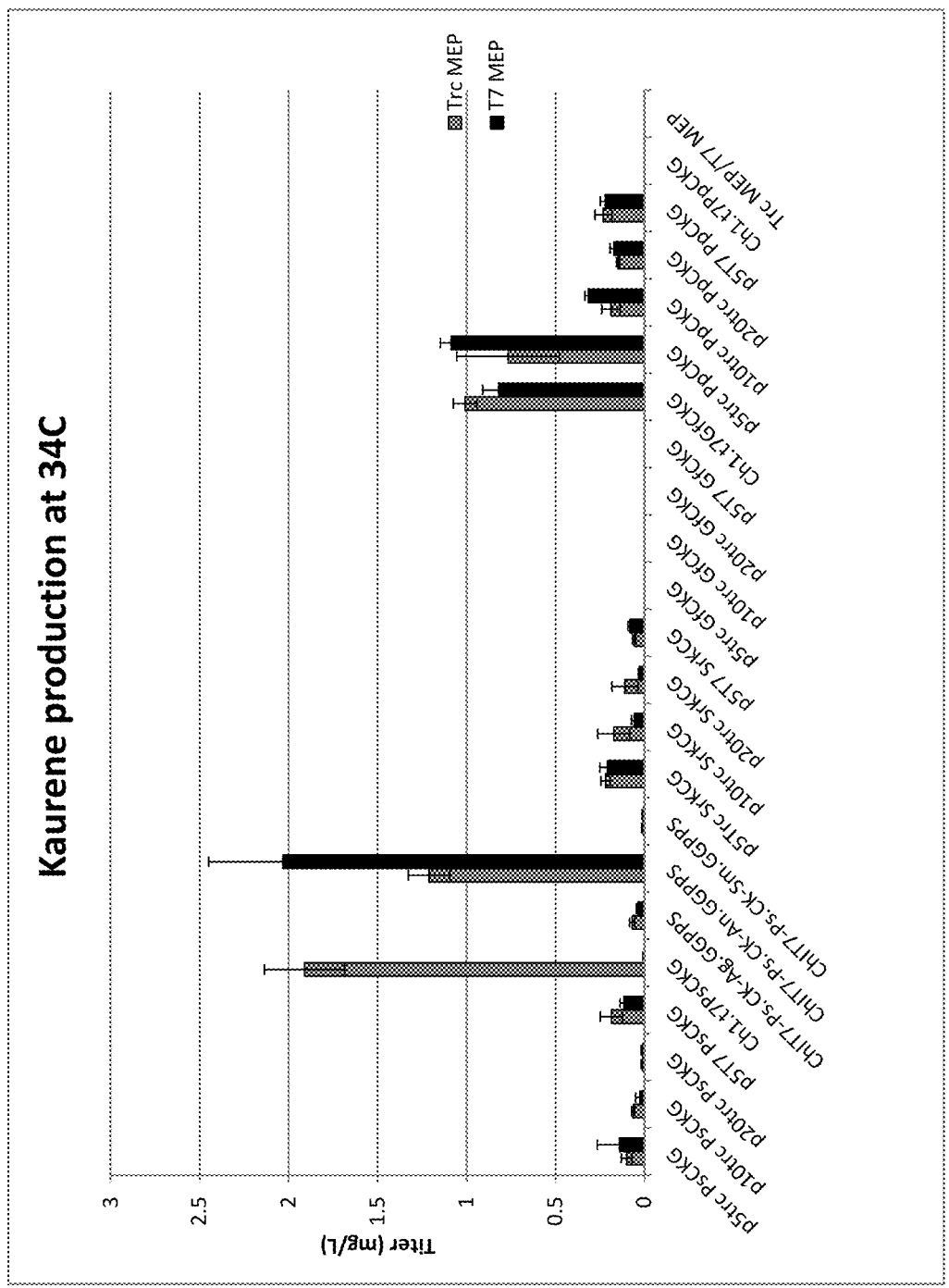
FIG. 48 shows kaurene production at 34° C. across various module constructs.

The effect of temperature on kaurene substrate production at 30 and 34° C. was tested. FIG. 47 shows kaurene production at 30° C. across various module constructs and FIG. 48 shows kaurene production at 34° C. across various module constructs. At 30° C., Ch1.T7-PsCK-AnGGPPS in T7MEP background gave highest kaurene titers (~15 mg/L). At 34° C., Ch1.T7-PsCK-AnGGPPS in T7MEP background showed the highest kaurene titers (~2 mg/L).

Figure 49:
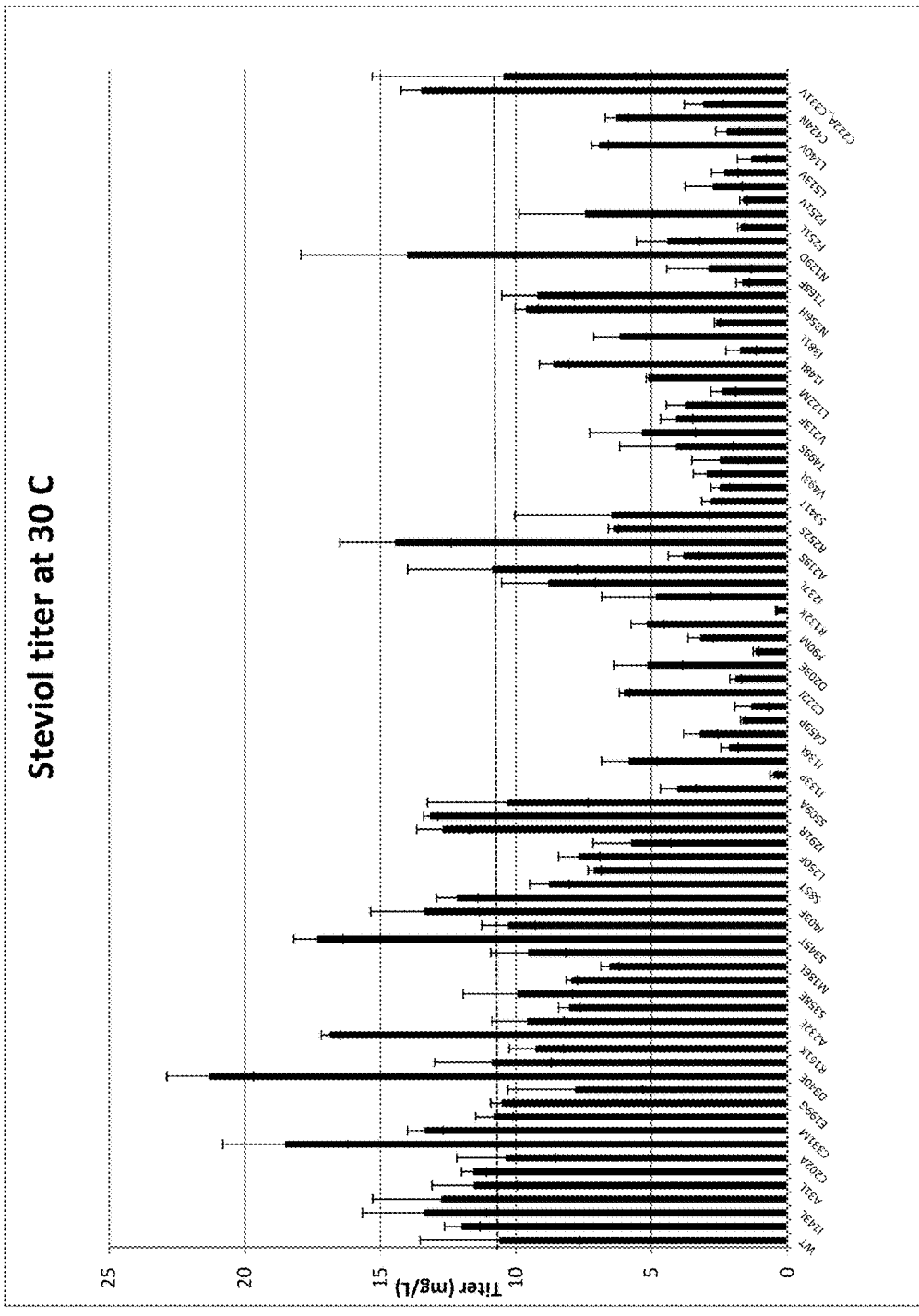
FIG. 49 shows production of Steviol at 30° C. across a library of AtKAH point mutations.
Figure 50:
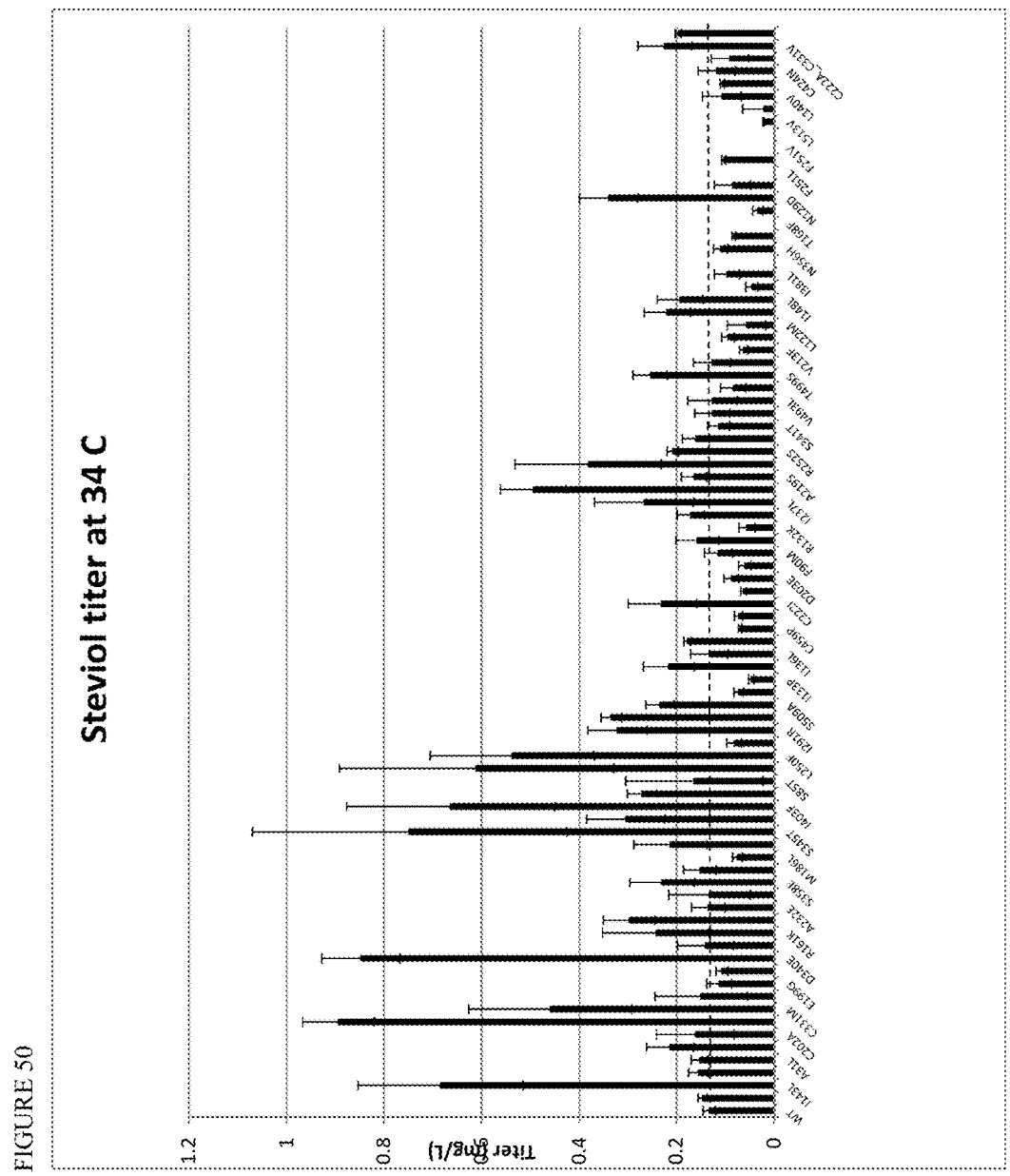
FIG. 50 shows production of Steviol at 34° C. across a library of AtKAH point mutations.

To investigate the thermotolerance of AtKAH, AtKAH point mutants were tested at 30° C. and 34° C. Conditions were: R media+glucose, 96 deep well plate, 3 days at 30° C. or 34° C. The strain background was p5Trc-(8RP) t14AtKAH-O-(8RP)t20SrKO-O-FLSrCPR. FIG. 49 shows production of Steviol at 30° C. across a library of AtKAH point mutations. FIG. 50 shows production of Steviol at 34° C. across a library of AtKAH point mutations. Various point mutations show improved thermotolerance that wild type, as shown by higher titers of steviol at 30 or 34° C.

Figure 51A:
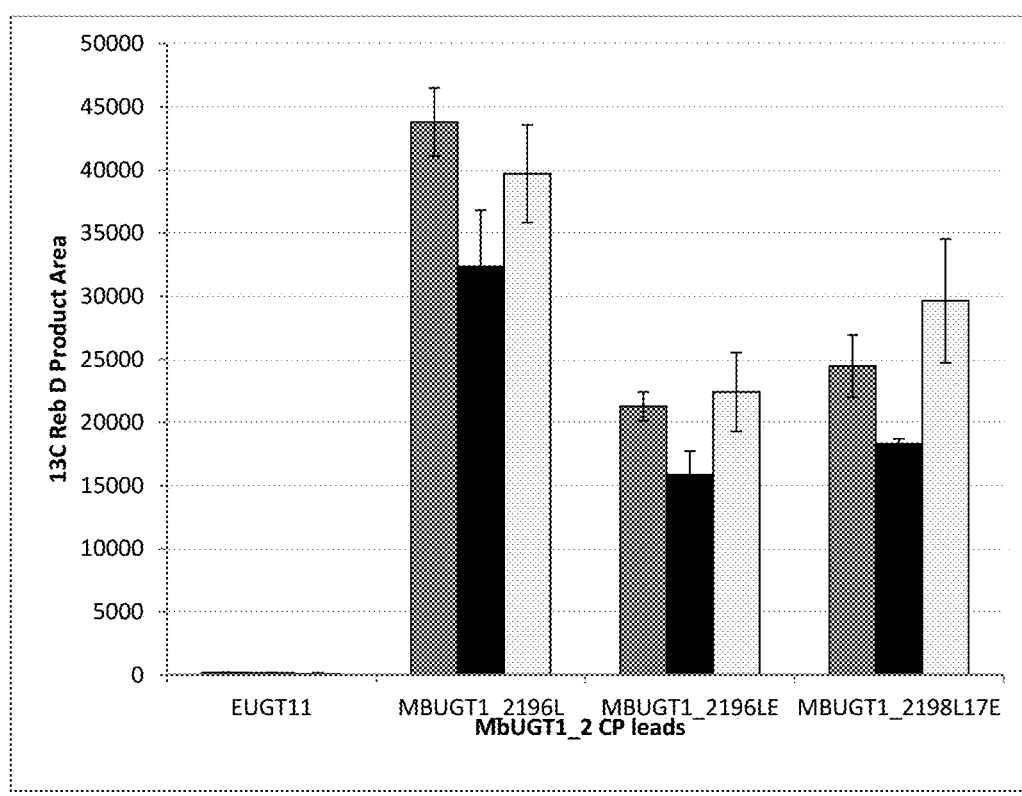
FIG. 51 shows activities of MbUGT1-2 circular permutants at 30° C., 34° C., and 37° C. Panel (A) shows conversion of Reb A to Reb D. Panel (B) shows conversion of Steviolmonoside to 13C Steviolbioside.
Figure 51B:
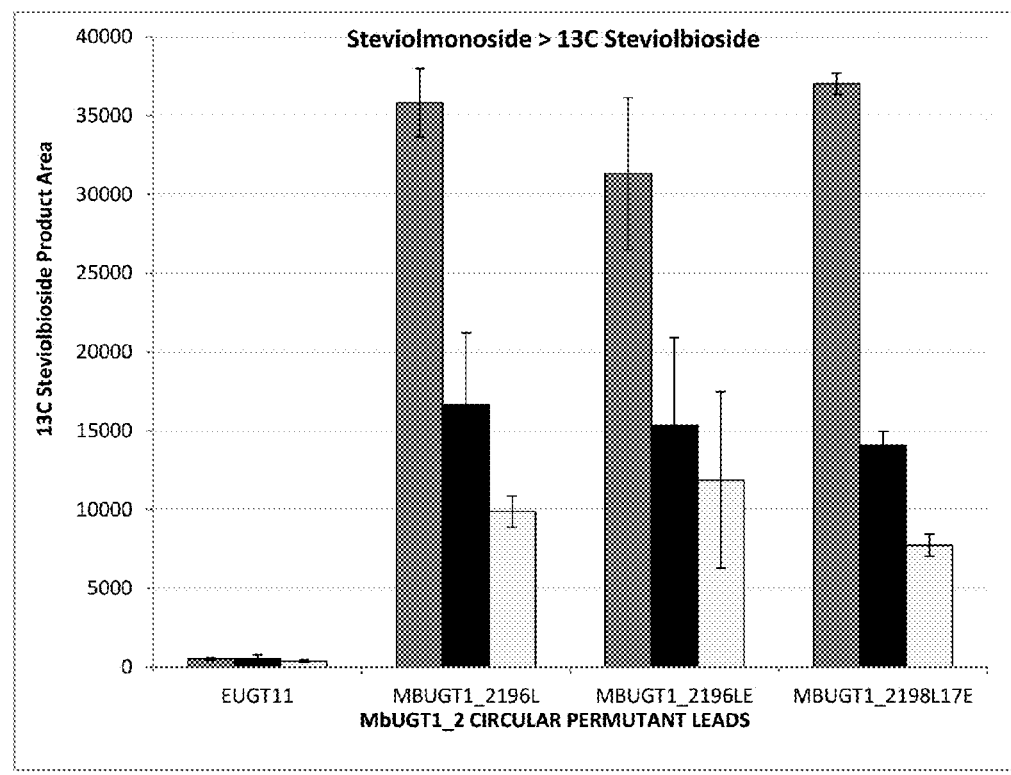

MbUGT1_2 circular permutants were tested for activity at 30, 33, and 37° C. FIG. 51(A),(B) shows activities of MbUGT1_2 circular permutants at 30° C., 34° C., and 37° C. Panel (A) shows conversion of Reb A to Reb D, while Panel (B) shows conversion of Steviolmonoside to 13C Steviolbioside. For both, expression of circular permutants was induced, followed by a four hour incubation period. As shown, EUGT11 lost its activity when induced at and above 30° C. In contrast, lead circular permutants seem to be most active at 30° C. MbUGT1_2 196L retains highest activity on both substrates.

Figure 52:
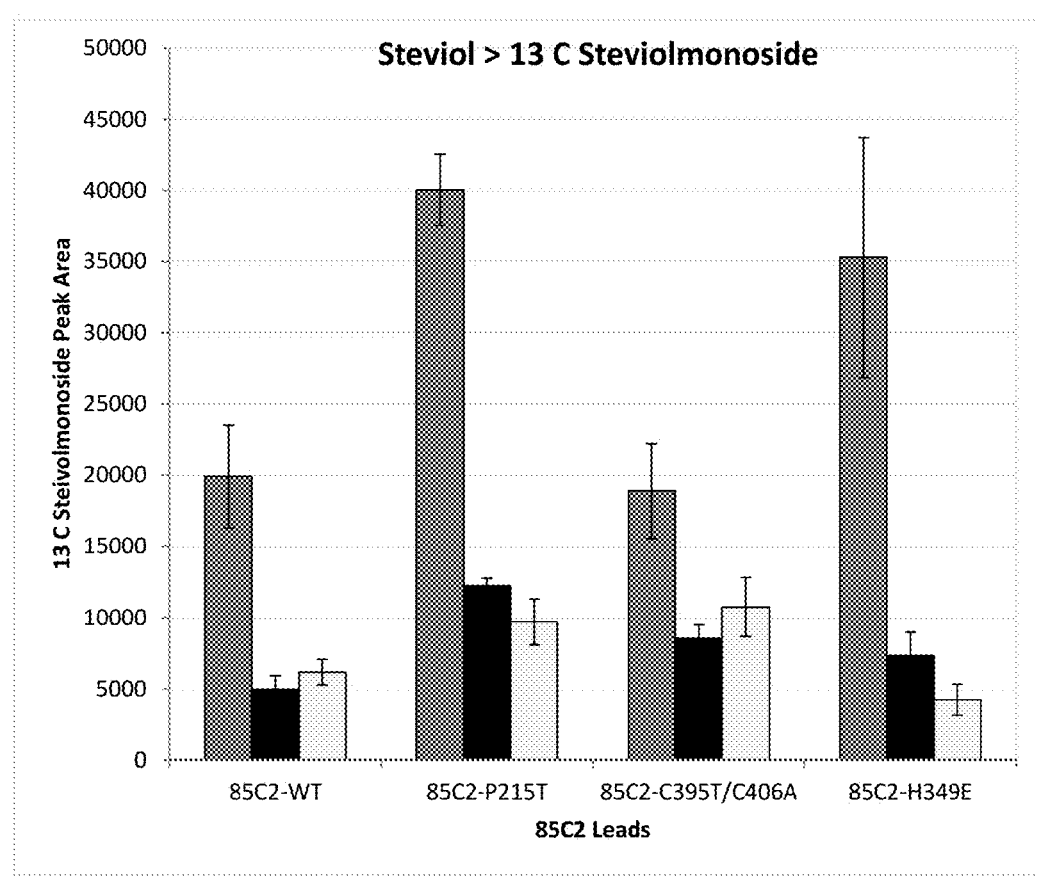
FIG. 52 shows activities of UGT85C2 mutants for conversion of Steviol to 13C Steviolmonoside at 30° C., 34° C., and 37° C.

FIG. 52 shows activities of UGT85C2 mutants for conversion of Steviol to 13C Steviolmonoside at 30° C., 34° C., and 37° C. Expression was induced, followed by a four hour incubation period. As shown, 85C2-WT and the leads retain comparable activity at 34° C. and 37° C., maintaining highest activity at 30° C.

Figure 53:
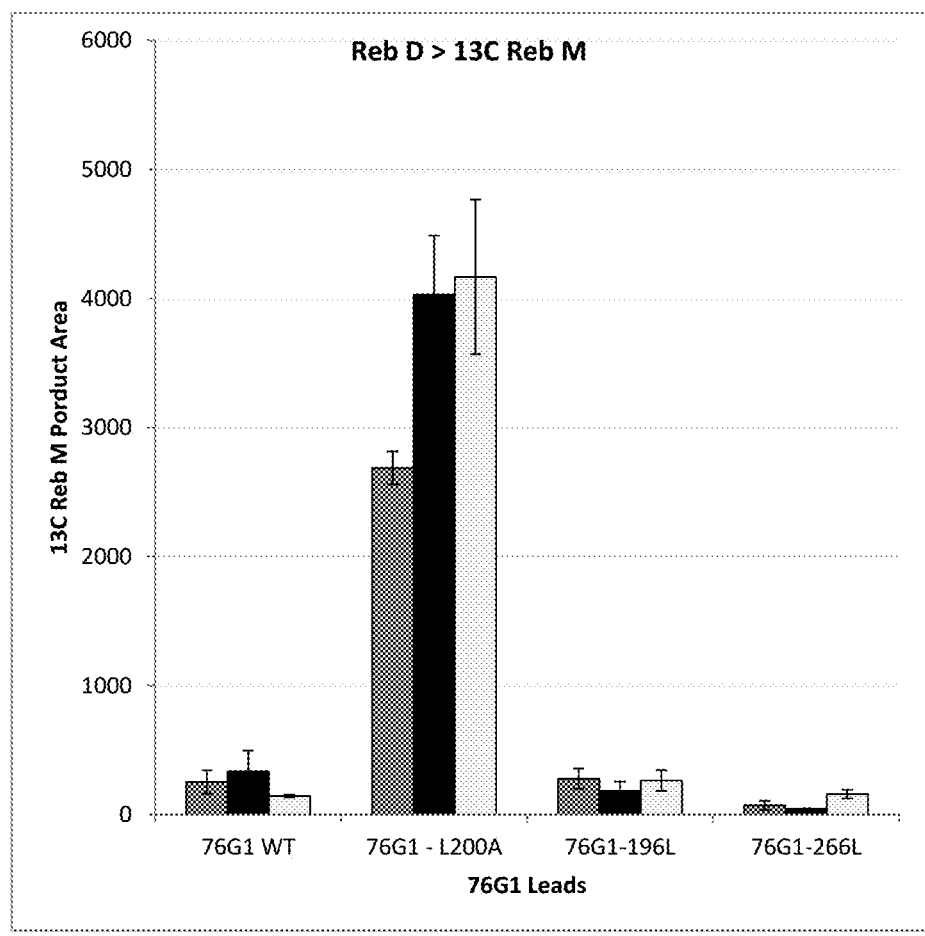
FIG. 53 shows activities of UGT76G1 mutants for conversion of Reb D to 13C Reb M at 30° C., 34° C., and 37° C.

FIG. 53 shows activities of UGT76G1 mutants for conversion of Reb D to 13C Reb M at 30° C., 34° C., and 37° C. Expression was induced, followed by a four hour incubation period. 76G1-L200A is particularly active when induced and assayed at the higher temperatures, possibly due to a greater amount of protein.

Figure 54:
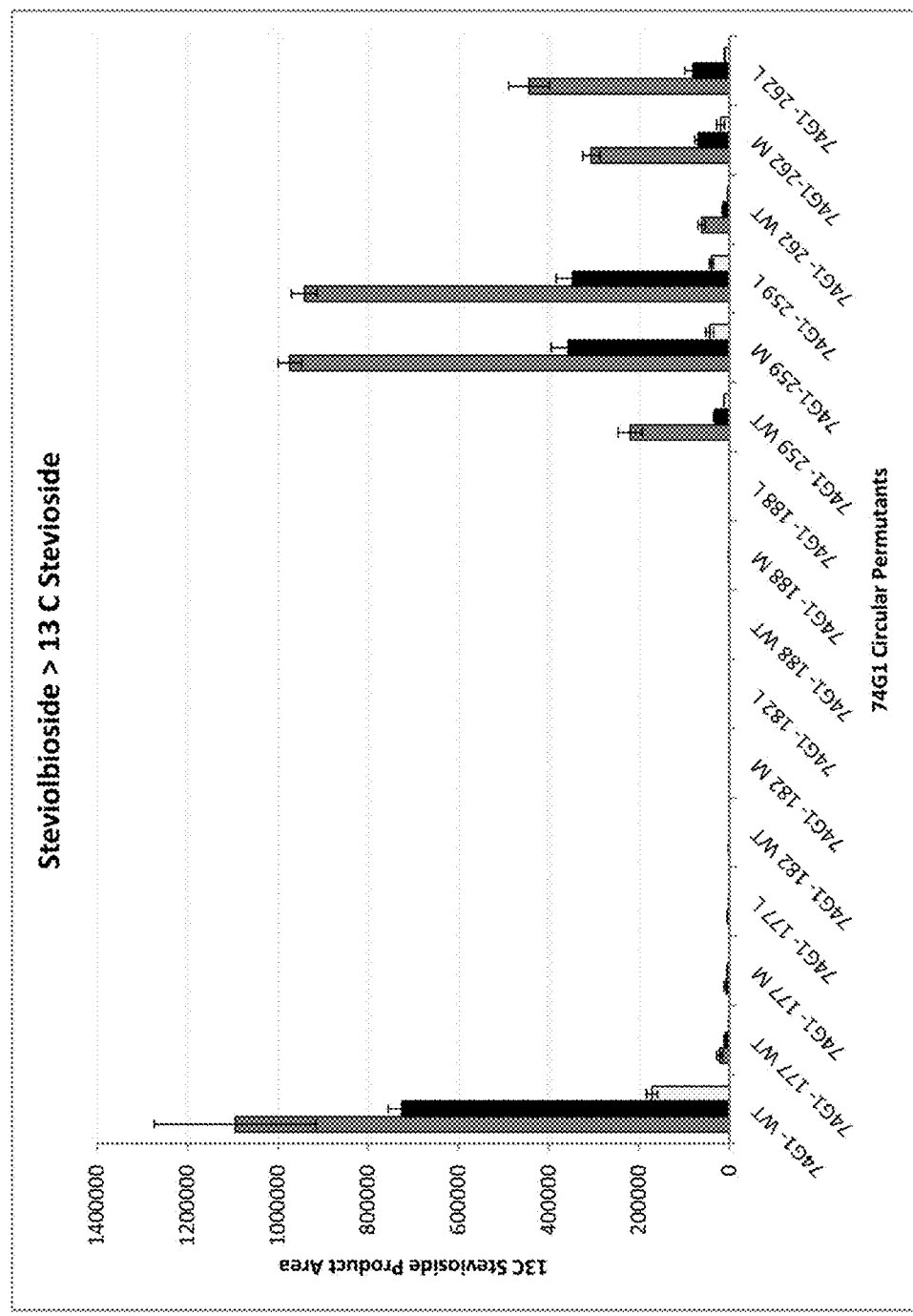
FIG. 54 shows activities of UGT74G1 circular permutants for conversion of Steviolbioside to 13C Stevioside at 30° C., 34° C., and 37° C.

FIG. 54 shows activities of UGT74G1 circular permutants for conversion of Steviolbioside to 13C Stevioside at 30° C., 34° C., and 37° C. 74G1-WT retains activity on Steviolbioside even when induced and assayed at 37 C. The circular permutants 74G1-259M and 74G1-259L show a significant drop in activity at higher temperatures.

REFERENCES

1. Sharma M, Thakral N K, & Thakral S (2009) *Chemistry and in vivo profile of ent-kaurene glycosides of Stevia rebaudiana Bertoni: An overview. Natural Product Radiance* 8(2):181-189.
2. Chang M C Y & Keasling J D (2006) *Production of isoprenoid pharmaceuticals by engineered microbes. Nature chemical biology* 2(12):674-681.
3. Ajikumar P K, et al. (2008) *Terpenoids: opportunities for biosynthesis of natural product drugs using engineered microorganisms. Molecular pharmaceutics* 5(2):167-190.
4. Ajikumar P K, et al. (2010) *Isoprenoid pathway optimization for Taxol precursor overproduction in Escherichia coli. Science* 330(6000):70-74.
5. Dugar D & Stephanopoulos G (2011) *Relative potential of biosynthetic pathways for biofuels and bio-based products. Nature Biotechnology* 29(12):1074-1078.
6. Leonard E, et al. (2010) *Combining metabolic and protein engineering of a terpenoid biosynthetic pathway for overproduction and selectivity control. Proceedings of the National Academy of Sciences* 107(31): 13654-13659.
7. Yadav V G, De Mey M, Giaw Lim C, Kumaran Ajikumar P, & Stephanopoulos G (2012) *The future of metabolic engineering and synthetic biology: Towards a systematic practice. Metabolic Engineering.*
8. Yadav S K & Guleria P (2012) *Steviol glycosides from Stevia: Biosynthesis pathway review and their application in foods and medicine. Critical Reviews in Food Science and Nutrition* 52(11):988-998.
9. Richman A S, Gijzen M, Starratt A N, Yang Z, & Brandle J E (1999) *Diterpene synthesis in Stevia rebaudiana: recruitment and up-regulation of key enzymes from the gibberellin biosynthetic pathway. The Plant Journal* 19(4):411-421.
10. Hayashi K, et al. (2006) *Identification and functional analysis of bifunctional ent-kaurene synthase from the moss Physcomitrella patens. FEBS letters* 580(26):6175-6181.
11. Toyomasu T, et al. (2000) *Cloning of a full-length cDNA encoding ent-kaurene synthase from Gibberella fujikuroi: functional analysis of a bifunctional diterpene cyclase. Bioscience, biotechnology, and biochemistry* 64(3):660-664.
12. Helliwell C A, Poole A, Peacock W J, & Dennis E S (1999) *Arabidopsis ent-kaurene oxidase catalyzes three steps of gibberellin biosynthesis. Plant Physiology* 119 (2):507-510.
13. Brandle J & Telmer P (2007) *Steviol glycoside biosynthesis. Phytochemistry* 68(14):1855-1863.
14. Richman A, Swanson A, Humphrey T, Chapman R, McGarvey B, Pocs R & Brandle J. (2005) *Functional genomics uncovers three glucosyltransferases involved in the synthesis of the major sweet glucosides of Stevia rebaudiana. The Plant Journal* 41(1):56-67.
15. Hefner J, Ketchum R E B, & Croteau R (1998) *Cloning and Functional Expression of a cDNA Encoding Geranylgeranyl Diphosphate Synthase from Taxus canadensis and Assessment of the Role of this Prenyltransferase in Cells Induced for Taxol Production. Archives of biochemistry and biophysics* 360(1): 62-74.
16. Burke C & Croteau R (2002) *Interaction with the small subunit of geranyl diphosphate synthase modifies the chain length specificity of geranylgeranyl diphosphate synthase to produce geranyl diphosphate. Journal of Biological Chemistry* 277(5):3141-3149.
17. Galagan J E, et al. (2005) *Sequencing of Aspergillus nidulans and comparative analysis with A. fumigatus and A. oryzae. Nature* 438(7071):1105-1115.
18. Kim S Y, et al. (2009) *Cloning and heterologous expression of the cyclooctatin biosynthetic gene cluster afford a diterpene cyclase and two P450 hydroxylases. Chemistry & biology* 16(7):736-743.
19. Kawaide H, Imai R, Sassa T, & Kamiya Y (1997) *ent-Kaurene Synthase from the Fungus Phaeosphaeria sp. L487. Journal of Biological Chemistry* 272(35):21706-21712.
20. Humphrey T V, Richman A S, Menassa R, & Brandle J E (2006) *Spatial organisation of four enzymes from Stevia rebaudiana that are involved in steviol glycoside synthesis. Plant molecular biology* 61(1):47-62.
21. Miyazaki S, Katsumata T, Natsume M, & Kawaide H (2011) *The CYP701B1 of Physcomitrella patens is an ent-kaurene oxidase that resists inhibition by uniconazole-P. FEBS letters* 585(12):1879-1883.
22. Mizutani M & Ohta D (1998) *Two Isoforms of NADPH: Cytochrome P450 Reductase in Arabidopsis thaliana: Gene Structure, Heterologous Expression in Insect Cells, and Differential Regulation. Plant Physiology* 116(1): 357-367.
23. Yamaguchi S, Nomura T, Magome H, Kamiya Y (2008) Method for producing steviol synthetase gene and steviol. US Patent Application Publication No. 2008/0271205.
24. Kim K K, Sawa Y, & Shibata H (1996) *Hydroxylation of ent-Kaurenoic Acid to Steviol in Stevia rebaudiana Bertoni-Purification and Partial Characterization of the Enzyme. Archives of biochemistry and biophysics* 332(2): 223-230.
25. Schuler M A (1996) *Plant cytochrome P450 monooxygenases. Critical reviews in plant sciences* 15(3):235-284.
26. Heinemann U & Hahn M. (1995) *Circular permutation of polypeptide chains: implications for protein folding and stability. Prog. Biophys. Molec. Biol.* 64(2-3):121-143.
27. Yu Y, Lutz S (2011) *Circular permutation: a different way to engineer enzyme structure and function. Trends Biotechnol* 29(1):18-25.
28. Houghton-Larsen J, et al. Recombinant production of steviol glycosides. PCT Publication No. WO 2013/022989.

TABLE 1

Summary of enzyme/gene sequences enabling biosynthesis of steviol.

| No. | Enzyme | Species | Gene ID | Protein ID |
|---|---|---|---|---|
| 1 | TcGGPPS | *Taxus canadensis* | AF081514.1 | AAD16018.1 |
| 2 | AgGGPPS | *Abies grandis* | AF425235.2 | AAL17614.2 |
| 3 | AnGGPPS | *Aspergillus nidulans* | XM_654104.1 | XP_659196.1 |
| 4 | SmGGPPS | *Streptomyces melanosporofaciens* | AB448947.1 | BAI44337.1 |
| 5 | MbGGPPS | *Marine bacterium* 443 | n/a | AAR37858.1 |
| 6 | PhGGPPS | *Paracoccus haeundaensis* | n/a | AAY28422.1 |
| 7 | CtGGPPS | *Chlorobium tepidum* TLS | NC_002932.3 | NP_661160.1 |
| 8 | SsGGPPS | *Synechococcus* sp. JA-3-3Ab | n/a | ABC98596.1 |
| 9 | Ss2GGPPS | *Synechocystis* sp. PCC 6803 | n/a | BAA16690.1 |
| 10 | TmGGPPS | *Thermotoga maritima* HB8 | n/a | NP_227976.1 |
| 11 | CgGGPPS | *Corynebacterium glutamicum* | n/a | NP_601376.2 |
| 12 | TtGGPPS | *Thermus thermophillus* HB27 | n/a | YP_143279.1 |
| 13 | PcGGPPS | *Pyrobaculum calidifontis* JCM 11548 | n/a | WP_011848845.1 |
| 14 | SrCPPS | *Stevia rebaudiana* | AF034545.1 | AAB87091.1 |
| 15 | EtCPPS | *Erwina tracheiphila* | n/a | WP_020322919.1 |
| 16 | SfCPPS | *Sinorhizobium fredii* | n/a | WP_010875301.1 |
| 17 | SrKS | *Stevia rebaudiana* | AF097311.1 | AAD34295.1 |
| 18 | EtKS | *Erwina tracheiphila* | n/a | WP_020322918.1 |
| 19 | SfKS | *Sinorhizobium fredii* | n/a | WP_010875302.1 |
| 20 | GfCPPS/KS | *Gibberella fujikuroi* | AB013295.1 | Q9UVY5.1 |
| 21 | PpCPPS/KS | *Physcomitrella patens* | AB302933.1 | BAF61135.1 |
| 22 | PsCPPS/KS | *Phaeosphaeria* sp. L487 | AB003395.1 | O13284.1 |
| 23 | AtKO | *Arabidopsis thaliana* | NM_122491.2 | NP_197962.1 |
| 24 | SrKO | *Stevia rebaudiana* | AY364317.1 | AAQ63464.1 |
| 25 | PpKO | *Physcomitrella patens* | AB618673.1 | BAK19917.1 |
| 26 | AtCPR | *Arabidopsis thaliana* | X66016.1 | CAA46814.1 |
| 27 | SrCPR | *Stevia rebaudiana* | DQ269454.4 | ABB88839.2 |
| 28 | AtKAH | *Arabidopsis thaliana* | NM_122399.2 | NP_197872.1 |
| 29 | SrKAH1 | *Stevia rebaudiana* | DQ398871.3 | ABD60225.1 |
| 30 | SrKAH2 | *Stevia rebaudiana* | n/a | n/a |

TABLE 2

Strains constructed to evaluate pathways for kaurene biosynthesis.

| Strain # | Upstream | Downstream |
|---|---|---|
| 1 | WT | Ch1.T7-KCG |
| 2 | Ch1.Trc-MEP | Ch1.T7-KCG |
| 3 | Ch1.T7-MEP | Ch1.T7-KCG |
| 4 | WT | p5-Trc-KCG |
| 5 | Ch1.Trc-MEP | p5-Trc-KCG |
| 6 | Ch1.T7-MEP | p5-Trc-KCG |
| 7 | WT | p10-Trc-KCG |
| 8 | Ch1.Trc-MEP | p10-Trc-KCG |
| 9 | Ch1.T7-MEP | p10-Trc-KCG |
| 10 | WT | p20-Trc-KCG |
| 11 | Ch1.Trc-MEP | p20-Trc-KCG |
| 12 | Ch1.T7-MEP | p20-Trc-KCG |
| 13 | WT | p5-T7-KCG |
| 14 | Ch1.Trc-MEP | p5-T7-KCG |
| 15 | Ch1.T7-MEP | p5-T7-KCG |
| 16 | WT | Ch1.T7-PpCKG |
| 17 | Ch1.Trc-MEP | Ch1.T7-PpCKG |
| 18 | Ch1.T7-MEP | Ch1.T7-PpCKG |
| 19 | WT | p5-Trc-PpCKG |
| 20 | Ch1.Trc-MEP | p5-Trc-PpCKG |
| 21 | Ch1.T7-MEP | p5-Trc-PpCKG |
| 22 | WT | p10-Trc-PpCKG |
| 23 | Ch1.Trc-MEP | p10-Trc-PpCKG |
| 24 | Ch1.T7-MEP | p10-Trc-PpCKG |
| 25 | WT | p20-Trc-PpCKG |
| 26 | Ch1.Trc-MEP | p20-Trc-PpCKG |
| 27 | Ch1.T7-MEP | p20-Trc-PpCKG |
| 28 | WT | p5-T7-PpCKG |
| 29 | Ch1.Trc-MEP | p5-T7-PpCKG |
| 30 | Ch1.T7-MEP | p5-T7-PpCKG |
| 31 | WT | Ch1.T7-GfCKG |
| 32 | Ch1.Trc-MEP | Ch1.T7-GfCKG |
| 33 | Ch1.T7-MEP | Ch1.T7-GfCKG |
| 34 | WT | p5-Trc-GfCKG |
| 35 | Ch1.Trc-MEP | p5-Trc-GfCKG |
| 36 | Ch1.T7-MEP | p5-Trc-GfCKG |
| 37 | WT | p10-Trc-GfCKG |
| 38 | Ch1.Trc-MEP | p10-Trc-GfCKG |
| 39 | Ch1.T7-MEP | p10-Trc-GfCKG |
| 40 | WT | p20-Trc-GfCKG |
| 41 | Ch1.Trc-MEP | p20-Trc-GfCKG |
| 42 | Ch1.T7-MEP | p20-Trc-GfCKG |
| 43 | WT | p5-T7-GfCKG |
| 44 | Ch1.Trc-MEP | p5-T7-GfCKG |
| 45 | Ch1.T7-MEP | p5-T7-GfCKG |
| 46 | WT | Ch1.T7-PsCKG |
| 47 | Ch1.Trc-MEP | Ch1.T7-PsCKG |
| 48 | Ch1.T7-MEP | Ch1.T7-PsCKG |
| 49 | WT | p5-Trc-PsCKG |
| 50 | Ch1.Trc-MEP | p5-Trc-PsCKG |
| 51 | Ch1.T7-MEP | p5-Trc-PsCKG |
| 52 | WT | p10-Trc-PsCKG |
| 53 | Ch1.Trc-MEP | p10-Trc-PsCKG |
| 54 | Ch1.T7-MEP | p10-Trc-PsCKG |
| 55 | WT | p20-Trc-PsCKG |
| 56 | Ch1.Trc-MEP | p20-Trc-PsCKG |
| 57 | Ch1.T7-MEP | p20-Trc-PsCKG |
| 58 | WT | p5-T7-PsCKG |

TABLE 2-continued

Strains constructed to evaluate pathways for kaurene biosynthesis.

| Strain # | Upstream | Downstream |
|---|---|---|
| 59 | Ch1.Trc-MEP | p5-T7-PsCKG |
| 60 | Ch1.T7-MEP | p5-T7-PsCKG |

TABLE 3

Combinations of upstream and downstream pathway configurations tested for KO ctivity and kaurenoic acid biosynthesis. Ch1 = 1 copy chromosomally integrated, p5/p10/p20 = plasmids of increasing copy number, Trc/T7 = promoters of increasing ranscriptional strength.

| Upstream/Downstream | Ch1.T7-MEP Ch1.T7-SrKCG | Ch1.T7-MEP p10Trc-SrKCG | Ch1.T7-MEP p20Trc-SrKCG |
|---|---|---|---|
| p5Trc-(8RP)t4SrKO-L-t69SrCPR | ✔ | ✔ | ✔ |
| p5Trc-(8RP)t20SrKO-L-t69SrCPR | ✔ | ✔ | ✔ |
| p5Trc-(8RP)t39SrKO-L-t69SrCPR | ✔ | ✔ | ✔ |
| p5Trc-(8RP)t39SrKO-(8RP)t69SrCPR | ✔ | ✔ | ✔ |
| p5Trc-(MA)t39SrKO-(8RP)t69SrCPR | ✔ | ✔ | ✔ |

TABLE 4

Fold-change in in vivo activity over parental enzyme for point mutants of SrKO. The fold increases describe the change in kaurene remaining in this strain, or the change in kaurenoic acid produced, both relative to the wild-type (non-mutated) enzyme-bearing parental strain.

| Wild-type residue | Position | Mutation | Fold increase in kaurene | Fold increase in kaurenoic acid |
|---|---|---|---|---|
| A | 116 | R | 1.0 | 1.8 |
| T | 119 | S | 0.9 | 1.9 |
| I | 183 | V | 1.0 | 1.7 |
| H | 382 | Y | 1.0 | 1.8 |

TABLE 5

Combinations of upstream and downstream pathway configurations tested for KO/KAH activity and steviol biosynthesis. Ch1 = 1 copy chromosomally integrated, p5 and p10 = plasmids of increasing copy number, Trc/T7 = promoters of increasing transcriptional strength.

| Expression module | | Steviol Detected |
|---|---|---|
| Ch1.T7-MEP Ch1.T7-(8RP)t69SrCPR p10Trc-SrKCG | p5Trc-(8RP)t39SrKO-(8RP)t7SrKAH | ++ |
| | p5Trc-(8RP)t39SrKO-(8RP)t21SrKAH | ++ |
| | p5Trc-(8RP)t39SrKO-(8RP)t29SrKAH | + |

TABLE 6

Fold-change in activity over parental enzyme for point mutants of AtKAH. The fold increases describe the change in kaurenoic acid remaining in this strain, or the change in steviol produced, both relative to the wild-type (non-mutated) enzyme-bearing parental strain.

| Wild-type residue | Position | Mutation | Wild-type residue | Position | Mutation | Fold increase kaurenoic acid | Fold increase steviol |
|---|---|---|---|---|---|---|---|
| A | 25 | L | | | | 0.7 | 1.6 |
| K | 37 | R | | | | 0.8 | 1.4 |
| S | 79 | T | | | | 0.7 | 1.6 |
| F | 84 | I | | | | 1.3 | 0.0 |
| F | 84 | M | | | | 1.2 | 0.2 |
| Y | 95 | F | | | | 1.1 | 1.0 |
| H | 104 | I | | | | 1.4 | 0.0 |
| I | 107 | M | | | | 1.0 | 1.2 |
| L | 116 | M | | | | 1.4 | 0.9 |
| T | 119 | C | | | | 0.7 | 1.5 |
| N | 123 | D | | | | 0.9 | 1.1 |
| R | 126 | K | | | | 1.4 | 0.0 |
| I | 127 | P | | | | 1.1 | 0.0 |
| I | 127 | V | | | | 1.1 | 0.1 |
| I | 130 | L | | | | 1.0 | 0.0 |
| L | 134 | V | | | | 1.3 | 0.7 |
| I | 137 | L | | | | 0.3 | 1.9 |
| I | 142 | L | | | | 1.2 | 0.8 |
| I | 142 | V | | | | 0.5 | 2.1 |
| I | 143 | L | | | | 1.7 | 0.0 |
| R | 155 | K | | | | 0.9 | 2.0 |
| T | 162 | F | | | | 1.4 | 0.0 |
| H | 163 | M | | | | 1.2 | 0.2 |
| I | 166 | V | | | | 0.3 | 1.2 |
| M | 180 | L | | | | 1.3 | 1.5 |
| V | 188 | I | | | | 1.0 | 1.1 |
| E | 193 | G | | | | 1.1 | 1.7 |
| C | 196 | A | | | | 0.9 | 1.5 |
| D | 197 | E | | | | 1.7 | 0.8 |
| V | 207 | F | | | | 1.4 | 0.5 |
| A | 213 | S | | | | 0.7 | 0.9 |
| C | 216 | A | C | 325 | V | 0.8 | 0.9 |
| C | 216 | I | | | | 1.1 | 1.0 |
| C | 216 | S | | | | 1.3 | 0.0 |
| A | 226 | E | | | | 0.9 | 1.5 |
| I | 231 | L | | | | 0.3 | 0.8 |

TABLE 6-continued

Fold-change in activity over parental enzyme for point mutants of AtKAH. The fold increases describe the change in kaurenoic acid remaining in this strain, or the change in steviol produced, both relative to the wild-type (non-mutated) enzyme-bearing parental strain.

| Wild-type residue | Position | Mutation | Wild-type residue | Position | Mutation | Fold increase kaurenoic acid | Fold increase steviol |
|---|---|---|---|---|---|---|---|
| L | 235 | Q |  |  |  | 0.3 | 2.4 |
| I | 238 | M |  |  |  | 1.5 | 0.2 |
| L | 244 | F |  |  |  | 0.9 | 1.4 |
| F | 245 | L |  |  |  | 1.6 | 0.0 |
| F | 245 | V |  |  |  | 1.5 | 0.0 |
| R | 246 | S |  |  |  | 1.1 | 0.8 |
| F | 247 | L |  |  |  | 1.0 | 1.1 |
| L | 272 | I |  |  |  | 1.7 | 0.0 |
| S | 274 | D |  |  |  | 1.0 | 1.3 |
| S | 275 | L |  |  |  | 0.6 | 1.2 |
| I | 285 | R |  |  |  | 0.6 | 1.7 |
| C | 287 | S |  |  |  | 0.7 | 1.7 |
| K | 292 | E |  |  |  | 1.2 | 0.6 |
| Q | 297 | E |  |  |  | 1.0 | 0.9 |
| C | 307 | S |  |  |  | 0.6 | 0.0 |
| V | 322 | I |  |  |  | 1.1 | 1.4 |
| C | 325 | I |  |  |  | 0.5 | 2.4 |
| C | 325 | M |  |  |  | 0.6 | 2.2 |
| F | 330 | L |  |  |  | 1.0 | 1.5 |
| D | 334 | E |  |  |  | 0.3 | 2.2 |
| S | 335 | T |  |  |  | 0.7 | 0.5 |
| S | 339 | T |  |  |  | 0.2 | 2.2 |
| N | 350 | H |  |  |  | 0.9 | 1.1 |
| S | 352 | E |  |  |  | 0.7 | 1.5 |
| S | 363 | E |  |  |  | 0.8 | 1.3 |
| E | 373 | D |  |  |  | 1.1 | 1.6 |
| I | 375 | L |  |  |  | 1.2 | 0.8 |
| V | 381 | L |  |  |  | 1.3 | 0.7 |
| M | 389 | L |  |  |  | 1.2 | 0.9 |
| I | 397 | F |  |  |  | 0.8 | 1.7 |
| C | 418 | N |  |  |  | 1.4 | 0.5 |
| S | 446 | A |  |  |  | 0.6 | 1.2 |
| E | 447 | N |  |  |  | 0.8 | 1.4 |
| C | 453 | P |  |  |  | 0.7 | 0.0 |
| I | 460 | M |  |  |  | 1.3 | 0.2 |
| V | 470 | L |  |  |  | 0.7 | 1.7 |
| G | 475 | A |  |  |  | 1.1 | 1.3 |
| M | 477 | V |  |  |  | 0.8 | 0.6 |
| V | 487 | L |  |  |  | 1.3 | 1.0 |
| T | 493 | S |  |  |  | 1.1 | 1.2 |
| T | 497 | N |  |  |  | 0.5 | 1.0 |
| Q | 499 | V |  |  |  | 0.6 | 1.6 |
| S | 503 | A |  |  |  | 0.3 | 1.0 |
| H | 504 | F |  |  |  | 1.1 | 0.2 |
| K | 505 | R |  |  |  | 0.5 | 0.9 |
| L | 506 | M |  |  |  | 1.6 | 0.0 |
| L | 507 | I |  |  |  | 1.5 | 0.0 |
| L | 507 | T |  |  |  | 1.6 | 0.0 |
| L | 507 | V |  |  |  | 1.5 | 0.0 |

TABLE 7

Modifications to *E. coli* strain to improve UDP-glucose substrate pools and support high-titer production of steviol glycosides.

| Modification | Type | Gene ID (BioCyc) |
|---|---|---|
| ΔgalE | Deletion | EG10362 |
| ΔgalT | Deletion | EG10366 |
| ΔgalK | Deletion | EG10363 |
| ΔgalM | Deletion | EG11698 |
| ΔushA | Deletion | EG11060 |
| Δagp | Deletion | EG10033 |
| Δpgm | Deletion | EG12144 |
| galU (*Escherichia coli* K-12 substr. MG1655) | Insertion | EG11319 |
| ugpA (*Bifidobacterium bifidum* PRL2010) | Insertion | BBPR_0976 |
| spl (*Bifidobacterium adolescentis* ATCC 15703) | Insertion | BAD_0078 |

TABLE 8

Enzymes known to catalyze reactions required for steviol glycoside biosynthesis [to RebM].

| Substrate | Product | Type of glycosylation | Enzyme 1 | Enzyme 2 | Enzyme 3 | Enzyme 4 |
|---|---|---|---|---|---|---|
| Steviol | Steviolmonoside | C13 | SrUGT85C2 | | | |
| Steviol | C19-Glu-Steviol | C19 | SrUGT74G1 | MbUGTc19 | | |
| Steviolmonoside | Steviolbioside | 1-2' | SrUGT91D1 | SrUGT91D2 | OsUGT1-2 | MbUGT1-2 |
| Steviolmonoside | Rubusoside | C19 | SrUGT74G1 | MbUGTc19 | | |
| C19-Glu-Steviol | Rubusoside | C13 | SrUGT85C2 | | | |
| Steviolbioside | Stevioside | C19 | SrUGT74G1 | MbUGTc19 | | |
| Steviolbioside | RebB | 1-3' | SrUGT76G1 | | | |
| Stevioside | RebE | 1-2' | SrUGT91D1 | SrUGT91D2 | OsUGT1-2 | MbUGT1-2 |
| Stevioside | RebA | 1-3' | SrUGT76G1 | | | |
| RebB | RebA | C19 | SrUGT74G1 | MbUGTc19 | | |
| RebE | RebD | 1-3' | SrUGT76G1 | | | |
| RebA | RebD | 1-2' | SrUGT91D1 | SrUGT91D2 | OsUGT1-2 | MbUGT1-2 |
| RebD | RebM | 1-3' | SrUGT76G1 | | | |

TABLE 9

Summary of enzyme/gene sequences for biosynthesis of steviol glycosides, including RebM.

| Type of glycosylation | Enzyme | Gene ID | Protein ID | Description |
|---|---|---|---|---|
| C13 | SrUGT85C2 | AY345978.1 | AAR06916.1 | |
| C19 | SrUGT74G1 | AY345982.1 | AAR06920.1 | |
| | MbUGTc19 | — | — | circular permutant of SrUGT74G1 |
| 1-2' | SrUGT91D1 | AY345980.1 | AAR06918.1 | |
| | SrUGT91D2 | ACE87855.1 | ACE87855.1 | |
| | SrUGT91D2e | — | — | US2011/038967 |
| | OsUGT1-2 | NM_001057542.1 | NP_001051007.2 | WO 2013/022989 |
| | MbUGT1-2 | — | — | circular permutant of OsUGT1-2 |
| 1-3' | SrUGT76G1 | FB917645.1 | CAX02464.1 | |

TABLE 10

Summary of steviol glycoside structures.

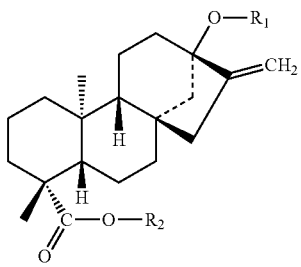

| Symbol | Common Name | R1 | R2 | Glycosylations |
|---|---|---|---|---|
| SG1 | Steviolmonoside | Glcβ1- | H— | 1 |
| SG2 | C19-glucopyranosyl steviol | H— | Glcβ1- | 1 |
| SG3 | Steviolbioside | Glcβ1-2Glcβ1- | H— | 2 |
| SG4 | — | H— | Glcβ1-2Glcβ1- | 2 |
| SG5 | Rubusoside | Glcβ1- | Glcβ1- | 2 |
| SG6 | — | Glcβ1-3Glcβ1- | H— | 2 |
| SG7 | — | H— | Glcβ1-3Glcβ1- | 2 |
| SG8 | Stevioside | Glcβ1-2Glcβ1- | Glcβ1- | 3 |
| SG9 | Rebaudioside G | Glcβ1-3Glcβ1- | Glcβ1- | 3 |
| SG10 | — | Glcβ1- | Glcβ1-2Glcβ1- | 3 |
| SG11 | — | Glcβ1- | Glcβ1-3Glcβ1- | 3 |
| SG12 | Rebaudioside B | Glcβ1-2(Glcβ1-3)Glcβ1- | H— | 3 |
| SG13 | — | H— | Glcβ1-2(Glcβ1-3)Glcβ1- | 3 |
| SG14 | Rebaudioside E | Glcβ1-2Glcβ1- | Glcβ1-2Glcβ1- | 4 |

TABLE 10-continued

Summary of steviol glycoside structures.

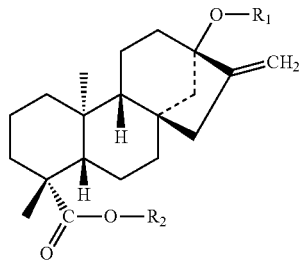

| Symbol | Common Name | R1 | R2 | Glycosylations |
|---|---|---|---|---|
| SG15 | — | Glcβ1-3Glcβ1- | Glcβ1-3Glcβ1- | 4 |
| SG16 | Rebaudioside A | Glcβ1-2(Glcβ1-3)Glcβ1- | Glcβ1- | 4 |
| SG17 | — | Glcβ1- | Glcβ1-2(Glcβ1-3)Glcβ1- | 4 |
| SG18 | — | Glcβ1-3Glcβ1-2(Glcβ1-3)Glcβ1- | H— | 4 |
| SG19 | — | H— | Glcβ1-3Glcβ1-2(Glcβ1-3)Glcβ1- | 4 |
| SG20 | — | Glcβ1-2Glcβ1- | Glcβ1-3Glcβ1- | 4 |
| SG21 | — | Glcβ1-3Glcβ1- | Glcβ1-2Glcβ1- | 4 |
| SG22 | — | Glcβ1-2(Glcb1-2Glcβ1-3)Glcβ1- | H— | 4 |
| SG23 | — | H— | Glcβ1-2(Glcb1-2Glcβ1-3)Glcβ1- | 4 |
| SG24 | Rebaudioside D | Glcβ1-2(Glcβ1-3)Glcβ1- | Glcβ1-2Glcβ1- | 5 |
| SG25 | — | Glcβ1-2Glcβ1- | Glcβ1-2(Glcβ1-3)Glcβ1- | 5 |
| SG26 | Rebaudioside I | Glcβ1-2(Glcβ1-3)Glcβ1- | Glcβ1-3Glcβ1- | 5 |
| SG27 | — | Glcβ1-3Glcβ1- | Glcβ1-2(Glcβ1-3)Glcβ1- | 5 |
| SG28 | — | Glcβ1-3Glcβ1-2(Glcβ1-3)Glcβ1- | Glcβ1- | 5 |
| SG29 | — | Glcβ1- | Glcβ1-3Glcβ1-2(Glcβ1-3)Glcβ1- | 5 |
| SG30 | — | Glcβ1-2(Glcb1-2Glcβ1-3)Glcβ1- | Glcβ1- | 5 |
| SG31 | — | Glcβ1- | Glcβ1-2(Glcb1-2Glcβ1-3)Glcβ1- | 5 |
| SG32 | Rebaudioside M | Glcβ1-2(Glcβ1-3)Glcβ1- | Glcβ1-2(Glcβ1-3)Glcβ1- | 6 |
| SG33 | — | Glcβ1-3Glcβ1-2(Glcβ1-3)Glcβ1- | Glcβ1-2Glcβ1- | 6 |
| SG34 | — | Glcβ1-3Glcβ1-2(Glcβ1-3)Glcβ1- | Glcβ1-3Glcβ1- | 6 |
| SG35 | — | Glcβ1-2Glcβ1- | Glcβ1-3Glcβ1-2(Glcβ1-3)Glcβ1- | 6 |
| SG36 | — | Glcβ1-3Glcβ1- | Glcβ1-3Glcβ1-2(Glcβ1-3)Glcβ1- | 6 |
| SG37 | — | Glcβ1-2(Glcb1-2Glcβ1-3)Glcβ1- | Glcβ1-2Glcβ1- | 6 |
| SG38 | — | Glcβ1-2(Glcb1-2Glcβ1-3)Glcβ1- | Glcβ1-3Glcβ1- | 6 |
| SG39 | — | Glcβ1-2Glcβ1- | Glcβ1-2(Glcb1-2Glcβ1-3)Glcβ1- | 6 |
| SG40 | — | Glcβ1-3Glcβ1- | Glcβ1-2(Glcb1-2Glcβ1-3)Glcβ1- | 6 |
| SG41 | — | Glcβ1-3Glcβ1-2(Glcβ1-3)Glcβ1- | Glcβ1-2(Glcβ1-3)Glcβ1- | 7 |
| SG42 | — | Glcβ1-2(Glcβ1-3)Glcβ1- | Glcβ1-3Glcβ1-2(Glcβ1-3)Glcβ1- | 7 |
| SG43 | — | Glcβ1-2(Glcb1-2Glcβ1-3)Glcβ1- | Glcβ1-2(Glcβ1-3)Glcβ1- | 7 |
| SG44 | — | Glcβ1-2(Glcβ1-3)Glcβ1- | Glcβ1-2(Glcb1-2Glcβ1-3)Glcβ1- | 7 |
| SG45 | — | Glcβ1-3Glcβ1-2(Glcβ1-3)Glcβ1- | Glcβ1-3Glcβ1-2(Glcβ1-3)Glcβ1- | 8 |
| SG46 | — | Glcβ1-2(Glcb1-2Glcβ1-3)Glcβ1- | Glcβ1-2(Glcb1-2Glcβ1-3)Glcβ1- | 8 |
| SG47 | — | Glcβ1-3Glcβ1-2(Glcβ1-3)Glcβ1- | Glcβ1-2(Glcb1-2Glcβ1-3)Glcβ1- | 8 |
| SG48 | — | Glcβ1-2(Glcb1-2Glcβ1-3)Glcβ1- | Glcβ1-3Glcβ1-2(Glcβ1-3)Glcβ1- | 8 |

TABLE 11

Fold-change in activity over parental enzyme for point mutants of SrUGT85C2 (C13-O-glycosylating activity).

| WT | Pos. | Mutation | WT | Pos. | Mutation | WT | Pos. | Mutation | WT | Pos. | Mutation | Fold increase steviolmonoside | Fold increase rubusoside |
|---|---|---|---|---|---|---|---|---|---|---|---|---|---|
| D | 2 | G | | | | | | | | | | 1.1 | |
| A | 3 | S | | | | | | | | | | 1.1 | |
| V | 13 | A | | | | | | | | | | 1.0 | |
| V | 13 | A | L | 40 | F | | | | | | | 1.1 | |
| V | 13 | I | L | 40 | H | | | | | | | 0.9 | |
| I | 14 | V | | | | | | | | | | 1.4 | |
| F | 15 | C | | | | | | | | | | 1.1 | |
| F | 18 | Y | | | | | | | | | | 1.2 | |
| S | 22 | G | | | | | | | | | | 0.6 | |
| S | 22 | G | A | 27 | P | | | | | | | 0.7 | |
| K | 25 | N | | | | | | | | | | 0.8 | |
| A | 26 | P | | | | | | | | | | 0.5 | |
| Q | 32 | K | | | | | | | | | | 1.0 | |
| K | 37 | R | | | | | | | | | | 1.0 | |
| L | 39 | F | | | | | | | | | | 1.1 | |
| Q | 40 | H | | | | | | | | | | 1.1 | |
| Q | 40 | R | | | | | | | | | | 1.0 | |
| D | 47 | E | | | | | | | | | | 1.3 | |
| F | 48 | Y | | | | | | | | | | 1.4 | |
| I | 49 | N | | | | | | | | | | 1.3 | |
| N | 51 | K | | | | | | | | | | 1.4 | |
| Q | 52 | R | | | | | | | | | | 1.1 | |
| F | 53 | L | | | | | | | | | | 1.4 | |
| E | 55 | K | | | | | | | | | | 1.0 | |
| S | 57 | R | | | | | | | | | | 1.0 | |
| H | 60 | N | | | | | | | | | | 1.4 | |
| C | 61 | A | | | | | | | | | | 1.2 | |
| A | 65 | L | | | | | | | | | | 1.1 | |
| G | 67 | D | | | | | | | | | | 0.8 | |
| V | 77 | L | | | | | | | | | | 0.9 | |
| S | 78 | P | | | | | | | | | | 1.0 | |
| H | 79 | P | | | | | | | | | | 0.9 | |
| P | 81 | D | | | | | | | | | | 1.0 | |
| A | 83 | D | | | | | | | | | | 1.1 | |
| S | 84 | A | | | | | | | | | | 0.9 | |
| I | 85 | T | | | | | | | | | | 1.1 | |
| P | 86 | Q | | | | | | | | | | 1.2 | |
| I | 87 | D | | | | | | | | | | 0.9 | |
| R | 88 | I | | | | | | | | | | 0.9 | |
| E | 89 | P | | | | | | | | | | 1.0 | |
| L | 92 | C | | | | | | | | | | 0.9 | |
| R | 93 | E | | | | | | | | | | 1.1 | |
| I | 95 | T | | | | | | | | | | 1.0 | |
| E | 96 | R | | | | | | | | | | 0.9 | |
| T | 97 | K | | | | | | | | | | 1.0 | |
| F | 99 | C | | | | | | | | | | 1.1 | |
| F | 99 | L | F | 127 | W | | | | | | | 1.1 | |
| D | 101 | A | | | | | | | | | | 1.1 | |
| R | 102 | P | | | | | | | | | | 1.2 | |
| I | 104 | E | | | | | | | | | | 1.1 | |
| I | 104 | R | | | | | | | | | | 0.7 | |
| I | 104 | R | K | 134 | E | | | | | | | 1.0 | |
| V | 107 | L | | | | | | | | | | 0.9 | |
| T | 108 | A | | | | | | | | | | 1.0 | |
| P | 111 | N | | | | | | | | | | 0.8 | |
| P | 114 | V | | | | | | | | | | 1.0 | 0.7 |
| I | 118 | V | | | | | | | | | | 1.0 | 0.7 |
| L | 123 | M | | | | | | | | | | 1.0 | 1.0 |
| I | 128 | L | | | | | | | | | | 1.0 | 1.1 |
| K | 132 | E | | | | | | | | | | 1.0 | 1.3 |
| K | 133 | E | | | | | | | | | | 1.0 | 0.8 |
| V | 138 | E | | | | | | | | | | 0.7 | 0.3 |
| V | 138 | R | | | | | | | | | | 0.6 | 0.2 |
| M | 139 | V | | | | | | | | | | 1.0 | 0.8 |
| M | 140 | L | | | | | | | | | | 0.9 | 0.7 |
| Y | 141 | F | | | | | | | | | | 1.0 | 0.9 |
| A | 145 | S | | | | | | | | | | 1.0 | 1.0 |
| F | 152 | Y | | | | | | | | | | 0.8 | 0.4 |
| Y | 153 | L | | | | | | | | | | 0.9 | 0.9 |
| I | 155 | Y | | | | | | | | | | 1.1 | 0.9 |
| H | 156 | R | | | | | | | | | | 1.0 | 1.1 |
| F | 163 | L | | | | | | | | | | 1.2 | 1.2 |
| A | 169 | E | | | | | | | | | | 1.1 | 1.2 |
| V | 184 | I | | | | | | | | | | 1.0 | 1.0 |

TABLE 11-continued

Fold-change in activity over parental enzyme for point mutants of SrUGT85C2 (C13-O-glycosylating activity).

| WT | Pos. | Mutation | WT | Pos. | Mutation | WT | Pos. | Mutation | WT | Pos. | Mutation | Fold increase steviolmonoside | Fold increase rubusoside |
|---|---|---|---|---|---|---|---|---|---|---|---|---|---|
| E | 188 | K | | | | | | | | | | 0.9 | 0.9 |
| G | 189 | N | | | | | | | | | | 1.1 | 1.1 |
| F | 195 | L | | | | | | | | | | 1.0 | 0.9 |
| L | 197 | F | | | | | | | | | | 0.8 | 0.6 |
| D | 198 | I | | | | | | | | | | 1.0 | 0.5 |
| W | 199 | R | | | | | | | | | | 1.0 | 0.8 |
| S | 200 | T | | | | | | | | | | 1.0 | 0.9 |
| L | 203 | P | | | | | | | | | | 0.8 | 0.7 |
| K | 206 | I | | | | | | | | | | 1.1 | 0.5 |
| V | 207 | M | | | | | | | | | | 0.9 | 0.5 |
| M | 209 | N | | | | | | | | | | 1.4 | 0.9 |
| A | 214 | E | | | | | | | | | | 1.0 | 0.5 |
| P | 215 | T | | | | | | | | | | 1.8 | 0.9 |
| Q | 216 | E | | | | | | | | | | 1.2 | 0.6 |
| S | 218 | A | | | | | | | | | | 1.1 | 0.7 |
| V | 221 | A | | | | | | | | | | 1.1 | 0.7 |
| H | 223 | A | | | | | | | | | | 1.2 | 0.8 |
| H | 224 | I | | | | | | | | | | 0.6 | 0.3 |
| I | 225 | L | M | 472 | F | | | | | | | 0.8 | 0.4 |
| F | 226 | L | | | | | | | | | | 1.0 | 0.7 |
| H | 227 | N | | | | | | | | | | 0.1 | 0.0 |
| S | 235 | D | | | | | | | | | | 1.2 | 0.8 |
| I | 236 | V | | | | | | | | | | 1.2 | 0.7 |
| I | 237 | L | | | | | | | | | | 1.2 | 0.8 |
| K | 238 | D | | | | | | | | | | 1.3 | 0.9 |
| T | 239 | A | | | | | | | | | | 1.1 | 0.9 |
| L | 242 | S | | | | | | | | | | 1.4 | 1.1 |
| R | 243 | I | | | | | | | | | | 0.8 | 0.6 |
| Y | 244 | L | | | | | | | | | | 1.3 | 0.7 |
| N | 245 | P | | | | | | | | | | 1.1 | 1.3 |
| H | 246 | P | | | | | | | | | | 0.7 | 0.6 |
| I | 247 | V | | | | | | | | | | 0.9 | 0.7 |
| D | 258 | N | | | | | | | | | | 0.9 | 0.7 |
| F | 285 | L | | | | | | | | | | 0.7 | 0.9 |
| Q | 289 | D | | | | | | | | | | 0.8 | 1.0 |
| K | 291 | Q | Y | 326 | R | | | | | | | 1.2 | 1.0 |
| K | 291 | Q | E | 293 | P | Y | 326 | R | | | | 1.3 | 0.9 |
| E | 292 | P | Y | 326 | R | | | | | | | 0.9 | 0.7 |
| T | 304 | I | | | | | | | | | | 1.3 | 0.9 |
| S | 308 | T | | | | | | | | | | 1.3 | 0.9 |
| D | 311 | Q | | | | | | | | | | 1.3 | 1.0 |
| M | 312 | L | | | | | | | | | | 1.1 | 0.9 |
| M | 312 | L | I | 331 | V | | | | | | | 1.6 | 1.1 |
| G | 316 | A | | | | | | | | | | 1.1 | 1.0 |
| A | 320 | E | H | 350 | R | | | | | | | 1.2 | 0.8 |
| A | 320 | E | E | 346 | G | H | 350 | R | | | | 1.3 | 0.6 |
| N | 323 | G | | | | | | | | | | 1.2 | 1.1 |
| Y | 325 | P | | | | | | | | | | 1.1 | 1.0 |
| I | 329 | V | | | | | | | | | | 1.1 | 1.0 |
| S | 332 | P | | | | | | | | | | 1.3 | 1.0 |
| N | 333 | D | | | | | | | | | | 1.3 | 1.2 |
| N | 339 | S | | | | | | | | | | 0.9 | 0.9 |
| E | 345 | G | | | | | | | | | | 0.9 | 0.9 |
| E | 345 | G | H | 350 | R | | | | | | | 1.4 | 0.9 |
| L | 346 | F | | | | | | | | | | 0.9 | 0.7 |
| L | 346 | F | I | 351 | T | | | | | | | 0.9 | 0.7 |
| H | 349 | E | | | | | | | | | | 1.5 | 1.0 |
| K | 352 | D | | | | | | | | | | 0.9 | 0.8 |
| F | 355 | L | | | | | | | | | | 1.1 | 0.8 |
| S | 361 | P | | | | | | | | | | 1.0 | 0.8 |
| K | 364 | Q | | | | | | | | | | 0.8 | 0.9 |
| L | 375 | V | | | | | | | | | | 0.9 | 1.0 |
| L | 375 | V | I | 395 | V | | | | | | | 0.9 | 0.8 |
| L | 375 | V | I | 395 | V | L | 432 | A | L | 436 | V | 0.2 | 0.7 |
| G | 381 | N | | | | | | | | | | 1.0 | 0.1 |
| I | 384 | L | | | | | | | | | | 1.3 | 0.7 |
| L | 387 | I | | | | | | | | | | 0.8 | 0.9 |
| L | 387 | I | V | 416 | I | | | | | | | 0.9 | 0.7 |
| S | 388 | C | | | | | | | | | | 0.8 | 0.7 |
| I | 394 | V | L | 432 | A | | | | | | | 0.6 | 0.7 |
| I | 394 | V | L | 436 | V | | | | | | | 1.2 | |
| C | 395 | A | | | | | | | | | | 1.4 | |
| C | 395 | A | C | 407 | A | | | | | | | 1.4 | |
| C | 395 | T | C | 407 | A | | | | | | | 1.5 | |

TABLE 11-continued

Fold-change in activity over parental enzyme for point mutants of SrUGT85C2 (C13-O-glycosylating activity).

| WT | Pos. | Mutation | WT | Pos. | Mutation | WT | Pos. | Mutation | WT | Pos. | Mutation | Fold increase steviolmonoside | Fold increase rubusoside |
|---|---|---|---|---|---|---|---|---|---|---|---|---|---|
| Y | 398 | F | | | | | | | | | | 0.9 | |
| S | 399 | F | | | | | | | | | | 1.0 | |
| W | 400 | A | | | | | | | | | | 0.9 | 0.3 |
| L | 403 | Q | | | | | | | | | | 1.0 | |
| I | 409 | V | | | | | | | | | | 0.9 | 0.9 |
| E | 414 | G | | | | | | | | | | 1.3 | |
| E | 414 | K | K | 443 | E | | | | | | | 0.4 | |
| V | 415 | I | | | | | | | | | | 0.5 | |
| L | 417 | M | | | | | | | | | | 0.7 | |
| M | 419 | I | | | | | | | | | | 1.0 | 0.8 |
| G | 420 | D | | | | | | | | | | 1.2 | |
| K | 422 | D | | | | | | | | | | 0.6 | |
| D | 426 | E | | | | | | | | | | 1.0 | |
| K | 429 | E | | | | | | | | | | 1.0 | |
| K | 429 | E | Q | 434 | R | | | | | | | 0.9 | |
| Q | 433 | R | | | | | | | | | | 0.4 | |
| G | 439 | K | | | | | | | | | | 0.9 | |
| H | 441 | K | | | | | | | | | | 1.0 | 1.0 |
| K | 442 | E | | | | | | | | | | 0.9 | 1.1 |
| K | 446 | R | D | 450 | E | | | | | | | 1.0 | 1.0 |
| D | 449 | E | | | | | | | | | | 0.8 | |
| W | 450 | L | | | | | | | | | | 1.1 | |
| E | 452 | K | | | | | | | | | | 0.9 | 1.0 |
| K | 453 | L | | | | | | | | | | 1.1 | |
| R | 455 | E | | | | | | | | | | 0.7 | |
| I | 456 | E | | | | | | | | | | 0.9 | |
| I | 458 | T | | | | | | | | | | 1.0 | |
| N | 461 | G | | | | | | | | | | 1.1 | |
| N | 461 | G | S | 466 | Y | | | | | | | 0.9 | 0.7 |
| I | 468 | L | | | | | | | | | | 0.4 | |
| M | 471 | L | | | | | | | | | | 0.7 | |
| I | 475 | V | | | | | | | | | | 1.0 | |
| T | 476 | L | | | | | | | | | | 0.5 | |
| V | 477 | L | | | | | | | | | | 0.6 | |

TABLE 12

Fold-change in activity over parental enzyme for point mutants of MbUGT1-2 (1-2' glycosylating activity).

| Wild-type residue | Position | Mutation | Insertion | Wild-type residue | Position | Mutation | Fold increase steviolbioside | Fold increase RebD |
|---|---|---|---|---|---|---|---|---|
| S | 14 | W | | | | | 1.8 | 2.4 |
| S | 14 | Y | | | | | 1.7 | 2.3 |
| V | 89 | A | | | | | | |
| G | 185 | A | | | | | 1.1 | 0.6 |
| V | 365 | I | | | | | 1.4 | 1.9 |
| E | 366 | P | | | | | 2.0 | 3.0 |
| V | 395 | Y | | F | 396 | T | 0.1 | 0.2 |
| G | 417 | T | | | | | 0.0 | 0.0 |
| H | 420 | E | | | | | 1.5 | 1.8 |
| M | 421 | F | | | | | 1.2 | 1.7 |
| M | 421 | I | | | | | 0.3 | 0.3 |
| M | 421 | A | | | | | 0.7 | 0.4 |
| S | 424 | D | | | | | 1.6 | 2.1 |
| S | 424 | Y | | | | | 0.8 | 0.4 |
| | | | GPS between 425 and 426 | | | | 0.9 | 1.5 |
| D | 427 | E | | | | | 1.2 | 1.5 |
| D | 427 | S | | | | | 1.1 | 1.0 |
| D | 427 | W | | | | | | |
| R | 428 | E | | | | | 1.4 | 1.9 |
| R | 428 | H | | | | | 1.0 | 1.1 |
| R | 428 | W | | | | | 0.8 | 0.5 |
| E | 431 | A | | | | | | |
| E | 431 | Y | | | | | 1.5 | 1.7 |
| R | 432 | H | | | | | 1.8 | 2.7 |
| R | 432 | W | | | | | 1.7 | 2.7 |

TABLE 12-continued

Fold-change in activity over parental enzyme for point mutants of MbUGT1-2 (1-2' glycosylating activity).

| Wild-type residue | Position | Mutation | Insertion | Wild-type residue | Position | Mutation | Fold increase steviolbioside | Fold increase RebD |
|---|---|---|---|---|---|---|---|---|
| K | 463 | D | | | | | 1.3 | 1.4 |
| K | 463 | E | | | | | 1.4 | 2.0 |

TABLE 13

Fold-change in activity over parental enzyme for point mutants of SrUGT76G1 (1-3' glycosylating activity).

| WT | Pos. | Mut. | Insert. | Delet. | WT | Pos. | Mut. | Delet. | WT | Pos. | Mut. | Delet. | WT | Pos. | Mut. | Fold increase RebA | Fold increase RebM |
|---|---|---|---|---|---|---|---|---|---|---|---|---|---|---|---|---|---|
| F | 22 | V | | | | | | | | | | | | | | 0.3 | 0.1 |
| S | 77 | A | | | | | | | | | | | | | | 1.4 | 1.5 |
| N | 78 | A | | | | | | | | | | | | | | 1.1 | 1.2 |
| T | 81 | A | | | | | | | | | | | | | | 1.0 | 1.3 |
| H | 82 | A | | | | | | | | | | | | | | 1.4 | 0.7 |
| G | 87 | V | | | | | | | | | | | | | | 0.0 | 0.1 |
| | | | | G87-P91 | | | | | | | | | | | | 0.1 | 1.0 |
| I | 90 | V | | | | | | | | | | | | | | 1.1 | 0.4 |
| P | 91 | A | | | | | | | | | | | | | | 0.6 | 0.5 |
| I | 93 | V | | | | | | | | | | | | | | 1.0 | 0.3 |
| N | 94 | G | | | | | | | | | | | | | | 1.3 | 0.5 |
| L | 126 | G | | | | | | | | | | | | | | 0.5 | 0.4 |
| W | 127 | F | | | | | | | | | | | | | | 0.9 | 0.2 |
| M | 145 | V | | | | | | | | | | | | | | 0.5 | 0.4 |
| S | 147 | G | | | | | | | | | | | | | | 1.2 | 0.4 |
| N | 151 | A | | | | | | | | | | | | | | 0.7 | 0.4 |
| H | 155 | A | | | | | | | | | | | | | | 0.7 | 0.3 |
| Y | 155 | Y | | | | | | | | | | | | | | 1.4 | 0.2 |
| S | 192 | A | | | | | | | | | | | | | | 1.0 | 1.1 |
| Y | 194 | G | | | | | | | | | | | | | | 0.8 | 0.1 |
| | | | G between 194 and 195 | | | | | | | | | | | | | 2.4 | 1.1 |
| W | 197 | P | | | | | | | | | | | | | | 1.7 | 0.7 |
| I | 199 | A | | | | | | | | | | | | | | 0.9 | 0.1 |
| L | 200 | A | | | T | 284 | A | | | | | | | | | 8.2 | 8.6 |
| L | 200 | A | | | L | 379 | G | | T | 284 | A | | S | 192 | A | 7.0 | 9.0 |
| L | 200 | A | | | L | 379 | G | | T | 284 | A | | | | | 9.4 | 9.2 |
| L | 200 | A | | | L | 379 | G | | | | | G87-P91 | | | | 0.5 | |
| L | 200 | A | | | L | 379 | G | | | | | | | | | 3.1 | 1.8 |
| L | 200 | A | | | | | | | | | | | | | | 8.0 | 17.0 |
| L | 200 | G | | | | | | | | | | | | | | 6.7 | 3.9 |
| L | 200 | V | | | | | | | | | | | | | | 1.1 | 0.1 |
| L | 200 | A | | | | | | G87-P91 | | | | | | | | 1.6 | 1.6 |
| E | 202 | D | | | | | | | | | | | | | | 1.2 | 0.1 |
| I | 203 | A | | | | | | | | | | | | | | 1.2 | 0.2 |
| L | 204 | A | | | | | | | | | | | | | | 0.6 | 0.2 |
| G | 205 | R | | | K | 206 | A | | K | 209 | E | | | | | 0.8 | 0.1 |
| G | 205 | A | | | | | | | | | | | | | | 1.4 | 0.4 |
| M | 207 | A | | | | | | | | | | | | | | 0.8 | 0.6 |
| T | 284 | A | | | | | | | | | | | | | | 1.0 | 1.5 |
| T | 284 | V | | | | | | | | | | | | | | 1.6 | 0.3 |
| L | 379 | G | | | T | 284 | A | | | | | | | | | 1.1 | 1.5 |
| L | 379 | G | | | | | | | | | | | | | | 0.6 | 2.0 |
| L | 379 | A | | | | | | | | | | | | | | 1.9 | 1.4 |
| L | 397 | V | | | | | | | | | | | | | | 2.1 | 0.9 |

The invention claimed is:

1. A method for making Rebaudioside M (RebM) or Rebaudioside D (RebD), comprising: providing a host cell producing RebM or RebD from steviol through a plurality of uridine diphosphate dependent glycosyltransferase enzymes (UGT), the UGT enzymes comprising one or more of:
   (a) a modified UGT enzyme having an increase in 1-2' glycosylating activity at C19 of Rebaudioside A (RebA) as compared to its parent UGT enzyme, without substantial loss of 1-2' glycosylating activity at C13 of steviolmonoside as compared to its parent UGT enzyme, and
   (b) a modified UGT enzyme having an increase in 1-3' glycosylating activity at C19 of Rebaudioside D (RebD) as compared to its parent UGT enzyme, without substantial loss of 1-3' glycosylating activity at C13 of stevioside as compared to its parent UGT enzyme;
   and culturing the host cell under conditions for producing the RebM or RebD;
   wherein the UGT enzyme having an increase in 1-2' glycosylating activity at C19 of RebA is a circular permutant of its parent UGT enzyme and the UGT enzyme having an increase in 1-3' glycosylating activity at C19 of RebD is a circular permutant of its parent UGT enzyme.

2. The method of claim 1, wherein:
   (a) the 1-2' glycosylating activity at C19 of Rebaudioside A (RebA) is equal to or better than the 1-2' glycosylating activity at C13 of steviolmonoside: and/or
   (b) the 1-3' glycosylating activity at C19 of Rebaudioside D (RebD) is equal to or better than the 1-3' glycosylating activity at C13 of stevioside.

3. The method of claim 1, wherein the cell expresses only one UGT enzyme having 1-2' glycosylating activity at C13 of steviolmonoside, and/or expresses only one UGT enzyme having 1-3' glycosylating activity at C13 of stevioside.

4. The method of claim 1, wherein the cell expresses both the UGT enzyme having an increase in 1-2' glycosylating activity at C19 of RebA that is a circular permutant of its parent UGT enzyme and the UGT enzyme having an increase in 1-3' glycosylating activity at C19 of RebD that is a circular permutant of its parent UGT enzyme.

5. The method of claim 1, wherein the UGT enzyme having 1-2' glycosylating activity is OsUGT1-2 or SrUGT91D2, or SrUGT91D1, or derivative thereof having increased glycosylating activity at C19 of RebA as compared to its parent UGT enzyme.

6. The method of claim 5, wherein the UGT enzyme having 1-2' glycosylating activity is a circular permutant of OsUGT1-2 comprising one or more amino acid substitutions, deletions, and/or insertions that increase 1-2' glycosylating activity at C19 of RebA as compared to its parent UGT enzyme.

7. The method of claim 6, wherein the UGT enzyme having 1-2' glycosylating activity is a circular permutant of OsUGT1-2 having a cut site corresponding to a position within 190 to 210 of SEQ ID NO: 7, and having a linker sequence between the amino acids that correspond to the N-terminal and C-terminal residues of SEQ ID NO: 7, and wherein the linker optionally has a length of from 2 to 25 amino acids.

8. The method of claim 5, wherein the UGT enzyme having 1-2' glycosylating activity is SrUGT91D2, and which is a circular permutant comprising one or more amino acid substitutions, insertions, and/or deletions that increase glycosylating activity of C19 of RebA as compared to its parent UGT enzyme.

9. The method of claim 1, wherein the UGT enzyme having 1-2' glycosylating activity is MbUGT1,2-2 (SEQ ID NO: 45) or derivative thereof.

10. The method of claim 1, wherein the UGT enzyme having 1-3' glycosylating activity is a derivative of SrUGT76G1, which is a circular permutant comprising one or more amino acid substitutions, insertions, and/or deletions increasing glycosylation activity of C19 of RebD as compared to its parent UGT enzyme.

11. The method of claim 1, wherein the UGT enzyme having 1-3' glycosylating activity is a derivative of SrUGT76G1 that includes an amino acid substitution at one or more of positions 200, 284, and/or 379, wherein amino acid positions are numbered according to SEQ ID NO:3.

12. The method of claim 1, wherein the host cell further comprises a UGT enzyme that converts steviol to steviolmonoside.

13. The method of claim 12, wherein the UGT enzyme that converts steviol to steviolmonoside is SrUGT85C2, or derivative thereof.

14. The method of claim 1, wherein the host cell further comprises a UGT enzyme that converts steviolbioside to stevioside.

15. The method of claim 14, wherein the UGT enzyme that converts steviolbioside to stevioside is SrUGT74G1, or derivative thereof.

16. The method of claim 1, wherein the host cell produces steviol substrate through an enzymatic pathway comprising a kaurene synthase (KS), kaurene oxidase (KO), and a kaurenoic acid hydroxylase (KAH), the host cell further comprising a cytochrome P450 reductase (CPR) for regenerating one or more of the KO and KAH enzymes.

17. The method of claim 1, wherein the host cell expresses a geranylgeranyl pyrophosphate synthase (GGPPS), which is optionally of *Taxus canadensis*, *Abies grandis*, *Aspergillus nidulans*, *Stevia rebaudiana*, *Gibberella fujikuroi*, Marine bacterium 443, *Paracoccus haeundaensis*, *Chlorobium tepidum*, *Mus musculus*, *Thalassiosira pseudonana*, *Streptomyces melanosporofaciens*, *Streptomyces clavuligerus*, *Sulfulubus acidocaldarius*, *Synechococcus* sp., *Synechocystis* sp., *Arabidopsis thaliana*, *Thermotogo maritime*, *Corynebacterium glutamicum*, *Therms thermophillus*, *Pyrobaculum calidifontis*, or derivatives thereof.

18. The method of claim 1, wherein the host cell expresses a pathway producing iso-pentenyl pyrophosphate (IPP) and dimethylallyl pyrophosphate (DMAPP).

19. The method of claim 18, wherein the host cell is prokaryotic or eukaryotic.

20. The method of claim 19, wherein the host cell is *E. coli*, *Bacillus subtillus*, or *Pseudomonas putida*.

21. The method of claim 19, wherein the host cell is a species of *Saccharomyces*, *Pichia*, or *Yarrowia*, including *Saccharomyces cerevisiae*, *Pichia pastoris*, and *Yarrowia lipolytica*.

22. The method of claim 1, wherein the host cell comprises the following heterologously expressed genes:
   *Taxus canadensis* GGPPS or derivative thereof,
   *Phaeosphaeria* sp. PsCK (a copalyl diphosphate-kaurene synthase) or derivative thereof,
   *Stevia rebaudiana* KO or derivative thereof,
   *Arabidopsis thaliana* KAH or derivative thereof,
   *Stevia rebaudiana* CPR or derivative thereof,
   *Stevia rebaudiana* UGT85C2 or derivative thereof,
   *Stevia rebaudiana* UGT74G1 or derivative thereof or MbUGTC 19 or derivative thereof,
   *Stevia rebaudiana* UGT76G1 or derivative thereof or MbUGT1-3 or derivative thereof, and Stevia rebaudiana UGT91 D2 or OsUGT1-2 or MbUGT1-2 or derivative thereof.

23. The method of claim 1, wherein the host cell comprises the following heterologously expressed genes:

Corynebacterium glutmnncun GGPS or derivative thereof,
Erwina tracheiphila copalyl diphosphate synthase (CPPS) or derivative thereof,
Erwina tracheiphila KS or derivative thereof,
Stevia rebaudiana KO or derivative thereof,
Arabidopsis thaliana KAH or derivative thereof,
Stevia rebaudiana CPR or derivative thereof,
Stevia rebaudiana UGT85C2 or derivative thereof,
Stevia rebaudiana UGT74G1 or derivative thereof or MbUGTC19 or derivative thereof or MbUGTC19-2 or derivative thereof,
Stevia rebaudiana UGT76G1 or derivative thereof or MbUGT1-3 or derivative thereof, and
Stevia rebaudiana UGT91 D2 or OsUGT1-2 or MbUGT1,2-2 or derivative thereof.

24. The method of claim 1, further comprising recovering the RebM or RebD from culture media.

* * * * *

UNITED STATES PATENT AND TRADEMARK OFFICE
CERTIFICATE OF CORRECTION

PATENT NO. : 10,463,062 B2
APPLICATION NO. : 15/524015
DATED : November 5, 2019
INVENTOR(S) : Ryan Philippe Page 1 of 1

It is certified that error appears in the above-identified patent and that said Letters Patent is hereby corrected as shown below:

In the Claims

Claim 22, Column 196, Line 64, change "UGT74G I ;" to -- UGT74G1 --;

Claim 22, Column 196, Line 65, change "MbUGTC 19 ;" to -- MbUGTC19 --;

Claim 22, Column 196, Line 66, change "UGT76G I ;" to -- UGT76G1 --;

Claim 22, Column 197, Line 1, change "UGT91 D2;" to -- UGT91D2 --;

Claim 22, Column 197, Line 1, after "OsUGT1-2;" insert -- , --;

Claim 23, Column 197, Line 19, change "UGT91 D2;" to -- UGT91D2 --.

Signed and Sealed this
Twenty-eighth Day of April, 2020

Andrei Iancu
*Director of the United States Patent and Trademark Office*

SEQUENCE LISTING

<160> NUMBER OF SEQ ID NOS: 63

<210> SEQ ID NO 1
<211> LENGTH: 481
<212> TYPE: PRT

<213> ORGANISM: Stevia rebaudiana

<400> SEQUENCE: 1

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400
```

```
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly Gly His Lys Met Arg Asn Lys Ala Lys
        435                 440                 445
Asp Trp Lys Glu Lys Ala Arg Ile Ala Ile Ala Pro Asn Gly Ser Ser
    450                 455                 460
Ser Leu Asn Ile Asp Lys Met Val Lys Glu Ile Thr Val Leu Ala Arg
465                 470                 475                 480
Asn

<210> SEQ ID NO 2
<211> LENGTH: 460
<212> TYPE: PRT
<213> ORGANISM: Stevia rebaudiana

<400> SEQUENCE: 2

Met Ala Glu Gln Gln Lys Ile Lys Lys Ser Pro His Val Leu Leu Ile
1               5                   10                  15
Pro Phe Pro Leu Gln Gly His Ile Asn Pro Phe Ile Gln Phe Gly Lys
            20                  25                  30
Arg Leu Ile Ser Lys Gly Val Lys Thr Thr Leu Val Thr Thr Ile His
        35                  40                  45
Thr Leu Asn Ser Thr Leu Asn His Ser Asn Thr Thr Thr Thr Ser Ile
    50                  55                  60
Glu Ile Gln Ala Ile Ser Asp Gly Cys Asp Glu Gly Gly Phe Met Ser
65                  70                  75                  80
Ala Gly Glu Ser Tyr Leu Glu Thr Phe Lys Gln Val Gly Ser Lys Ser
                85                  90                  95
Leu Ala Asp Leu Ile Lys Lys Leu Gln Ser Glu Gly Thr Thr Ile Asp
            100                 105                 110
Ala Ile Ile Tyr Asp Ser Met Thr Glu Trp Val Leu Asp Val Ala Ile
        115                 120                 125
Glu Phe Gly Ile Asp Gly Gly Ser Phe Thr Gln Ala Cys Val Val
    130                 135                 140
Asn Ser Leu Tyr Tyr His Val His Lys Gly Leu Ile Ser Leu Pro Leu
145                 150                 155                 160
Gly Glu Thr Val Ser Val Pro Gly Phe Pro Val Leu Gln Arg Trp Glu
                165                 170                 175
Thr Pro Leu Ile Leu Gln Asn His Glu Gln Ile Gln Ser Pro Trp Ser
            180                 185                 190
Gln Met Leu Phe Gly Gln Phe Ala Asn Ile Asp Gln Ala Arg Trp Val
        195                 200                 205
Phe Thr Asn Ser Phe Tyr Lys Leu Glu Glu Glu Val Ile Glu Trp Thr
    210                 215                 220
Arg Lys Ile Trp Asn Leu Lys Val Ile Gly Pro Thr Leu Pro Ser Met
225                 230                 235                 240
Tyr Leu Asp Lys Arg Leu Asp Asp Asp Lys Asp Asn Gly Phe Asn Leu
                245                 250                 255
Tyr Lys Ala Asn His His Glu Cys Met Asn Trp Leu Asp Asp Lys Pro
            260                 265                 270
Lys Glu Ser Val Val Tyr Val Ala Phe Gly Ser Leu Val Lys His Gly
        275                 280                 285
```

```
Pro Glu Gln Val Glu Glu Ile Thr Arg Ala Leu Ile Asp Ser Asp Val
    290                 295                 300

Asn Phe Leu Trp Val Ile Lys His Lys Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
                355                 360                 365

Pro Val Val Ala Met Pro Gln Phe Ser Asp Gln Thr Thr Asn Ala Lys
370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
                420                 425                 430

Lys Asp Leu Ala Lys Val Ala Val His Glu Gly Gly Ser Ser Asp Asn
                435                 440                 445

Asp Ile Val Glu Phe Val Ser Glu Leu Ile Lys Ala
450                 455                 460

<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
                115                 120                 125

Phe Ala Gln Ser Val Ala Asp Ser Leu Asn Leu Arg Arg Leu Val Leu
                130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
                195                 200                 205
```

```
Lys Gln Thr Lys Ala Ser Ser Gly Val Ile Trp Asn Ser Phe Lys Glu
            210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
450                 455
```

<210> SEQ ID NO 4
<211> LENGTH: 485
<212> TYPE: PRT
<213> ORGANISM: Stevia rebaudiana

<400> SEQUENCE: 4

```
Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65              70                  75                  80

Leu Thr Leu Pro Arg Val Gln Glu Leu Pro Glu Asp Ala Glu Ala Thr
                85                  90                  95

Thr Asp Val His Pro Glu Asp Ile Gln Tyr Leu Lys Lys Ala Val Asp
            100                 105                 110

Gly Leu Gln Pro Glu Val Thr Arg Phe Leu Glu Gln His Ser Pro Asp
```

```
                   115                 120                 125
Trp Ile Ile Tyr Asp Phe Thr His Tyr Trp Leu Pro Ser Ile Ala Ala
            130                 135                 140

Ser Leu Gly Ile Ser Arg Ala Tyr Phe Cys Val Ile Thr Pro Trp Thr
145                 150                 155                 160

Ile Ala Tyr Leu Ala Pro Ser Ser Asp Ala Met Ile Asn Asp Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Met Glu
            195                 200                 205

Pro Tyr Glu Ala Pro Gly Ile Ser Asp Gly Tyr Arg Met Gly Met Val
        210                 215                 220

Phe Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
            275                 280                 285

Val Val Tyr Val Ala Leu Gly Ser Glu Ala Leu Val Ser Gln Thr Glu
        290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
            355                 360                 365

Gly Phe Leu Thr His Cys Gly Ser Gly Ser Ile Val Glu Gly Leu Met
        370                 375                 380

Phe Gly His Pro Leu Ile Met Leu Pro Ile Phe Cys Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Val Glu Asn Glu Gly Glu Ile Tyr Lys Ala Asn Ala
            435                 440                 445

Arg Ala Leu Ser Lys Ile Tyr Asn Asp Thr Lys Val Glu Lys Glu Tyr
        450                 455                 460

Val Ser Gln Phe Val Asp Tyr Leu Glu Lys Asn Ala Arg Ala Val Ala
465                 470                 475                 480

Ile Asp His Glu Ser
                485

<210> SEQ ID NO 5
<211> LENGTH: 473
<212> TYPE: PRT
<213> ORGANISM: Stevia rebaudiana

<400> SEQUENCE: 5
```

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Val Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
```

```
            420                 425                 430
Lys Ala Asn Ala Arg Glu Leu Ser Lys Ile Tyr Asn Asp Thr Lys Val
                435                 440                 445
Glu Lys Glu Tyr Val Ser Gln Phe Val Asp Tyr Leu Glu Lys Asn Thr
    450                 455                 460
Arg Ala Val Ala Ile Asp His Glu Ser
465                 470

<210> SEQ ID NO 6
<211> LENGTH: 473
<212> TYPE: PRT
<213> ORGANISM: Stevia rebaudiana

<400> SEQUENCE: 6

Met Ala Thr Ser Asp Ser Ile Val Asp Asp Arg Lys Gln Leu His Val
1               5                   10                  15
Ala Thr Phe Pro Trp Leu Ala Phe Gly His Ile Leu Pro Tyr Leu Gln
                20                  25                  30
Leu Ser Lys Leu Ile Ala Glu Lys Gly His Lys Val Ser Phe Leu Ser
            35                  40                  45
Thr Thr Arg Asn Ile Gln Arg Leu Ser Ser His Ile Ser Pro Leu Ile
        50                  55                  60
Asn Val Val Gln Leu Thr Leu Pro Arg Val Gln Glu Leu Pro Glu Asp
65                  70                  75                  80
Ala Glu Ala Thr Thr Asp Val His Pro Glu Asp Ile Pro Tyr Leu Lys
                85                  90                  95
Lys Ala Ser Asp Gly Leu Gln Pro Glu Val Thr Arg Phe Leu Glu Gln
                100                 105                 110
His Ser Pro Asp Trp Ile Ile Tyr Asp Tyr Thr His Tyr Trp Leu Pro
            115                 120                 125
Ser Ile Ala Ala Ser Leu Gly Ile Ser Arg Ala His Phe Ser Val Thr
        130                 135                 140
Thr Pro Trp Ala Ile Ala Tyr Met Gly Pro Ser Ala Asp Ala Met Ile
145                 150                 155                 160
Asn Gly Ser Asp Gly Arg Thr Thr Val Glu Asp Leu Thr Thr Pro Pro
                165                 170                 175
Lys Trp Phe Pro Phe Pro Thr Lys Val Cys Trp Arg Lys His Asp Leu
            180                 185                 190
Ala Arg Leu Val Pro Tyr Lys Ala Pro Gly Ile Ser Asp Gly Tyr Arg
        195                 200                 205
Met Gly Leu Val Leu Lys Gly Ser Asp Cys Leu Leu Ser Lys Cys Tyr
        210                 215                 220
His Glu Phe Gly Thr Gln Trp Leu Pro Leu Leu Glu Thr Leu His Gln
225                 230                 235                 240
Val Pro Val Val Pro Val Gly Leu Leu Pro Pro Glu Ile Pro Gly Asp
                245                 250                 255
Glu Lys Asp Glu Thr Trp Val Ser Ile Lys Lys Trp Leu Asp Gly Lys
                260                 265                 270
Gln Lys Gly Ser Val Val Tyr Val Ala Leu Gly Ser Glu Val Leu Val
            275                 280                 285
Ser Gln Thr Glu Val Val Glu Leu Ala Leu Gly Leu Glu Leu Ser Gly
        290                 295                 300
Leu Pro Phe Val Trp Ala Tyr Arg Lys Pro Lys Gly Pro Ala Lys Ser
305                 310                 315                 320
```

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Lys Gln Val Gly Ile
385                 390                 395                 400

Glu Ile Pro Arg Asn Glu Glu Asp Gly Cys Leu Thr Lys Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 7
<211> LENGTH: 462
<212> TYPE: PRT
<213> ORGANISM: Oryza sativa

<400> SEQUENCE: 7

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
                165                 170                 175

Gln Gly Arg Pro Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

```
Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
                340                 345                 350

Ala Phe Leu Thr His Cys Gly Trp Asn Ser Thr Ile Glu Gly Leu Met
                355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
                420                 425                 430

Ala Lys Lys Leu Gln Glu Ile Val Ala Asp Met Ala Cys His Glu Arg
                435                 440                 445

Tyr Ile Asp Gly Phe Ile Gln Gln Leu Arg Ser Tyr Lys Asp
    450                 455                 460
```

<210> SEQ ID NO 8
<211> LENGTH: 463
<212> TYPE: PRT
<213> ORGANISM: Artificial sequence
<220> FEATURE:
<223> OTHER INFORMATION: Synthetic sequence

<400> SEQUENCE: 8

```
Met Ala Glu Cys Met Asn Trp Leu Asp Asp Lys Pro Lys Glu Ser Val
1               5                   10                  15

Val Tyr Val Ala Phe Gly Ser Leu Val Lys His Gly Pro Glu Gln Val
                20                  25                  30

Glu Glu Ile Thr Arg Ala Leu Ile Asp Ser Asp Val Asn Phe Leu Trp
            35                  40                  45

Val Ile Lys His Lys Glu Glu Gly Lys Leu Pro Glu Asn Leu Ser Glu
        50                  55                  60

Val Ile Lys Thr Gly Lys Gly Leu Ile Val Ala Trp Cys Lys Gln Leu
65                  70                  75                  80

Asp Val Leu Ala His Glu Ser Val Gly Cys Phe Val Thr His Cys Gly
                85                  90                  95

Phe Asn Ser Thr Leu Glu Ala Ile Ser Leu Gly Val Pro Val Val Ala
                100                 105                 110

Met Pro Gln Phe Ser Asp Gln Thr Thr Asn Ala Lys Leu Leu Asp Glu
                115                 120                 125
```

```
Ile Leu Gly Val Gly Val Arg Val Lys Ala Asp Glu Asn Gly Ile Val
    130                 135                 140

Arg Arg Gly Asn Leu Ala Ser Cys Ile Lys Met Ile Met Glu Glu Glu
145                 150                 155                 160

Arg Gly Val Ile Ile Arg Lys Asn Ala Val Lys Trp Lys Asp Leu Ala
                165                 170                 175

Lys Val Ala Val His Glu Gly Gly Ser Ser Asp Asn Asp Ile Val Glu
            180                 185                 190

Phe Val Ser Glu Leu Ile Lys Ala Gly Ser Gly Glu Gln Gln Lys Ile
        195                 200                 205

Lys Lys Ser Pro His Val Leu Leu Ile Pro Phe Pro Leu Gln Gly His
    210                 215                 220

Ile Asn Pro Phe Ile Gln Phe Gly Lys Arg Leu Ile Ser Lys Gly Val
225                 230                 235                 240

Lys Thr Thr Leu Val Thr Thr Ile His Thr Leu Asn Ser Thr Leu Asn
                245                 250                 255

His Ser Asn Thr Thr Thr Ser Ile Glu Ile Gln Ala Ile Ser Asp
            260                 265                 270

Gly Cys Asp Glu Gly Gly Phe Met Ser Ala Gly Glu Ser Tyr Leu Glu
        275                 280                 285

Thr Phe Lys Gln Val Gly Ser Lys Ser Leu Ala Asp Leu Ile Lys Lys
    290                 295                 300

Leu Gln Ser Glu Gly Thr Thr Ile Asp Ala Ile Ile Tyr Asp Ser Met
305                 310                 315                 320

Thr Glu Trp Val Leu Asp Val Ala Ile Glu Phe Gly Ile Asp Gly Gly
                325                 330                 335

Ser Phe Phe Thr Gln Ala Cys Val Val Asn Ser Leu Tyr Tyr His Val
            340                 345                 350

His Lys Gly Leu Ile Ser Leu Pro Leu Gly Glu Thr Val Ser Val Pro
        355                 360                 365

Gly Phe Pro Val Leu Gln Arg Trp Glu Thr Pro Leu Ile Leu Gln Asn
    370                 375                 380

His Glu Gln Ile Gln Ser Pro Trp Ser Gln Met Leu Phe Gly Gln Phe
385                 390                 395                 400

Ala Asn Ile Asp Gln Ala Arg Trp Val Phe Thr Asn Ser Phe Tyr Lys
                405                 410                 415

Leu Glu Glu Glu Val Ile Glu Trp Thr Arg Lys Ile Trp Asn Leu Lys
            420                 425                 430

Val Ile Gly Pro Thr Leu Pro Ser Met Tyr Leu Asp Lys Arg Leu Asp
        435                 440                 445

Asp Asp Lys Asp Asn Gly Phe Asn Leu Tyr Lys Ala Asn His His
    450                 455                 460

<210> SEQ ID NO 9
<211> LENGTH: 463
<212> TYPE: PRT
<213> ORGANISM: Artificial sequence
<220> FEATURE:
<223> OTHER INFORMATION: Synthetic sequence

<400> SEQUENCE: 9

Met Ala Gly Ser Ser Gly Met Ser Leu Ala Glu Arg Phe Ser Leu Thr
1               5                   10                  15

Leu Ser Arg Ser Ser Leu Val Val Gly Arg Ser Cys Val Glu Phe Glu
            20                  25                  30
```

```
Pro Glu Thr Val Pro Leu Leu Ser Thr Leu Arg Gly Lys Pro Ile Thr
            35                  40                  45

Phe Leu Gly Leu Met Pro Pro Leu His Glu Gly Arg Arg Glu Asp Gly
 50                  55                  60

Glu Asp Ala Thr Val Arg Trp Leu Asp Ala Gln Pro Ala Lys Ser Val
 65                  70                  75                  80

Val Tyr Val Ala Leu Gly Ser Glu Val Pro Leu Gly Val Glu Lys Val
                 85                  90                  95

His Glu Leu Ala Leu Gly Leu Glu Leu Ala Gly Thr Arg Phe Leu Trp
            100                 105                 110

Ala Leu Arg Lys Pro Thr Gly Val Ser Asp Ala Asp Leu Leu Pro Ala
            115                 120                 125

Gly Phe Glu Glu Arg Thr Arg Gly Arg Gly Val Val Ala Thr Arg Trp
            130                 135                 140

Val Pro Gln Met Ser Ile Leu Ala His Ala Ala Val Gly Ala Phe Leu
145                 150                 155                 160

Thr His Cys Gly Trp Asn Ser Thr Ile Glu Gly Leu Met Phe Gly His
                    165                 170                 175

Pro Leu Ile Met Leu Pro Ile Phe Gly Asp Gln Gly Pro Asn Ala Arg
            180                 185                 190

Leu Ile Glu Ala Lys Asn Ala Gly Leu Gln Val Ala Arg Asn Asp Gly
            195                 200                 205

Asp Gly Ser Phe Asp Arg Glu Gly Val Ala Ala Ile Arg Ala Val
            210                 215                 220

Ala Val Glu Glu Glu Ser Ser Lys Val Phe Gln Ala Lys Ala Lys Lys
225                 230                 235                 240

Leu Gln Glu Ile Val Ala Asp Met Ala Cys His Glu Arg Tyr Ile Asp
                    245                 250                 255

Gly Phe Ile Gln Gln Leu Arg Ser Tyr Lys Asp Asp Ser Gly Tyr Ser
                260                 265                 270

Ser Ser Tyr Ala Ala Ala Ala Gly Met His Val Val Ile Cys Pro Trp
            275                 280                 285

Leu Ala Phe Gly His Leu Leu Pro Cys Leu Asp Leu Ala Gln Arg Leu
            290                 295                 300

Ala Ser Arg Gly His Arg Val Ser Phe Val Ser Thr Pro Arg Asn Ile
305                 310                 315                 320

Ser Arg Leu Pro Pro Val Arg Pro Ala Leu Ala Pro Leu Val Ala Phe
                    325                 330                 335

Val Ala Leu Pro Leu Pro Arg Val Glu Gly Leu Pro Asp Gly Ala Glu
                340                 345                 350

Ser Thr Asn Asp Val Pro His Asp Arg Pro Asp Met Val Glu Leu His
            355                 360                 365

Arg Arg Ala Phe Asp Gly Leu Ala Ala Pro Phe Ser Glu Phe Leu Gly
370                 375                 380

Thr Ala Cys Ala Asp Trp Val Ile Val Asp Val Phe His His Trp Ala
385                 390                 395                 400

Ala Ala Ala Ala Leu Glu His Lys Val Pro Cys Ala Met Met Leu Leu
                405                 410                 415

Gly Ser Ala His Met Ile Ala Ser Ile Ala Asp Arg Arg Leu Glu Arg
                420                 425                 430

Ala Glu Thr Glu Ser Pro Ala Ala Ala Gly Gln Gly Arg Pro Ala Ala
            435                 440                 445
```

Ala Pro Thr Phe Glu Val Ala Arg Met Lys Leu Ile Arg Thr Lys
    450                 455                 460

<210> SEQ ID NO 10
<211> LENGTH: 459
<212> TYPE: PRT
<213> ORGANISM: Artificial sequence
<220> FEATURE:
<223> OTHER INFORMATION: Synthetic sequence

<400> SEQUENCE: 10

Met Ala Asn Trp Gln Ile Leu Lys Glu Ile Leu Gly Lys Met Ile Lys
1               5                   10                  15

Gln Thr Lys Ala Ser Ser Gly Val Ile Trp Asn Ser Phe Lys Glu Leu
            20                  25                  30

Glu Glu Ser Glu Leu Glu Thr Val Ile Arg Glu Ile Pro Ala Pro Ser
        35                  40                  45

Phe Leu Ile Pro Leu Pro Lys His Leu Thr Ala Ser Ser Ser Ser Leu
    50                  55                  60

Leu Asp His Asp Arg Thr Val Phe Gln Trp Leu Asp Gln Gln Pro Pro
65                  70                  75                  80

Ser Ser Val Leu Tyr Val Ser Phe Gly Ser Thr Ser Glu Val Asp Glu
                85                  90                  95

Lys Asp Phe Leu Glu Ile Ala Arg Gly Leu Val Asp Ser Lys Gln Ser
            100                 105                 110

Phe Leu Trp Val Val Arg Pro Gly Phe Val Lys Gly Ser Thr Trp Val
        115                 120                 125

Glu Pro Leu Pro Asp Gly Phe Leu Gly Glu Arg Gly Arg Ile Val Lys
    130                 135                 140

Trp Val Pro Gln Gln Glu Val Leu Ala His Gly Ala Ile Gly Ala Phe
145                 150                 155                 160

Trp Thr His Ser Gly Trp Asn Ser Thr Leu Glu Ser Val Cys Glu Gly
                165                 170                 175

Val Pro Met Ile Phe Ser Asp Phe Gly Leu Asp Gln Pro Leu Asn Ala
            180                 185                 190

Arg Tyr Met Ser Asp Val Leu Lys Val Gly Val Tyr Leu Glu Asn Gly
        195                 200                 205

Trp Glu Arg Gly Glu Ile Ala Asn Ala Ile Arg Arg Val Met Val Asp
    210                 215                 220

Glu Glu Gly Glu Tyr Ile Arg Gln Asn Ala Arg Val Leu Lys Gln Lys
225                 230                 235                 240

Ala Asp Val Ser Leu Met Lys Gly Gly Ser Ser Tyr Glu Ser Leu Glu
                245                 250                 255

Ser Leu Val Ser Tyr Ile Ser Ser Leu Glu Asn Lys Thr Glu Thr Thr
            260                 265                 270

Val Arg Arg Arg Arg Ile Ile Leu Phe Pro Val Pro Phe Gln Gly
        275                 280                 285

His Ile Asn Pro Ile Leu Gln Leu Ala Asn Val Leu Tyr Ser Lys Gly
    290                 295                 300

Phe Ser Ile Thr Ile Phe His Thr Asn Phe Asn Lys Pro Lys Thr Ser
305                 310                 315                 320

Asn Tyr Pro His Phe Thr Phe Arg Phe Ile Leu Asp Asn Asp Pro Gln
                325                 330                 335

Asp Glu Arg Ile Ser Asn Leu Pro Thr His Gly Pro Leu Ala Gly Met
            340                 345                 350

Arg Ile Pro Ile Ile Asn Glu His Gly Ala Asp Glu Leu Arg Arg Glu
        355                 360                 365

Leu Glu Leu Leu Met Leu Ala Ser Gly Glu Asp Glu Val Ser Cys
    370                 375                 380

Leu Ile Thr Asp Ala Leu Trp Tyr Phe Ala Gln Ser Val Ala Asp Ser
385                 390                 395                 400

Leu Asn Leu Arg Arg Leu Val Leu Met Thr Ser Ser Leu Phe Asn Phe
                405                 410                 415

His Ala His Val Ser Leu Pro Gln Phe Asp Glu Leu Gly Tyr Leu Asp
            420                 425                 430

Pro Asp Asp Lys Thr Arg Leu Glu Glu Gln Ala Ser Gly Phe Pro Met
        435                 440                 445

Leu Lys Val Lys Asp Ile Lys Ser Ala Tyr Ser
    450                 455

<210> SEQ ID NO 11
<211> LENGTH: 392
<212> TYPE: PRT
<213> ORGANISM: Taxus canadensis

<400> SEQUENCE: 11

Met Tyr Thr Ala Met Ala Ala Gly Thr Gln Ser Leu Gln Leu Arg Thr
1               5                   10                  15

Val Ala Ser Tyr Gln Glu Cys Asn Ser Met Arg Ser Cys Phe Lys Leu
            20                  25                  30

Thr Pro Phe Lys Ser Phe His Gly Val Asn Phe Asn Val Pro Ser Leu
        35                  40                  45

Gly Ala Ala Asn Cys Glu Ile Met Gly His Leu Lys Leu Gly Ser Leu
    50                  55                  60

Pro Tyr Lys Gln Cys Ser Val Ser Ser Lys Ser Thr Lys Thr Met Ala
65                  70                  75                  80

Gln Leu Val Asp Leu Ala Glu Thr Glu Lys Ala Glu Gly Lys Asp Ile
                85                  90                  95

Glu Phe Asp Phe Asn Glu Tyr Met Lys Ser Lys Ala Val Ala Val Asp
            100                 105                 110

Ala Ala Leu Asp Lys Ala Ile Pro Leu Glu Tyr Pro Glu Lys Ile His
        115                 120                 125

Glu Ser Met Arg Tyr Ser Leu Leu Ala Gly Gly Lys Arg Val Arg Pro
    130                 135                 140

Ala Leu Cys Ile Ala Ala Cys Glu Leu Val Gly Gly Ser Gln Asp Leu
145                 150                 155                 160

Ala Met Pro Thr Ala Cys Ala Met Glu Met Ile His Thr Met Ser Leu
                165                 170                 175

Ile His Asp Asp Leu Pro Cys Met Asp Asn Asp Phe Arg Arg Gly
            180                 185                 190

Lys Pro Thr Asn His Lys Val Phe Gly Glu Asp Thr Ala Val Leu Ala
        195                 200                 205

Gly Asp Ala Leu Leu Ser Phe Ala Phe Glu His Ile Ala Val Ala Thr
    210                 215                 220

Ser Lys Thr Val Pro Ser Asp Arg Thr Leu Arg Val Ile Ser Glu Leu
225                 230                 235                 240

Gly Lys Thr Ile Gly Ser Gln Gly Leu Val Gly Gly Gln Val Val Asp
                245                 250                 255

Ile Thr Ser Glu Gly Asp Ala Asn Val Asp Leu Lys Thr Leu Glu Trp
            260                 265                 270

Ile His Ile His Lys Thr Ala Val Leu Leu Glu Cys Ser Val Val Ser
        275                 280                 285

Gly Gly Ile Leu Gly Gly Ala Thr Glu Asp Glu Ile Ala Arg Ile Arg
        290                 295                 300

Arg Tyr Ala Arg Cys Val Gly Leu Leu Phe Gln Val Val Asp Asp Ile
305                 310                 315                 320

Leu Asp Val Thr Lys Ser Ser Glu Glu Leu Gly Lys Thr Ala Gly Lys
                325                 330                 335

Asp Leu Leu Thr Asp Lys Ala Thr Tyr Pro Lys Leu Met Gly Leu Glu
                340                 345                 350

Lys Ala Lys Glu Phe Ala Ala Glu Leu Ala Thr Arg Ala Lys Glu Glu
                355                 360                 365

Leu Ser Ser Phe Asp Gln Ile Lys Ala Ala Pro Leu Leu Gly Leu Ala
                370                 375                 380

Asp Tyr Ile Ala Phe Arg Gln Asn
385                 390

<210> SEQ ID NO 12
<211> LENGTH: 296
<212> TYPE: PRT
<213> ORGANISM: Taxus canadensis

<400> SEQUENCE: 12

Met Ala Asp Phe Asn Glu Tyr Met Lys Ser Lys Ala Val Ala Val Asp
1               5                   10                  15

Ala Ala Leu Asp Lys Ala Ile Pro Leu Glu Tyr Pro Glu Lys Ile His
                20                  25                  30

Glu Ser Met Arg Tyr Ser Leu Leu Ala Gly Gly Lys Arg Val Arg Pro
            35                  40                  45

Ala Leu Cys Ile Ala Ala Cys Glu Leu Val Gly Gly Ser Gln Asp Leu
        50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95

Lys Pro Thr Asn His Lys Val Phe Gly Glu Asp Thr Ala Val Leu Ala
                100                 105                 110

Gly Asp Ala Leu Leu Ser Phe Ala Phe Glu His Ile Ala Val Ala Thr
            115                 120                 125

Ser Lys Thr Val Pro Ser Asp Arg Thr Leu Arg Val Ile Cys Glu Leu
        130                 135                 140

Gly Lys Thr Ile Gly Ser Gln Gly Leu Val Gly Gly Gln Val Val Asp
145                 150                 155                 160

Ile Thr Ser Glu Gly Asp Ala Asn Val Asp Leu Lys Thr Leu Glu Trp
                165                 170                 175

Ile His Ile His Lys Thr Ala Val Leu Leu Glu Cys Ser Val Val Ser
                180                 185                 190

Gly Gly Ile Leu Gly Asp Ala Thr Glu Asp Glu Ile Ala Arg Ile Arg
            195                 200                 205

Arg Tyr Ala Arg Cys Val Gly Leu Leu Phe Gln Val Val Asp Asp Ile
        210                 215                 220

Leu Asp Val Thr Lys Ser Ser Glu Glu Leu Gly Lys Thr Ala Gly Lys
225                 230                 235                 240

Asp Leu Leu Thr Asp Lys Ala Thr Tyr Pro Lys Leu Met Gly Leu Glu

```
                    245                 250                 255
Lys Ala Lys Glu Phe Ala Ala Glu Leu Ala Thr Arg Ala Lys Glu Glu
            260                 265                 270

Leu Ser Ser Phe Asp Gln Ile Lys Val Ala Pro Leu Leu Gly Leu Ala
            275                 280                 285

Asp Tyr Ile Ala Phe Arg Gln Asn
            290                 295

<210> SEQ ID NO 13
<211> LENGTH: 383
<212> TYPE: PRT
<213> ORGANISM: Abies grandis

<400> SEQUENCE: 13

Met Ala Tyr Ser Gly Met Ala Thr Ser Tyr His Gly Leu His Phe Met
1               5                   10                  15

Asn Ile Ala Thr Gln Glu Cys Asn Leu Lys Arg Leu Ser Ile Pro Ser
            20                  25                  30

Arg Arg Phe His Gly Val Ser Pro Ser Leu Trp Ala Ser Asn Gly Phe
            35                  40                  45

Gln Gly His Leu Lys Arg Glu Leu Ser Ala Asn Ser Phe Leu Val Ser
        50                  55                  60

Ser Ser Arg Tyr Ser Asn Thr Ile Ala Lys Phe Thr Asn Leu Pro Glu
65                  70                  75                  80

Lys Val Lys Glu Lys Val Ile Glu Phe Asp Phe Lys Glu Tyr Leu Arg
                85                  90                  95

Ser Lys Ala Met Ala Val Asn Glu Ala Leu Asp Arg Ala Val Pro Leu
            100                 105                 110

Arg Tyr Pro Glu Arg Ile His Glu Ala Met Arg Tyr Ser Leu Leu Ala
            115                 120                 125

Gly Gly Lys Arg Val Arg Pro Val Leu Cys Ile Ser Ala Cys Glu Leu
        130                 135                 140

Val Gly Gly Thr Glu Glu Val Ala Met Pro Thr Ala Cys Ala Met Glu
145                 150                 155                 160

Met Ile His Thr Met Ser Leu Ile His Asp Asp Leu Pro Cys Met Asp
                165                 170                 175

Asn Asp Asp Phe Arg Arg Gly Lys Pro Thr Asn His Lys Val Phe Gly
            180                 185                 190

Glu Gly Thr Ala Ile Leu Ala Gly Asp Ala Leu Leu Ser Phe Ala Phe
            195                 200                 205

Glu His Ile Ala Val Ser Thr Ser Lys Ser Val Gly Thr Asp Arg Ile
        210                 215                 220

Leu Arg Val Val Ser Glu Leu Gly Arg Thr Ile Gly Ser Gln Gly Leu
225                 230                 235                 240

Val Gly Gly Gln Val Ala Asp Ile Thr Ser Glu Gly Asp Ala Ser Val
                245                 250                 255

Asp Leu Asp Thr Leu Glu Trp Ile His Ile His Lys Thr Ala Val Leu
            260                 265                 270

Leu Glu Cys Ser Val Met Cys Gly Ala Ile Ile Ser Gly Ala Ser Asp
            275                 280                 285

Asn Glu Ile Glu Arg Ile Gln Arg Tyr Ala Arg Ser Val Gly Leu Leu
        290                 295                 300

Phe Gln Val Val Asp Asp Ile Leu Asp Val Thr Lys Ser Ser Lys Glu
305                 310                 315                 320
```

```
Leu Gly Lys Thr Ala Gly Lys Asp Leu Ile Ser Asp Lys Ala Thr Tyr
            325                 330                 335

Pro Lys Leu Met Gly Leu Glu Lys Ala Lys Gln Phe Ala Ser Asp Leu
            340                 345                 350

Leu Ile Arg Ala Lys Glu Asp Leu Ser Cys Phe Asp Pro Met Lys Ala
            355                 360                 365

Ala Pro Leu Leu Gly Leu Ala Asp Tyr Ile Ala Phe Arg Gln Asn
            370                 375                 380

<210> SEQ ID NO 14
<211> LENGTH: 397
<212> TYPE: PRT
<213> ORGANISM: Aspergillus nidulans

<400> SEQUENCE: 14

Met Ser Pro Pro Leu Asp Ser Ala Leu Glu Pro Leu Ser Glu Tyr Lys
1               5                   10                  15

Glu Thr Ala Phe Pro Arg Thr Glu Lys Asp Pro Ser Gln Tyr Lys Glu
            20                  25                  30

His Asp Leu Val Thr Pro Glu Lys Glu Ile Gln Thr Gly Tyr Phe Ser
            35                  40                  45

Pro Arg Gly Ser His Ser Ser His Gly Ser His Asp Ser Ser Ala Ser
        50                  55                  60

Ser Asn Ile Ser Leu Asp Asp Ala Arg Met Ser Asp Val Asn Asn Ser
65                  70                  75                  80

Pro Asn Val Phe His Asp Asp Pro Asp Thr Ile Asp Glu Lys Leu Ser
                85                  90                  95

Met Tyr Trp Lys Ala Ala Asn Glu Thr Val Ile Arg Glu Pro Tyr Asp
            100                 105                 110

Tyr Ile Ala Gly Ile Pro Gly Lys Glu Ile Arg Arg Lys Leu Leu Glu
            115                 120                 125

Ala Phe Asn His Trp Tyr Lys Val Asp Glu Gln Ser Cys Gln Ala Ile
        130                 135                 140

Ala Thr Thr Val Gly Met Ala His Asn Ala Ser Leu Leu Ile Asp Asp
145                 150                 155                 160

Ile Gln Asp Ser Ser Lys Leu Arg Arg Gly Val Pro Cys Ala His Glu
                165                 170                 175

Val Phe Gly Ile Ala Gln Thr Ile Asn Ser Ala Asn Tyr Val Tyr Phe
            180                 185                 190

Leu Ala Gln Asn Gln Leu Phe Arg Leu Arg Ser Trp Pro Gln Ala Ile
            195                 200                 205

Ser Val Phe Asn Glu Glu Met Val Asn Leu His Arg Gly Gln Gly Met
        210                 215                 220

Glu Leu Phe Trp Arg Asp Asn Leu Leu Pro Pro Ser Met Asp Asp Tyr
225                 230                 235                 240

Leu Gln Met Ile Ala Asn Lys Thr Gly Gly Leu Phe Arg Met Ile Val
                245                 250                 255

Arg Leu Leu Gln Thr Ser Ser Arg Gln Val Ile Asp Val Glu Gln Leu
            260                 265                 270

Val Asp Val Leu Gly Leu Tyr Phe Gln Ile Leu Asp Asp Tyr Lys Asn
            275                 280                 285

Ile Arg Glu Glu Lys Met Ala Ala Gln Lys Gly Phe Phe Glu Asp Leu
        290                 295                 300

Thr Glu Gly Lys Phe Ser Phe Pro Ile Cys His Ala Ile Gly Glu Gly
305                 310                 315                 320
```

```
Ala Lys Asn Arg Thr Ala Leu Leu His Met Leu Arg Leu Lys Thr Asp
            325                 330                 335

Asp Met Lys Ile Lys Gln Glu Ala Val Cys Ile Leu Asp Asn Ala Gly
            340                 345                 350

Ser Leu Asp Tyr Thr Arg Glu Val Leu Tyr Gly Leu Asp Arg Lys Ala
            355                 360                 365

Arg Ser Leu Leu Arg Glu Phe Lys Thr Pro Asn Pro Phe Met Glu Ala
            370                 375                 380

Leu Leu Asp Ala Met Leu Ser Ser Leu Gln Ala Cys His
385                 390                 395

<210> SEQ ID NO 15
<211> LENGTH: 359
<212> TYPE: PRT
<213> ORGANISM: Streptomyces melanosporofaciens

<400> SEQUENCE: 15

Met Thr Thr Pro Thr Leu Ser Pro Gly Arg Leu Asp Ala Asp Thr Val
1               5                   10                  15

Arg Lys Ser Val Asp Val Leu Glu Asp Phe Leu Thr Ala Lys Ala
            20                  25                  30

His Thr Thr Pro Gln His His Leu Pro Tyr Leu Ser Gly Leu Leu Lys
            35                  40                  45

Asp Phe Leu Ser Gly Gly Lys Arg Ile Arg Pro Leu Leu Cys Val Thr
50                  55                  60

Gly Trp Gln Ala Val Gly Gly Glu Asp Thr Glu Pro Val Phe Arg
65                  70                  75                  80

Val Ala Ala Cys Leu Glu Met Phe His Ala Phe Ala Leu Ile His Asp
            85                  90                  95

Asp Val Met Asp Asp Ser Asp Thr Arg Arg Gly Arg Pro Thr Ile His
            100                 105                 110

Arg Thr Leu Ala Ala Leu Cys Ala Thr Asp Arg Arg Pro Glu Gln Ile
            115                 120                 125

Glu Arg Phe Gly Val Ser Gly Ala Val Leu Leu Gly Asp Leu Ala Leu
            130                 135                 140

Thr Trp Ser Asp Glu Leu Leu His Ser Ala Gly Leu Thr Pro Val Gln
145                 150                 155                 160

Phe Asp Ala Val Leu Pro Leu Ser Glu Met Arg Thr Glu Val Met
            165                 170                 175

Leu Gly Gln Tyr Leu Asp Leu Gln Ala Thr Gly Glu Leu Thr Asp Asp
            180                 185                 190

Val Glu Ala Thr Leu Thr Val Asn Arg Tyr Lys Thr Ala Lys Tyr Thr
            195                 200                 205

Ile Glu Arg Pro Leu His Val Gly Ala Ala Ile Ala Gly Ala Gly Pro
    210                 215                 220

Glu Ala Met Glu Ala Phe Thr Ala Tyr Ala Leu Pro Leu Gly Glu Ala
225                 230                 235                 240

Phe Gln Leu Arg Asp Asp Leu Leu Gly Val Tyr Gly Asp Pro Glu Ser
            245                 250                 255

Thr Gly Lys Ser Gln Leu Asp Asp Leu Arg Ala Gly Lys Asn Thr Thr
            260                 265                 270

Leu Ile Ala Leu Ala Leu Arg Gly Ser Asp Ser Thr Gln Ala Ala Arg
    275                 280                 285

Leu Arg Ser Leu Ile Gly Asn Pro Leu Leu Asp Glu Arg Asp Ala Ala
```

```
                290                 295                 300
Thr Ile Gln Glu Ile Phe Ala Thr Thr Ala Arg Asp Ala Val Glu
305                 310                 315                 320

Gln Met Ile Asp Asp Arg Arg Thr Gln Ala Leu Arg Ala Leu Asp Asp
                325                 330                 335

Ala Pro Phe Thr Ala Asp Ala Val Asn Ala Leu Lys Gln Ile Ala Arg
                340                 345                 350

Leu Ala Thr Val Arg Asn Ser
        355

<210> SEQ ID NO 16
<211> LENGTH: 787
<212> TYPE: PRT
<213> ORGANISM: Stevia rebaudiana

<400> SEQUENCE: 16

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
                20                  25                  30

Ser Thr Gly Ile Val Ala Leu Arg Asp Ile Asn Phe Arg Cys Lys Ala
            35                  40                  45

Val Ser Lys Glu Tyr Ser Asp Leu Leu Gln Lys Asp Glu Ala Ser Phe
    50                  55                  60

Thr Lys Trp Asp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
                100                 105                 110

Asp Thr Ala Trp Val Ala Leu Val Gln Asp Val Asp Gly Ser Gly Ser
            115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
                180                 185                 190

Lys Leu Glu Asp Glu Asn Ala Glu His Met Pro Ile Gly Phe Glu Val
            195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
                260                 265                 270

Leu Lys Leu Gln Cys Lys Asp Gly Ser Phe Leu Phe Ser Pro Ser Ser
            275                 280                 285

Thr Ala Phe Ala Leu Met Gln Thr Lys Asp Glu Lys Cys Leu Gln Tyr
    290                 295                 300
```

-continued

```
Leu Thr Asn Ile Val Thr Lys Phe Asn Gly Gly Val Pro Asn Val Tyr
305                 310                 315                 320

Pro Val Asp Leu Phe Glu His Ile Trp Val Asp Arg Leu Gln Arg
                325                 330                 335

Leu Gly Ile Ala Arg Tyr Phe Lys Ser Glu Ile Lys Asp Cys Val Glu
                340                 345                 350

Tyr Ile Asn Lys Tyr Trp Thr Lys Asn Gly Ile Cys Trp Ala Arg Asn
                355                 360                 365

Thr His Val Gln Asp Ile Asp Thr Ala Met Gly Phe Arg Val Leu
                370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
                420                 425                 430

Glu Arg Ile Leu Glu Asp Ala Lys Lys Phe Ser Tyr Asn Tyr Leu Lys
                435                 440                 445

Glu Lys Gln Ser Thr Asn Glu Leu Leu Asp Lys Trp Ile Ile Ala Lys
                450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
                500                 505                 510

Ser Asn Asn Thr Tyr Leu Glu Met Ala Lys Leu Asp Tyr Asn Asn Tyr
                515                 520                 525

Val Ala Val Leu Gln Leu Glu Trp Tyr Thr Ile Gln Gln Trp Tyr Val
                530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ala Ser Ile Phe Glu Pro Glu Arg Ser
                565                 570                 575

Lys Glu Arg Ile Ala Trp Ala Lys Thr Thr Ile Leu Val Asp Lys Ile
                580                 585                 590

Thr Ser Ile Phe Asp Ser Ser Gln Ser Ser Lys Glu Asp Ile Thr Ala
                595                 600                 605

Phe Ile Asp Lys Phe Arg Asn Lys Ser Ser Ser Lys Lys His Ser Ile
                610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
                660                 665                 670

Gly Val Asp Val Thr Ala Glu Leu Met Val Gln Met Ile Asn Met Thr
                675                 680                 685

Ala Gly Arg Trp Val Ser Lys Glu Leu Leu Thr His Pro Gln Tyr Gln
                690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
```

```
              725                 730                 735
Leu Val Gln Leu Val Phe Ser Asp Thr Pro Asp Asp Leu Asp Gln Asp
            740                 745                 750

Met Lys Gln Thr Phe Leu Thr Val Met Lys Thr Phe Tyr Tyr Lys Ala
            755                 760                 765

Trp Cys Asp Pro Asn Thr Ile Asn Asp His Ile Ser Lys Val Phe Glu
            770                 775                 780

Ile Val Ile
785

<210> SEQ ID NO 17
<211> LENGTH: 784
<212> TYPE: PRT
<213> ORGANISM: Stevia rebaudiana

<400> SEQUENCE: 17

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Met Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
    290                 295                 300
```

```
Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
            340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Glu Asp Phe Tyr Thr Cys
450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
```

```
            725                 730                 735
Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
            755                 760                 765

Ile Ile Tyr Asn Pro Leu Val Leu Val Asn Glu Asn Glu Glu Gln Arg
770                 775                 780

<210> SEQ ID NO 18
<211> LENGTH: 952
<212> TYPE: PRT
<213> ORGANISM: Gibberella fujikuroi

<400> SEQUENCE: 18

Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
            100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
    130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
            180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
    210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Ile Ser Gly Thr
            260                 265                 270

Phe Pro Thr Thr His Phe Glu Cys Ser Trp Ile Ile Ala Thr Leu Leu
        275                 280                 285

Lys Val Gly Phe Thr Leu Lys Gln Ile Asp Gly Asp Gly Leu Arg Gly
    290                 295                 300

Leu Ser Thr Ile Leu Leu Glu Ala Leu Arg Asp Glu Asn Gly Val Ile
305                 310                 315                 320
```

```
Gly Phe Ala Pro Arg Thr Ala Asp Val Asp Asp Thr Ala Lys Ala Leu
            325                 330                 335

Leu Ala Leu Ser Leu Val Asn Gln Pro Val Ser Pro Asp Ile Met Ile
            340                 345                 350

Lys Val Phe Glu Gly Lys Asp His Phe Thr Thr Phe Gly Ser Glu Arg
            355                 360                 365

Asp Pro Ser Leu Thr Ser Asn Leu His Val Leu Leu Ser Leu Leu Lys
            370                 375                 380

Gln Ser Asn Leu Ser Gln Tyr His Pro Gln Ile Leu Lys Thr Thr Leu
385                 390                 395                 400

Phe Thr Cys Arg Trp Trp Gly Ser Asp His Cys Val Lys Asp Lys
            405                 410                 415

Trp Asn Leu Ser His Leu Tyr Pro Thr Met Leu Leu Val Glu Ala Phe
            420                 425                 430

Thr Glu Val Leu His Leu Ile Asp Gly Gly Glu Leu Ser Ser Leu Phe
            435                 440                 445

Asp Glu Ser Phe Lys Cys Lys Ile Gly Leu Ser Ile Phe Gln Ala Val
            450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
            485                 490                 495

Val Cys Phe Phe Thr His Met Val Asp Arg Leu Gln Ser Cys Val Asp
            500                 505                 510

Arg Gly Phe Ser Trp Leu Lys Ser Cys Ser Phe His Ser Gln Asp Leu
            515                 520                 525

Thr Trp Thr Ser Lys Thr Ala Tyr Glu Val Gly Phe Val Ala Glu Ala
            530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
            565                 570                 575

Lys Tyr Met Arg Leu Val Arg Lys Thr Ala Leu Phe Ser Pro Leu Asp
            580                 585                 590

Glu Trp Gly Leu Met Ala Ser Ile Ile Glu Ser Ser Phe Phe Val Pro
            595                 600                 605

Leu Leu Gln Ala Gln Arg Val Glu Ile Tyr Pro Arg Asp Asn Ile Lys
            610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
            645                 650                 655

Met Met Tyr Leu Ser Leu Leu Gly Tyr Gln Thr Asp Glu Tyr Met Glu
            660                 665                 670

Ala Val Ala Gly Pro Val Phe Gly Asp Val Ser Leu Leu His Gln Thr
            675                 680                 685

Ile Asp Lys Val Ile Asp Asn Thr Met Gly Asn Leu Ala Arg Ala Asn
            690                 695                 700

Gly Thr Val His Ser Gly Asn Gly His Gln Glu Ser Pro Asn Ile
705                 710                 715                 720

Gly Gln Val Glu Asp Thr Leu Thr Arg Phe Thr Asn Ser Val Leu Asn
            725                 730                 735

His Lys Asp Val Leu Asn Ser Ser Ser Asp Gln Asp Thr Leu Arg
```

```
                    740                 745                 750
Arg Glu Phe Arg Thr Phe Met His Ala His Ile Thr Gln Ile Glu Asp
            755                 760                 765
Asn Ser Arg Phe Ser Lys Gln Ala Ser Ser Asp Ala Phe Ser Ser Pro
        770                 775                 780
Glu Gln Ser Tyr Phe Gln Trp Val Asn Ser Thr Gly Gly Ser His Val
785                 790                 795                 800
Ala Cys Ala Tyr Ser Phe Ala Phe Ser Asn Cys Leu Met Ser Ala Asn
            805                 810                 815
Leu Leu Gln Gly Lys Asp Ala Phe Pro Ser Gly Thr Gln Lys Tyr Leu
        820                 825                 830
Ile Ser Ser Val Met Arg His Ala Thr Asn Met Cys Arg Met Tyr Asn
            835                 840                 845
Asp Phe Gly Ser Ile Ala Arg Asp Asn Ala Glu Arg Asn Val Asn Ser
        850                 855                 860
Ile His Phe Pro Glu Phe Thr Leu Cys Asn Gly Thr Ser Gln Asn Leu
865                 870                 875                 880
Asp Glu Arg Lys Glu Arg Leu Leu Lys Ile Ala Thr Tyr Glu Gln Gly
            885                 890                 895
Tyr Leu Asp Arg Ala Leu Glu Ala Leu Glu Arg Gln Ser Arg Asp Asp
        900                 905                 910
Ala Gly Asp Arg Ala Gly Ser Lys Asp Met Arg Lys Leu Lys Ile Val
            915                 920                 925
Lys Leu Phe Cys Asp Val Thr Asp Leu Tyr Asp Gln Leu Tyr Val Ile
        930                 935                 940
Lys Asp Leu Ser Ser Ser Met Lys
945                 950

<210> SEQ ID NO 19
<211> LENGTH: 881
<212> TYPE: PRT
<213> ORGANISM: Physcomitrella patens

<400> SEQUENCE: 19

Met Ala Ser Ser Thr Leu Ile Gln Asn Arg Ser Cys Gly Val Thr Ser
1               5                   10                  15
Ser Met Ser Ser Phe Gln Ile Phe Arg Gly Gln Pro Leu Arg Phe Pro
            20                  25                  30
Gly Thr Arg Thr Pro Ala Ala Val Gln Cys Leu Lys Lys Arg Arg Cys
        35                  40                  45
Leu Arg Pro Thr Glu Ser Val Leu Glu Ser Ser Pro Gly Ser Gly Ser
    50                  55                  60
Tyr Arg Ile Val Thr Gly Pro Ser Gly Ile Asn Pro Ser Ser Asn Gly
65                  70                  75                  80
His Leu Gln Glu Gly Ser Leu Thr His Arg Leu Pro Ile Pro Met Glu
            85                  90                  95
Lys Ser Ile Asp Asn Phe Gln Ser Thr Leu Tyr Val Ser Asp Ile Trp
        100                 105                 110
Ser Glu Thr Leu Gln Arg Thr Glu Cys Leu Leu Gln Val Thr Glu Asn
    115                 120                 125
Val Gln Met Asn Glu Trp Ile Glu Glu Ile Arg Met Tyr Phe Arg Asn
            130                 135                 140
Met Thr Leu Gly Glu Ile Ser Met Ser Pro Tyr Asp Thr Ala Trp Val
145                 150                 155                 160
```

-continued

```
Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
    210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285

Pro Met Ala Met Val Tyr Lys Tyr Pro Thr Thr Leu Leu His Ser Leu
    290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

Leu Met Tyr Thr Lys Asp Val Lys Cys Phe Asp Tyr Leu Asn Gln Leu
            340                 345                 350

Leu Ile Lys Phe Asp His Ala Cys Pro Asn Val Tyr Pro Val Asp Leu
        355                 360                 365

Phe Glu Arg Leu Trp Met Val Asp Arg Leu Gln Arg Leu Gly Ile Ser
    370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
        435                 440                 445

Phe Phe Cys Phe Ala Gly Gln Ser Ser Gln Ala Val Thr Gly Met Phe
    450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
            500                 505                 510

Glu Val Glu Tyr Asn Leu Thr Phe Pro Trp Tyr Ala Ser Leu Pro Arg
        515                 520                 525

Leu Glu His Arg Thr Tyr Leu Asp Gln Tyr Gly Ile Asp Asp Ile Trp
    530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
```

```
                580             585             590
Asp Leu Glu Phe Ala Arg Gln Lys Ser Val Glu Cys Tyr Phe Ala Gly
            595                 600             605

Ala Ala Thr Met Phe Glu Pro Glu Met Val Gln Ala Arg Leu Val Trp
        610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
                645                 650                 655

Trp Asn Pro Glu Leu Ile Asn Gly Leu Pro Glu Gln Ala Lys Ile Leu
            660                 665                 670

Phe Met Gly Leu Tyr Lys Thr Val Asn Thr Ile Ala Glu Glu Ala Phe
        675                 680                 685

Met Ala Gln Lys Arg Asp Val His His His Leu Lys His Tyr Trp Asp
    690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
                725                 730                 735

Ala Leu Glu Pro Ile Val Cys Ser Thr Leu Phe Ala Gly His Arg
            740                 745                 750

Leu Asp Glu Asp Val Leu Asp Ser Tyr Asp Tyr His Leu Val Met His
        755                 760                 765

Leu Val Asn Arg Val Gly Arg Ile Leu Asn Asp Ile Gln Gly Met Lys
    770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
                805                 810                 815

Glu Leu Val Asp Asn Ser Met Gln Gln Leu Thr Tyr Glu Val Leu Arg
            820                 825                 830

Phe Thr Ala Val Pro Lys Ser Cys Lys Arg Ile His Leu Asn Met Ala
        835                 840                 845

Lys Ile Met His Ala Phe Tyr Lys Asp Thr Asp Gly Phe Ser Ser Leu
    850                 855                 860

Thr Ala Met Thr Gly Phe Val Lys Val Leu Phe Glu Pro Val Pro
865                 870                 875                 880

Glu

<210> SEQ ID NO 20
<211> LENGTH: 946
<212> TYPE: PRT
<213> ORGANISM: Phaeosphaeria sp.

<400> SEQUENCE: 20

Met Phe Ala Lys Phe Asp Met Leu Glu Glu Ala Arg Ala Leu Val
1               5                   10                  15

Arg Lys Val Gly Asn Ala Val Asp Pro Ile Tyr Gly Phe Ser Thr Thr
            20                  25                  30

Ser Cys Gln Ile Tyr Asp Thr Ala Trp Ala Ala Met Ile Ser Lys Glu
        35                  40                  45

Glu His Gly Asp Lys Val Trp Leu Phe Pro Glu Ser Phe Lys Tyr Leu
    50                  55                  60

Leu Glu Lys Gln Gly Glu Asp Gly Ser Trp Glu Arg His Pro Arg Ser
```

```
                65                  70                  75                  80
Lys Thr Val Gly Val Leu Asn Thr Ala Ala Ala Cys Leu Ala Leu Leu
                    85                  90                  95

Arg His Val Lys Asn Pro Leu Gln Leu Gln Asp Ile Ala Ala Gln Asp
                    100                 105                 110

Ile Glu Leu Arg Ile Gln Arg Gly Leu Arg Ser Leu Glu Glu Gln Leu
                    115                 120                 125

Ile Ala Trp Asp Asp Val Leu Asp Thr Asn His Ile Gly Val Glu Met
                130                 135                 140

Ile Val Pro Ala Leu Leu Asp Tyr Leu Gln Ala Glu Asp Glu Asn Val
145                 150                 155                 160

Asp Phe Glu Phe Glu Ser His Ser Leu Leu Met Gln Met Tyr Lys Glu
                    165                 170                 175

Lys Met Ala Arg Phe Ser Pro Glu Ser Leu Tyr Arg Ala Arg Pro Ser
                    180                 185                 190

Ser Ala Leu His Asn Leu Glu Ala Leu Ile Gly Lys Leu Asp Phe Asp
                    195                 200                 205

Lys Val Gly His His Leu Tyr Asn Gly Ser Met Met Ala Ser Pro Ser
                210                 215                 220

Ser Thr Ala Ala Phe Leu Met His Ala Ser Pro Trp Ser His Glu Ala
225                 230                 235                 240

Glu Ala Tyr Leu Arg His Val Phe Glu Ala Gly Thr Gly Lys Gly Ser
                    245                 250                 255

Gly Gly Phe Pro Gly Thr Tyr Pro Thr Thr Tyr Phe Glu Leu Asn Trp
                    260                 265                 270

Val Leu Ser Thr Leu Met Lys Ser Gly Phe Thr Leu Ser Asp Leu Glu
                    275                 280                 285

Cys Asp Glu Leu Ser Ser Ile Ala Asn Thr Ile Ala Glu Gly Phe Glu
                    290                 295                 300

Cys Asp His Gly Val Ile Gly Phe Ala Pro Arg Ala Val Asp Val Asp
305                 310                 315                 320

Asp Thr Ala Lys Gly Leu Leu Thr Leu Thr Leu Leu Gly Met Asp Glu
                    325                 330                 335

Gly Val Ser Pro Ala Pro Met Ile Ala Met Phe Glu Ala Lys Asp His
                    340                 345                 350

Phe Leu Thr Phe Leu Gly Glu Arg Asp Pro Ser Phe Thr Ser Asn Cys
                    355                 360                 365

His Val Leu Leu Ser Leu Leu His Arg Thr Asp Leu Leu Gln Tyr Leu
                    370                 375                 380

Pro Gln Ile Arg Lys Thr Thr Thr Phe Leu Cys Glu Ala Trp Trp Ala
385                 390                 395                 400

Cys Asp Gly Gln Ile Lys Asp Lys Trp His Leu Ser His Leu Tyr Pro
                    405                 410                 415

Thr Met Leu Met Val Gln Ala Phe Ala Glu Ile Leu Leu Lys Ser Ala
                    420                 425                 430

Glu Gly Glu Pro Leu His Asp Ala Phe Asp Ala Ala Thr Leu Ser Arg
                    435                 440                 445

Val Ser Ile Cys Val Phe Gln Ala Cys Leu Arg Thr Leu Leu Ala Gln
                    450                 455                 460

Ser Gln Asp Gly Ser Trp His Gly Gln Pro Glu Ala Ser Cys Tyr Ala
465                 470                 475                 480

Val Leu Thr Leu Ala Glu Ser Gly Arg Leu Val Leu Leu Gln Ala Leu
                    485                 490                 495
```

```
Gln Pro Gln Ile Ala Ala Ala Met Glu Lys Ala Ala Asp Val Met Gln
            500                 505                 510

Ala Gly Arg Trp Ser Cys Ser Asp His Asp Cys Asp Trp Thr Ser Lys
        515                 520                 525

Thr Ala Tyr Arg Val Asp Leu Val Ala Ala Ala Tyr Arg Leu Ala Ala
    530                 535                 540

Met Lys Ala Ser Ser Asn Leu Thr Phe Thr Val Asp Asp Asn Val Ser
545                 550                 555                 560

Lys Arg Ser Asn Gly Phe Gln Gln Leu Val Gly Arg Thr Asp Leu Phe
                565                 570                 575

Ser Gly Val Pro Ala Trp Glu Leu Gln Ala Ser Phe Leu Glu Ser Ala
            580                 585                 590

Leu Phe Val Pro Leu Leu Arg Asn His Arg Leu Asp Val Phe Asp Arg
        595                 600                 605

Asp Asp Ile Lys Val Ser Lys Asp His Tyr Leu Asp Met Ile Pro Phe
    610                 615                 620

Thr Trp Val Gly Cys Asn Asn Arg Ser Arg Thr Tyr Val Ser Thr Ser
625                 630                 635                 640

Phe Leu Phe Asp Met Met Ile Ile Ser Met Leu Gly Tyr Gln Ile Asp
                645                 650                 655

Glu Phe Phe Glu Ala Glu Ala Ala Pro Ala Phe Ala Gln Cys Ile Gly
            660                 665                 670

Gln Leu His Gln Val Val Asp Lys Val Val Asp Glu Val Ile Asp Glu
        675                 680                 685

Val Val Asp Lys Val Val Gly Lys Val Val Gly Lys Val Val Gly Lys
    690                 695                 700

Val Val Asp Glu Arg Val Asp Ser Pro Thr His Glu Ala Ile Ala Ile
705                 710                 715                 720

Cys Asn Ile Glu Ala Ser Leu Arg Arg Phe Val Asp His Val Leu His
                725                 730                 735

His Gln His Val Leu His Ala Ser Gln Gln Glu Gln Asp Ile Leu Trp
            740                 745                 750

Arg Glu Leu Arg Ala Phe Leu His Ala His Val Gln Met Ala Asp
        755                 760                 765

Asn Ser Thr Leu Ala Pro Pro Gly Arg Thr Phe Phe Asp Trp Val Arg
    770                 775                 780

Thr Thr Ala Ala Asp His Val Ala Cys Ala Tyr Ser Phe Ala Phe Ala
785                 790                 795                 800

Cys Cys Ile Thr Ser Ala Thr Ile Gly Gln Gly Ser Met Phe Ala
                805                 810                 815

Thr Val Asn Glu Leu Tyr Leu Val Gln Ala Ala Ala Arg His Met Thr
            820                 825                 830

Thr Met Cys Arg Met Cys Asn Asp Ile Gly Ser Val Asp Arg Asp Phe
        835                 840                 845

Ile Glu Ala Asn Ile Asn Ser Val His Phe Pro Glu Phe Ser Thr Leu
    850                 855                 860

Ser Leu Val Ala Asp Lys Lys Ala Leu Ala Arg Leu Ala Ala Tyr
865                 870                 875                 880

Glu Lys Ser Cys Leu Thr His Thr Leu Asp Gln Phe Glu Asn Glu Val
                885                 890                 895

Leu Gln Ser Pro Arg Val Ser Ser Ala Ala Ser Gly Asp Phe Arg Thr
            900                 905                 910
```

```
Arg Lys Val Ala Val Arg Phe Ala Asp Val Thr Asp Phe Tyr
            915                 920                 925

Asp Gln Leu Tyr Ile Leu Arg Asp Leu Ser Ser Leu Lys His Val
    930                 935                 940

Gly Thr
945

<210> SEQ ID NO 21
<211> LENGTH: 513
<212> TYPE: PRT
<213> ORGANISM: Stevia rebaudiana

<400> SEQUENCE: 21

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335
```

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile

<210> SEQ ID NO 22
<211> LENGTH: 501
<212> TYPE: PRT
<213> ORGANISM: Artificial sequence
<220> FEATURE:
<223> OTHER INFORMATION: Synthetic sequence

<400> SEQUENCE: 22

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
        35                  40                  45

Asn Leu Leu Gln Leu Lys Glu Lys Lys Pro Tyr Met Thr Phe Thr Arg
    50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
        115                 120                 125

Tyr His Lys Thr Val Lys Arg His Ile Leu Thr Ala Val Leu Gly Pro
    130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

```
Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
        195                 200                 205

Leu Lys Ile Thr Met Asn Arg Asp Glu Ile Phe Gln Val Leu Val Val
        210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
                260                 265                 270

Lys Lys Arg Ile Ala Ser Gly Glu Lys Leu Asn Ser Tyr Ile Asp Tyr
            275                 280                 285

Leu Leu Ser Glu Ala Gln Thr Leu Thr Asp Gln Gln Leu Leu Met Ser
        290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
        370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
                485                 490                 495

Ile Lys Pro Arg Ile
            500

<210> SEQ ID NO 23
<211> LENGTH: 509
<212> TYPE: PRT
<213> ORGANISM: Arabidopsis thaliana

<400> SEQUENCE: 23

Met Ala Phe Phe Ser Met Ile Ser Ile Leu Leu Gly Phe Val Ile Ser
1               5                   10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45
```

-continued

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Leu Ile Val Leu Asn Ser Thr Glu Thr
                85                  90                  95

Ala Lys Glu Ala Met Val Thr Arg Phe Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
                500                 505

<210> SEQ ID NO 24
<211> LENGTH: 546
<212> TYPE: PRT
<213> ORGANISM: Physcomitrella patens

<400> SEQUENCE: 24

Met Ala Lys His Leu Ala Thr Gln Leu Leu Gln Gln Trp Asn Glu Ala
1               5                   10                  15

Leu Lys Thr Met Pro Pro Gly Phe Arg Thr Ala Gly Lys Ile Leu Val
                20                  25                  30

Trp Glu Glu Leu Ala Ser Asn Lys Val Leu Ile Thr Ile Ala Leu Ala
            35                  40                  45

Trp Val Leu Leu Phe Val Ala Arg Thr Cys Leu Arg Asn Lys Lys Arg
50                  55                  60

Leu Pro Pro Ala Ile Pro Gly Gly Leu Pro Val Leu Gly Asn Leu Leu
65                  70                  75                  80

Gln Leu Thr Glu Lys Lys Pro His Arg Thr Phe Thr Ala Trp Ser Lys
                85                  90                  95

Glu His Gly Pro Ile Phe Thr Ile Lys Val Gly Ser Val Pro Gln Ala
            100                 105                 110

Val Val Asn Asn Ser Glu Ile Ala Lys Glu Val Leu Val Thr Lys Phe
        115                 120                 125

Ala Ser Ile Ser Lys Arg Gln Met Pro Met Ala Leu Arg Val Leu Thr
    130                 135                 140

Arg Asp Lys Thr Met Val Ala Met Ser Asp Tyr Gly Glu Glu His Arg
145                 150                 155                 160

Met Leu Lys Lys Leu Val Met Thr Asn Leu Leu Gly Pro Thr Thr Gln
                165                 170                 175

Asn Lys Asn Arg Ser Leu Arg Asp Asp Ala Leu Ile Gly Met Ile Glu
            180                 185                 190

Gly Val Leu Ala Glu Leu Lys Ala Ser Pro Thr Ser Pro Lys Val Val
        195                 200                 205

Asn Val Arg Asp Tyr Val Gln Arg Ser Leu Phe Pro Phe Ala Leu Gln
    210                 215                 220

Gln Val Phe Gly Tyr Ile Pro Asp Gln Val Glu Val Leu Glu Leu Gly
225                 230                 235                 240

Thr Cys Val Ser Thr Trp Asp Met Phe Asp Ala Leu Val Val Ala Pro
                245                 250                 255

Leu Ser Ala Val Ile Asn Val Asp Trp Arg Asp Phe Phe Pro Ala Leu
            260                 265                 270

Arg Trp Ile Pro Asn Arg Ser Val Glu Asp Leu Val Arg Thr Val Asp
        275                 280                 285

Phe Lys Arg Asn Ser Ile Met Lys Ala Leu Ile Arg Ala Gln Arg Met
    290                 295                 300

Arg Leu Ala Asn Leu Lys Glu Pro Pro Arg Cys Tyr Ala Asp Ile Ala
305                 310                 315                 320

Leu Thr Glu Ala Thr His Leu Thr Glu Lys Gln Leu Glu Met Ser Leu
                325                 330                 335

```
Trp Glu Pro Ile Ile Glu Ser Ala Asp Thr Thr Leu Val Thr Ser Glu
            340                 345                 350

Trp Ala Met Tyr Glu Ile Ala Lys Asn Pro Asp Cys Gln Asp Arg Leu
        355                 360                 365

Tyr Arg Glu Ile Val Ser Val Ala Gly Thr Arg Met Val Thr Glu
    370                 375                 380

Asp Asp Leu Pro Asn Met Pro Tyr Leu Gly Ala Ile Ile Lys Glu Thr
385                 390                 395                 400

Leu Arg Lys Tyr Thr Pro Val Pro Leu Ile Pro Ser Arg Phe Val Glu
                405                 410                 415

Glu Asp Ile Thr Leu Gly Gly Tyr Asp Ile Pro Lys Gly Tyr Gln Ile
            420                 425                 430

Leu Val Asn Leu Phe Ala Ile Ala Asn Asp Pro Ala Val Trp Ser Asn
        435                 440                 445

Pro Glu Lys Trp Asp Pro Glu Arg Met Leu Ala Asn Lys Lys Val Asp
    450                 455                 460

Met Gly Phe Arg Asp Phe Ser Leu Met Pro Phe Gly Ala Gly Lys Arg
465                 470                 475                 480

Met Cys Ala Gly Ile Thr Gln Ala Met Phe Ile Ile Pro Met Asn Val
                485                 490                 495

Ala Ala Leu Val Gln His Cys Glu Trp Arg Leu Ser Pro Gln Glu Ile
            500                 505                 510

Ser Asn Ile Asn Asn Lys Ile Glu Asp Val Val Tyr Leu Thr Thr His
        515                 520                 525

Lys Leu Ser Pro Leu Ser Cys Glu Ala Thr Pro Arg Ile Ser His Arg
    530                 535                 540

Leu Pro
545

<210> SEQ ID NO 25
<211> LENGTH: 476
<212> TYPE: PRT
<213> ORGANISM: Stevia rebaudiana

<400> SEQUENCE: 25

Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
```

```
                145                 150                 155                 160
Trp Arg Gly Lys Glu Glu Val Asn Val Phe Gln Thr Val Lys Leu Tyr
                165                 170                 175
Ala Phe Glu Leu Ala Cys Arg Leu Phe Met Asn Leu Asp Asp Pro Asn
                180                 185                 190
His Ile Ala Lys Leu Gly Ser Leu Phe Asn Ile Phe Leu Lys Gly Ile
                195                 200                 205
Ile Glu Leu Pro Ile Asp Val Pro Gly Thr Arg Phe Tyr Ser Ser Lys
                210                 215                 220
Lys Ala Ala Ala Ile Arg Ile Glu Leu Lys Lys Leu Ile Lys Ala
225                 230                 235                 240
Arg Lys Leu Glu Leu Lys Glu Gly Lys Ala Ser Ser Gln Asp Leu
                245                 250                 255
Leu Ser His Leu Leu Thr Ser Pro Asp Glu Asn Gly Met Phe Leu Thr
                260                 265                 270
Glu Glu Glu Ile Val Asp Asn Ile Leu Leu Leu Phe Ala Gly His
                275                 280                 285
Asp Thr Ser Ala Leu Ser Ile Thr Leu Leu Met Lys Thr Leu Gly Glu
290                 295                 300
His Ser Asp Val Tyr Asp Lys Val Leu Lys Glu Gln Leu Glu Ile Ser
305                 310                 315                 320
Lys Thr Lys Glu Ala Trp Glu Ser Leu Lys Trp Glu Asp Ile Gln Lys
                325                 330                 335
Met Lys Tyr Ser Trp Ser Val Ile Cys Glu Val Met Arg Leu Asn Pro
                340                 345                 350
Pro Val Ile Gly Thr Tyr Arg Glu Ala Leu Val Asp Ile Asp Tyr Ala
                355                 360                 365
Gly Tyr Thr Ile Pro Lys Gly Trp Lys Leu His Trp Ser Ala Val Ser
                370                 375                 380
Thr Gln Arg Asp Glu Ala Asn Phe Glu Asp Val Thr Arg Phe Asp Pro
385                 390                 395                 400
Ser Arg Phe Glu Gly Ala Gly Pro Thr Pro Phe Thr Phe Val Pro Phe
                405                 410                 415
Gly Gly Gly Pro Arg Met Cys Leu Gly Lys Glu Phe Ala Arg Leu Glu
                420                 425                 430
Val Leu Ala Phe Leu His Asn Ile Val Thr Asn Phe Lys Trp Asp Leu
                435                 440                 445
Leu Ile Pro Asp Glu Lys Ile Glu Tyr Asp Pro Met Ala Thr Pro Ala
                450                 455                 460
Lys Gly Leu Pro Ile Arg Leu His Pro His Gln Val
465                 470                 475

<210> SEQ ID NO 26
<211> LENGTH: 522
<212> TYPE: PRT
<213> ORGANISM: Stevia rebaudiana

<400> SEQUENCE: 26

Met Gly Leu Phe Pro Leu Glu Asp Ser Tyr Ala Leu Val Phe Glu Gly
1               5                   10                  15
Leu Ala Ile Thr Leu Ala Leu Tyr Tyr Leu Leu Ser Phe Ile Tyr Lys
                20                  25                  30
Thr Ser Lys Lys Thr Cys Thr Pro Pro Lys Ala Ser Gly Glu His Pro
                35                  40                  45
```

-continued

```
Ile Thr Gly His Leu Asn Leu Leu Ser Gly Ser Ser Gly Leu Pro His
    50                  55                  60

Leu Ala Leu Ala Ser Leu Ala Asp Arg Cys Gly Pro Ile Phe Thr Ile
65                  70                  75                  80

Arg Leu Gly Ile Arg Arg Val Leu Val Val Ser Asn Trp Glu Ile Ala
                85                  90                  95

Lys Glu Ile Phe Thr Thr His Asp Leu Ile Val Ser Asn Arg Pro Lys
            100                 105                 110

Tyr Leu Ala Ala Lys Ile Leu Gly Phe Asn Tyr Val Ser Phe Ser Phe
        115                 120                 125

Ala Pro Tyr Gly Pro Tyr Trp Val Gly Ile Arg Lys Ile Ile Ala Thr
    130                 135                 140

Lys Leu Met Ser Ser Ser Arg Leu Gln Lys Leu Gln Phe Val Arg Val
145                 150                 155                 160

Phe Glu Leu Glu Asn Ser Met Lys Ser Ile Arg Glu Ser Trp Lys Glu
                165                 170                 175

Lys Lys Asp Glu Glu Gly Lys Val Leu Val Glu Met Lys Lys Trp Phe
            180                 185                 190

Trp Glu Leu Asn Met Asn Ile Val Leu Arg Thr Val Ala Gly Lys Gln
        195                 200                 205

Tyr Thr Gly Thr Val Asp Asp Ala Asp Ala Lys Arg Ile Ser Glu Leu
    210                 215                 220

Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
            260                 265                 270

Glu His Arg Lys Lys Gln Ala Asn Asp Asp Lys Lys Glu Asp Met Asp
        275                 280                 285

Phe Met Asp Ile Met Ile Ser Met Thr Glu Ala Asn Ser Pro Leu Glu
    290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
                325                 330                 335

Leu Leu Leu Asn Asn Arg Asp Thr Leu Lys Lys Ala Gln Glu Glu Leu
            340                 345                 350

Asp Met Cys Val Gly Lys Gly Arg Gln Val Asn Glu Ser Asp Leu Val
        355                 360                 365

Asn Leu Ile Tyr Leu Glu Ala Val Leu Lys Glu Ala Leu Arg Leu Tyr
    370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
                405                 410                 415

Trp Lys Leu His Arg Asp Pro Asn Ile Trp Ser Asp Pro Cys Glu Phe
            420                 425                 430

Lys Pro Glu Arg Phe Leu Thr Pro Asn Gln Lys Asp Val Asp Val Ile
        435                 440                 445

Gly Met Asp Phe Glu Leu Ile Pro Phe Gly Ala Gly Arg Arg Tyr Cys
    450                 455                 460

Pro Gly Thr Arg Leu Ala Leu Gln Met Leu His Ile Val Leu Ala Thr
```

-continued

```
            465                 470                 475                 480
Leu Leu Gln Asn Phe Glu Met Ser Thr Pro Asn Asp Ala Pro Val Asp
                485                 490                 495

Met Thr Ala Ser Val Gly Met Thr Asn Ala Lys Ala Ser Pro Leu Glu
                500                 505                 510

Val Leu Ser Pro Arg Val Lys Trp Ser
                515                 520

<210> SEQ ID NO 27
<211> LENGTH: 525
<212> TYPE: PRT
<213> ORGANISM: Arabidopsis thaliana

<400> SEQUENCE: 27

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
                20                  25                  30

Val Glu Gln Trp Arg Met Arg Arg Ser Leu Lys Leu Gln Gly Val Lys
                35                  40                  45

Gly Pro Pro Pro Ser Ile Phe Asn Gly Asn Val Ser Glu Met Gln Arg
    50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Ile Glu Cys Lys Asp Thr His Lys Lys Asp Leu Met Gln Leu
    290                 295                 300

Ile Leu Glu Gly Ala Met Arg Ser Cys Asp Gly Asn Leu Trp Asp Lys
305                 310                 315                 320
```

```
Ser Ala Tyr Arg Arg Phe Val Val Asp Asn Cys Lys Ser Ile Tyr Phe
            325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
            355                 360                 365

Ser Ser Cys Lys Asn Gly Ile Pro Asp Ala Glu Ser Ile Pro Asn Leu
            370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
            405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
            435                 440                 445

Glu Arg Phe Ser Glu Gly Ile Ser Lys Ala Cys Lys Tyr Pro Gln Ser
            450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
            485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
            515                 520                 525

<210> SEQ ID NO 28
<211> LENGTH: 507
<212> TYPE: PRT
<213> ORGANISM: Artificial sequence
<220> FEATURE:
<223> OTHER INFORMATION: Synthetic sequence

<400> SEQUENCE: 28

Met Ala Leu Leu Leu Ala Val Phe Val Tyr Gly Arg Ala Val Val Glu
1               5                   10                  15

Gln Trp Arg Met Arg Arg Ser Leu Lys Leu Gln Gly Val Lys Gly Pro
            20                  25                  30

Pro Pro Ser Ile Phe Asn Gly Asn Val Ser Glu Met Gln Arg Ile Gln
            35                  40                  45

Ser Glu Ala Lys His Cys Ser Gly Asp Asn Ile Ile Ser His Asp Tyr
        50                  55                  60

Ser Ser Ser Leu Phe Pro His Phe Asp His Trp Arg Lys Gln Tyr Gly
65                  70                  75                  80

Arg Ile Tyr Thr Tyr Ser Thr Gly Leu Lys Gln His Leu Tyr Ile Asn
            85                  90                  95

His Pro Glu Met Val Lys Glu Leu Ser Gln Thr Asn Thr Leu Asn Leu
            100                 105                 110

Gly Arg Ile Thr His Ile Thr Lys Arg Leu Asn Pro Ile Leu Gly Asn
            115                 120                 125

Gly Ile Ile Thr Ser Asn Gly Pro His Trp Ala His Gln Arg Arg Ile
        130                 135                 140

Ile Ala Tyr Glu Phe Thr His Asp Lys Ile Lys Gly Met Val Gly Leu
145                 150                 155                 160
```

Met Val Glu Ser Ala Met Pro Met Leu Asn Lys Trp Glu Glu Met Val
                165                 170                 175

Lys Arg Gly Gly Glu Met Gly Cys Asp Ile Arg Val Asp Glu Asp Leu
            180                 185                 190

Lys Asp Val Ser Ala Asp Val Ile Ala Lys Ala Cys Phe Gly Ser Ser
        195                 200                 205

Phe Ser Lys Gly Lys Ala Ile Phe Ser Met Ile Arg Asp Leu Leu Thr
    210                 215                 220

Ala Ile Thr Lys Arg Ser Val Leu Phe Arg Phe Asn Gly Phe Thr Asp
225                 230                 235                 240

Met Val Phe Gly Ser Lys Lys His Gly Asp Val Asp Ile Asp Ala Leu
                245                 250                 255

Glu Met Glu Leu Glu Ser Ser Ile Trp Glu Thr Val Lys Glu Arg Glu
            260                 265                 270

Ile Glu Cys Lys Asp Thr His Lys Lys Asp Leu Met Gln Leu Ile Leu
        275                 280                 285

Glu Gly Ala Met Arg Ser Cys Asp Gly Asn Leu Trp Asp Lys Ser Ala
    290                 295                 300

Tyr Arg Arg Phe Val Val Asp Asn Cys Lys Ser Ile Tyr Phe Ala Gly
305                 310                 315                 320

His Asp Ser Thr Ala Val Ser Val Ser Trp Cys Leu Met Leu Leu Ala
                325                 330                 335

Leu Asn Pro Ser Trp Gln Val Lys Ile Arg Asp Glu Ile Leu Ser Ser
            340                 345                 350

Cys Lys Asn Gly Ile Pro Asp Ala Glu Ser Ile Pro Asn Leu Lys Thr
        355                 360                 365

Val Thr Met Val Ile Gln Glu Thr Met Arg Leu Tyr Pro Pro Ala Pro
    370                 375                 380

Ile Val Gly Arg Glu Ala Ser Lys Asp Ile Arg Leu Gly Asp Leu Val
385                 390                 395                 400

Val Pro Lys Gly Val Cys Ile Trp Thr Leu Ile Pro Ala Leu His Arg
                405                 410                 415

Asp Pro Glu Ile Trp Gly Pro Asp Ala Asn Asp Phe Lys Pro Glu Arg
            420                 425                 430

Phe Ser Glu Gly Ile Ser Lys Ala Cys Lys Tyr Pro Gln Ser Tyr Ile
        435                 440                 445

Pro Phe Gly Leu Gly Pro Arg Thr Cys Val Gly Lys Asn Phe Gly Met
    450                 455                 460

Met Glu Val Lys Val Leu Val Ser Leu Ile Val Ser Lys Phe Ser Phe
465                 470                 475                 480

Thr Leu Ser Pro Thr Tyr Gln His Ser Pro Ser His Lys Leu Leu Val
                485                 490                 495

Glu Pro Gln His Gly Val Val Ile Arg Val Val
            500                 505

<210> SEQ ID NO 29
<211> LENGTH: 519
<212> TYPE: PRT
<213> ORGANISM: Artificial sequence
<220> FEATURE:
<223> OTHER INFORMATION: Synthetic sequence

<400> SEQUENCE: 29

Met Ala Leu Leu Leu Ala Val Phe Ile Val Ile Val Gly Ile Phe Ser
1               5                   10                  15

```
Val Gly Tyr His Val Tyr Gly Arg Ala Val Val Glu Gln Trp Arg Met
            20                  25                  30

Arg Arg Ser Leu Lys Leu Gln Gly Val Lys Gly Pro Pro Ser Ile
        35                  40                  45

Phe Asn Gly Asn Val Ser Glu Met Gln Arg Ile Gln Ser Glu Ala Lys
    50                  55                  60

His Cys Ser Gly Asp Asn Ile Ile Ser His Asp Tyr Ser Ser Leu
65                  70                  75                  80

Phe Pro His Phe Asp His Trp Arg Lys Gln Tyr Gly Arg Ile Tyr Thr
                85                  90                  95

Tyr Ser Thr Gly Leu Lys Gln His Leu Tyr Ile Asn His Pro Glu Met
            100                 105                 110

Val Lys Glu Leu Ser Gln Thr Asn Thr Leu Asn Leu Gly Arg Ile Thr
        115                 120                 125

His Ile Thr Lys Arg Leu Asn Pro Ile Leu Gly Asn Gly Ile Ile Thr
    130                 135                 140

Ser Asn Gly Pro His Trp Ala His Gln Arg Ile Ile Ala Tyr Glu
145                 150                 155                 160

Phe Thr His Asp Lys Ile Lys Gly Met Val Gly Leu Met Val Glu Ser
                165                 170                 175

Ala Met Pro Met Leu Asn Lys Trp Glu Glu Met Val Lys Arg Gly Gly
            180                 185                 190

Glu Met Gly Cys Asp Ile Arg Val Asp Glu Asp Leu Lys Asp Val Ser
        195                 200                 205

Ala Asp Val Ile Ala Lys Ala Cys Phe Gly Ser Ser Phe Ser Lys Gly
210                 215                 220

Lys Ala Ile Phe Ser Met Ile Arg Asp Leu Leu Thr Ala Ile Thr Lys
225                 230                 235                 240

Arg Ser Val Leu Phe Arg Phe Asn Gly Phe Thr Asp Met Val Phe Gly
                245                 250                 255

Ser Lys Lys His Gly Asp Val Asp Ile Asp Ala Leu Glu Met Glu Leu
            260                 265                 270

Glu Ser Ser Ile Trp Glu Thr Val Lys Glu Arg Glu Ile Glu Cys Lys
        275                 280                 285

Asp Thr His Lys Lys Asp Leu Met Gln Leu Ile Leu Glu Gly Ala Met
290                 295                 300

Arg Ser Cys Asp Gly Asn Leu Trp Asp Lys Ser Ala Tyr Arg Arg Phe
305                 310                 315                 320

Val Val Asp Asn Cys Lys Ser Ile Tyr Phe Ala Gly His Asp Ser Thr
                325                 330                 335

Ala Val Ser Val Ser Trp Cys Leu Met Leu Leu Ala Leu Asn Pro Ser
            340                 345                 350

Trp Gln Val Lys Ile Arg Asp Glu Ile Leu Ser Ser Cys Lys Asn Gly
        355                 360                 365

Ile Pro Asp Ala Glu Ser Ile Pro Asn Leu Lys Thr Val Thr Met Val
370                 375                 380

Ile Gln Glu Thr Met Arg Leu Tyr Pro Pro Ala Pro Ile Val Gly Arg
385                 390                 395                 400

Glu Ala Ser Lys Asp Ile Arg Leu Gly Asp Leu Val Val Pro Lys Gly
                405                 410                 415

Val Cys Ile Trp Thr Leu Ile Pro Ala Leu His Arg Asp Pro Glu Ile
            420                 425                 430

Trp Gly Pro Asp Ala Asn Asp Phe Lys Pro Glu Arg Phe Ser Glu Gly
```

```
                435                 440                 445
Ile Ser Lys Ala Cys Lys Tyr Pro Gln Ser Tyr Ile Pro Phe Gly Leu
    450                 455                 460

Gly Pro Arg Thr Cys Val Gly Lys Asn Phe Gly Met Met Glu Val Lys
465                 470                 475                 480

Val Leu Val Ser Leu Ile Val Ser Lys Phe Ser Phe Thr Leu Ser Pro
                485                 490                 495

Thr Tyr Gln His Ser Pro Ser His Lys Leu Leu Val Glu Pro Gln His
                500                 505                 510

Gly Val Val Ile Arg Val Val
            515

<210> SEQ ID NO 30
<211> LENGTH: 710
<212> TYPE: PRT
<213> ORGANISM: Stevia rebaudiana

<400> SEQUENCE: 30

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
                20                  25                  30

Asp Pro Thr Thr Leu Pro Ala Leu Lys Met Leu Val Glu Asn Arg Glu
            35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Lys Lys Lys Glu Lys Glu Ser Glu
                85                  90                  95

Val Asp Asp Gly Lys Lys Val Ser Ile Phe Tyr Gly Thr Gln Thr
                100                 105                 110

Gly Thr Ala Glu Gly Phe Ala Lys Ala Leu Val Glu Glu Ala Lys Val
            115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Lys Gly Glu Trp
                180                 185                 190

Leu Lys Lys Leu Gln Tyr Gly Val Phe Gly Leu Gly Asn Arg Gln Tyr
            195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Thr Ser Val Thr Thr Pro
                260                 265                 270

Tyr Thr Ala Ala Val Leu Glu Tyr Arg Val Val Tyr His Asp Lys Pro
            275                 280                 285
```

```
Ala Asp Ser Tyr Ala Glu Asp Gln Thr His Thr Asn Gly His Val Val
290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
                340                 345                 350

Tyr Ser Glu Asn Leu Ser Glu Val Val Asp Glu Ala Leu Lys Leu Leu
                355                 360                 365

Gly Leu Ser Pro Asp Thr Tyr Phe Ser Val His Ala Asp Lys Glu Asp
370                 375                 380

Gly Thr Pro Ile Gly Gly Ala Ser Leu Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
                420                 425                 430

Glu Ala Asp Arg Leu Lys Phe Leu Ala Ser Pro Ala Gly Lys Asp Glu
                435                 440                 445

Tyr Ala Gln Trp Ile Val Ala Asn Gln Arg Ser Leu Leu Glu Val Met
450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
                500                 505                 510

Thr Thr Pro Ala Gly Arg Ile His Arg Gly Leu Cys Ser Thr Trp Met
                515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Phe Gly Cys Arg Asn Arg Lys Val Asp Phe Ile
                595                 600                 605

Tyr Glu Asp Glu Leu Asn Asn Phe Val Glu Thr Gly Ala Leu Ser Glu
610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
                675                 680                 685

Ser Ser Lys Ala Glu Leu Tyr Val Lys Asn Leu Gln Met Ser Gly Arg
690                 695                 700

Tyr Leu Arg Asp Val Trp
```

<210> SEQ ID NO 31
<211> LENGTH: 692
<212> TYPE: PRT
<213> ORGANISM: Arabidopsis thaliana

<400> SEQUENCE: 31

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
                20                  25                  30

Thr Thr Ser Leu Ala Leu Val Ala Gly Phe Val Val Leu Leu Trp Lys
            35                  40                  45

Lys Thr Ala Asp Arg Ser Gly Glu Leu Lys Pro Leu Met Ile Pro
    50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
                100                 105                 110

Lys Ala Ala Val Lys Val Ile Asp Leu Asp Asp Tyr Ala Ala Asp Asp
                115                 120                 125

Asp Gln Tyr Glu Glu Lys Leu Lys Lys Glu Thr Leu Ala Phe Phe Cys
130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
                180                 185                 190

Asn Lys Ile Gly Ile Val Leu Asp Glu Glu Leu Cys Lys Lys Gly Ala
            195                 200                 205

Lys Arg Leu Ile Glu Val Gly Leu Gly Asp Asp Asp Gln Ser Ile Glu
210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
                260                 265                 270

Gln Lys Ser Met Glu Ser Asn Val Ala Asn Gly Asn Thr Thr Ile Asp
            275                 280                 285

Ile His His Pro Cys Arg Val Asp Val Ala Val Gln Lys Glu Leu His
290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
                340                 345                 350

Ser Leu Asp Leu Val Phe Ser Ile His Ala Asp Lys Glu Asp Gly Ser
            355                 360                 365
```

Pro Leu Glu Ser Ala Val Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690

<210> SEQ ID NO 32
<211> LENGTH: 524
<212> TYPE: PRT
<213> ORGANISM: Erwina tracheiphila

<400> SEQUENCE: 32

Met Ala His Ala Leu Ala Glu Asn Ile Leu Thr Glu Leu Asn Thr Leu
1               5                   10                  15

Leu Ser Asp Met Asp Asp Gly Gly Tyr Val Gly Pro Ser Val Tyr Asp
            20                  25                  30

Thr Ala Gln Leu Leu Arg Phe His Pro Asn Pro Pro Asp Arg Ala Gly
        35                  40                  45

-continued

```
Ile Tyr Arg Trp Leu Ile Lys Gln Gln His Glu Asp Gly Gly Trp Gly
 50                  55                  60

Ser Pro Asp Phe Pro Leu His Arg Gln Val Pro Thr Val Ala Ala Ile
 65                  70                  75                  80

Leu Ala Leu His Glu Ala Gln Pro Gln Pro Glu Gly Ala Ala Ala Ala
                 85                  90                  95

Leu Ala Ala Ala Ala Val Tyr Leu Ala Gln Glu Arg Asp Leu Tyr Ala
                100                 105                 110

Asp Thr Ile Pro Asp Asp Ala Pro Ile Gly Ala Glu Leu Ile Leu Pro
                115                 120                 125

Gln Leu Cys Arg Gln Ala Ala Leu Phe Pro His Leu Ala Tyr Pro
130                 135                 140

Arg Tyr Gly Ala Leu Tyr Glu Ala Glu Ala Arg Leu Gly Lys Val
145                 150                 155                 160

Glu Ser Leu Thr Ala Val Pro Ser Gly His Pro Leu Leu His Ser Trp
                165                 170                 175

Glu Ser Trp Gly Arg Ser Ser Thr Glu Val Thr Pro Asp Val Phe Gly
                180                 185                 190

Ser Ile Gly Ile Ser Pro Ser Ala Thr Ala Val Trp Leu Gly Arg Ala
                195                 200                 205

Cys Ala Glu Asn Pro Ala Cys Leu Pro Glu His Ala Thr Arg Tyr Leu
                210                 215                 220

His Asn Ala Ser Arg Ala Thr Gly Val Gly Ile Asp Gly Val Val Pro
225                 230                 235                 240

Asn Val Trp Pro Ile Asp Val Phe Glu Pro Cys Trp Ser Leu Tyr Ser
                245                 250                 255

Leu His Leu Ala Gly Leu Phe Ser His Pro Gly Leu Ser Thr Val Val
                260                 265                 270

Gln Asn Ile Ala Thr Asn Ile Gln Ala Ile Leu Thr Pro Leu Gly Leu
                275                 280                 285

Gly Pro Ala Leu Ser Phe Ala Ser Asp Ala Asp Thr Ala Ile Ala
                290                 295                 300

Ala Ala Val Val Gln Leu Ser Gly His Ser Leu Thr Cys Tyr Pro Leu
305                 310                 315                 320

His Gln Phe Glu Lys Gly Asp Leu Phe Val Thr Phe Pro Gly Glu Arg
                325                 330                 335

Asn Pro Ser Leu Ser Thr Thr Ile His Ala Val His Ala Leu Ser Leu
                340                 345                 350

Leu Gly Thr Thr Ala Pro Asp Ala Arg Ala Tyr Ile Glu Asn Ser Lys
                355                 360                 365

Ser Ala Asp Gly Val Trp Lys Asn Glu Lys Trp His Ala Ser Trp Leu
370                 375                 380

Tyr Pro Thr Ser His Ala Val Ala Ala Leu Ala His Gly Met Pro Ser
385                 390                 395                 400

Trp Arg Asp Asn Asp Val Leu Tyr Lys Ile Leu Glu Ala Gln His Leu
                405                 410                 415

Ser Gly Gly Trp Gly Ala Gly Ala Ala Pro Thr Gln Glu Thr Ala
                420                 425                 430

Tyr Ala Leu Phe Ala Leu His Val Met Asn Asp Arg Val Asn Ala Pro
                435                 440                 445

Leu Arg Glu Lys Leu Val Ser Ala Val Ala Arg Ala Arg Glu Trp Leu
450                 455                 460
```

```
Leu Val Arg Tyr Gln Ser Asn Gln Leu Pro Ile Thr Pro Leu Trp Ile
465                 470                 475                 480

Gly Lys Glu Leu Tyr Cys Pro Gln Arg Val Val Arg Val Thr Glu Leu
            485                 490                 495

Thr Gly Leu Trp Leu Ala Leu Asn Trp Asn Pro Ser His Ser Asp Val
        500                 505                 510

Ser Asp Thr Arg Thr Glu Thr Pro Gly Glu Arg Ile
        515                 520

<210> SEQ ID NO 33
<211> LENGTH: 317
<212> TYPE: PRT
<213> ORGANISM: Erwina tracheiphila

<400> SEQUENCE: 33

Met Ala Thr Ser His Asp Asp Ala Cys Gln Gln Val Lys Val Trp Gly
1               5                   10                  15

Glu Thr Leu Phe Gly Phe Leu Asp Glu His Ala Val Glu Ala Val Arg
            20                  25                  30

Gly Gly Gln Phe Ile Leu Arg His Ile Arg Pro Glu Leu Ala Ala Ile
        35                  40                  45

Ser Ala Arg Thr Gly Arg Asp Pro Asp Asp Glu Ala Arg Glu Leu Ala
    50                  55                  60

Phe Tyr Gln Glu Met Ala Leu Leu Phe Trp Ile Asp Asp Cys His Asp
65                  70                  75                  80

Arg Gly Val Met Ser Pro Asp Asp Tyr Ala Val Val Glu Gly Ile Leu
                85                  90                  95

Val Gly Arg Met Pro Asp Ala Pro Thr Pro Ser Val Gly Cys Ser Phe
            100                 105                 110

Leu Arg His Arg Leu Ala Gln Leu Ala Ser His Lys His Asp Tyr Ser
        115                 120                 125

Gln Leu Leu Ala Asp Thr Gln Ala Tyr Ser Thr Ala Leu Arg Asn Gly
    130                 135                 140

Lys Arg Leu Ala Ser Asp Pro Asp Arg Trp Ser Tyr Ser Glu His Leu
145                 150                 155                 160

Arg Asn Gly Val Asp Ser Ile Gly Tyr Gln Asn Val Phe Gly Cys Leu
                165                 170                 175

Ser Leu Leu Trp Gly Leu Asp Met Pro Arg Trp Arg Thr Glu Pro Ala
            180                 185                 190

Phe Gln Asn Ala Leu Ser Phe Leu Cys Ala Ile Gly Arg Leu Gln Asn
        195                 200                 205

Asp Leu His Gly Leu Ala Asn Asp Arg Thr Leu Gly Glu Ala Asp Asn
    210                 215                 220

Leu Ala Val Gln Leu Glu Arg Arg Tyr Pro Thr Leu Asp Ala Val Glu
225                 230                 235                 240

Phe Leu Gln Thr Glu Ile Thr Gly Tyr Glu Arg Met Leu Arg Pro Leu
                245                 250                 255

Leu Glu Thr Ala Asn Phe Asp Pro Val Trp Val Arg Leu Met Glu Thr
            260                 265                 270

Met Leu Thr Val Ser Asp Gln Tyr Tyr Ala Thr Ser Thr Leu Arg Tyr
        275                 280                 285

Arg Ile Asp Asp Thr Ala Thr Thr Ala Pro Ser Cys Asp Thr Arg His
    290                 295                 300

Ala Ser Gly Ala Val Thr Gly Ser Gly Asn Glu Thr Glu
305                 310                 315
```

<210> SEQ ID NO 34
<211> LENGTH: 517
<212> TYPE: PRT
<213> ORGANISM: Sinorhizobium fredii

<400> SEQUENCE: 34

```
Met Ala Asn Ala Leu Ser Glu Gln Ile Leu Phe Glu Leu Arg His Leu
1               5                   10                  15

Leu Ser Glu Met Ser Asp Gly Gly Val Gly Pro Ser Val Tyr Asp
            20                  25                  30

Thr Ala Arg Ala Leu Gln Phe Gly Gly Asn Val Thr Gly Arg Gln Asp
            35                  40                  45

Ala Tyr Ala Trp Leu Leu Ala Gln Gln Gln Ala Asp Gly Gly Trp Gly
        50                  55                  60

Ser Ala Asp Phe Pro Leu Phe Arg His Ala Pro Thr Trp Ala Ala Leu
65                  70                  75                  80

Leu Ala Leu Gln Arg Ala Asp Pro Leu Pro Gly Ala Ala Asp Ala Val
                85                  90                  95

Gln Ala Ala Thr Arg Phe Leu Glu Arg Gln Ala Asp Pro Tyr Ala His
            100                 105                 110

Ala Val Pro Glu Asp Ala Pro Ile Gly Ala Glu Leu Ile Leu Pro Gln
        115                 120                 125

Leu Cys Gly Glu Ala Ala Ser Leu Leu Gly Gly Val Ala Phe Pro Arg
130                 135                 140

His Pro Ala Leu Leu Pro Leu Arg Gln Ala Cys Leu Val Lys Leu Gly
145                 150                 155                 160

Ala Val Ala Thr Leu Pro Ser Gly His Pro Leu Leu His Ser Trp Glu
                165                 170                 175

Ala Trp Gly Thr Trp Pro Thr Ala Ala Cys Pro Asp Asp Gly Ser
            180                 185                 190

Ile Gly Ile Ser Pro Ala Ala Thr Ala Ala Trp Arg Ala His Ala Val
        195                 200                 205

Thr Gln Gly Ser Thr Pro Gln Val Gly Arg Ala Asp Ala Tyr Leu Gln
    210                 215                 220

Ala Ala Ser Arg Ala Thr Arg Ser Gly Ile Glu Gly Val Val Pro Asn
225                 230                 235                 240

Val Trp Pro Ile Asn Val Phe Glu Pro Cys Trp Ser Leu Tyr Thr Leu
                245                 250                 255

His Leu Ala Gly Leu Phe Ala His Pro Ala Leu Asp Glu Ala Val Arg
            260                 265                 270

Val Ile Val Ala Gln Leu Asp Ala Arg Leu Gly Val Arg Gly Leu Gly
        275                 280                 285

Pro Ala Leu His Phe Ala Ala Asp Ala Asp Thr Ala Val Ala Leu
    290                 295                 300

Cys Val Leu Arg Leu Ala Gly Arg Asp Pro Ala Val Asp Ala Leu Arg
305                 310                 315                 320

His Phe Glu Ile Gly Glu Leu Phe Val Thr Phe Pro Gly Glu Arg Asn
                325                 330                 335

Ala Ser Val Ser Thr Asn Ile His Ala Leu His Ala Leu Arg Leu Leu
            340                 345                 350

Gly Lys Pro Ala Ala Gly Thr Ser Ala Tyr Val Glu Ala Asn Arg Asn
        355                 360                 365

Pro His Gly Leu Trp Asp Asn Glu Lys Trp His Val Ser Trp Leu Tyr
```

```
                370                 375                 380
Pro Thr Ala His Ala Val Ala Ala Leu Ala Gln Gly Lys Pro Gln Trp
385                 390                 395                 400

Arg Asp Glu Arg Ala Leu Ala Ala Leu Leu Gln Ala Gln Arg Asp Asp
                405                 410                 415

Gly Gly Trp Gly Ala Gly Arg Ala Ser Thr Phe Glu Glu Thr Ala Tyr
            420                 425                 430

Ala Leu Phe Ala Leu His Val Met Asp Gly Ser Glu Glu Pro Thr Gly
            435                 440                 445

Arg Arg Arg Ile Ala Gln Ala Val Ala Arg Ala Leu Glu Trp Met Leu
            450                 455                 460

Ala Arg His Ala Ala Pro Ala Leu Pro Gln Met Pro Leu Trp Ile Gly
465                 470                 475                 480

Lys Glu Leu Tyr Cys Pro Ile Arg Val Val Arg Val Ala Glu Leu Ala
                485                 490                 495

Gly Leu Trp Leu Ala Leu Arg Trp Gly Pro Arg Val Pro Ala Glu Gly
            500                 505                 510

Ala Gly Ala Ala Pro
            515

<210> SEQ ID NO 35
<211> LENGTH: 302
<212> TYPE: PRT
<213> ORGANISM: Sinorhizobium fredii

<400> SEQUENCE: 35

Met Ala Ile Pro Thr Glu Arg Gly Leu Gln Gln Val Leu Glu Trp Gly
1               5                   10                  15

Arg Ser Leu Thr Gly Phe Ala Asp Glu His Ala Ala Glu Ala Val Arg
            20                  25                  30

Gly Gly Gln Tyr Ile Leu Gln Arg Ile His Pro Ser Leu Arg Asp Thr
        35                  40                  45

Ser Ala Arg Thr Gly Arg Asp Pro Gln Asp Glu Thr Leu Ile Val Ala
    50                  55                  60

Phe Tyr Arg Glu Leu Ala Leu Leu Phe Trp Leu Asp Asp Cys Asn Asp
65                  70                  75                  80

Leu Asp Leu Ile Ala Pro Glu Gln Leu Ala Ala Val Glu Gln Ala Leu
                85                  90                  95

Gly Gln Gly Val Pro Cys Ala Leu Pro Gly Phe Glu Gly Cys Ala Val
            100                 105                 110

Leu Arg Ala Ser Leu Ala Ala Leu Ala Tyr Asp Arg Arg Asp Tyr Ala
        115                 120                 125

Gln Leu Leu Asp Asp Thr Arg Cys Tyr Cys Ala Ala Leu Arg Ala Gly
    130                 135                 140

His Ala Gln Ala Ala Gly Ala Ala Glu Arg Trp Ser Tyr Ala Glu Tyr
145                 150                 155                 160

Leu His Asn Gly Ile Asp Ser Ile Ala Tyr Ala Asn Val Phe Cys Cys
                165                 170                 175

Leu Ser Leu Leu Trp Gly Leu Asp Met Ala Thr Leu Arg Ala Arg Pro
            180                 185                 190

Ala Phe Arg Gln Val Leu Arg Leu Ile Ser Ala Ile Gly Arg Leu Gln
        195                 200                 205

Asn Asp Leu His Gly Arg Asp Lys Asp Arg Ser Ala Gly Glu Ala Asp
    210                 215                 220
```

```
Asn Ala Ala Ile Leu Leu Leu Glu Arg Tyr Pro Ala Met Pro Val Val
225                 230                 235                 240

Glu Phe Leu Asn Asp Glu Leu Ala Gly His Thr Arg Met Leu His Arg
            245                 250                 255

Val Met Ala Glu Glu Arg Phe Pro Ala Pro Trp Gly Pro Leu Ile Glu
            260                 265                 270

Ala Met Ala Ala Ile Arg Ala His Tyr Tyr Gln Thr Ser Thr Ser Arg
            275                 280                 285

Tyr Arg Ser Asp Ala Ala Gly Gly Gly Gln His Ala Pro Ala
            290                 295                 300

<210> SEQ ID NO 36
<211> LENGTH: 295
<212> TYPE: PRT
<213> ORGANISM: Marine bacterium 443

<400> SEQUENCE: 36

Met Ala Glu Asn Gly Leu Leu Asp Cys Glu Gln Tyr Leu Glu Glu Ala
1               5                   10                  15

Met Ala Glu His Ala Thr Ala Gln Cys Pro Pro Leu Leu Ala Gln Ala
            20                  25                  30

Leu Asn Tyr Ala Val Phe Pro Gly Gly Ala Arg Val Arg Pro Lys Ile
        35                  40                  45

Cys Lys Ala Val Ala Leu Ala Asn Asn Ser Ser Asp Val Gly Leu Ala
    50                  55                  60

Asn Ala Ala Ser Ala Ile Glu Leu Leu His Cys Ala Ser Leu Val
65                  70                  75                  80

His Asp Asp Leu Pro Cys Phe Asp Ala Thr Gln Arg Arg Gly Lys
                85                  90                  95

Pro Ser Val His Ala Lys Phe Gly Glu Arg Ile Ala Val Leu Thr Gly
            100                 105                 110

Asp Ala Leu Ile Val Ala Ala Phe Gln Thr Leu Ala Thr His Ala Ile
            115                 120                 125

His Ala Val Arg Thr Glu Arg Val Pro Leu Val Thr Ala Ile Val Ala
    130                 135                 140

Arg Gly Val Gly Ala Pro His Gly Ile Cys Ala Gly Gln Ala Trp Glu
145                 150                 155                 160

Cys Glu Arg Ser Val Asp Leu Ser Arg Tyr His Arg Ala Lys Thr Gly
                165                 170                 175

Ala Leu Phe Val Ala Ala Thr Cys Ala Gly Ala Ala Ala Gly Val
            180                 185                 190

Asp Pro Gly Pro Trp Val Asn Leu Gly Ala Ser Ile Gly Glu Ala Tyr
        195                 200                 205

Gln Val Ala Asp Asp Ile Lys Asp Ala Ile Ser Asp Pro Glu Thr Leu
    210                 215                 220

Gly Lys Pro Thr Gly Ile Asp Val Lys Leu Asp Arg Pro Ser Ala Val
225                 230                 235                 240

Arg Glu Leu Gly Leu Asp Gly Ala Val Thr Arg Leu Lys Gln Cys Leu
                245                 250                 255

Glu Ala Gly Leu Asp Ser Met Pro Ala Cys Ala Gly Gln Asp Leu Leu
            260                 265                 270

Gln Lys Ile Val Arg Ala Gln Ala Ser Arg Phe Val Pro Glu Lys Ile
        275                 280                 285

Ala Gln Val Ala Ala Val Asp
    290                 295
```

<210> SEQ ID NO 37
<211> LENGTH: 296
<212> TYPE: PRT
<213> ORGANISM: Paracoccus haeundaensis

<400> SEQUENCE: 37

| Met | Ala | Arg | Arg | Asp | Val | Asn | Pro | Ile | His | Ala | Thr | Leu | Leu | Gln | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Arg Leu Glu Glu Ile Ala Gln Gly Phe Gly Ala Val Ser Gln Pro Leu
                20                  25                  30

Gly Ala Ala Met Ser His Gly Ala Leu Ser Ser Gly Arg Arg Phe Arg
            35                  40                  45

Gly Met Leu Met Leu Leu Ala Ala Glu Ala Ser Gly Gly Val Cys Asp
        50                  55                  60

Thr Ile Val Asp Ala Ala Cys Ala Val Glu Met Val His Ala Ala Ser
65                  70                  75                  80

Leu Ile Phe Asp Asp Leu Pro Cys Met Asp Asp Ala Gly Leu Arg Arg
                85                  90                  95

Gly Arg Pro Ala Thr His Val Ala His Gly Glu Ser Arg Ala Val Leu
            100                 105                 110

Gly Gly Ile Ala Leu Ile Thr Glu Ala Met Ala Leu Leu Ala Gly Ala
        115                 120                 125

Arg Gly Ala Ser Gly Thr Val Arg Ala Gln Leu Val Arg Ile Leu Ser
    130                 135                 140

Arg Ser Leu Gly Pro Gln Gly Leu Cys Ala Gly Gln Asp Leu Asp Leu
145                 150                 155                 160

His Ala Ala Lys Asn Gly Ala Gly Val Glu Gln Glu Gln Asp Leu Lys
                165                 170                 175

Thr Gly Val Leu Phe Ile Ala Gly Leu Glu Met Leu Ala Val Ile Lys
            180                 185                 190

Glu Phe Asp Ala Glu Gln Thr Gln Met Ile Asp Phe Gly Arg Gln
        195                 200                 205

Leu Gly Arg Val Phe Gln Ser Tyr Asp Asp Leu Leu Asp Val Val Gly
    210                 215                 220

Asp Gln Ala Ala Leu Gly Lys Asp Thr Gly Arg Asp Ala Ala Ala Pro
225                 230                 235                 240

Gly Pro Arg Arg Gly Leu Leu Ala Val Ser Asp Leu Gln Asn Val Ser
                245                 250                 255

Arg His Tyr Glu Ala Ser Arg Ala Gln Leu Asp Ala Met Leu Arg Ser
            260                 265                 270

Lys Arg Leu Gln Ala Pro Glu Ile Ala Ala Leu Leu Glu Arg Val Leu
        275                 280                 285

Pro Tyr Ala Ala Arg Ala Val Asp
    290                 295

<210> SEQ ID NO 38
<211> LENGTH: 335
<212> TYPE: PRT
<213> ORGANISM: Clorobium tepidum TLS

<400> SEQUENCE: 38

Met Ala Ser Ser Pro Ile Thr Gln Ala Gln Val Glu Ser Lys Tyr Arg
1               5                   10                  15

Gln Tyr His Ala Lys Ile Asn Glu Ala Leu Ala Ala Cys Phe Pro Lys
            20                  25                  30

Glu Lys Pro Ala Thr Leu Tyr Asp Pro Ala Arg Tyr Ile Leu Glu Gly
            35                  40                  45

Lys Gly Lys Arg Ile Arg Pro Phe Leu Thr Leu Leu Ala Ala Glu Ala
 50                  55                  60

Val Ser Gly Lys Ser Asp Asn Ala Leu Gly Val Ala Leu Gly Ile Glu
 65                  70                  75                  80

Val Leu His Asn Phe Thr Leu Met His Asp Asp Ile Met Asp Gln Ala
                    85                  90                  95

Asp Leu Arg His Gly Arg Pro Thr Val His Lys Gln Trp Asn Val Asn
                100                 105                 110

Ala Ala Ile Leu Ser Gly Asp Met Met Ile Ala Tyr Ala Tyr Glu Leu
                115                 120                 125

Ala Leu Lys Ala Ile Ser Ser Arg His Ala Glu Ile Ile His Ile Phe
            130                 135                 140

Asn Asp Ala Asn Ile Thr Ile Cys Glu Gly Gln Ala Leu Asp Met Glu
145                 150                 155                 160

Leu Glu Gln Arg Lys Asp Val Thr Ile Ala Asp Tyr Leu Asp Met Ile
                165                 170                 175

Ser Lys Lys Thr Gly Arg Leu Ile Ser Ala Ala Leu Glu Ala Gly Gly
                180                 185                 190

Val Ala Gly Asp Gly Thr Pro Glu Gln Ile Ala Ala Leu Val Thr Phe
            195                 200                 205

Gly Glu Lys Ile Gly Arg Ala Phe Gln Ile Gln Asp Asp Tyr Leu Asp
        210                 215                 220

Ile Met Ala Gly Asp Gly Lys Ser Gly Lys Val Pro Gly Gly Asp Val
225                 230                 235                 240

Ile Asn Gly Lys Lys Thr Trp Leu Leu Leu Arg Ser Leu Glu Leu Ala
                245                 250                 255

Glu Gly Ala Asp Arg Glu Leu Leu Gln Ser Ile Phe Asp Asn Asn Gly
                260                 265                 270

Thr Ser Pro Asp Asn Val Pro Ala Val Lys Ala Ile Phe Glu Lys Cys
            275                 280                 285

Gly Val Leu Asn Glu Thr Arg Ala Lys Ile Asn Glu Asp Thr Glu Ala
        290                 295                 300

Ala Leu Ala Ala Leu Asp Ala Leu Pro Phe Glu Glu Gly Arg Gly Tyr
305                 310                 315                 320

Leu Arg Gly Phe Ala Asn Ile Leu Met Lys Arg Asp Phe Val Asp
                325                 330                 335

<210> SEQ ID NO 39
<211> LENGTH: 300
<212> TYPE: PRT
<213> ORGANISM: Synechoccus sp. JA-3-3Ab

<400> SEQUENCE: 39

Met Ala Val Ala Gln Thr Phe Asn Leu Asp Thr Tyr Leu Ser Gln Arg
 1               5                  10                  15

Gln Gln Gln Val Glu Glu Ala Leu Ser Ala Ala Leu Val Pro Ala Tyr
                20                  25                  30

Pro Glu Arg Ile Tyr Glu Ala Met Arg Tyr Ser Leu Leu Ala Gly Gly
            35                  40                  45

Lys Arg Leu Arg Pro Ile Leu Cys Leu Ala Ala Cys Glu Leu Ala Gly
 50                  55                  60

Gly Ser Val Glu Gln Ala Met Pro Thr Ala Cys Ala Leu Glu Met Ile

```
            65                  70                  75                  80
His Thr Met Ser Leu Ile His Asp Asp Leu Pro Ala Met Asp Asn Asp
                85                  90                  95

Asp Phe Arg Arg Gly Lys Pro Thr Asn His Lys Val Phe Gly Glu Asp
            100                 105                 110

Ile Ala Ile Leu Ala Gly Asp Ala Leu Leu Ala Tyr Ala Phe Glu His
            115                 120                 125

Ile Ala Ser Gln Thr Arg Gly Val Pro Pro Gln Leu Val Leu Gln Val
        130                 135                 140

Ile Ala Arg Ile Gly His Ala Val Ala Ala Thr Gly Leu Val Gly Gly
145                 150                 155                 160

Gln Val Val Asp Leu Glu Ser Glu Gly Lys Ala Ile Ser Leu Glu Thr
                165                 170                 175

Leu Glu Tyr Ile His Ser His Lys Thr Gly Ala Leu Leu Glu Ala Ser
            180                 185                 190

Val Val Ser Gly Gly Ile Leu Ala Gly Ala Asp Glu Glu Leu Leu Ala
        195                 200                 205

Arg Leu Ser His Tyr Ala Arg Asp Ile Gly Leu Ala Phe Gln Ile Val
210                 215                 220

Asp Asp Ile Leu Asp Val Thr Ala Thr Ser Glu Gln Leu Gly Lys Thr
225                 230                 235                 240

Ala Gly Lys Asp Gln Ala Ala Lys Ala Thr Tyr Pro Ser Leu Leu
                245                 250                 255

Gly Leu Glu Ala Ser Arg Gln Lys Ala Glu Glu Leu Ile Gln Ser Ala
            260                 265                 270

Lys Glu Ala Leu Arg Pro Tyr Gly Ser Gln Ala Glu Pro Leu Leu Ala
        275                 280                 285

Leu Ala Asp Phe Ile Thr Arg Arg Gln His Val Asp
        290                 295                 300

<210> SEQ ID NO 40
<211> LENGTH: 305
<212> TYPE: PRT
<213> ORGANISM: Synechocystis sp. PCC 6803

<400> SEQUENCE: 40

Met Ala Val Ala Gln Gln Thr Arg Thr Asp Phe Asp Leu Ala Gln Tyr
1               5                   10                  15

Leu Gln Val Lys Lys Gly Val Val Glu Ala Ala Leu Asp Ser Ser Leu
            20                  25                  30

Ala Ile Ala Arg Pro Glu Lys Ile Tyr Glu Ala Met Arg Tyr Ser Leu
        35                  40                  45

Leu Ala Gly Gly Lys Arg Leu Arg Pro Ile Leu Cys Ile Thr Ala Cys
    50                  55                  60

Glu Leu Cys Gly Gly Asp Glu Ala Leu Ala Leu Pro Thr Ala Cys Ala
65                  70                  75                  80

Leu Glu Met Ile His Thr Met Ser Leu Ile His Asp Asp Leu Pro Ser
                85                  90                  95

Met Asp Asn Asp Asp Phe Arg Arg Gly Lys Pro Thr Asn His Lys Val
            100                 105                 110

Tyr Gly Glu Asp Ile Ala Ile Leu Ala Gly Asp Gly Leu Leu Ala Tyr
        115                 120                 125

Ala Phe Glu Tyr Val Val Thr His Thr Pro Gln Ala Asp Pro Gln Ala
    130                 135                 140
```

-continued

```
Leu Leu Gln Val Ile Ala Arg Leu Gly Arg Thr Val Gly Ala Ala Gly
145                 150                 155                 160

Leu Val Gly Gly Gln Val Leu Asp Leu Glu Ser Glu Gly Arg Thr Asp
            165                 170                 175

Ile Thr Pro Glu Thr Leu Thr Phe Ile His Thr His Lys Thr Gly Ala
        180                 185                 190

Leu Leu Glu Ala Ser Val Leu Thr Gly Ala Ile Leu Ala Gly Ala Thr
            195                 200                 205

Gly Glu Gln Gln Gln Arg Leu Ala Arg Tyr Ala Gln Asn Ile Gly Leu
        210                 215                 220

Ala Phe Gln Val Val Asp Asp Ile Leu Asp Ile Thr Ala Thr Gln Glu
225                 230                 235                 240

Glu Leu Gly Lys Thr Ala Gly Lys Asp Val Lys Ala Gln Lys Ala Thr
            245                 250                 255

Tyr Pro Ser Leu Leu Gly Leu Glu Ala Ser Arg Ala Gln Ala Gln Ser
            260                 265                 270

Leu Ile Asp Gln Ala Ile Val Ala Leu Glu Pro Phe Gly Pro Ser Ala
        275                 280                 285

Glu Pro Leu Gln Ala Ile Ala Glu Tyr Ile Val Ala Arg Lys Tyr Val
    290                 295                 300

Asp
305

<210> SEQ ID NO 41
<211> LENGTH: 275
<212> TYPE: PRT
<213> ORGANISM: Thermotoga maritima HB8

<400> SEQUENCE: 41

Met Ala Lys Lys Glu Lys Val Glu Glu Arg Ile Arg Glu Ile Leu Arg
1               5                   10                  15

Pro Gly Trp Asp Leu Leu Thr Glu Glu Ala Met Leu Tyr Ser Ala Thr
            20                  25                  30

Val Gly Gly Lys Arg Ile Arg Pro Leu Leu Val Leu Thr Leu Gly Glu
        35                  40                  45

Asp Leu Gly Val Glu Glu Glu Lys Leu Leu Asp Val Ala Val Ala Val
    50                  55                  60

Glu Leu Phe His Thr Ala Ser Leu Ile His Asp Asp Leu Pro Pro Ile
65                  70                  75                  80

Asp Asn Ala Asp Phe Arg Arg Gly Lys Pro Ser Cys His Arg Thr Tyr
                85                  90                  95

Gly Glu Asp Ile Ala Leu Leu Ala Gly Asp Gly Leu Phe Phe Leu Ala
            100                 105                 110

Phe Ser Gln Ile Ser Lys Ile Gly Asn Ser Lys Ile Phe Glu Glu Phe
        115                 120                 125

Ser Glu Thr Ala Tyr Lys Leu Leu Leu Gly Glu Ala Met Asp Val Glu
    130                 135                 140

Phe Glu Arg Arg Lys Met Glu Val Ser Gln Glu Met Val Glu Arg Met
145                 150                 155                 160

Tyr Ala Phe Lys Thr Gly Ala Leu Phe Ala Phe Cys Phe Ser Ala Pro
                165                 170                 175

Phe Ile Leu Lys Gly Lys Asp His Thr Lys Met Lys Leu Leu Gly Glu
            180                 185                 190

Lys Phe Gly Val Ala Phe Gln Ile Tyr Asp Asp Leu Lys Asp Ile Leu
        195                 200                 205
```

```
Gly Ser Phe Glu Lys Val Gly Lys Asp Leu Gly Lys Asp Thr Glu Lys
    210                 215                 220

Val Thr Leu Val Lys Lys Val Gly Ile Gln Lys Ala Arg Glu Met Ala
225                 230                 235                 240

Asp Lys Tyr Tyr Glu Glu Val Leu Lys Gly Ile Glu Ser Glu Gly Leu
                245                 250                 255

Phe Arg Thr Leu Phe Leu Lys Glu Leu Lys Gln Met Val Glu Glu
                260                 265                 270

Arg Val Asp
        275

<210> SEQ ID NO 42
<211> LENGTH: 374
<212> TYPE: PRT
<213> ORGANISM: Corynebacterium glutamicum

<400> SEQUENCE: 42

Met Ala Lys Asp Val Ser Leu Ser Ser Phe Asp Ala His Asp Leu Asp
1               5                   10                  15

Leu Asp Lys Phe Pro Glu Val Val Arg Asp Arg Leu Thr Gln Phe Leu
                20                  25                  30

Asp Ala Gln Glu Leu Thr Ile Ala Asp Ile Gly Ala Pro Val Thr Asp
            35                  40                  45

Ala Val Ala His Leu Arg Ser Phe Val Leu Asn Gly Gly Lys Arg Ile
50                  55                  60

Arg Pro Leu Tyr Ala Trp Ala Gly Phe Leu Ala Ala Gln Gly His Lys
65                  70                  75                  80

Asn Ser Ser Glu Lys Leu Glu Ser Val Leu Asp Ala Ala Ser Leu
                85                  90                  95

Glu Phe Ile Gln Ala Cys Ala Leu Ile His Asp Asp Ile Ile Asp Ser
                100                 105                 110

Ser Asp Thr Arg Arg Gly Ala Pro Thr Val His Arg Ala Val Glu Ala
            115                 120                 125

Asp His Arg Ala Asn Asn Phe Glu Gly Asp Pro Glu His Phe Gly Val
130                 135                 140

Ser Val Ser Ile Leu Ala Gly Asp Met Ala Leu Val Trp Ala Glu Asp
145                 150                 155                 160

Met Leu Gln Asp Ser Gly Leu Ser Ala Glu Ala Leu Ala Arg Thr Arg
                165                 170                 175

Asp Ala Trp Arg Gly Met Arg Thr Glu Val Ile Gly Gly Gln Leu Leu
            180                 185                 190

Asp Ile Tyr Leu Glu Ser His Ala Asn Glu Ser Val Glu Leu Ala Asp
        195                 200                 205

Ser Val Asn Arg Phe Lys Thr Ala Ala Tyr Thr Ile Ala Arg Pro Leu
210                 215                 220

His Leu Gly Ala Ser Ile Ala Gly Gly Ser Pro Gln Leu Ile Asp Ala
225                 230                 235                 240

Leu Leu His Tyr Gly His Asp Ile Gly Ile Ala Phe Gln Leu Arg Asp
                245                 250                 255

Asp Leu Leu Gly Val Phe Gly Asp Pro Ala Ile Thr Gly Lys Pro Ala
            260                 265                 270

Gly Asp Asp Ile Arg Glu Gly Lys Arg Thr Val Leu Leu Ala Leu Ala
        275                 280                 285

Leu Gln Arg Ala Asp Lys Gln Ser Pro Glu Ala Ala Thr Ala Ile Arg
```

```
            290                 295                 300
Ala Gly Val Gly Lys Val Thr Ser Pro Glu Asp Ile Ala Val Ile Thr
305                 310                 315                 320

Glu His Ile Arg Ala Thr Gly Ala Glu Glu Val Glu Gln Arg Ile
                325                 330                 335

Ser Gln Leu Thr Glu Ser Gly Leu Ala His Leu Asp Asp Val Asp Ile
            340                 345                 350

Pro Asp Glu Val Arg Ala Gln Leu Arg Ala Leu Ala Ile Arg Ser Thr
                355                 360                 365

Glu Arg Arg Met Val Asp
        370

<210> SEQ ID NO 43
<211> LENGTH: 333
<212> TYPE: PRT
<213> ORGANISM: Thermus thermophillus HB27

<400> SEQUENCE: 43

Met Ala Val Pro Ala Pro Glu Ala Ile Arg Gln Ala Leu Gln Glu Arg
1               5                   10                  15

Leu Leu Ala Arg Leu Asp His Pro Asp Pro Leu Tyr Arg Asp Leu Leu
            20                  25                  30

Gln Asp Tyr Pro Arg Arg Gly Gly Lys Met Leu Arg Gly Leu Leu Thr
        35                  40                  45

Val Tyr Ser Ala Leu Ala His Gly Ala Pro Leu Glu Ala Gly Leu Glu
    50                  55                  60

Ala Ala Thr Ala Leu Glu Leu Phe Gln Asn Trp Val Leu Val His Asp
65                  70                  75                  80

Asp Ile Glu Asp Gly Ser Glu Glu Arg Arg Gly Arg Pro Ala Leu His
                85                  90                  95

Arg Leu His Pro Met Pro Leu Ala Leu Asn Ala Gly Asp Ala Met His
            100                 105                 110

Ala Glu Met Trp Gly Leu Leu Ala Glu Gly Leu Ala Arg Gly Leu Phe
        115                 120                 125

Pro Pro Glu Val Leu Leu Glu Phe His Glu Val Arg Arg Thr Ala
    130                 135                 140

Tyr Gly Gln His Leu Asp Leu Leu Trp Thr Leu Gly Gly Thr Phe Asp
145                 150                 155                 160

Leu Arg Pro Glu Asp Tyr Phe Arg Met Val Ala His Lys Ala Ala Tyr
                165                 170                 175

Tyr Thr Ala Val Ala Pro Leu Arg Leu Gly Ala Leu Leu Ala Gly Lys
            180                 185                 190

Thr Pro Pro Ala Ala Tyr Glu Glu Gly Gly Leu Arg Leu Gly Thr Ala
        195                 200                 205

Phe Gln Ile Val Asp Asp Val Leu Asn Leu Glu Gly Gly Glu Ala Tyr
    210                 215                 220

Gly Lys Glu Arg Ala Gly Asp Leu Tyr Glu Gly Lys Arg Thr Leu Ile
225                 230                 235                 240

Leu Leu Arg Phe Leu Glu Glu Ala Pro Pro Glu Glu Arg Ala Arg Ala
                245                 250                 255

Leu Ala Leu Leu Ala Leu Pro Arg Glu Ala Lys Pro Glu Ala Glu Val
            260                 265                 270

Gly Trp Leu Leu Glu Arg Leu Leu Ala Ser Arg Ala Leu Ala Trp Ala
        275                 280                 285
```

```
Lys Ala Glu Ala Lys Arg Leu Gln Ala Glu Gly Ala Leu Leu Glu
290                 295                 300

Ala Ala Phe Gln Asp Leu Pro Gly Lys Glu Ala Leu Asp His Leu Arg
305                 310                 315                 320

Gly Leu Leu Ala Ala Leu Val Glu Arg Arg Ala Val Asp
                325                 330

<210> SEQ ID NO 44
<211> LENGTH: 335
<212> TYPE: PRT
<213> ORGANISM: Pyrobaculum calidifontis JCM 11548

<400> SEQUENCE: 44

Met Ala Asp Val Val Ser Arg Leu His Gln Lys Tyr Gly Ala Glu Val
1               5                   10                  15

Glu Lys Ala Leu Val Arg Tyr Leu Ser Ile Gly Leu Ala Glu Asp Phe
                20                  25                  30

Arg Glu Ala Val Leu Tyr Gln Val Lys Thr Gly Gly Lys Arg Leu Arg
            35                  40                  45

Pro Leu Leu Thr Leu Ala Ala Ala Glu Ala Val Ser Gly Gln Trp Arg
        50                  55                  60

Pro Ala Leu Pro Ala Ala Ala Ile Val Glu Leu Ile His Asn Tyr Ser
65                  70                  75                  80

Leu Ile Tyr Asp Asp Ile Ile Asp Arg Gly Asp Val Arg Arg Gly Leu
                85                  90                  95

Pro Thr Val Arg Lys Ala Phe Gly Asp Asn Ala Ala Ile Leu Val Gly
            100                 105                 110

Ile Trp Tyr Arg Glu Ala Ile Glu Glu Ala Val Leu Asp Thr Pro Lys
        115                 120                 125

Pro Thr Leu Phe Ala Lys Glu Val Ala Glu Val Ile Lys Ala Ile Asp
    130                 135                 140

Glu Gly Glu Arg Leu Asp Ile Leu Phe Glu Ala Ala Gly Arg Ser Asp
145                 150                 155                 160

Pro Tyr Phe Val Gln Ala Arg Trp Arg Glu Val Thr Leu Asp Asp Tyr
                165                 170                 175

Ile Lys Met Val Ser Leu Lys Thr Gly Ala Leu Ile Ala Ala Ala Ala
            180                 185                 190

Lys Trp Gly Val Leu Ser Val Ser Asp Asp Arg Gly Leu Ala Glu Ala
        195                 200                 205

Ala Trp Asn Phe Gly Met Ala Ala Gly Val Ala Phe Gln Ile Ile Asp
    210                 215                 220

Asp Val Leu Asp Ile Tyr Gly Asp Pro Lys Lys Phe Gly Lys Glu Ile
225                 230                 235                 240

Gly Lys Asp Ile Lys Glu His Lys Arg Gly Asn Ala Val Val Ala Val
                245                 250                 255

Ala Leu Ser His Leu Gly Glu Gly Glu Arg Arg Arg Leu Leu Glu Ile
            260                 265                 270

Leu Ala Arg Glu Val Val Glu Glu Ala Asp Val Arg Glu Ala Val Ala
        275                 280                 285

Leu Leu Asp Ser Val Gly Ala Arg Glu Glu Ala Leu Arg Leu Ala Ala
    290                 295                 300

Arg Tyr Arg Glu Glu Ala Glu Arg His Leu Ala Lys Ile Pro Asn Asn
305                 310                 315                 320

Gly Thr Leu Lys Glu Leu Leu Asp Phe Ile Val Ala Arg Glu Tyr
                325                 330                 335
```

```
<210> SEQ ID NO 45
<211> LENGTH: 463
<212> TYPE: PRT
<213> ORGANISM: Artificial sequence
<220> FEATURE:
<223> OTHER INFORMATION: Synthetic sequence

<400> SEQUENCE: 45

Met Ala Thr Lys Gly Ser Ser Gly Met Ser Leu Ala Glu Arg Phe Trp
1               5                   10                  15

Leu Thr Leu Ser Arg Ser Ser Leu Val Val Gly Arg Ser Cys Val Glu
            20                  25                  30

Phe Glu Pro Glu Thr Val Pro Leu Leu Ser Thr Leu Arg Gly Lys Pro
        35                  40                  45

Ile Thr Phe Leu Gly Leu Met Pro Pro Leu His Glu Gly Arg Arg Glu
    50                  55                  60

Asp Gly Glu Asp Ala Thr Val Arg Trp Leu Asp Ala Gln Pro Ala Lys
65                  70                  75                  80

Ser Val Val Tyr Val Ala Leu Gly Ser Glu Val Pro Leu Gly Val Glu
                85                  90                  95

Lys Val His Glu Leu Ala Leu Gly Leu Glu Leu Ala Gly Thr Arg Phe
            100                 105                 110

Leu Trp Ala Leu Arg Lys Pro Thr Gly Val Ser Asp Ala Asp Leu Leu
        115                 120                 125

Pro Ala Gly Phe Glu Glu Arg Thr Arg Gly Arg Gly Val Val Ala Thr
    130                 135                 140

Arg Trp Val Pro Gln Met Ser Ile Leu Ala His Ala Ala Val Gly Ala
145                 150                 155                 160

Phe Leu Thr His Cys Gly Trp Asn Ser Thr Ile Glu Gly Leu Met Phe
                165                 170                 175

Gly His Pro Leu Ile Met Leu Pro Ile Phe Gly Asp Gln Gly Pro Asn
            180                 185                 190

Ala Arg Leu Ile Glu Ala Lys Asn Ala Gly Leu Gln Val Ala Arg Asn
        195                 200                 205

Asp Gly Asp Gly Ser Phe Asp Arg Glu Gly Val Ala Ala Ile Arg
    210                 215                 220

Ala Val Ala Val Glu Glu Glu Ser Ser Lys Val Phe Gln Ala Lys Ala
225                 230                 235                 240

Lys Lys Leu Gln Glu Ile Val Ala Asp Met Ala Cys His Glu Arg Tyr
                245                 250                 255

Ile Asp Gly Phe Ile Gln Gln Leu Arg Ser Tyr Lys Asp Asp Ser Gly
            260                 265                 270

Tyr Ser Ser Tyr Ala Ala Ala Gly Met His Val Val Ile Cys
        275                 280                 285

Pro Trp Leu Ala Phe Gly His Leu Leu Pro Cys Leu Asp Leu Ala Gln
    290                 295                 300

Arg Leu Ala Ser Arg Gly His Arg Val Ser Phe Val Ser Thr Pro Arg
305                 310                 315                 320

Asn Ile Ser Arg Leu Pro Pro Val Arg Pro Ala Leu Ala Pro Leu Val
                325                 330                 335

Ala Phe Val Ala Leu Pro Leu Pro Arg Val Glu Gly Leu Pro Asp Gly
            340                 345                 350

Ala Glu Ser Thr Asn Asp Val Pro His Asp Arg Pro Asp Met Val Glu
        355                 360                 365
```

```
Leu His Arg Arg Ala Phe Asp Gly Leu Ala Ala Pro Phe Ser Glu Phe
        370                 375                 380

Leu Gly Thr Ala Cys Ala Asp Trp Val Ile Val Asp Val Phe His His
385                 390                 395                 400

Trp Ala Ala Ala Ala Leu Glu His Lys Val Pro Cys Ala Met Met
                405                 410                 415

Leu Leu Gly Ser Ala Glu Met Ile Ala Ser Ile Ala Asp Glu Arg Leu
            420                 425                 430

Glu His Ala Glu Thr Glu Ser Pro Ala Ala Gly Gln Gly Arg Pro
        435                 440                 445

Ala Ala Ala Pro Thr Phe Glu Val Ala Arg Met Lys Leu Ile Arg
        450                 455                 460

<210> SEQ ID NO 46
<211> LENGTH: 463
<212> TYPE: PRT
<213> ORGANISM: Artificial sequence
<220> FEATURE:
<223> OTHER INFORMATION: Synthetic sequence

<400> SEQUENCE: 46

Met Ala Asn His His Glu Cys Met Asn Trp Leu Asp Asp Lys Pro Lys
1               5                   10                  15

Glu Ser Val Val Tyr Val Ala Phe Gly Ser Leu Val Lys His Gly Pro
            20                  25                  30

Glu Gln Val Glu Glu Ile Thr Arg Ala Leu Ile Asp Ser Asp Val Asn
        35                  40                  45

Phe Leu Trp Val Ile Lys His Lys Glu Glu Gly Lys Leu Pro Glu Asn
50                  55                  60

Leu Ser Glu Val Ile Lys Thr Gly Lys Gly Leu Ile Val Ala Trp Cys
65                  70                  75                  80

Lys Gln Leu Asp Val Leu Ala His Glu Ser Val Gly Cys Phe Val Thr
                85                  90                  95

His Cys Gly Phe Asn Ser Thr Leu Glu Ala Ile Ser Leu Gly Val Pro
            100                 105                 110

Val Val Ala Met Pro Gln Phe Ser Asp Gln Thr Thr Asn Ala Lys Leu
        115                 120                 125

Leu Asp Glu Ile Leu Gly Val Gly Val Arg Val Lys Ala Asp Glu Asn
    130                 135                 140

Gly Ile Val Arg Arg Gly Asn Leu Ala Ser Cys Ile Lys Met Ile Met
145                 150                 155                 160

Glu Glu Glu Arg Gly Val Ile Ile Arg Lys Asn Ala Val Lys Trp Lys
                165                 170                 175

Asp Leu Ala Lys Val Ala Val His Glu Gly Gly Ser Ser Asp Asn Asp
            180                 185                 190

Ile Val Glu Phe Val Ser Glu Leu Ile Lys Ala Gly Ser Gly Glu Gln
        195                 200                 205

Gln Lys Ile Lys Lys Ser Pro His Val Leu Leu Ile Pro Phe Pro Leu
    210                 215                 220

Gln Gly His Ile Asn Pro Phe Ile Gln Phe Gly Lys Arg Leu Ile Ser
225                 230                 235                 240

Lys Gly Val Lys Thr Thr Leu Val Thr Thr Ile His Thr Leu Asn Ser
                245                 250                 255

Thr Leu Asn His Ser Asn Thr Thr Thr Ser Ile Glu Ile Gln Ala
            260                 265                 270
```

```
Ile Ser Asp Gly Cys Asp Glu Gly Gly Phe Met Ser Ala Gly Glu Ser
        275                 280                 285

Tyr Leu Glu Thr Phe Lys Gln Val Gly Ser Lys Ser Leu Ala Asp Leu
    290                 295                 300

Ile Lys Lys Leu Gln Ser Glu Gly Thr Thr Ile Asp Ala Ile Ile Tyr
305                 310                 315                 320

Asp Ser Met Thr Glu Trp Val Leu Asp Val Ala Ile Glu Phe Gly Ile
                325                 330                 335

Asp Gly Gly Ser Phe Phe Thr Gln Ala Cys Val Val Asn Ser Leu Tyr
                340                 345                 350

Tyr His Val His Lys Gly Leu Ile Ser Leu Pro Leu Gly Glu Thr Val
                355                 360                 365

Ser Val Pro Gly Phe Pro Val Leu Gln Arg Trp Glu Thr Pro Leu Ile
        370                 375                 380

Leu Gln Asn His Glu Gln Ile Gln Ser Pro Trp Ser Gln Met Leu Phe
385                 390                 395                 400

Gly Gln Phe Ala Asn Ile Asp Gln Ala Arg Trp Val Phe Thr Asn Ser
                405                 410                 415

Phe Tyr Lys Leu Glu Glu Val Ile Glu Trp Thr Arg Lys Ile Trp
            420                 425                 430

Asn Leu Lys Val Ile Gly Pro Thr Leu Pro Ser Met Tyr Leu Asp Lys
            435                 440                 445

Arg Leu Asp Asp Lys Asp Asn Gly Phe Asn Leu Tyr Lys Ala
        450                 455                 460

<210> SEQ ID NO 47
<211> LENGTH: 8
<212> TYPE: PRT
<213> ORGANISM: Artificial sequence
<220> FEATURE:
<223> OTHER INFORMATION: Synthetic sequence

<400> SEQUENCE: 47

Met Ala Leu Leu Leu Ala Val Phe
1               5

<210> SEQ ID NO 48
<211> LENGTH: 17
<212> TYPE: PRT
<213> ORGANISM: Artificial sequence
<220> FEATURE:
<223> OTHER INFORMATION: Synthetic sequence

<400> SEQUENCE: 48

Tyr Lys Asp Asp Ser Gly Tyr Ser Ser Ser Tyr Ala Ala Ala Ala Gly
1               5                   10                  15

Met

<210> SEQ ID NO 49
<211> LENGTH: 7
<212> TYPE: PRT
<213> ORGANISM: Artificial sequence
<220> FEATURE:
<223> OTHER INFORMATION: Synthetic sequence

<400> SEQUENCE: 49

Tyr Lys Asp Ala Ala Gly Met
1               5
```

```
<210> SEQ ID NO 50
<211> LENGTH: 5
<212> TYPE: PRT
<213> ORGANISM: Artificial sequence
<220> FEATURE:
<223> OTHER INFORMATION: Synthetic sequence

<400> SEQUENCE: 50

Tyr Gly Ser Gly Met
1               5

<210> SEQ ID NO 51
<211> LENGTH: 482
<212> TYPE: PRT
<213> ORGANISM: Artificial sequence
<220> FEATURE:
<223> OTHER INFORMATION: Synthetic sequence

<400> SEQUENCE: 51

Met Ala Asp Ala Met Ala Thr Thr Glu Lys Lys Pro His Val Ile Phe
1               5                   10                  15

Ile Pro Phe Pro Ala Gln Ser His Ile Lys Ala Met Leu Lys Leu Ala
                20                  25                  30

Gln Leu Leu His His Lys Gly Leu Gln Ile Thr Phe Val Asn Thr Asp
            35                  40                  45

Phe Ile His Asn Gln Phe Leu Glu Ser Ser Gly Pro His Cys Leu Asp
        50                  55                  60

Gly Ala Pro Gly Phe Arg Phe Glu Thr Ile Pro Asp Gly Val Ser His
65                  70                  75                  80

Ser Pro Glu Ala Ser Ile Pro Ile Arg Glu Ser Leu Leu Arg Ser Ile
                85                  90                  95

Glu Thr Asn Phe Leu Asp Arg Phe Ile Asp Leu Val Thr Lys Leu Pro
            100                 105                 110

Asp Pro Pro Thr Cys Ile Ile Ser Asp Gly Phe Leu Ser Val Phe Thr
        115                 120                 125

Ile Asp Ala Ala Lys Lys Leu Gly Ile Pro Val Met Met Tyr Trp Thr
130                 135                 140

Leu Ala Ala Cys Gly Phe Met Gly Phe Tyr His Ile His Ser Leu Ile
145                 150                 155                 160

Glu Lys Gly Phe Ala Pro Leu Lys Asp Ala Ser Tyr Leu Thr Asn Gly
                165                 170                 175

Tyr Leu Asp Thr Val Ile Asp Trp Val Pro Gly Met Glu Gly Ile Arg
            180                 185                 190

Leu Lys Asp Phe Pro Leu Asp Trp Ser Thr Asp Leu Asn Asp Lys Val
        195                 200                 205

Leu Met Phe Thr Thr Glu Ala Thr Gln Arg Ser His Lys Val Ser His
    210                 215                 220

His Ile Phe His Thr Phe Asp Glu Leu Glu Pro Ser Ile Ile Lys Thr
225                 230                 235                 240

Leu Ser Leu Arg Tyr Asn His Ile Tyr Thr Ile Gly Pro Leu Gln Leu
                245                 250                 255

Leu Leu Asp Gln Ile Pro Glu Glu Lys Lys Gln Thr Gly Ile Thr Ser
            260                 265                 270

Leu His Gly Tyr Ser Leu Val Lys Glu Glu Pro Glu Cys Phe Gln Trp
        275                 280                 285

Leu Gln Ser Lys Glu Pro Asn Ser Val Val Tyr Val Asn Phe Gly Ser
    290                 295                 300
```

```
Thr Thr Val Met Ser Leu Glu Asp Met Thr Glu Phe Gly Trp Gly Leu
305                 310                 315                 320

Ala Asn Ser Asn His Tyr Phe Leu Trp Ile Ile Arg Ser Asn Leu Val
            325                 330                 335

Ile Gly Glu Asn Ala Val Leu Pro Pro Glu Leu Glu Glu His Ile Lys
        340                 345                 350

Lys Arg Gly Phe Ile Ala Ser Trp Cys Ser Gln Glu Lys Val Leu Lys
            355                 360                 365

His Pro Ser Val Gly Gly Phe Leu Thr His Cys Gly Trp Gly Ser Thr
    370                 375                 380

Ile Glu Ser Leu Ser Ala Gly Val Pro Met Ile Cys Trp Pro Tyr Ser
385                 390                 395                 400

Trp Asp Gln Leu Thr Asn Cys Arg Tyr Ile Cys Lys Glu Trp Glu Val
            405                 410                 415

Gly Leu Glu Met Gly Thr Lys Val Lys Arg Asp Glu Val Lys Arg Leu
        420                 425                 430

Val Gln Glu Leu Met Gly Glu Gly Gly His Lys Met Arg Asn Lys Ala
            435                 440                 445

Lys Asp Trp Lys Glu Lys Ala Arg Ile Ala Ile Ala Pro Asn Gly Ser
    450                 455                 460

Ser Ser Leu Asn Ile Asp Lys Met Val Lys Glu Ile Thr Val Leu Ala
465                 470                 475                 480

Arg Asn

<210> SEQ ID NO 52
<211> LENGTH: 44
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
```

<221> NAME/KEY: misc_feature
<222> LOCATION: (35)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid

<400> SEQUENCE: 52

Trp Xaa Pro Gln Xaa Xaa Xaa Leu Xaa His Xaa Xaa Xaa Xaa Ala Phe
1               5                   10                  15

Xaa Xaa His Xaa Gly Xaa Xaa Xaa Xaa Xaa Glu Xaa Xaa Xaa Xaa Gly
            20                  25                  30

Xaa Pro Xaa Xaa Xaa Xaa Pro Xaa Phe Xaa Xaa Gln
        35                  40

<210> SEQ ID NO 53
<211> LENGTH: 57
<212> TYPE: PRT
<213> ORGANISM: Artificial Sequence
<220> FEATURE:
<223> OTHER INFORMATION: Synthetic sequence

<400> SEQUENCE: 53

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro
    50                  55

<210> SEQ ID NO 54
<211> LENGTH: 61
<212> TYPE: PRT
<213> ORGANISM: Artificial Sequence
<220> FEATURE:
<223> OTHER INFORMATION: Synthetic sequence

<400> SEQUENCE: 54

Met Ala Leu Leu Leu Ala Val Phe Thr Gly Leu Leu Thr Val Pro Ala
1               5                   10                  15

Thr Ala Ile Thr Ile Gly Gly Thr Ala Val Ala Leu Ala Val Ala Leu
            20                  25                  30

Ile Phe Trp Tyr Leu Lys Ser Tyr Thr Ser Ala Arg Arg Ser Gln Ser
        35                  40                  45

Asn His Leu Pro Arg Val Pro Glu Val Pro Gly Val Pro
    50                  55                  60

<210> SEQ ID NO 55
<211> LENGTH: 37
<212> TYPE: PRT
<213> ORGANISM: Artificial Sequence
<220> FEATURE:
<223> OTHER INFORMATION: Synthetic sequence

<400> SEQUENCE: 55

Ala Val Ala Leu Ala Val Ala Leu Ile Phe Trp Tyr Leu Lys Ser Tyr
1               5                   10                  15

Thr Ser Ala Arg Arg Ser Gln Ser Asn His Leu Pro Arg Val Pro Glu
            20                  25                  30

Val Pro Gly Val Pro
        35

<210> SEQ ID NO 56
<211> LENGTH: 18
<212> TYPE: PRT
<213> ORGANISM: Artificial Sequence
<220> FEATURE:
<223> OTHER INFORMATION: Synthetic sequence

<400> SEQUENCE: 56

Arg Arg Ser Gln Ser Asn His Leu Pro Arg Val Pro Glu Val Pro Gly
1               5                   10                  15

Val Pro

<210> SEQ ID NO 57
<211> LENGTH: 18
<212> TYPE: PRT
<213> ORGANISM: Artificial Sequence
<220> FEATURE:
<223> OTHER INFORMATION: Synthetic sequence

<400> SEQUENCE: 57

Arg Arg Ser Gln Ser Asn His Leu Pro Arg Val Pro Glu Val Pro Gly
1               5                   10                  15

Val Pro

<210> SEQ ID NO 58
<211> LENGTH: 480
<212> TYPE: PRT
<213> ORGANISM: Artificial Sequence
<220> FEATURE:
<223> OTHER INFORMATION: Synthetic sequence

<400> SEQUENCE: 58

Met Glu Glu Ser Lys Thr Pro His Val Ala Ile Ile Pro Ser Pro Gly
1               5                   10                  15

Met Gly His Leu Ile Pro Leu Val Glu Phe Ala Lys Arg Leu Val His
            20                  25                  30

Leu His Gly Leu Thr Val Thr Phe Val Ile Ala Gly Glu Gly Pro Pro
        35                  40                  45

Ser Lys Ala Gln Arg Thr Val Leu Asp Ser Leu Pro Ser Ser Ile Ser
    50                  55                  60

Ser Val Phe Leu Pro Pro Val Asp Leu Thr Asp Leu Ser Ser Ser Thr
65                  70                  75                  80

Arg Ile Glu Ser Arg Ile Ser Leu Thr Val Thr Arg Ser Asn Pro Glu
                85                  90                  95

Leu Arg Lys Val Phe Asp Ser Phe Val Glu Gly Gly Arg Leu Pro Thr
            100                 105                 110

Ala Leu Val Val Asp Leu Phe Gly Thr Asp Ala Phe Asp Val Ala Val
        115                 120                 125

Glu Phe His Val Pro Pro Tyr Ile Phe Tyr Pro Thr Thr Ala Asn Val
    130                 135                 140

Leu Ser Phe Phe Leu His Leu Pro Lys Leu Asp Glu Thr Val Ser Cys
145                 150                 155                 160

Glu Phe Arg Glu Leu Thr Glu Pro Leu Met Leu Pro Gly Cys Val Pro
                165                 170                 175

-continued

Val Ala Gly Lys Asp Phe Leu Asp Pro Ala Gln Asp Arg Lys Asp Asp
                180                 185                 190

Ala Tyr Lys Trp Leu Leu His Asn Thr Lys Arg Tyr Lys Glu Ala Glu
            195                 200                 205

Gly Ile Leu Val Asn Thr Phe Phe Glu Leu Pro Asn Ala Ile Lys
        210                 215                 220

Ala Leu Gln Glu Pro Gly Leu Asp Lys Pro Val Tyr Pro Val Gly
225                 230                 235                 240

Pro Leu Val Asn Ile Gly Lys Gln Glu Ala Lys Gln Thr Glu Glu Ser
                245                 250                 255

Glu Cys Leu Lys Trp Leu Asp Asn Gln Pro Leu Gly Ser Val Leu Tyr
            260                 265                 270

Val Ser Phe Gly Ser Gly Gly Thr Leu Thr Cys Glu Gln Leu Asn Glu
        275                 280                 285

Leu Ala Leu Gly Leu Ala Asp Ser Glu Gln Arg Phe Leu Trp Val Ile
    290                 295                 300

Arg Ser Pro Ser Gly Ile Ala Asn Ser Ser Tyr Phe Asp Ser His Ser
305                 310                 315                 320

Gln Thr Asp Pro Leu Thr Phe Leu Pro Pro Gly Phe Leu Glu Arg Thr
                325                 330                 335

Lys Lys Arg Gly Phe Val Ile Pro Phe Trp Ala Pro Gln Ala Gln Val
            340                 345                 350

Leu Ala His Pro Ser Thr Gly Gly Phe Leu Thr His Cys Gly Trp Asn
        355                 360                 365

Ser Thr Leu Glu Ser Val Val Ser Gly Ile Pro Leu Ile Ala Trp Pro
    370                 375                 380

Leu Tyr Ala Glu Gln Lys Met Asn Ala Val Leu Leu Ser Glu Asp Ile
385                 390                 395                 400

Arg Ala Ala Leu Arg Pro Arg Ala Gly Asp Asp Gly Leu Val Arg Arg
                405                 410                 415

Glu Glu Val Ala Arg Val Val Lys Gly Leu Met Glu Gly Glu Glu Gly
            420                 425                 430

Lys Gly Val Arg Asn Lys Met Lys Glu Leu Lys Glu Ala Ala Cys Arg
        435                 440                 445

Val Leu Lys Asp Asp Gly Thr Ser Thr Lys Ala Leu Ser Leu Val Ala
    450                 455                 460

Leu Lys Trp Lys Ala His Lys Lys Glu Leu Glu Gln Asn Gly Asn His
465                 470                 475                 480

<210> SEQ ID NO 59
<211> LENGTH: 465
<212> TYPE: PRT
<213> ORGANISM: Artificial Sequence
<220> FEATURE:
<223> OTHER INFORMATION: Synthetic sequence

<400> SEQUENCE: 59

Met Ser Met Ser Asp Ile Asn Lys Asn Ser Glu Leu Ile Phe Ile Pro
1               5                   10                  15

Ala Pro Gly Ile Gly His Leu Ala Ser Ala Leu Glu Phe Ala Lys Leu
            20                  25                  30

Leu Thr Asn His Asp Lys Asn Leu Tyr Ile Thr Val Phe Cys Ile Lys
        35                  40                  45

Phe Pro Gly Met Pro Phe Ala Asp Ser Tyr Ile Lys Ser Val Leu Ala
    50                  55                  60

```
Ser Gln Pro Gln Ile Gln Leu Ile Asp Leu Pro Glu Val Glu Pro Pro
 65                  70                  75                  80

Pro Gln Glu Leu Leu Lys Ser Pro Glu Phe Tyr Ile Leu Thr Phe Leu
                 85                  90                  95

Glu Ser Leu Ile Pro His Val Lys Ala Thr Ile Lys Thr Ile Leu Ser
                100                 105                 110

Asn Lys Val Val Gly Leu Val Leu Asp Phe Phe Cys Val Ser Met Ile
                115                 120                 125

Asp Val Gly Asn Glu Phe Gly Ile Pro Ser Tyr Leu Phe Leu Thr Ser
                130                 135                 140

Asn Val Gly Phe Leu Ser Leu Met Leu Ser Leu Lys Asn Arg Gln Ile
145                 150                 155                 160

Glu Glu Val Phe Asp Asp Ser Asp Arg Asp His Gln Leu Leu Asn Ile
                165                 170                 175

Pro Gly Ile Ser Asn Gln Val Pro Ser Asn Val Leu Pro Asp Ala Cys
                180                 185                 190

Phe Asn Lys Asp Gly Gly Tyr Ile Ala Tyr Lys Leu Ala Glu Arg
                195                 200                 205

Phe Arg Asp Thr Lys Gly Ile Ile Val Asn Thr Phe Ser Asp Leu Glu
210                 215                 220

Gln Ser Ser Ile Asp Ala Leu Tyr Asp His Asp Glu Lys Ile Pro Pro
225                 230                 235                 240

Ile Tyr Ala Val Gly Pro Leu Leu Asp Leu Lys Gly Gln Pro Asn Pro
                245                 250                 255

Lys Leu Asp Gln Ala Gln His Asp Leu Ile Leu Lys Trp Leu Asp Glu
                260                 265                 270

Gln Pro Asp Lys Ser Val Val Phe Leu Cys Phe Gly Ser Met Gly Val
                275                 280                 285

Ser Phe Gly Pro Ser Gln Ile Arg Glu Ile Ala Leu Gly Leu Lys His
290                 295                 300

Ser Gly Val Arg Phe Leu Trp Ser Asn Ser Ala Glu Lys Lys Val Phe
305                 310                 315                 320

Pro Glu Gly Phe Leu Glu Trp Met Glu Leu Glu Gly Lys Gly Met Ile
                325                 330                 335

Cys Gly Trp Ala Pro Gln Val Glu Val Leu Ala His Lys Ala Ile Gly
                340                 345                 350

Gly Phe Val Ser His Cys Gly Trp Asn Ser Ile Leu Glu Ser Met Trp
                355                 360                 365

Phe Gly Val Pro Ile Leu Thr Trp Pro Ile Tyr Ala Glu Gln Gln Leu
                370                 375                 380

Asn Ala Phe Arg Leu Val Lys Glu Trp Gly Val Gly Leu Gly Leu Arg
385                 390                 395                 400

Val Asp Tyr Arg Lys Gly Ser Asp Val Val Ala Ala Glu Glu Ile Glu
                405                 410                 415

Lys Gly Leu Lys Asp Leu Met Asp Lys Asp Ser Ile Val His Lys Lys
                420                 425                 430

Val Gln Glu Met Lys Glu Met Ser Arg Asn Ala Val Val Asp Gly Gly
                435                 440                 445

Ser Ser Leu Ile Ser Val Gly Lys Leu Ile Asp Asp Ile Thr Gly Ser
                450                 455                 460

Asn
465
```

```
<210> SEQ ID NO 60
<211> LENGTH: 456
<212> TYPE: PRT
<213> ORGANISM: Artificial Sequence
<220> FEATURE:
<223> OTHER INFORMATION: Synthetic sequence

<400> SEQUENCE: 60

Met Ser Gln Thr Thr Asn Pro His Val Ala Val Leu Ala Phe Pro
1               5                   10                  15

Phe Ser Thr His Ala Ala Pro Leu Leu Ala Val Val Arg Arg Leu Ala
                20                  25                  30

Ala Ala Ala Pro His Ala Val Phe Ser Phe Ser Thr Ser Gln Ser
            35                  40                  45

Asn Ala Ser Ile Phe His Asp Ser Met His Thr Met Gln Cys Asn Ile
            50                  55                  60

Lys Ser Tyr Asp Ile Ser Asp Gly Val Pro Glu Gly Tyr Val Phe Ala
65              70                  75                  80

Gly Arg Pro Gln Glu Asp Ile Glu Leu Phe Thr Arg Ala Ala Pro Glu
                85                  90                  95

Ser Phe Arg Gln Gly Met Val Met Ala Val Ala Glu Thr Gly Arg Pro
                100                 105                 110

Val Ser Cys Leu Val Ala Asp Ala Phe Ile Trp Phe Ala Ala Asp Met
                115                 120                 125

Ala Ala Glu Met Gly Val Ala Trp Leu Pro Phe Trp Thr Ala Gly Pro
            130                 135                 140

Asn Ser Leu Ser Thr His Val Tyr Ile Asp Glu Ile Arg Glu Lys Ile
145                 150                 155                 160

Gly Val Ser Gly Ile Gln Gly Arg Glu Asp Glu Leu Leu Asn Phe Ile
                165                 170                 175

Pro Gly Met Ser Lys Val Arg Phe Arg Asp Leu Gln Glu Gly Ile Val
                180                 185                 190

Phe Gly Asn Leu Asn Ser Leu Phe Ser Arg Met Leu His Arg Met Gly
                195                 200                 205

Gln Val Leu Pro Lys Ala Thr Ala Val Phe Ile Asn Ser Phe Glu Glu
            210                 215                 220

Leu Asp Asp Ser Leu Thr Asn Asp Leu Lys Ser Lys Leu Lys Thr Tyr
225                 230                 235                 240

Leu Asn Ile Gly Pro Phe Asn Leu Ile Thr Pro Pro Val Val Pro
                245                 250                 255

Asn Thr Thr Gly Cys Leu Gln Trp Leu Lys Glu Arg Lys Pro Thr Ser
                260                 265                 270

Val Val Tyr Ile Ser Phe Gly Thr Val Thr Thr Pro Pro Ala Glu
                275                 280                 285

Val Val Ala Leu Ser Glu Ala Leu Glu Ala Ser Arg Val Pro Phe Ile
                290                 295                 300

Trp Ser Leu Arg Asp Lys Ala Arg Val His Leu Pro Glu Gly Phe Leu
305                 310                 315                 320

Glu Lys Thr Arg Gly Tyr Gly Met Val Val Pro Trp Ala Pro Gln Ala
                325                 330                 335

Glu Val Leu Ala His Glu Ala Val Gly Ala Phe Val Thr His Cys Gly
                340                 345                 350

Trp Asn Ser Leu Trp Glu Ser Val Ala Gly Gly Val Pro Leu Ile Cys
                355                 360                 365
```

Arg Pro Phe Phe Gly Asp Gln Arg Leu Asn Gly Arg Met Val Glu Asp
            370                 375                 380

Val Leu Glu Ile Gly Val Arg Ile Glu Gly Gly Val Phe Thr Lys Ser
385                 390                 395                 400

Gly Leu Met Ser Cys Phe Asp Gln Ile Leu Ser Gln Glu Lys Gly Lys
                405                 410                 415

Lys Leu Arg Glu Asn Leu Arg Ala Leu Arg Glu Thr Ala Asp Arg Ala
            420                 425                 430

Val Gly Pro Lys Gly Ser Ser Thr Glu Asn Phe Ile Thr Leu Val Asp
            435                 440                 445

Leu Val Ser Lys Pro Lys Asp Val
    450                 455

<210> SEQ ID NO 61
<211> LENGTH: 482
<212> TYPE: PRT
<213> ORGANISM: Artificial Sequence
<220> FEATURE:
<223> OTHER INFORMATION: Synthetic sequence

<400> SEQUENCE: 61

Met Gly Asn Phe Ala Asn Arg Lys Pro His Val Val Met Ile Pro Tyr
1               5                   10                  15

Pro Val Gln Gly His Ile Asn Pro Leu Phe Lys Leu Ala Lys Leu Leu
            20                  25                  30

His Leu Arg Gly Phe His Ile Thr Phe Val Asn Thr Glu Tyr Asn His
        35                  40                  45

Lys Arg Leu Leu Lys Ser Arg Gly Pro Lys Ala Phe Asp Gly Phe Thr
    50                  55                  60

Asp Phe Asn Phe Glu Ser Ile Pro Asp Gly Leu Thr Pro Met Glu Gly
65                  70                  75                  80

Asp Gly Asp Val Ser Gln Asp Val Pro Thr Leu Cys Gln Ser Val Arg
                85                  90                  95

Lys Asn Phe Leu Lys Pro Tyr Cys Glu Leu Leu Thr Arg Leu Asn His
            100                 105                 110

Ser Thr Asn Val Pro Pro Val Thr Cys Leu Val Ser Asp Cys Cys Met
        115                 120                 125

Ser Phe Thr Ile Gln Ala Ala Glu Glu Phe Glu Leu Pro Asn Val Leu
    130                 135                 140

Tyr Phe Ser Ser Ser Ala Cys Ser Leu Leu Asn Val Met His Phe Arg
145                 150                 155                 160

Ser Phe Val Glu Arg Gly Ile Ile Pro Phe Lys Asp Glu Ser Tyr Leu
                165                 170                 175

Thr Asn Gly Cys Leu Glu Thr Lys Val Asp Trp Ile Pro Gly Leu Lys
            180                 185                 190

Asn Phe Arg Leu Lys Asp Ile Val Asp Phe Ile Arg Thr Thr Asn Pro
        195                 200                 205

Asn Asp Ile Met Leu Glu Phe Phe Ile Glu Val Ala Asp Arg Val Asn
    210                 215                 220

Lys Asp Thr Thr Ile Leu Leu Asn Thr Phe Asn Glu Leu Glu Ser Asp
225                 230                 235                 240

Val Ile Asn Ala Leu Ser Ser Thr Ile Pro Ser Ile Tyr Pro Ile Gly
                245                 250                 255

Pro Leu Pro Ser Leu Leu Lys Gln Thr Pro Gln Ile His Gln Leu Asp
            260                 265                 270

```
Ser Leu Asp Ser Asn Leu Trp Lys Glu Asp Thr Glu Cys Leu Asp Trp
            275                 280                 285

Leu Glu Ser Lys Glu Pro Gly Ser Val Val Tyr Val Asn Phe Gly Ser
        290                 295                 300

Thr Thr Val Met Thr Pro Glu Gln Leu Leu Glu Phe Ala Trp Gly Leu
305                 310                 315                 320

Ala Asn Cys Lys Lys Ser Phe Leu Trp Ile Ile Arg Pro Asp Leu Val
                325                 330                 335

Ile Gly Gly Ser Val Ile Phe Ser Ser Glu Phe Thr Asn Glu Ile Ala
                340                 345                 350

Asp Arg Gly Leu Ile Ala Ser Trp Cys Pro Gln Asp Lys Val Leu Asn
                355                 360                 365

His Pro Ser Ile Gly Gly Phe Leu Thr His Cys Gly Trp Asn Ser Thr
            370                 375                 380

Thr Glu Ser Ile Cys Ala Gly Val Pro Met Leu Cys Trp Pro Phe Phe
385                 390                 395                 400

Ala Asp Gln Pro Thr Asp Cys Arg Phe Ile Cys Asn Glu Trp Glu Ile
                405                 410                 415

Gly Met Glu Ile Asp Thr Asn Val Lys Arg Glu Glu Leu Ala Lys Leu
            420                 425                 430

Ile Asn Glu Val Ile Ala Gly Asp Lys Gly Lys Lys Met Lys Gln Lys
            435                 440                 445

Ala Met Glu Leu Lys Lys Lys Ala Glu Glu Asn Thr Arg Pro Gly Gly
            450                 455                 460

Cys Ser Tyr Met Asn Leu Asn Lys Val Ile Lys Asp Val Leu Leu Lys
465                 470                 475                 480

Gln Asn

<210> SEQ ID NO 62
<211> LENGTH: 454
<212> TYPE: PRT
<213> ORGANISM: Artificial Sequence
<220> FEATURE:
<223> OTHER INFORMATION: Synthetic sequence

<400> SEQUENCE: 62

Met Ser Thr Phe Lys Asn Glu Met Asn Gly Asn Asn Leu Leu His Val
1               5                   10                  15

Ala Val Leu Ala Phe Pro Phe Gly Thr His Ala Ala Pro Leu Leu Ser
            20                  25                  30

Leu Val Lys Lys Ile Ala Thr Glu Ala Pro Lys Val Thr Phe Ser Phe
        35                  40                  45

Phe Cys Thr Thr Thr Thr Asn Asp Thr Leu Phe Ser Arg Ser Asn Glu
    50                  55                  60

Phe Leu Pro Asn Ile Lys Tyr Tyr Asn Val His Asp Gly Leu Pro Lys
65                  70                  75                  80

Gly Tyr Val Ser Ser Gly Asn Pro Arg Glu Pro Ile Phe Leu Phe Ile
                85                  90                  95

Lys Ala Met Gln Glu Asn Phe Lys His Val Ile Asp Glu Ala Val Ala
            100                 105                 110

Glu Thr Gly Lys Asn Ile Thr Cys Leu Val Thr Asp Ala Phe Phe Trp
        115                 120                 125

Phe Gly Ala Asp Leu Ala Glu Glu Met His Ala Lys Trp Val Pro Leu
    130                 135                 140

Trp Thr Ala Gly Pro His Ser Leu Leu Thr His Val Tyr Thr Asp Leu
```

```
145                 150                 155                 160
Ile Arg Glu Lys Thr Gly Ser Lys Glu Val His Asp Val Lys Ser Ile
                165                 170                 175

Asp Val Leu Pro Gly Phe Pro Glu Leu Lys Ala Ser Asp Leu Pro Glu
            180                 185                 190

Gly Val Ile Lys Asp Ile Asp Val Pro Phe Ala Thr Met Leu His Lys
            195                 200                 205

Met Gly Leu Glu Leu Pro Arg Ala Asn Ala Val Ala Ile Asn Ser Phe
    210                 215                 220

Ala Thr Ile His Pro Leu Ile Glu Asn Glu Leu Asn Ser Lys Phe Lys
225                 230                 235                 240

Leu Leu Leu Asn Val Gly Pro Phe Asn Leu Thr Thr Pro Gln Arg Lys
                245                 250                 255

Val Ser Asp Glu His Gly Cys Leu Glu Trp Leu Asp Gln His Glu Asn
            260                 265                 270

Ser Ser Val Val Tyr Ile Ser Phe Gly Ser Val Val Thr Pro Pro Pro
            275                 280                 285

His Glu Leu Thr Ala Leu Ala Glu Ser Leu Glu Glu Cys Gly Phe Pro
    290                 295                 300

Phe Ile Trp Ser Phe Arg Gly Asp Pro Lys Glu Lys Leu Pro Lys Gly
305                 310                 315                 320

Phe Leu Glu Arg Thr Lys Thr Lys Gly Lys Ile Val Ala Trp Ala Pro
                325                 330                 335

Gln Val Glu Ile Leu Lys His Ser Ser Val Gly Val Phe Leu Thr His
            340                 345                 350

Ser Gly Trp Asn Ser Val Leu Glu Cys Ile Val Gly Gly Val Pro Met
            355                 360                 365

Ile Ser Arg Pro Phe Phe Gly Asp Gln Gly Leu Asn Thr Ile Leu Thr
    370                 375                 380

Glu Ser Val Leu Glu Ile Gly Val Gly Val Asp Asn Gly Val Leu Thr
385                 390                 395                 400

Lys Glu Ser Ile Lys Lys Ala Leu Glu Leu Thr Met Ser Ser Glu Lys
                405                 410                 415

Gly Gly Ile Met Arg Gln Lys Ile Val Lys Leu Lys Glu Ser Ala Phe
            420                 425                 430

Lys Ala Val Glu Gln Asn Gly Thr Ser Ala Met Asp Phe Thr Thr Leu
            435                 440                 445

Ile Gln Ile Val Thr Ser
    450

<210> SEQ ID NO 63
<211> LENGTH: 446
<212> TYPE: PRT
<213> ORGANISM: Artificial Sequence
<220> FEATURE:
<223> OTHER INFORMATION: Synthetic sequence

<400> SEQUENCE: 63

Met Lys Asn Lys Gln His Val Ala Ile Phe Pro Phe Pro Phe Gly Ser
1               5                   10                  15

His Leu Pro Pro Leu Leu Asn Leu Val Leu Lys Leu Ala His Ile Ala
            20                  25                  30

Pro Asn Thr Ser Phe Ser Phe Ile Gly Thr His Ser Ser Asn Ala Phe
        35                  40                  45

Leu Phe Thr Lys Arg His Ile Pro Asn Asn Ile Arg Val Phe Thr Ile
```

```
                 50                  55                  60
Ser Asp Gly Ile Pro Glu Gly His Val Pro Ala Asn Asn Pro Ile Glu
65                   70                  75                  80

Lys Leu Asp Leu Phe Leu Ser Thr Gly Pro Asp Asn Leu Arg Lys Gly
                 85                  90                  95

Ile Glu Leu Ala Val Ala Glu Thr Lys Gln Ser Val Thr Cys Ile Ile
                100                 105                 110

Ala Asp Ala Phe Val Thr Ser Ser Leu Leu Val Ala Gln Thr Leu Asn
                115                 120                 125

Val Pro Trp Ile Ala Phe Trp Pro Asn Val Ser Cys Ser Leu Ser Leu
130                 135                 140

Tyr Phe Asn Ile Asp Leu Ile Arg Asp Lys Cys Ser Lys Asp Ala Lys
145                 150                 155                 160

Asn Ala Thr Leu Asp Phe Leu Pro Gly Leu Ser Lys Leu Arg Val Glu
                165                 170                 175

Asp Val Pro Gln Asp Met Leu Asp Val Gly Glu Lys Glu Thr Leu Phe
                180                 185                 190

Ser Arg Thr Leu Asn Ser Leu Gly Val Val Leu Pro Gln Ala Lys Ala
                195                 200                 205

Val Val Val Asn Phe Phe Ala Glu Leu Asp Pro Pro Leu Phe Val Lys
210                 215                 220

Tyr Met Arg Ser Lys Leu Gln Ser Leu Leu Tyr Val Val Pro Leu Pro
225                 230                 235                 240

Cys Pro Gln Leu Leu Leu Pro Glu Ile Asp Ser Asn Gly Cys Leu Ser
                245                 250                 255

Trp Leu Asp Ser Lys Ser Ser Arg Ser Val Ala Tyr Val Cys Phe Gly
                260                 265                 270

Thr Val Val Ser Pro Pro Gln Glu Val Val Ala Val Ala Glu Ala
                275                 280                 285

Leu Glu Glu Ser Gly Phe Pro Phe Val Trp Ala Leu Lys Glu Ser Leu
290                 295                 300

Leu Ser Ile Leu Pro Lys Gly Phe Val Glu Arg Thr Ser Thr Arg Gly
305                 310                 315                 320

Lys Val Val Ser Trp Val Pro Gln Ser His Val Leu Ser His Gly Ser
                325                 330                 335

Val Gly Val Phe Val Thr His Cys Gly Ala Asn Ser Val Met Glu Ser
                340                 345                 350

Val Ser Asn Gly Val Pro Met Ile Cys Arg Pro Phe Phe Gly Asp Gln
                355                 360                 365

Gly Ile Ala Ala Arg Val Ile Gln Asp Ile Trp Glu Val Gly Val Ile
                370                 375                 380

Val Glu Gly Lys Val Phe Thr Lys Asn Gly Phe Val Lys Ser Leu Asn
385                 390                 395                 400

Leu Ile Leu Val Gln Glu Asp Gly Lys Lys Ile Arg Asp Asn Ala Leu
                405                 410                 415

Lys Val Lys Gln Ile Val Gln Asp Ala Val Gly Pro His Gly Gln Ala
                420                 425                 430

Ala Glu Asp Phe Asn Thr Leu Val Glu Val Ile Ser Ser Ser
                435                 440                 445
```